United States Patent
Behzadi et al.

(10) Patent No.: US 11,744,481 B2
(45) Date of Patent: Sep. 5, 2023

(54) SYSTEM, APPARATUS AND METHODS FOR DATA COLLECTION AND ASSESSING OUTCOMES

(71) Applicant: OTSUKA PHARMACEUTICAL CO., LTD., Tokyo (JP)

(72) Inventors: Yashar Behzadi, Anaheim, CA (US); Alireza Akhbardeh, Redwood City, CA (US); Clifford Lewis, Albuquerque, NM (US)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 757 days.

(21) Appl. No.: 14/895,726

(22) PCT Filed: Jun. 2, 2014

(86) PCT No.: PCT/US2014/040570
§ 371 (c)(1),
(2) Date: Dec. 3, 2015

(87) PCT Pub. No.: WO2014/197402
PCT Pub. Date: Dec. 11, 2014

(65) Prior Publication Data
US 2016/0106339 A1 Apr. 21, 2016

Related U.S. Application Data

(60) Provisional application No. 61/831,075, filed on Jun. 4, 2013.

(51) Int. Cl.
*A61B 5/07* (2006.01)
*A61B 5/00* (2006.01)
(Continued)

(52) U.S. Cl.
CPC ............ *A61B 5/073* (2013.01); *A61B 5/0022* (2013.01); *A61B 5/1116* (2013.01);
(Continued)

(58) Field of Classification Search
CPC .......... A61B 2560/0204; A61B 5/0022; A61B 5/073; A61M 15/008; A61M 2205/3592
See application file for complete search history.

(56) References Cited

U.S. PATENT DOCUMENTS 3,218,638 A 11/1965 Honig
3,345,989 A 10/1967 Reynolds
(Continued)

FOREIGN PATENT DOCUMENTS

CA 2953847 11/2006
CN 1588649 3/2005
(Continued)

OTHER PUBLICATIONS

AADE, "AADE 37th Annual Meeting San Antonio Aug. 4-7, 2010" American Association of Diabetes Educators Aug. 2010; http://www.diabeteseducator.org/annualmeeting/2010/index.html; 2 pp.
(Continued)

*Primary Examiner* — Tse W Chen
*Assistant Examiner* — Michael A Catina
(74) *Attorney, Agent, or Firm* — Pillsbury Winthrop Shaw Pittman LLP

(57) ABSTRACT

A computer-implemented method is disclosed. The computer-implemented method comprises receiving, by a computer system, ingestible event marker (IEM) system information from a receiver worn by a subject, the IEM system information comprising information associated with ingestion of medication by the subject, wherein the receiver is configured to communicate with the computer system; receiving, by the computer system, contextual information
(Continued)

associated with the subject; and calculating, by the computer system, a composite risk score based on the IEM system information and the contextual information associated with the subject.

15 Claims, 49 Drawing Sheets

(51) Int. Cl.
*A61B 5/11* (2006.01)
*G16H 50/30* (2018.01)
*G16H 20/10* (2018.01)
*A61B 5/145* (2006.01)
*A61B 5/0205* (2006.01)

(52) U.S. Cl.
CPC .......... *A61B 5/4857* (2013.01); *A61B 5/6861* (2013.01); *A61B 5/7264* (2013.01); *A61B 5/7275* (2013.01); *A61B 5/7282* (2013.01); *G16H 20/10* (2018.01); *G16H 50/30* (2018.01); *A61B 5/0024* (2013.01); *A61B 5/02055* (2013.01); *A61B 5/14539* (2013.01); *A61B 5/4833* (2013.01); *A61B 2560/0204* (2013.01); *A61B 2560/0475* (2013.01); *A61B 2562/0219* (2013.01)

(56) References Cited

U.S. PATENT DOCUMENTS

| | | |
|---|---|---|
| 3,353,539 A | 11/1967 | Preston |
| 3,409,721 A | 11/1968 | Applezweig |
| 3,419,736 A | 12/1968 | Walsh |
| 3,589,943 A | 6/1971 | Grubb et al. |
| 3,607,788 A | 9/1971 | Adolph |
| 3,628,669 A | 12/1971 | McKinnis et al. |
| 3,642,008 A | 2/1972 | Bolduc |
| 3,679,480 A | 7/1972 | Brown et al. |
| 3,682,160 A | 8/1972 | Murata |
| 3,719,183 A | 3/1973 | Schwartz |
| 3,727,616 A | 4/1973 | Lenzkes |
| 3,799,802 A | 3/1974 | Schneble, Jr. et al. |
| 3,825,016 A | 7/1974 | Lale et al. |
| 3,828,766 A | 8/1974 | Krasnow |
| 3,837,339 A | 9/1974 | Aisenberg et al. |
| 3,893,111 A | 7/1975 | Cotter |
| 3,944,064 A | 3/1976 | Bashaw et al. |
| 3,967,202 A | 6/1976 | Batz |
| 3,989,050 A | 11/1976 | Buchalter |
| 4,017,856 A | 4/1977 | Wiegand |
| 4,055,178 A | 10/1977 | Harrigan |
| 4,062,750 A | 12/1977 | Butler |
| 4,077,397 A | 3/1978 | Ellis |
| 4,077,398 A | 3/1978 | Ellis |
| 4,082,087 A | 4/1978 | Howson |
| 4,090,752 A | 5/1978 | Long |
| 4,105,023 A | 8/1978 | Merchese et al. |
| 4,106,348 A | 8/1978 | Auphan |
| 4,129,125 A | 12/1978 | Lester |
| 4,133,730 A | 1/1979 | DuBois et al. |
| 4,141,349 A | 2/1979 | Ory et al. |
| 4,166,453 A | 9/1979 | McClelland |
| 4,239,046 A | 12/1980 | Ong |
| 4,251,795 A | 2/1981 | Shibasaki et al. |
| 4,269,189 A | 5/1981 | Abraham |
| 4,281,664 A | 8/1981 | Duggan |
| 4,331,654 A | 5/1982 | Morris |
| 4,345,588 A | 8/1982 | Widder et al. |
| 4,418,697 A | 12/1983 | Tama |
| 4,425,117 A | 1/1984 | Hugemann |
| 4,439,196 A | 3/1984 | Higuchi |
| 4,494,950 A | 1/1985 | Fischell |
| 4,526,474 A | 7/1985 | Simon |
| 4,547,391 A | 10/1985 | Jenkins |
| 4,559,950 A | 12/1985 | Vaughan |
| 4,564,363 A | 1/1986 | Bagnall et al. |
| 4,578,061 A | 3/1986 | Lemelson |
| 4,618,533 A | 10/1986 | Steuck |
| 4,635,641 A | 1/1987 | Hoffman |
| 4,654,165 A | 3/1987 | Eisenber |
| 4,663,250 A | 5/1987 | Ong et al. |
| 4,669,479 A | 6/1987 | Dunseath |
| 4,681,111 A | 7/1987 | Silvian |
| 4,687,660 A | 8/1987 | Baker et al. |
| 4,725,997 A | 2/1988 | Urquhart et al. |
| 4,749,575 A | 6/1988 | Rotman et al. |
| 4,763,659 A | 8/1988 | Dunseath |
| 4,767,627 A | 8/1988 | Caldwell et al. |
| 4,784,162 A | 11/1988 | Ricks |
| 4,793,825 A | 12/1988 | Benjamin et al. |
| 4,809,705 A | 3/1989 | Ascher |
| 4,835,373 A | 5/1989 | Adams et al. |
| 4,844,076 A | 7/1989 | Lesho |
| 4,871,974 A | 10/1989 | Davis et al. |
| 4,876,093 A | 10/1989 | Theeuwes et al. |
| 4,896,261 A | 1/1990 | Nolan |
| 4,975,230 A | 12/1990 | Pinkhasov |
| 4,987,897 A | 1/1991 | Funke |
| 5,000,957 A | 3/1991 | Eckenhoff et al. |
| 5,016,634 A | 5/1991 | Vock et al. |
| 5,079,006 A | 1/1992 | Urquhart |
| 5,167,626 A | 12/1992 | Casper |
| 5,176,626 A | 1/1993 | Soehendra |
| 5,179,578 A | 1/1993 | Ishizu |
| 5,245,332 A | 9/1993 | Katzenstein et al. |
| 5,261,402 A | 11/1993 | DiSabito |
| 5,263,481 A | 11/1993 | Axelgaard et al. |
| 5,276,710 A | 1/1994 | Iwasaki |
| 5,279,607 A | 1/1994 | Schentag et al. |
| 5,281,287 A | 1/1994 | Lloyd |
| 5,283,136 A | 2/1994 | Peled et al. |
| 5,288,564 A | 2/1994 | Klein |
| 5,305,745 A | 4/1994 | Zacouto |
| 5,318,557 A | 6/1994 | Gross |
| 5,394,882 A | 3/1995 | Mawhinney |
| 5,395,366 A | 3/1995 | D'Andrea et al. |
| 5,411,535 A | 5/1995 | Fujii et al. |
| 5,412,372 A | 5/1995 | Parkhurst et al. |
| 5,428,961 A | 7/1995 | Sakakibara |
| 5,436,091 A | 7/1995 | Shackle et al. |
| 5,443,461 A | 8/1995 | Atkinson et al. |
| 5,443,843 A | 8/1995 | Curatolo et al. |
| 5,458,141 A | 10/1995 | Neil et al. |
| 5,468,222 A | 11/1995 | Altchuler |
| 5,485,841 A | 1/1996 | Watkin et al. |
| 5,511,548 A | 4/1996 | Riazzi et al. |
| 5,538,007 A | 7/1996 | Gorman |
| 5,551,953 A | 9/1996 | Lattin et al. |
| 5,567,210 A | 10/1996 | Bates et al. |
| 5,596,302 A | 1/1997 | Mastrocola et al. |
| D377,983 S | 2/1997 | Sabri et al. |
| 5,600,548 A | 2/1997 | Nguyen et al. |
| 5,634,466 A | 6/1997 | Gruner |
| 5,634,468 A | 6/1997 | Platt |
| 5,638,406 A | 6/1997 | Sogabe |
| 5,645,063 A | 7/1997 | Straka et al. |
| 5,705,189 A | 1/1998 | Lehmann et al. |
| 5,720,771 A | 2/1998 | Snell |
| 5,738,708 A | 4/1998 | Peachey et al. |
| 5,740,811 A | 4/1998 | Hedberg |
| 5,757,326 A | 5/1998 | Koyama et al. |
| 5,792,048 A | 8/1998 | Schaefer |
| 5,802,467 A | 9/1998 | Salazar |
| 5,833,716 A | 11/1998 | Bar-Or |
| 5,836,474 A | 11/1998 | Wessberg |
| 5,845,265 A | 12/1998 | Woolston |
| 5,862,803 A | 1/1999 | Besson |
| 5,862,808 A | 1/1999 | Albarello |
| 5,868,136 A | 2/1999 | Fox |
| 5,914,701 A | 6/1999 | Gersheneld et al. |
| 5,917,346 A | 6/1999 | Gord |
| 5,921,925 A | 7/1999 | Cartmell et al. |

(56) References Cited

U.S. PATENT DOCUMENTS

| | | |
|---|---|---|
| 5,925,030 A | 7/1999 | Gross et al. |
| 5,925,066 A | 7/1999 | Kroll et al. |
| 5,957,854 A | 9/1999 | Besson et al. |
| 5,963,132 A | 10/1999 | Yoakum et al. |
| 5,965,629 A | 10/1999 | Jung et al. |
| 5,974,124 A | 10/1999 | Schlueter, Jr. et al. |
| 5,981,166 A | 11/1999 | Mandecki |
| 5,999,846 A | 12/1999 | Pardey et al. |
| 6,009,350 A | 12/1999 | Renken |
| 6,023,631 A | 2/2000 | Cartmell et al. |
| 6,038,464 A | 3/2000 | Axelgaard et al. |
| 6,042,710 A | 3/2000 | Dubrow |
| 6,047,203 A | 4/2000 | Sackner |
| 6,076,016 A | 6/2000 | Feierbach et al. |
| 6,081,734 A | 6/2000 | Batz |
| 6,083,248 A | 7/2000 | Thompson |
| 6,090,489 A | 7/2000 | Hayakawa et al. |
| 6,091,975 A | 7/2000 | Daddona et al. |
| 6,095,985 A | 8/2000 | Raymond et al. |
| 6,099,482 A | 8/2000 | Brune et al. |
| 6,115,636 A | 9/2000 | Ryan |
| 6,117,077 A | 9/2000 | Del Mar et al. |
| 6,122,351 A | 9/2000 | Schlueter, Jr. et al. |
| 6,141,592 A | 10/2000 | Pauly |
| 6,149,940 A | 11/2000 | Maggi et al. |
| 6,200,265 B1 | 3/2001 | Walsh et al. |
| 6,204,764 B1 | 3/2001 | Maloney |
| 6,206,702 B1 | 3/2001 | Hayden et al. |
| 6,217,744 B1 | 4/2001 | Crosby |
| 6,231,593 B1 | 5/2001 | Meserol |
| 6,245,057 B1 | 6/2001 | Sieben et al. |
| 6,269,058 B1 | 7/2001 | Yamanoi et al. |
| 6,275,476 B1 | 8/2001 | Wood |
| 6,285,897 B1 | 9/2001 | Kilcoyne et al. |
| 6,287,252 B1 | 9/2001 | Lugo |
| 6,288,629 B1 | 9/2001 | Cofino et al. |
| 6,289,238 B1 | 9/2001 | Besson et al. |
| 6,315,719 B1 | 11/2001 | Rode et al. |
| 6,342,774 B1 | 1/2002 | Kreisinger et al. |
| 6,344,824 B1 | 2/2002 | Takasugi et al. |
| 6,358,202 B1 | 3/2002 | Arent |
| 6,364,834 B1 | 4/2002 | Reuss |
| 6,366,206 B1 | 4/2002 | Ishikawa et al. |
| 6,368,190 B1 | 4/2002 | Easter et al. |
| 6,371,927 B1 | 4/2002 | Brune |
| 6,374,670 B1 | 4/2002 | Spelman |
| 6,380,858 B1 | 4/2002 | Yarin et al. |
| 6,390,088 B1 | 5/2002 | Noehl et al. |
| 6,394,953 B1 | 5/2002 | Devlin et al. |
| 6,394,997 B1 | 5/2002 | Lemelson |
| 6,409,674 B1 | 6/2002 | Brockway et al. |
| 6,411,567 B1 | 6/2002 | Niemiec et al. |
| 6,426,863 B1 | 7/2002 | Munshi |
| 6,432,292 B1 | 8/2002 | Pinto et al. |
| 6,440,069 B1 | 8/2002 | Raymond et al. |
| 6,441,747 B1 | 8/2002 | Khair |
| 6,453,199 B1 | 9/2002 | Kobozev |
| 6,477,424 B1 | 11/2002 | Thompson et al. |
| 6,482,156 B2 | 11/2002 | Lliff |
| 6,494,829 B1 | 12/2002 | New et al. |
| 6,496,705 B1 | 12/2002 | Ng et al. |
| 6,505,077 B1 | 1/2003 | Kast et al. |
| 6,525,996 B1 | 2/2003 | Miyazawa |
| 6,526,315 B1 | 2/2003 | Inagawa |
| 6,531,026 B1 | 3/2003 | Takeichi et al. |
| 6,540,699 B1 | 4/2003 | Smith |
| 6,544,174 B2 | 4/2003 | West |
| 6,564,079 B1 | 5/2003 | Cory |
| 6,572,636 B1 | 6/2003 | Hagen et al. |
| 6,574,425 B1 | 6/2003 | Weiss et al. |
| 6,577,893 B1 | 6/2003 | Besson et al. |
| 6,579,231 B1 | 6/2003 | Phipps |
| 6,595,929 B2 | 7/2003 | Stivoric |
| 6,599,284 B2 | 7/2003 | Faour et al. |
| 6,605,038 B1 | 8/2003 | Teller |
| 6,605,046 B1 | 8/2003 | Del Mar |
| 6,609,018 B2 | 8/2003 | Cory |
| 6,612,984 B1 | 9/2003 | Kerr |
| 6,632,175 B1 | 10/2003 | Marshall |
| 6,632,216 B2 | 10/2003 | Houzego et al. |
| 6,635,279 B2 | 10/2003 | Kolter et al. |
| 6,638,231 B2 | 10/2003 | Govari et al. |
| 6,643,541 B2 | 11/2003 | Mok et al. |
| 6,650,718 B1 | 11/2003 | Fujimura et al. |
| 6,654,638 B1 | 11/2003 | Sweeney |
| 6,663,846 B1 | 12/2003 | McCombs |
| 6,673,474 B2 | 1/2004 | Yamamoto |
| 6,679,830 B2 | 1/2004 | Kolarovic et al. |
| 6,680,923 B1 | 1/2004 | Leon |
| 6,683,493 B1 | 1/2004 | Fujimora et al. |
| 6,689,117 B2 | 2/2004 | Sweeney et al. |
| 6,694,161 B2 | 2/2004 | Mehrotra |
| 6,704,602 B2 | 3/2004 | Berg et al. |
| 6,720,923 B1 | 4/2004 | Hayward et al. |
| 6,738,671 B2 | 5/2004 | Christophersom et al. |
| 6,740,033 B1 | 5/2004 | Olejniczak et al. |
| 6,745,082 B2 | 6/2004 | Axelgaard et al. |
| 6,755,783 B2 | 6/2004 | Cosentino |
| 6,757,523 B2 | 6/2004 | Fry |
| 6,759,968 B2 | 7/2004 | Zierolf |
| 6,771,174 B2 | 8/2004 | Broas |
| 6,773,429 B2 | 8/2004 | Sheppard et al. |
| 6,800,060 B2 | 10/2004 | Marshall |
| 6,801,137 B2 | 10/2004 | Eggers et al. |
| 6,804,558 B2 | 10/2004 | Haller et al. |
| 6,814,706 B2 | 11/2004 | Barton et al. |
| 6,822,554 B2 | 11/2004 | Vrijens et al. |
| 6,836,862 B1 | 12/2004 | Erekson et al. |
| 6,839,659 B2 | 1/2005 | Tarassenko et al. |
| 6,840,904 B2 | 1/2005 | Goldberg |
| 6,842,636 B2 | 1/2005 | Perrault |
| 6,845,272 B1 | 1/2005 | Thomsen |
| 6,864,780 B2 | 3/2005 | Doi |
| 6,879,810 B2 | 4/2005 | Bouet |
| 6,882,881 B1 | 4/2005 | Lesser et al. |
| 6,897,788 B2 | 5/2005 | Khair et al. |
| 6,909,878 B2 | 6/2005 | Haller |
| 6,922,592 B2 | 7/2005 | Thompson et al. |
| 6,928,370 B2 | 8/2005 | Anuzis et al. |
| 6,929,636 B1 | 8/2005 | Von Alten |
| 6,937,150 B2 | 8/2005 | Medema |
| 6,939,292 B2 | 9/2005 | Mizuno |
| 6,942,616 B2 | 9/2005 | Kerr |
| 6,951,536 B2 | 10/2005 | Yokoi |
| 6,957,107 B2 | 10/2005 | Rogers et al. |
| 6,959,929 B2 | 11/2005 | Pugnet et al. |
| 6,968,153 B1 | 11/2005 | Heinonen |
| 6,987,965 B2 | 1/2006 | Ng et al. |
| 6,990,082 B1 | 1/2006 | Zehavi et al. |
| 7,002,476 B2 | 2/2006 | Rapchak |
| 7,004,395 B2 | 2/2006 | Koenck |
| 7,009,634 B2 | 3/2006 | Iddan et al. |
| 7,009,946 B1 | 3/2006 | Kardach |
| 7,013,162 B2 | 3/2006 | Gorsuch |
| 7,016,648 B2 | 3/2006 | Haller |
| 7,020,508 B2 | 3/2006 | Stivoric |
| 7,023,940 B2 | 4/2006 | Nakamura et al. |
| 7,024,248 B2 | 4/2006 | Penner et al. |
| 7,031,745 B2 | 4/2006 | Shen |
| 7,031,857 B2 | 4/2006 | Tarassenko et al. |
| 7,039,453 B2 | 5/2006 | Mullick |
| 7,044,911 B2 | 5/2006 | Drinan et al. |
| 7,046,649 B2 | 5/2006 | Awater et al. |
| 7,050,419 B2 | 5/2006 | Azenkot et al. |
| 7,062,308 B1 | 6/2006 | Jackson |
| 7,069,062 B2 | 6/2006 | Minotani et al. |
| 7,076,437 B1 | 7/2006 | Levy |
| 7,081,693 B2 | 7/2006 | Hamel et al. |
| 7,091,726 B2 | 8/2006 | Sano et al. |
| 7,118,531 B2 | 10/2006 | Krill |
| 7,125,382 B2 | 10/2006 | Zhou et al. |
| 7,127,300 B2 | 10/2006 | Mazar et al. |
| 7,146,228 B2 | 12/2006 | Nielsen |
| 7,146,449 B2 | 12/2006 | Do et al. |

(56) References Cited

U.S. PATENT DOCUMENTS

| | | |
|---|---|---|
| 7,149,581 B2 | 12/2006 | Goedeke et al. |
| 7,154,071 B2 | 12/2006 | Sattler et al. |
| 7,155,232 B2 | 12/2006 | Godfrey et al. |
| 7,160,258 B2 | 1/2007 | Imran |
| 7,161,484 B2 | 1/2007 | Tsoukalis |
| 7,164,942 B2 | 1/2007 | Avrahami |
| 7,171,166 B2 | 1/2007 | Ng et al. |
| 7,171,177 B2 | 1/2007 | Park et al. |
| 7,171,259 B2 | 1/2007 | Rytky |
| 7,176,784 B2 | 2/2007 | Gilbert et al. |
| 7,187,960 B2 | 3/2007 | Abreu |
| 7,188,767 B2 | 3/2007 | Penuela |
| 7,194,038 B1 | 3/2007 | Inkinen |
| 7,206,630 B1 | 4/2007 | Tarler |
| 7,209,790 B2 | 4/2007 | Thompson et al. |
| 7,215,660 B2 | 5/2007 | Perlman |
| 7,215,991 B2 | 5/2007 | Besson |
| 7,218,967 B2 | 5/2007 | Bergelson |
| 7,231,451 B2 | 6/2007 | Law |
| 7,243,118 B2 | 7/2007 | Lou |
| 7,246,521 B2 | 7/2007 | Kim |
| 7,249,212 B2 | 7/2007 | Do |
| 7,252,792 B2 | 8/2007 | Perrault |
| 7,253,716 B2 | 8/2007 | Lovoi et al. |
| 7,261,690 B2 | 8/2007 | Teller |
| 7,270,633 B1 | 9/2007 | Goscha |
| 7,273,454 B2 | 9/2007 | Raymond et al. |
| 7,285,090 B2 | 10/2007 | Stivoric et al. |
| 7,289,855 B2 | 10/2007 | Nghiem |
| 7,291,014 B2 | 11/2007 | Chung et al. |
| 7,291,497 B2 | 11/2007 | Holmes |
| 7,292,139 B2 | 11/2007 | Mazar et al. |
| 7,294,105 B1 | 11/2007 | Islam |
| 7,295,877 B2 | 11/2007 | Govari |
| 7,311,665 B2 | 12/2007 | Hawthorne |
| 7,313,163 B2 | 12/2007 | Liu |
| 7,317,378 B2 | 1/2008 | Jarvis et al. |
| 7,318,808 B2 | 1/2008 | Tarassenko et al. |
| 7,336,732 B1 | 2/2008 | Wiss |
| 7,336,929 B2 | 2/2008 | Yasuda |
| 7,342,895 B2 | 3/2008 | Serpa |
| 7,346,380 B2 | 3/2008 | Axelgaard et al. |
| 7,349,722 B2 | 3/2008 | Witkowski et al. |
| 7,352,998 B2 | 4/2008 | Palin |
| 7,353,258 B2 | 4/2008 | Washburn |
| 7,357,891 B2 | 4/2008 | Yang et al. |
| 7,359,674 B2 | 4/2008 | Markki |
| 7,366,558 B2 | 4/2008 | Virtanen et al. |
| 7,366,675 B1 | 4/2008 | Walker et al. |
| 7,368,190 B2 | 5/2008 | Heller et al. |
| 7,368,191 B2 | 5/2008 | Andelman et al. |
| 7,373,196 B2 | 5/2008 | Ryu et al. |
| 7,375,739 B2 | 5/2008 | Robbins |
| 7,376,435 B2 | 5/2008 | McGowan |
| 7,382,247 B2 | 6/2008 | Welch et al. |
| 7,382,263 B2 | 6/2008 | Danowski et al. |
| 7,387,607 B2 | 6/2008 | Holt |
| 7,388,903 B2 | 6/2008 | Godfrey et al. |
| 7,389,088 B2 | 6/2008 | Kim |
| 7,392,015 B1 | 6/2008 | Farlow |
| 7,395,106 B2 | 7/2008 | Ryu et al. |
| 7,396,330 B2 | 7/2008 | Banet |
| 7,404,968 B2 | 7/2008 | Abrams et al. |
| 7,413,544 B2 | 8/2008 | Kerr |
| 7,414,534 B1 | 8/2008 | Kroll et al. |
| 7,414,543 B2 | 8/2008 | Rye et al. |
| 7,415,242 B1 | 8/2008 | Ngan |
| 7,419,468 B2 | 9/2008 | Shimizu et al. |
| 7,424,268 B2 | 9/2008 | Diener |
| 7,424,319 B2 | 9/2008 | Muehlsteff |
| 7,427,266 B2 | 9/2008 | Ayer et al. |
| 7,433,731 B2 | 10/2008 | Matsumura et al. |
| 7,449,262 B2 | 11/2008 | Christie et al. |
| 7,462,150 B1 * | 12/2008 | Bharmi .............. A61B 5/02405 600/300 |
| 7,471,665 B2 | 12/2008 | Perlman |
| 7,485,093 B2 | 2/2009 | Glukhovsky |
| 7,485,095 B2 | 2/2009 | Shusterman |
| 7,499,674 B2 | 3/2009 | Salokannel |
| 7,502,643 B2 | 3/2009 | Farringdon et al. |
| 7,505,795 B1 | 3/2009 | Lim et al. |
| 7,508,248 B2 | 3/2009 | Yoshida |
| 7,510,121 B2 | 3/2009 | Koenck |
| 7,512,448 B2 | 3/2009 | Malick |
| 7,512,860 B2 | 3/2009 | Miyazaki et al. |
| 7,515,043 B2 | 4/2009 | Welch |
| 7,519,416 B2 | 4/2009 | Sula et al. |
| 7,523,756 B2 | 4/2009 | Minai |
| 7,525,426 B2 | 4/2009 | Edelstein |
| 7,527,807 B2 | 5/2009 | Choi et al. |
| 7,539,533 B2 | 5/2009 | Tran |
| 7,542,878 B2 | 6/2009 | Nanikashvili |
| 7,547,278 B2 | 6/2009 | Miyazaki et al. |
| 7,551,590 B2 | 6/2009 | Haller |
| 7,554,452 B2 | 6/2009 | Cole |
| 7,558,620 B2 | 7/2009 | Ishibashi |
| 7,558,622 B2 | 7/2009 | Tran |
| 7,558,965 B2 | 7/2009 | Wheeler et al. |
| 7,575,005 B2 | 8/2009 | Mumford |
| 7,614,743 B2 | 11/2009 | Geiger |
| 7,616,111 B2 | 11/2009 | Covannon |
| 7,616,710 B2 | 11/2009 | Kim et al. |
| 7,617,001 B2 | 11/2009 | Penner et al. |
| 7,639,473 B2 | 12/2009 | Hsu et al. |
| 7,640,802 B2 | 1/2010 | King et al. |
| 7,647,112 B2 | 1/2010 | Tracey |
| 7,647,185 B2 | 1/2010 | Tarassenko et al. |
| 7,653,031 B2 | 1/2010 | Godfrey et al. |
| 7,668,437 B1 | 2/2010 | Yamada et al. |
| 7,683,761 B2 | 2/2010 | Burghard et al. |
| 7,672,703 B2 | 3/2010 | Yeo et al. |
| 7,672,714 B2 | 3/2010 | Kuo |
| 7,673,679 B2 | 3/2010 | Harrison et al. |
| 7,678,043 B2 | 3/2010 | Gilad |
| 7,689,437 B1 | 3/2010 | Teller et al. |
| 7,689,833 B2 | 3/2010 | Lange |
| 7,697,994 B2 | 4/2010 | VanDanacker et al. |
| 7,712,288 B2 | 5/2010 | Ramasubramanian et al. |
| 7,720,036 B2 | 5/2010 | Sadri |
| 7,729,776 B2 | 6/2010 | Von Arx et al. |
| 7,733,224 B2 | 6/2010 | Tran |
| 7,736,318 B2 | 6/2010 | Costentino |
| 7,747,454 B2 | 6/2010 | Bartfeld et al. |
| 7,756,587 B2 | 7/2010 | Penner et al. |
| 7,764,996 B2 | 7/2010 | Zhang et al. |
| 7,779,614 B1 | 8/2010 | McGonagle et al. |
| 7,796,043 B2 | 9/2010 | Euliano et al. |
| 7,797,033 B2 | 9/2010 | D'Andrea et al. |
| 7,806,852 B1 | 10/2010 | Jursen |
| 7,809,399 B2 | 10/2010 | Lu |
| 7,811,231 B2 | 10/2010 | Jin et al. |
| 7,844,341 B2 | 11/2010 | Von Arx et al. |
| 7,857,766 B2 | 12/2010 | Lasater et al. |
| 7,860,731 B2 | 12/2010 | Jackson et al. |
| 7,871,734 B2 | 1/2011 | Hertz et al. |
| 7,899,526 B2 | 3/2011 | Benditt et al. |
| 7,904,133 B2 | 3/2011 | Gehman et al. |
| D639,437 S | 6/2011 | Bishay et al. |
| 7,978,064 B2 | 7/2011 | Zdeblick et al. |
| 8,025,149 B2 | 9/2011 | Sterry et al. |
| 8,036,731 B2 | 10/2011 | Kimchy et al. |
| 8,036,748 B2 | 10/2011 | Zdeblick et al. |
| 8,055,334 B2 | 11/2011 | Savage et al. |
| 8,060,249 B2 | 11/2011 | Bear et al. |
| 8,073,707 B2 | 12/2011 | Teller et al. |
| 8,083,128 B2 | 12/2011 | Dembo et al. |
| 8,123,576 B2 | 2/2012 | Kim |
| 8,135,596 B2 | 3/2012 | Jung et al. |
| 8,142,513 B2 | 3/2012 | Shalon et al. |
| 8,177,611 B2 | 5/2012 | Kang |
| 8,180,425 B2 | 5/2012 | Selvitelli et al. |
| 8,185,191 B1 | 5/2012 | Shapiro et al. |
| 8,185,646 B2 | 5/2012 | Headley |
| 8,200,320 B2 | 6/2012 | Kovacs |

(56) References Cited

U.S. PATENT DOCUMENTS

| | | |
|---|---|---|
| 8,209,018 B2 | 6/2012 | Osorio et al. |
| 8,214,007 B2 | 7/2012 | Baker et al. |
| 8,224,667 B1 | 7/2012 | Miller et al. |
| 8,238,998 B2 | 8/2012 | Park |
| 8,249,686 B2 | 8/2012 | Libbus et al. |
| 8,253,586 B1 | 8/2012 | Matak |
| 8,254,853 B2 | 8/2012 | Rofougaran |
| 8,258,962 B2 | 9/2012 | Robertson et al. |
| 8,262,394 B2 | 9/2012 | Walker et al. |
| 8,271,106 B2 | 9/2012 | Wehba et al. |
| 8,285,356 B2 | 10/2012 | Bly et al. |
| 8,290,574 B2 | 10/2012 | Felid et al. |
| 8,301,232 B2 | 10/2012 | Albert et al. |
| 8,308,640 B2 | 11/2012 | Baldus et al. |
| 8,314,619 B2 | 11/2012 | Takiguchi |
| 8,315,687 B2 | 11/2012 | Cross et al. |
| 8,343,068 B2 | 1/2013 | Najafi et al. |
| 8,369,936 B2 | 2/2013 | Farringdon et al. |
| 8,386,009 B2 | 2/2013 | Lindberg et al. |
| 8,389,003 B2 | 3/2013 | Mintchev et al. |
| 8,404,275 B2 | 3/2013 | Habboushe |
| 8,440,274 B2 | 5/2013 | Wang |
| 8,454,528 B2 | 6/2013 | Yuen et al. |
| 8,454,561 B2 | 6/2013 | Uber, III et al. |
| 8,514,086 B2 | 8/2013 | Harper et al. |
| 8,542,123 B2 | 9/2013 | Robertson |
| 8,564,432 B2 | 10/2013 | Covannon et al. |
| 8,564,627 B2 | 10/2013 | Suzuki et al. |
| 8,583,227 B2 | 11/2013 | Savage et al. |
| 8,597,186 B2 | 12/2013 | Hafezi et al. |
| 8,634,838 B2 | 1/2014 | Hellwig et al. |
| 8,660,645 B2 | 2/2014 | Stevenson et al. |
| 8,668,280 B2 | 3/2014 | Heller et al. |
| 8,668,643 B2 | 3/2014 | Kinast |
| 8,718,193 B2 | 5/2014 | Arne et al. |
| 8,722,085 B2 | 5/2014 | McKinney et al. |
| 8,762,733 B2 | 6/2014 | Derchak et al. |
| 8,771,183 B2 | 7/2014 | Sloan |
| 8,810,260 B1 | 8/2014 | Zhou |
| 8,810,409 B2 | 8/2014 | Robertson et al. |
| 8,823,510 B2 | 9/2014 | Downey et al. |
| 8,836,513 B2 | 9/2014 | Hafezi et al. |
| 8,838,217 B2 | 9/2014 | Myr |
| 8,858,432 B2 | 10/2014 | Robertson |
| 8,868,453 B2 | 10/2014 | Zdeblick |
| 8,908,943 B2 | 12/2014 | Berry et al. |
| 8,926,509 B2 | 1/2015 | Magar et al. |
| 8,932,221 B2 | 1/2015 | Colliou et al. |
| 8,945,005 B2 | 2/2015 | Hafezi et al. |
| 8,956,287 B2 | 2/2015 | Zdeblick et al. |
| 8,966,973 B1 | 3/2015 | Milone |
| 8,989,837 B2 | 3/2015 | Weinstein et al. |
| 9,031,658 B2 | 5/2015 | Chiao et al. |
| 9,047,746 B1 | 6/2015 | Euliano et al. |
| 9,060,708 B2 | 6/2015 | Robertson et al. |
| 9,083,589 B2 | 7/2015 | Arne et al. |
| 9,088,168 B2 | 7/2015 | Mach et al. |
| 9,125,868 B2 | 9/2015 | McKinney et al. |
| 9,189,941 B2 | 11/2015 | Eschelman et al. |
| 9,198,608 B2 | 12/2015 | Hafezi et al. |
| 9,226,663 B2 | 1/2016 | Fei |
| 9,226,679 B2 | 1/2016 | Balda |
| 9,235,683 B2 | 1/2016 | Robertson et al. |
| 9,270,025 B2 | 2/2016 | Robertson et al. |
| 9,277,864 B2 | 3/2016 | Yang et al. |
| 9,278,177 B2 | 3/2016 | Edwards et al. |
| 9,320,455 B2 | 4/2016 | Hafezi et al. |
| 9,433,371 B2 | 9/2016 | Hafezi et al. |
| 9,439,582 B2 | 9/2016 | Berkman et al. |
| 9,439,599 B2 | 9/2016 | Thompson et al. |
| 9,517,012 B2 | 12/2016 | Lane et al. |
| 9,603,550 B2 | 3/2017 | Behzadi |
| 9,756,874 B2 | 9/2017 | Arne et al. |
| 9,883,819 B2 | 2/2018 | Jensen et al. |
| 10,772,522 B2 | 9/2020 | Zadig |
| 2001/0027331 A1 | 10/2001 | Thompson |
| 2001/0031071 A1 | 10/2001 | Nichols et al. |
| 2001/0039503 A1 | 11/2001 | Chan et al. |
| 2001/0044588 A1 | 11/2001 | Mault |
| 2001/0051766 A1 | 12/2001 | Gazdinski |
| 2001/0056262 A1 | 12/2001 | Cabiri et al. |
| 2002/0002326 A1 | 1/2002 | Causey et al. |
| 2002/0019586 A1 | 2/2002 | Teller et al. |
| 2002/0026111 A1 | 2/2002 | Ackerman |
| 2002/0032384 A1 | 3/2002 | Raymond et al. |
| 2002/0032385 A1 | 3/2002 | Raymond et al. |
| 2002/0040278 A1 | 4/2002 | Anuzis et al. |
| 2002/0067270 A1 | 6/2002 | Yarin et al. |
| 2002/0077620 A1 | 6/2002 | Sweeney et al. |
| 2002/0128934 A1 | 9/2002 | Shaer |
| 2002/0132226 A1 | 9/2002 | Nair |
| 2002/0138009 A1 | 9/2002 | Brockway et al. |
| 2002/0184415 A1 | 12/2002 | Naghavi et al. |
| 2002/0192159 A1 | 12/2002 | Reitberg |
| 2002/0193669 A1 | 12/2002 | Glukhovsky |
| 2002/0193846 A1 | 12/2002 | Pool et al. |
| 2002/0198470 A1 | 12/2002 | Imran et al. |
| 2003/0017826 A1 | 1/2003 | Fishman |
| 2003/0023150 A1 | 1/2003 | Yokoi et al. |
| 2003/0028226 A1 | 2/2003 | Thompson |
| 2003/0037063 A1 | 2/2003 | Schwartz |
| 2003/0063522 A1 | 4/2003 | Sagar |
| 2003/0065536 A1 | 4/2003 | Hansen |
| 2003/0076179 A1 | 4/2003 | Branch et al. |
| 2003/0083559 A1 | 5/2003 | Thompson |
| 2003/0126593 A1 | 7/2003 | Mault |
| 2003/0130714 A1 | 7/2003 | Nielsen et al. |
| 2003/0135128 A1 | 7/2003 | Suffin et al. |
| 2003/0135392 A1 | 7/2003 | Vrijens et al. |
| 2003/0152622 A1 | 8/2003 | Louie-Helm et al. |
| 2003/0158466 A1 | 8/2003 | Lynn et al. |
| 2003/0158756 A1 | 8/2003 | Abramson |
| 2003/0162556 A1 | 8/2003 | Libes |
| 2003/0164401 A1 | 9/2003 | Andreasson et al. |
| 2003/0167000 A1 | 9/2003 | Mullick et al. |
| 2003/0171791 A1 | 9/2003 | KenKnight |
| 2003/0171898 A1 | 9/2003 | Tarassenko et al. |
| 2003/0181788 A1 | 9/2003 | Yokoi et al. |
| 2003/0181815 A1 | 9/2003 | Ebner et al. |
| 2003/0185286 A1 | 10/2003 | Yuen |
| 2003/0187337 A1 | 10/2003 | Tarassenko et al. |
| 2003/0187338 A1 | 10/2003 | Say et al. |
| 2003/0195403 A1 | 10/2003 | Berner et al. |
| 2003/0198619 A1 | 10/2003 | Dong et al. |
| 2003/0213495 A1 | 11/2003 | Fujita et al. |
| 2003/0214579 A1 | 11/2003 | Iddan |
| 2003/0216622 A1 | 11/2003 | Meron et al. |
| 2003/0216625 A1 | 11/2003 | Phipps |
| 2003/0216666 A1 | 11/2003 | Ericson et al. |
| 2003/0216729 A1 | 11/2003 | Marchitto |
| 2003/0216793 A1 | 11/2003 | Karlsson et al. |
| 2003/0229382 A1 | 12/2003 | Sun et al. |
| 2003/0232895 A1 | 12/2003 | Omidian et al. |
| 2004/0008123 A1 | 1/2004 | Carrender et al. |
| 2004/0018476 A1 | 1/2004 | LaDue |
| 2004/0019172 A1 | 1/2004 | Yang et al. |
| 2004/0034295 A1 | 2/2004 | Salganicoff |
| 2004/0049245 A1 | 3/2004 | Gass |
| 2004/0073095 A1 | 4/2004 | Causey et al. |
| 2004/0073454 A1 | 4/2004 | Urquhart et al. |
| 2004/0077995 A1 | 4/2004 | Ferek-Petric |
| 2004/0082982 A1 | 4/2004 | Gord et al. |
| 2004/0087839 A1 | 5/2004 | Raymond et al. |
| 2004/0092801 A1 | 5/2004 | Drakulic |
| 2004/0106859 A1 | 6/2004 | Say et al. |
| 2004/0111011 A1 | 6/2004 | Uchiyama et al. |
| 2004/0115507 A1 | 6/2004 | Potter et al. |
| 2004/0115517 A1 | 6/2004 | Fukada et al. |
| 2004/0121015 A1 | 6/2004 | Chidlaw et al. |
| 2004/0122296 A1 | 6/2004 | Hatlestad |
| 2004/0122297 A1 | 6/2004 | Stahmann et al. |
| 2004/0138558 A1 | 7/2004 | Dunki-Jacobs et al. |
| 2004/0147326 A1 | 7/2004 | Stiles |
| 2004/0148140 A1 | 7/2004 | Tarassenko et al. |

(56) References Cited

U.S. PATENT DOCUMENTS

| | | |
|---|---|---|
| 2004/0153007 A1 | 8/2004 | Harris |
| 2004/0167226 A1 | 8/2004 | Serafini |
| 2004/0167801 A1 | 8/2004 | Say et al. |
| 2004/0171914 A1 | 9/2004 | Avni |
| 2004/0193020 A1 | 9/2004 | Chiba |
| 2004/0193029 A1 | 9/2004 | Glukhovsky |
| 2004/0193446 A1 | 9/2004 | Mayer et al. |
| 2004/0199222 A1 | 10/2004 | Sun et al. |
| 2004/0215084 A1 | 10/2004 | Shimizu et al. |
| 2004/0218683 A1 | 11/2004 | Batra |
| 2004/0220643 A1 | 11/2004 | Schmidt |
| 2004/0224644 A1 | 11/2004 | Wu |
| 2004/0225199 A1 | 11/2004 | Evanyk |
| 2004/0253304 A1 | 12/2004 | Gross et al. |
| 2004/0258571 A1 | 12/2004 | Lee et al. |
| 2004/0259899 A1 | 12/2004 | Sanghvi et al. |
| 2004/0260154 A1 | 12/2004 | Sidelnik |
| 2004/0267240 A1 | 12/2004 | Gross et al. |
| 2005/0017841 A1 | 1/2005 | Doi |
| 2005/0020887 A1 | 1/2005 | Goldberg |
| 2005/0021103 A1 | 1/2005 | DiLorenzo |
| 2005/0021370 A1 | 1/2005 | Riff |
| 2005/0021372 A1 | 1/2005 | Mikkelsen |
| 2005/0024198 A1 | 2/2005 | Ward |
| 2005/0027175 A1 | 2/2005 | Yang |
| 2005/0027205 A1 | 2/2005 | Tarassenko et al. |
| 2005/0038321 A1 | 2/2005 | Fujita et al. |
| 2005/0038680 A1 | 2/2005 | McMahon |
| 2005/0043583 A1 | 2/2005 | Killman et al. |
| 2005/0043634 A1 | 2/2005 | Yokoi et al. |
| 2005/0043894 A1 | 2/2005 | Fernandez |
| 2005/0054897 A1 | 3/2005 | Hashimoto et al. |
| 2005/0055014 A1 | 3/2005 | Coppeta et al. |
| 2005/0062644 A1 | 3/2005 | Leci |
| 2005/0065407 A1 | 3/2005 | Nakamura et al. |
| 2005/0070778 A1 | 3/2005 | Lackey |
| 2005/0075145 A1 | 4/2005 | Dvorak et al. |
| 2005/0090753 A1 | 4/2005 | Goor et al. |
| 2005/0092108 A1 | 5/2005 | Andermo |
| 2005/0096514 A1 | 5/2005 | Starkebaum |
| 2005/0096562 A1 | 5/2005 | Delalic et al. |
| 2005/0101843 A1 | 5/2005 | Quinn |
| 2005/0101872 A1 | 5/2005 | Sattler |
| 2005/0115561 A1 | 6/2005 | Stahmann et al. |
| 2005/0116820 A1 | 6/2005 | Goldreich |
| 2005/0117389 A1 | 6/2005 | Worledge |
| 2005/0121322 A1 | 6/2005 | Say et al. |
| 2005/0131281 A1 | 6/2005 | Ayer et al. |
| 2005/0137480 A1 | 6/2005 | Alt et al. |
| 2005/0143623 A1 | 6/2005 | Kojima |
| 2005/0146594 A1 | 7/2005 | Nakatani et al. |
| 2005/0148883 A1 | 7/2005 | Boesen |
| 2005/0151625 A1 | 7/2005 | Lai |
| 2005/0154277 A1 | 7/2005 | Tang et al. |
| 2005/0154428 A1 | 7/2005 | Bruinsma |
| 2005/0156709 A1 | 7/2005 | Gilbert et al. |
| 2005/0159789 A1 | 7/2005 | Brockway |
| 2005/0165323 A1 | 7/2005 | Montgomery |
| 2005/0177069 A1 | 8/2005 | Takizawa |
| 2005/0182389 A1 | 8/2005 | LaPorte |
| 2005/0187789 A1 | 8/2005 | Hatlestad et al. |
| 2005/0192489 A1 | 9/2005 | Marshall |
| 2005/0197680 A1 | 9/2005 | DelMain et al. |
| 2005/0228268 A1 | 10/2005 | Cole |
| 2005/0234307 A1 | 10/2005 | Heinonen |
| 2005/0240305 A1 | 10/2005 | Bogash et al. |
| 2005/0245794 A1 | 11/2005 | Dinsmoor |
| 2005/0245839 A1 | 11/2005 | Stivoric et al. |
| 2005/0259768 A1 | 11/2005 | Yang et al. |
| 2005/0261559 A1 | 11/2005 | Mumford |
| 2005/0267550 A1 | 12/2005 | Hess et al. |
| 2005/0267556 A1 | 12/2005 | Shuros et al. |
| 2005/0267756 A1 | 12/2005 | Schultz et al. |
| 2005/0277912 A1 | 12/2005 | John |
| 2005/0277999 A1 | 12/2005 | Strother et al. |
| 2005/0280539 A1 | 12/2005 | Pettus |
| 2005/0285732 A1 | 12/2005 | Sengupta et al. |
| 2005/0285746 A1 | 12/2005 | Sengupta |
| 2005/0288594 A1 | 12/2005 | Lewkowicz et al. |
| 2006/0001496 A1 | 1/2006 | Abrosimov et al. |
| 2006/0028727 A1 | 2/2006 | Moon et al. |
| 2006/0036134 A1 | 2/2006 | Tarassenko et al. |
| 2006/0058602 A1 | 3/2006 | Kwiatkowski et al. |
| 2006/0061472 A1 | 3/2006 | Lovoi et al. |
| 2006/0065713 A1 | 3/2006 | Kingery |
| 2006/0068006 A1 | 3/2006 | Begleiter |
| 2006/0074283 A1 | 4/2006 | Henderson |
| 2006/0074319 A1 | 4/2006 | Barnes et al. |
| 2006/0078765 A1 | 4/2006 | Yang et al. |
| 2006/0089858 A1 | 4/2006 | Ling |
| 2006/0095091 A1 | 5/2006 | Drew |
| 2006/0095093 A1 | 5/2006 | Bettesh et al. |
| 2006/0100533 A1 | 5/2006 | Han |
| 2006/0109058 A1 | 5/2006 | Keating |
| 2006/0110962 A1 | 5/2006 | Powell |
| 2006/0122474 A1 | 6/2006 | Teller et al. |
| 2006/0122525 A1* | 6/2006 | Shusterman ........ A61B 5/04007 600/513 |
| 2006/0122667 A1 | 6/2006 | Chavan et al. |
| 2006/0129060 A1 | 6/2006 | Lee et al. |
| 2006/0136266 A1 | 6/2006 | Tarassenko et al. |
| 2006/0142648 A1 | 6/2006 | Banet |
| 2006/0145876 A1 | 7/2006 | Kimura |
| 2006/0148254 A1 | 7/2006 | McLean |
| 2006/0149339 A1 | 7/2006 | Burnes |
| 2006/0155174 A1 | 7/2006 | Glukhovsky et al. |
| 2006/0155183 A1 | 7/2006 | Kroecker |
| 2006/0158820 A1 | 7/2006 | Takiguchi |
| 2006/0161225 A1 | 7/2006 | Sormann et al. |
| 2006/0179949 A1 | 8/2006 | Kim |
| 2006/0183992 A1 | 8/2006 | Kawashima |
| 2006/0183993 A1 | 8/2006 | Horn |
| 2006/0184092 A1 | 8/2006 | Atanasoska et al. |
| 2006/0204738 A1 | 9/2006 | Dubrow et al. |
| 2006/0204764 A1 | 9/2006 | Hirao et al. |
| 2006/0210626 A1 | 9/2006 | Spaeder |
| 2006/0216603 A1 | 9/2006 | Choi |
| 2006/0218011 A1 | 9/2006 | Walker |
| 2006/0229053 A1 | 10/2006 | Sivard |
| 2006/0235489 A1 | 10/2006 | Drew |
| 2006/0243288 A1 | 11/2006 | Kim et al. |
| 2006/0247505 A1 | 11/2006 | Siddiqui |
| 2006/0253004 A1 | 11/2006 | Frisch et al. |
| 2006/0253005 A1 | 11/2006 | Drinan |
| 2006/0255064 A1 | 11/2006 | Donaldson |
| 2006/0265246 A1 | 11/2006 | Hoag |
| 2006/0267774 A1 | 11/2006 | Feinberg et al. |
| 2006/0270346 A1 | 11/2006 | Ibrahim |
| 2006/0273882 A1 | 12/2006 | Posamentier |
| 2006/0276702 A1 | 12/2006 | McGinnis |
| 2006/0280227 A1 | 12/2006 | Pinkney |
| 2006/0282001 A1 | 12/2006 | Noel |
| 2006/0285607 A1 | 12/2006 | Strodtbeck et al. |
| 2006/0287693 A1 | 12/2006 | Kraft et al. |
| 2006/0289640 A1 | 12/2006 | Mercure |
| 2006/0293607 A1 | 12/2006 | Alt |
| 2007/0000776 A1 | 1/2007 | Karube et al. |
| 2007/0002038 A1 | 1/2007 | Suzuki |
| 2007/0006636 A1 | 1/2007 | King et al. |
| 2007/0008113 A1 | 1/2007 | Spoonhower et al. |
| 2007/0016089 A1 | 1/2007 | Fischell et al. |
| 2007/0027386 A1 | 2/2007 | Such |
| 2007/0027388 A1 | 2/2007 | Chou |
| 2007/0038054 A1 | 2/2007 | Zhou |
| 2007/0049339 A1 | 3/2007 | Barak et al. |
| 2007/0055098 A1 | 3/2007 | Shimizu et al. |
| 2007/0060797 A1 | 3/2007 | Ball |
| 2007/0060800 A1 | 3/2007 | Drinan et al. |
| 2007/0066929 A1 | 3/2007 | Ferren et al. |
| 2007/0072156 A1 | 3/2007 | Kaufman et al. |
| 2007/0073353 A1 | 3/2007 | Rooney et al. |
| 2007/0088194 A1 | 4/2007 | Tahar |
| 2007/0096765 A1 | 5/2007 | Kagan |
| 2007/0106346 A1 | 5/2007 | Bergelson |

(56) References Cited

U.S. PATENT DOCUMENTS

| | | |
|---|---|---|
| 2007/0123772 A1 | 5/2007 | Euliano |
| 2007/0129622 A1 | 6/2007 | Bourget |
| 2007/0130287 A1 | 6/2007 | Kumar |
| 2007/0135691 A1 | 6/2007 | Zingelewicz et al. |
| 2007/0135803 A1 | 6/2007 | Belson |
| 2007/0142721 A1 | 6/2007 | Berner et al. |
| 2007/0156016 A1 | 7/2007 | Betesh |
| 2007/0160789 A1 | 7/2007 | Merical |
| 2007/0162089 A1 | 7/2007 | Mosesov |
| 2007/0162090 A1 | 7/2007 | Penner |
| 2007/0167495 A1 | 7/2007 | Brown et al. |
| 2007/0167848 A1 | 7/2007 | Kuo et al. |
| 2007/0172424 A1 | 7/2007 | Roser |
| 2007/0173701 A1 | 7/2007 | Al-Ali |
| 2007/0179347 A1 | 8/2007 | Tarassenko et al. |
| 2007/0179371 A1 | 8/2007 | Peyser et al. |
| 2007/0180047 A1 | 8/2007 | Dong et al. |
| 2007/0185393 A1 | 8/2007 | Zhou |
| 2007/0191002 A1 | 8/2007 | Ge |
| 2007/0196456 A1 | 8/2007 | Stevens |
| 2007/0207793 A1 | 9/2007 | Myer |
| 2007/0207858 A1 | 9/2007 | Breving |
| 2007/0208233 A1 | 9/2007 | Kovacs |
| 2007/0213659 A1 | 9/2007 | Trovato et al. |
| 2007/0237719 A1 | 10/2007 | Jones |
| 2007/0244370 A1 | 10/2007 | Kuo et al. |
| 2007/0244810 A1 | 10/2007 | Rudolph |
| 2007/0249946 A1 | 10/2007 | Kumar et al. |
| 2007/0255198 A1 | 11/2007 | Leong et al. |
| 2007/0255330 A1 | 11/2007 | Lee |
| 2007/0270672 A1 | 11/2007 | Hayter |
| 2007/0279217 A1 | 12/2007 | Venkatraman |
| 2007/0282174 A1 | 12/2007 | Sabatino |
| 2007/0282177 A1 | 12/2007 | Pilz |
| 2007/0291715 A1 | 12/2007 | Laroia et al. |
| 2007/0299480 A1 | 12/2007 | Hill |
| 2008/0004503 A1 | 1/2008 | Nisani et al. |
| 2008/0014866 A1 | 1/2008 | Lipowshi |
| 2008/0015421 A1 | 1/2008 | Penner |
| 2008/0015494 A1 | 1/2008 | Santini et al. |
| 2008/0015893 A1 | 1/2008 | Miller et al. |
| 2008/0020037 A1 | 1/2008 | Robertson et al. |
| 2008/0021519 A1 | 1/2008 | DeGeest |
| 2008/0021521 A1 | 1/2008 | Shah |
| 2008/0027679 A1 | 1/2008 | Shklarski |
| 2008/0033273 A1 | 2/2008 | Zhou |
| 2008/0033301 A1 | 2/2008 | Dellavecchia et al. |
| 2008/0038588 A1 | 2/2008 | Lee |
| 2008/0039700 A1 | 2/2008 | Drinan et al. |
| 2008/0045843 A1 | 2/2008 | Tsuji et al. |
| 2008/0046038 A1 | 2/2008 | Hill |
| 2008/0051647 A1 | 2/2008 | Wu et al. |
| 2008/0051667 A1 | 2/2008 | Goldreich |
| 2008/0051767 A1 | 2/2008 | Rossing et al. |
| 2008/0058614 A1 | 3/2008 | Banet |
| 2008/0062856 A1 | 3/2008 | Feher |
| 2008/0065168 A1 | 3/2008 | Bitton et al. |
| 2008/0074307 A1 | 3/2008 | Boric-Lubecke |
| 2008/0077015 A1 | 3/2008 | Botic-Lubecke |
| 2008/0077028 A1 | 3/2008 | Schaldach et al. |
| 2008/0077188 A1 | 3/2008 | Denker et al. |
| 2008/0077430 A1 | 3/2008 | Singer et al. |
| 2008/0091089 A1 | 4/2008 | Guillory et al. |
| 2008/0091114 A1 | 4/2008 | Min |
| 2008/0097549 A1 | 4/2008 | Colbaugh |
| 2008/0097917 A1 | 4/2008 | Dicks |
| 2008/0099366 A1 | 5/2008 | Niemic et al. |
| 2008/0103440 A1 | 5/2008 | Ferren et al. |
| 2008/0112885 A1 | 5/2008 | Okunev et al. |
| 2008/0114224 A1 | 5/2008 | Bandy et al. |
| 2008/0119705 A1 | 5/2008 | Patel |
| 2008/0119716 A1 | 5/2008 | Boric-Lubecke |
| 2008/0121825 A1 | 5/2008 | Trovato et al. |
| 2008/0137566 A1 | 6/2008 | Marholev |
| 2008/0139907 A1 | 6/2008 | Rao et al. |
| 2008/0140403 A1 | 6/2008 | Hughes et al. |
| 2008/0146871 A1 | 6/2008 | Arneson et al. |
| 2008/0146889 A1 | 6/2008 | Young |
| 2008/0146892 A1 | 6/2008 | LeBeouf |
| 2008/0154104 A1 | 6/2008 | Lamego |
| 2008/0166992 A1 | 7/2008 | Ricordi |
| 2008/0175898 A1 | 7/2008 | Jones et al. |
| 2008/0183245 A1 | 7/2008 | Van Oort |
| 2008/0188763 A1 | 8/2008 | John et al. |
| 2008/0188837 A1* | 8/2008 | Belsky ............... A61K 9/0053 604/890.1 |
| 2008/0194912 A1 | 8/2008 | Trovato et al. |
| 2008/0208009 A1 | 8/2008 | Shklarski |
| 2008/0214901 A1 | 9/2008 | Gehman |
| 2008/0214903 A1 | 9/2008 | Orbach |
| 2008/0214985 A1 | 9/2008 | Yanaki |
| 2008/0223936 A1 | 9/2008 | Mickle et al. |
| 2008/0243020 A1 | 10/2008 | Chou |
| 2008/0249360 A1 | 10/2008 | Li |
| 2008/0262320 A1 | 10/2008 | Schaefer et al. |
| 2008/0262336 A1 | 10/2008 | Ryu |
| 2008/0269664 A1 | 10/2008 | Trovato et al. |
| 2008/0275312 A1 | 11/2008 | Mosesov |
| 2008/0281636 A1 | 11/2008 | Jung et al. |
| 2008/0284599 A1 | 11/2008 | Zdeblick et al. |
| 2008/0288026 A1 | 11/2008 | Cross et al. |
| 2008/0288027 A1 | 11/2008 | Kroll |
| 2008/0294020 A1 | 11/2008 | Sapounas |
| 2008/0299197 A1 | 12/2008 | Toneguzzo et al. |
| 2008/0300572 A1 | 12/2008 | Rankers |
| 2008/0303638 A1 | 12/2008 | Nguyen |
| 2008/0303665 A1 | 12/2008 | Naik et al. |
| 2008/0306357 A1 | 12/2008 | Korman |
| 2008/0306359 A1 | 12/2008 | Zdeblick et al. |
| 2008/0306360 A1 | 12/2008 | Robertson et al. |
| 2008/0306362 A1 | 12/2008 | Davis |
| 2008/0311852 A1 | 12/2008 | Hansen |
| 2008/0312522 A1 | 12/2008 | Rowlandson |
| 2008/0316020 A1 | 12/2008 | Robertson |
| 2009/0006133 A1 | 1/2009 | Weinert |
| 2009/0009330 A1 | 1/2009 | Sakama et al. |
| 2009/0009332 A1 | 1/2009 | Nunez et al. |
| 2009/0024045 A1 | 1/2009 | Prakash |
| 2009/0024112 A1 | 1/2009 | Edwards et al. |
| 2009/0030293 A1 | 1/2009 | Cooper et al. |
| 2009/0030297 A1 | 1/2009 | Miller |
| 2009/0034209 A1 | 2/2009 | Joo |
| 2009/0043171 A1 | 2/2009 | Rule |
| 2009/0048498 A1 | 2/2009 | Riskey |
| 2009/0062634 A1 | 3/2009 | Say et al. |
| 2009/0062670 A1 | 3/2009 | Sterling |
| 2009/0062730 A1 | 3/2009 | Woo |
| 2009/0069642 A1 | 3/2009 | Gao |
| 2009/0069655 A1 | 3/2009 | Say et al. |
| 2009/0069656 A1 | 3/2009 | Say et al. |
| 2009/0069657 A1 | 3/2009 | Say et al. |
| 2009/0069658 A1 | 3/2009 | Say et al. |
| 2009/0076340 A1 | 3/2009 | Libbus et al. |
| 2009/0076343 A1 | 3/2009 | James |
| 2009/0076350 A1 | 3/2009 | Bly et al. |
| 2009/0076397 A1 | 3/2009 | Libbus et al. |
| 2009/0082645 A1 | 3/2009 | Hafezi et al. |
| 2009/0087483 A1 | 4/2009 | Sison |
| 2009/0088618 A1 | 4/2009 | Arneson |
| 2009/0099435 A1 | 4/2009 | Say et al. |
| 2009/0105561 A1 | 4/2009 | Boydon et al. |
| 2009/0110148 A1 | 4/2009 | Zhang |
| 2009/0112626 A1 | 4/2009 | Talbot |
| 2009/0124871 A1 | 5/2009 | Arshak |
| 2009/0131774 A1 | 5/2009 | Sweitzer |
| 2009/0134181 A1 | 5/2009 | Wachman et al. |
| 2009/0135886 A1 | 5/2009 | Robertson et al. |
| 2009/0142853 A1 | 6/2009 | Warrington et al. |
| 2009/0149708 A1 | 6/2009 | Hyde et al. |
| 2009/0149839 A1 | 6/2009 | Hyde et al. |
| 2009/0157113 A1 | 6/2009 | Marcotte |
| 2009/0157358 A1 | 6/2009 | Kim |
| 2009/0161602 A1 | 6/2009 | Matsumoto |
| 2009/0163789 A1 | 6/2009 | Say et al. |

(56) References Cited

U.S. PATENT DOCUMENTS

| | | |
|---|---|---|
| 2009/0171180 A1 | 7/2009 | Pering |
| 2009/0173628 A1 | 7/2009 | Say et al. |
| 2009/0177055 A1 | 7/2009 | Say et al. |
| 2009/0177056 A1 | 7/2009 | Say et al. |
| 2009/0177057 A1 | 7/2009 | Say et al. |
| 2009/0177058 A1 | 7/2009 | Say et al. |
| 2009/0177059 A1 | 7/2009 | Say et al. |
| 2009/0177060 A1 | 7/2009 | Say et al. |
| 2009/0177061 A1 | 7/2009 | Say et al. |
| 2009/0177062 A1 | 7/2009 | Say et al. |
| 2009/0177063 A1 | 7/2009 | Say et al. |
| 2009/0177064 A1 | 7/2009 | Say et al. |
| 2009/0177065 A1 | 7/2009 | Say et al. |
| 2009/0177066 A1 | 7/2009 | Say et al. |
| 2009/0182206 A1 | 7/2009 | Najafi |
| 2009/0182207 A1 | 7/2009 | Riskey et al. |
| 2009/0182212 A1 | 7/2009 | Say et al. |
| 2009/0182213 A1 | 7/2009 | Say et al. |
| 2009/0182214 A1 | 7/2009 | Say et al. |
| 2009/0182215 A1 | 7/2009 | Say et al. |
| 2009/0182388 A1 | 7/2009 | Von Arx |
| 2009/0187088 A1 | 7/2009 | Say et al. |
| 2009/0187089 A1 | 7/2009 | Say et al. |
| 2009/0187090 A1 | 7/2009 | Say et al. |
| 2009/0187091 A1 | 7/2009 | Say et al. |
| 2009/0187092 A1 | 7/2009 | Say et al. |
| 2009/0187093 A1 | 7/2009 | Say et al. |
| 2009/0187094 A1 | 7/2009 | Say et al. |
| 2009/0187095 A1 | 7/2009 | Say et al. |
| 2009/0187381 A1 | 7/2009 | King et al. |
| 2009/0192351 A1 | 7/2009 | Nishino |
| 2009/0192368 A1 | 7/2009 | Say et al. |
| 2009/0192369 A1 | 7/2009 | Say et al. |
| 2009/0192370 A1 | 7/2009 | Say et al. |
| 2009/0192371 A1 | 7/2009 | Say et al. |
| 2009/0192372 A1 | 7/2009 | Say et al. |
| 2009/0192373 A1 | 7/2009 | Say et al. |
| 2009/0192374 A1 | 7/2009 | Say et al. |
| 2009/0192375 A1 | 7/2009 | Say et al. |
| 2009/0192376 A1 | 7/2009 | Say et al. |
| 2009/0192377 A1 | 7/2009 | Say et al. |
| 2009/0192378 A1 | 7/2009 | Say et al. |
| 2009/0192379 A1 | 7/2009 | Say et al. |
| 2009/0198115 A1 | 8/2009 | Say et al. |
| 2009/0198116 A1 | 8/2009 | Say et al. |
| 2009/0198175 A1 | 8/2009 | Say et al. |
| 2009/0203964 A1 | 8/2009 | Shimizu et al. |
| 2009/0203971 A1 | 8/2009 | Sciarappa |
| 2009/0203972 A1 | 8/2009 | Heneghan |
| 2009/0203978 A1 | 8/2009 | Say et al. |
| 2009/0204265 A1 | 8/2009 | Hackett |
| 2009/0210164 A1 | 8/2009 | Say et al. |
| 2009/0216101 A1 | 8/2009 | Say et al. |
| 2009/0216102 A1 | 8/2009 | Say et al. |
| 2009/0227204 A1 | 9/2009 | Robertson et al. |
| 2009/0227876 A1 | 9/2009 | Tran |
| 2009/0227940 A1 | 9/2009 | Say et al. |
| 2009/0227941 A1 | 9/2009 | Say et al. |
| 2009/0227988 A1 | 9/2009 | Wood et al. |
| 2009/0228214 A1 | 9/2009 | Say et al. |
| 2009/0231125 A1 | 9/2009 | Baldus |
| 2009/0234200 A1 | 9/2009 | Husheer |
| 2009/0234203 A1 | 9/2009 | Arita |
| 2009/0243833 A1 | 10/2009 | Huang |
| 2009/0247836 A1 | 10/2009 | Cole et al. |
| 2009/0253960 A1 | 10/2009 | Takenaka et al. |
| 2009/0264714 A1 | 10/2009 | Chou |
| 2009/0264964 A1 | 10/2009 | Abrahamson |
| 2009/0265186 A1 | 10/2009 | Tarassenko et al. |
| 2009/0273467 A1 | 11/2009 | Elixmann |
| 2009/0277815 A1 | 11/2009 | Kohl et al. |
| 2009/0281539 A1 | 11/2009 | Selig |
| 2009/0287109 A1 | 11/2009 | Ferren et al. |
| 2009/0292194 A1 | 11/2009 | Libbus et al. |
| 2009/0295548 A1 | 12/2009 | Ronkka |
| 2009/0296677 A1 | 12/2009 | Mahany |
| 2009/0301925 A1 | 12/2009 | Alloro et al. |
| 2009/0303920 A1 | 12/2009 | Mahany |
| 2009/0306633 A1 | 12/2009 | Trovato et al. |
| 2009/0312619 A1 | 12/2009 | Say et al. |
| 2009/0318303 A1 | 12/2009 | Delamarche et al. |
| 2009/0318761 A1 | 12/2009 | Rabinovitz |
| 2009/0318779 A1 | 12/2009 | Tran |
| 2009/0318783 A1 | 12/2009 | Rohde |
| 2009/0318793 A1 | 12/2009 | Datta |
| 2010/0001841 A1 | 1/2010 | Cardullo |
| 2010/0006585 A1 | 1/2010 | Flowers et al. |
| 2010/0010330 A1 | 1/2010 | Rankers |
| 2010/0015584 A1 | 1/2010 | Singer et al. |
| 2010/0033324 A1 | 2/2010 | Shimizu et al. |
| 2010/0036269 A1 | 2/2010 | Ferren et al. |
| 2010/0049004 A1 | 2/2010 | Edman et al. |
| 2010/0049006 A1 | 2/2010 | Magar |
| 2010/0049012 A1 | 2/2010 | Dijksman et al. |
| 2010/0049069 A1 | 2/2010 | Tarassenko et al. |
| 2010/0056878 A1 | 3/2010 | Partin |
| 2010/0056891 A1 | 3/2010 | Say et al. |
| 2010/0056939 A1 | 3/2010 | Tarassenko et al. |
| 2010/0057041 A1 | 3/2010 | Hayter |
| 2010/0062709 A1 | 3/2010 | Kato |
| 2010/0063438 A1 | 3/2010 | Bengtsson |
| 2010/0063841 A1 | 3/2010 | D'Ambrosia et al. |
| 2010/0069002 A1 | 3/2010 | Rong |
| 2010/0069717 A1 | 3/2010 | Hafezi et al. |
| 2010/0082367 A1 | 4/2010 | Hains et al. |
| 2010/0099967 A1 | 4/2010 | Say et al. |
| 2010/0099968 A1 | 4/2010 | Say et al. |
| 2010/0099969 A1 | 4/2010 | Say et al. |
| 2010/0100077 A1 | 4/2010 | Rush |
| 2010/0100078 A1 | 4/2010 | Say et al. |
| 2010/0100237 A1 | 4/2010 | Ratnakar |
| 2010/0106001 A1 | 4/2010 | Say et al. |
| 2010/0118853 A1 | 5/2010 | Godfrey |
| 2010/0131434 A1* | 5/2010 | Magent .......... G06Q 10/06 706/11 |
| 2010/0139672 A1 | 6/2010 | Kroll et al. |
| 2010/0160742 A1 | 6/2010 | Seidl et al. |
| 2010/0168659 A1 | 7/2010 | Say et al. |
| 2010/0179398 A1 | 7/2010 | Say et al. |
| 2010/0183199 A1 | 7/2010 | Smith et al. |
| 2010/0191073 A1 | 7/2010 | Tarassenko et al. |
| 2010/0203394 A1 | 8/2010 | Bae et al. |
| 2010/0210299 A1 | 8/2010 | Gorbachov |
| 2010/0217100 A1 | 8/2010 | LeBoeuf et al. |
| 2010/0222652 A1 | 9/2010 | Cho |
| 2010/0228113 A1 | 9/2010 | Solosko |
| 2010/0233026 A1 | 9/2010 | Ismagliov et al. |
| 2010/0234706 A1 | 9/2010 | Gilland |
| 2010/0234715 A1 | 9/2010 | Shin |
| 2010/0234914 A1 | 9/2010 | Shen |
| 2010/0245091 A1 | 9/2010 | Singh |
| 2010/0249541 A1 | 9/2010 | Geva et al. |
| 2010/0249881 A1 | 9/2010 | Corndorf |
| 2010/0256461 A1 | 10/2010 | Mohamedali |
| 2010/0259543 A1 | 10/2010 | Tarassenko et al. |
| 2010/0268048 A1 | 10/2010 | Say et al. |
| 2010/0268049 A1 | 10/2010 | Say et al. |
| 2010/0268050 A1 | 10/2010 | Say et al. |
| 2010/0268288 A1 | 10/2010 | Hunter et al. |
| 2010/0274111 A1 | 10/2010 | Say et al. |
| 2010/0280345 A1 | 11/2010 | Say et al. |
| 2010/0280346 A1 | 11/2010 | Say et al. |
| 2010/0295694 A1 | 11/2010 | Kauffman et al. |
| 2010/0298668 A1 | 11/2010 | Hafezi et al. |
| 2010/0298730 A1 | 11/2010 | Tarassenko et al. |
| 2010/0299155 A1 | 11/2010 | Findlay et al. |
| 2010/0312188 A1 | 12/2010 | Robertson et al. |
| 2010/0312577 A1 | 12/2010 | Goodnow et al. |
| 2010/0312580 A1 | 12/2010 | Tarassenko et al. |
| 2010/0332443 A1 | 12/2010 | Gartenberg |
| 2011/0004079 A1 | 1/2011 | Ali et al. |
| 2011/0009715 A1 | 1/2011 | O'Reilly et al. |
| 2011/0021983 A1 | 1/2011 | Jurson |
| 2011/0029622 A1 | 2/2011 | Walker et al. |

(56) References Cited

U.S. PATENT DOCUMENTS

| | | |
|---|---|---|
| 2011/0050431 A1 | 3/2011 | Hood et al. |
| 2011/0054265 A1 | 3/2011 | Hafezi et al. |
| 2011/0065983 A1 | 3/2011 | Hafezi et al. |
| 2011/0077660 A1 | 3/2011 | Janik et al. |
| 2011/0081860 A1 | 4/2011 | Brown et al. |
| 2011/0105864 A1 | 5/2011 | Robertson et al. |
| 2011/0112686 A1 | 5/2011 | Nolan et al. |
| 2011/0124983 A1 | 5/2011 | Kroll et al. |
| 2011/0144470 A1 | 6/2011 | Mazar et al. |
| 2011/0160549 A1 | 6/2011 | Saroka et al. |
| 2011/0212782 A1 | 9/2011 | Thompson et al. |
| 2011/0224912 A1 | 9/2011 | Bhavaraju et al. |
| 2011/0230732 A1 | 9/2011 | Edman et al. |
| 2011/0237924 A1 | 9/2011 | McGusty et al. |
| 2011/0270112 A1 | 11/2011 | Manera et al. |
| 2011/0270135 A1 | 11/2011 | Dooley et al. |
| 2011/0279963 A1 | 11/2011 | Kumar et al. |
| 2012/0024889 A1 | 2/2012 | Robertson et al. |
| 2012/0029309 A1 | 2/2012 | Paquet et al. |
| 2012/0032816 A1 | 2/2012 | Cho et al. |
| 2012/0062371 A1 | 3/2012 | Radivojevic et al. |
| 2012/0071743 A1 | 3/2012 | Todorov et al. |
| 2012/0083715 A1 | 4/2012 | Yuen et al. |
| 2012/0089000 A1 | 4/2012 | Bishay et al. |
| 2012/0101396 A1 | 4/2012 | Solosko et al. |
| 2012/0116184 A1 | 5/2012 | Shieh |
| 2012/0179004 A1 | 7/2012 | Roesicke et al. |
| 2012/0197144 A1 | 8/2012 | Christ et al. |
| 2012/0214140 A1 | 8/2012 | Brynelson et al. |
| 2012/0265544 A1 | 10/2012 | Hwang et al. |
| 2012/0310070 A1 | 12/2012 | Kumar et al. |
| 2012/0316413 A1 | 12/2012 | Liu et al. |
| 2013/0002423 A1 | 1/2013 | Robertson et al. |
| 2013/0030259 A1 | 1/2013 | Thomsen et al. |
| 2013/0057385 A1 | 3/2013 | Murakami et al. |
| 2013/0060115 A1 | 3/2013 | Gehman et al. |
| 2013/0073312 A1 | 3/2013 | Thompson et al. |
| 2013/0117696 A1 | 5/2013 | Robertson et al. |
| 2013/0171596 A1 | 7/2013 | French |
| 2013/0185228 A1 | 7/2013 | Dresner |
| 2013/0196012 A1 | 8/2013 | Dill |
| 2013/0275296 A1 | 10/2013 | Tietzen et al. |
| 2013/0328416 A1 | 12/2013 | Whitworth et al. |
| 2013/0338452 A1 | 12/2013 | Robertson et al. |
| 2014/0004492 A1 | 1/2014 | O'Reilly et al. |
| 2014/0039445 A1 | 2/2014 | Austin et al. |
| 2014/0051965 A1 | 2/2014 | Zdeblick et al. |
| 2014/0203950 A1 | 7/2014 | Zdeblick et al. |
| 2014/0280125 A1 | 9/2014 | Bhardwaj et al. |
| 2014/0308930 A1 | 10/2014 | Tran |
| 2014/0315170 A1 | 10/2014 | Ionescu et al. |
| 2014/0349256 A1 | 11/2014 | Connor |
| 2014/0374276 A1 | 12/2014 | Guthrie et al. |
| 2015/0051465 A1 | 2/2015 | Robertson et al. |
| 2015/0080677 A1 | 3/2015 | Thompson et al. |
| 2015/0080678 A1 | 3/2015 | Frank et al. |
| 2015/0080679 A1 | 3/2015 | Frank et al. |
| 2015/0080680 A1 | 3/2015 | Zdeblick et al. |
| 2015/0080681 A1 | 3/2015 | Hafezi et al. |
| 2015/0127737 A1 | 5/2015 | Thompson et al. |
| 2015/0127738 A1 | 5/2015 | Thompson et al. |
| 2015/0149375 A1 | 5/2015 | Thompson et al. |
| 2015/0165313 A1 | 6/2015 | Thompson et al. |
| 2015/0171924 A1 | 6/2015 | Zdeblick |
| 2015/0182463 A1 | 7/2015 | Hafezi et al. |
| 2015/0193593 A1 | 7/2015 | Zdeblick et al. |
| 2015/0230728 A1 | 8/2015 | Hafezi et al. |
| 2015/0318901 A1 | 11/2015 | Robertson et al. |
| 2015/0365115 A1 | 12/2015 | Arne et al. |
| 2016/0155316 A1 | 6/2016 | Hafezi et al. |
| 2017/0215761 A1 | 8/2017 | Zdeblick |
| 2017/0270779 A1 | 9/2017 | Zdeblick et al. |
| 2017/0290513 A1 | 10/2017 | O'Reilly et al. |
| 2017/0303818 A1 | 10/2017 | Behzadi et al. |
| 2018/0026680 A1 | 1/2018 | Shirvani et al. |
| 2018/0184698 A1 | 7/2018 | Arne et al. |
| 2019/0133958 A1 | 5/2019 | Hafezi et al. |
| 2019/0158151 A1 | 5/2019 | Shirvani et al. |

FOREIGN PATENT DOCUMENTS

| | | |
|---|---|---|
| CN | 2748032 | 12/2005 |
| CN | 1991868 | 7/2007 |
| CN | 101005470 | 7/2007 |
| CN | 201076456 | 6/2008 |
| CN | 101524267 | 9/2009 |
| DE | 10313005 | 10/2004 |
| EP | 0344939 | 12/1989 |
| EP | 0526166 | 2/1993 |
| EP | 1199670 | 4/2002 |
| EP | 1246356 | 10/2002 |
| EP | 1342447 | 9/2003 |
| EP | 1534054 | 5/2005 |
| EP | 1702553 | 9/2006 |
| EP | 1098591 | 1/2007 |
| EP | 1789128 | 5/2007 |
| EP | 2143369 | 1/2010 |
| GB | 775071 | 5/1957 |
| GB | 2432862 | 6/2007 |
| IL | 172917 | 6/2010 |
| JP | 2000506410 | 5/1912 |
| JP | S6117949 | 1/1986 |
| JP | S63280393 | 11/1988 |
| JP | H01285247 | 11/1989 |
| JP | 05228128 | 9/1993 |
| JP | H0884779 | 4/1996 |
| JP | 09330159 | 12/1997 |
| JP | 1014898 | 1/1998 |
| JP | H11195415 | 7/1999 |
| JP | 2001078974 | 3/2001 |
| JP | 2002224053 | 8/2002 |
| JP | 2002263185 | 9/2002 |
| JP | 2002282218 | 10/2002 |
| JP | 2002282219 | 10/2002 |
| JP | 2002291684 | 10/2002 |
| JP | 2003210395 | 7/2003 |
| JP | 3454525 | 10/2003 |
| JP | 2003325440 | 11/2003 |
| JP | 2004007187 | 1/2004 |
| JP | 2004507188 | 3/2004 |
| JP | 2004134384 | 4/2004 |
| JP | 2004274452 | 9/2004 |
| JP | 2004313242 | 11/2004 |
| JP | 2004318534 | 11/2004 |
| JP | 2004-538572 A | 12/2004 |
| JP | 2004364016 | 12/2004 |
| JP | 2005031840 | 2/2005 |
| JP | 2005073886 | 3/2005 |
| JP | 2005304880 | 4/2005 |
| JP | 2005124708 | 5/2005 |
| JP | 2005148021 | 6/2005 |
| JP | 2005152037 | 6/2005 |
| JP | 2005287691 | 10/2005 |
| JP | 2005532841 | 11/2005 |
| JP | 2005532849 | 11/2005 |
| JP | 2005343515 | 12/2005 |
| JP | 2006006377 | 1/2006 |
| JP | 2006509574 | 3/2006 |
| JP | 2006177699 | 7/2006 |
| JP | 2006187611 | 7/2006 |
| JP | 2006278091 | 10/2006 |
| JP | 2006346000 | 12/2006 |
| JP | 3876573 | 1/2007 |
| JP | 2007151809 | 6/2007 |
| JP | 2007159631 | 6/2007 |
| JP | 2007-212421 A | 8/2007 |
| JP | 2007200739 | 8/2007 |
| JP | 2007313340 | 12/2007 |
| JP | 2007330677 | 12/2007 |
| JP | 2008011865 | 1/2008 |
| JP | 2008501415 | 1/2008 |
| JP | 2008176434 | 7/2008 |
| JP | 2008191955 | 8/2008 |
| JP | 2008289724 | 12/2008 |

(56) References Cited

FOREIGN PATENT DOCUMENTS

| | | |
|---|---|---|
| JP | 2009034345 | 2/2009 |
| JP | 2009050541 | 3/2009 |
| JP | 2009061236 | 3/2009 |
| JP | 2009065726 | 3/2009 |
| JP | 2010-533546 A | 11/2010 |
| JP | 2011015817 | 1/2011 |
| JP | 2011519583 | 7/2011 |
| JP | 2016-515022 A | 5/2016 |
| KR | 20020015907 | 3/2002 |
| KR | 20020061744 | 7/2002 |
| KR | 200600977523 | 7/2006 |
| KR | 100927471 | 11/2009 |
| KR | 20110137001 | 12/2011 |
| KR | 10-2012-099995 | 9/2012 |
| TW | 200301864 | 7/2003 |
| TW | 553735 | 9/2003 |
| TW | 200724094 | 7/2007 |
| TW | 200812556 | 3/2008 |
| TW | 201120673 | 6/2011 |
| WO | WO1988002237 | 4/1988 |
| WO | WO1992021307 | 12/1992 |
| WO | WO1993008734 | 5/1993 |
| WO | WO1993019667 | 10/1993 |
| WO | WO1994001165 | 1/1994 |
| WO | WO9516393 | 6/1995 |
| WO | WO1997014112 | 4/1997 |
| WO | WO1997039963 | 10/1997 |
| WO | WO1998043537 | 10/1998 |
| WO | WO1999037290 | 7/1999 |
| WO | WO1999059465 | 11/1999 |
| WO | WO2000033246 | 6/2000 |
| WO | WO2001000085 | 1/2001 |
| WO | WO2001047466 | 7/2001 |
| WO | WO2001049364 | 7/2001 |
| WO | WO2001074011 | 10/2001 |
| WO | WO2001080731 | 11/2001 |
| WO | 01/97092 | 12/2001 |
| WO | WO0235997 | 5/2002 |
| WO | WO2002045489 | 6/2002 |
| WO | WO2002058330 | 7/2002 |
| WO | WO2002062276 | 8/2002 |
| WO | WO2002087681 | 11/2002 |
| WO | WO2002095351 | 11/2002 |
| WO | WO2003005877 | 1/2003 |
| WO | WO2003050643 | 6/2003 |
| WO | WO2003068061 | 8/2003 |
| WO | WO2004014225 | 2/2004 |
| WO | WO2004019172 | 3/2004 |
| WO | WO2004039256 | 5/2004 |
| WO | WO2004059551 | 7/2004 |
| WO | WO2004066833 | 8/2004 |
| WO | WO2004066834 | 8/2004 |
| WO | WO2004066903 | 8/2004 |
| WO | WO2004068748 | 8/2004 |
| WO | WO2004068881 | 8/2004 |
| WO | WO2004075751 | 9/2004 |
| WO | WO2004109316 | 12/2004 |
| WO | WO2004110555 | 12/2004 |
| WO | WO2005011237 | 2/2005 |
| WO | WO2005020023 | 3/2005 |
| WO | WO2005024687 | 3/2005 |
| WO | WO2005041767 | 5/2005 |
| WO | WO2005047837 | 5/2005 |
| WO | WO2005051166 | 6/2005 |
| WO | WO2005053517 | 6/2005 |
| WO | WO2005069887 | 8/2005 |
| WO | WO2005082436 | 9/2005 |
| WO | WO2005083621 | 9/2005 |
| WO | WO2005110238 | 11/2005 |
| WO | WO2005117697 | 12/2005 |
| WO | WO2006009404 | 1/2006 |
| WO | WO2006016370 | 2/2006 |
| WO | WO2006021932 | 3/2006 |
| WO | WO2006027586 | 3/2006 |
| WO | WO2006028347 | 3/2006 |
| WO | WO2006035351 | 4/2006 |
| WO | WO2006037802 | 4/2006 |
| WO | WO2006046648 | 5/2006 |
| WO | WO2006055892 | 5/2006 |
| WO | WO2006055956 | 5/2006 |
| WO | WO2006059338 | 6/2006 |
| WO | WO2006075016 | 7/2006 |
| WO | WO2006100620 | 9/2006 |
| WO | WO2006104843 | 10/2006 |
| WO | WO2006109072 | 10/2006 |
| WO | WO2006/123346 | 11/2006 |
| WO | WO2006116718 | 11/2006 |
| WO | WO2006119345 | 11/2006 |
| WO | WO2006127355 | 11/2006 |
| WO | WO2007001724 | 1/2007 |
| WO | WO2007001742 | 1/2007 |
| WO | WO2007013952 | 2/2007 |
| WO | WO2007014084 | 2/2007 |
| WO | WO2007014527 | 2/2007 |
| WO | WO2007021496 | 2/2007 |
| WO | WO2007027660 | 3/2007 |
| WO | WO2007028035 | 3/2007 |
| WO | WO2007036687 | 4/2007 |
| WO | WO2007036741 | 4/2007 |
| WO | WO2007036746 | 4/2007 |
| WO | WO2007040878 | 4/2007 |
| WO | WO2007067054 | 6/2007 |
| WO | WO2007071180 | 6/2007 |
| WO | WO2007096810 | 8/2007 |
| WO | WO2007101141 | 9/2007 |
| WO | WO2007115087 | 10/2007 |
| WO | WO2007120946 | 10/2007 |
| WO | WO2007123923 | 11/2007 |
| WO | WO2007127316 | 11/2007 |
| WO | WO2007127879 | 11/2007 |
| WO | WO2007127945 | 11/2007 |
| WO | WO2007128165 | 11/2007 |
| WO | WO2007130491 | 11/2007 |
| WO | WO2007133526 | 11/2007 |
| WO | WO2007143535 | 12/2007 |
| WO | WO2007149546 | 12/2007 |
| WO | WO2008008281 | 1/2008 |
| WO | WO2008012700 | 1/2008 |
| WO | WO2008030482 | 3/2008 |
| WO | WO2008039030 | 4/2008 |
| WO | WO2008052136 | 5/2008 |
| WO | WO2008061138 | 5/2008 |
| WO | WO2008063626 | 5/2008 |
| WO | WO2008066617 | 6/2008 |
| WO | WO2008076464 | 6/2008 |
| WO | WO2008085131 | 7/2008 |
| WO | WO2008089232 | 7/2008 |
| WO | WO2008091683 | 7/2008 |
| WO | WO2008095183 | 8/2008 |
| WO | WO2008097652 | 8/2008 |
| WO | WO2008101107 | 8/2008 |
| WO | WO2008112577 | 9/2008 |
| WO | WO2008112578 | 9/2008 |
| WO | WO2008120156 | 10/2008 |
| WO | WO2008133394 | 11/2008 |
| WO | WO2008134185 | 11/2008 |
| WO | WO2008150633 | 12/2008 |
| WO | WO2009001108 | 12/2008 |
| WO | WO2009005759 | 1/2009 |
| WO | WO2009006615 | 1/2009 |
| WO | 2009/021378 A1 | 2/2009 |
| WO | WO2009022343 | 2/2009 |
| WO | WO2009029453 | 3/2009 |
| WO | WO2009032381 | 3/2009 |
| WO | WO2009036334 | 3/2009 |
| WO | 2009-513183 A | 4/2009 |
| WO | WO2009051829 | 4/2009 |
| WO | WO2009051830 | 4/2009 |
| WO | WO2009063377 | 5/2009 |
| WO | WO2009081348 | 7/2009 |
| WO | WO2009111664 | 9/2009 |
| WO | WO2009146082 | 12/2009 |
| WO | 2010/005877 | 1/2010 |
| WO | WO2010009100 | 1/2010 |

(56) References Cited

FOREIGN PATENT DOCUMENTS

| WO | WO2010011833 | 1/2010 |
|---|---|---|
| WO | WO2010019778 | 2/2010 |
| WO | WO2010057049 | 5/2010 |
| WO | WO2010075115 | 7/2010 |
| WO | WO2010080765 | 7/2010 |
| WO | WO2010080843 | 7/2010 |
| WO | WO2010107563 | 9/2010 |
| WO | WO2010107980 | 9/2010 |
| WO | WO2010115194 | 10/2010 |
| WO | WO2010132331 | 11/2010 |
| WO | WO2010135516 | 11/2010 |
| WO | WO2011024560 | 3/2011 |
| WO | WO2011068963 | 6/2011 |
| WO | WO2011133799 | 10/2011 |
| WO | WO2011159336 | 12/2011 |
| WO | WO2011159337 | 12/2011 |
| WO | WO2011159338 | 12/2011 |
| WO | WO2011159339 | 12/2011 |
| WO | WO2012104657 | 8/2012 |
| WO | WO2012158190 | 11/2012 |
| WO | WO2013012869 | 1/2013 |
| WO | 2013/070914 A2 | 5/2013 |
| WO | WO2015112603 | 7/2015 |

OTHER PUBLICATIONS

Arshak et al., A Review and Adaptation of Methods of Object Tracking to Telemetry Capsules IC-Med; Jan. 2007 vol. 1, No. 1, Issue 1, 12pp.
"ASGE Technology Status Evaluation Report: wireless capsule endoscopy" American Soc. For Gastrointestinal Endoscopy; Apr. 2006 vol. 63, No. 4; 7 pp.
Au-Yeung, K., et al., "A Networked System for Self-Management of Drug Therapy and Wellness", Wireless Health '10, Oct. 5-7, 2010, San Diego, 9 pages.
Aydin et al., "Design and implementation considerations for an advanced wireless interface in miniaturized integrated sensor Microsystems" Sch. of Eng. & Electron., Edinburgh Univ., UK; Sep. 2003; Abstract Only.
Barrie, Heidelberg pH capsule gastric analysis. Texbook of Natural Medicine, (1992), Pizzorno, Murray & Barrie.
Baskiyar, S. "A Real-time Fault Tolerant Intra-body Network" Dept. of Comp. Sci & Soft Eng; Auburn University; Proceedings of the 27th Annual IEEE Conference; 0742-1303/02 (2002) IEEE; 6 pp.
Bohidar et al., "Dielectric Behavior of Gelatin Solutions and Gels" Colloid Polym Sci (1998) 276:81-86.
Brock, "Smart Medicine: The Application of Auto-ID Technology to Healthcare" Auto-ID Labs (2002) http://www.autoidlabs.org/uploads/media/MIT-AUTOID-WH-010.pdf.
Carlson et al., "Evaluation of a non-invasive respiratory monitoring system for sleeping subjects" Physiological Measurement (1999) 20(1): 53.
Consolvo, Sunny et al., "Design Requirement for Technologies that Encourage Physical Activity," CHI 2006 Proceedings, Designing for Tangible Interactions, Apr. 22, 2006, Montreal, Quebec, Canada, pp. 457-466.
Coury, L. "Conductance Measurement Part 1: Theory"; Current Separations, 18:3 (1999) p. 91-96.
Delvaux et al., "Capsule endoscopy: Technique and indications" Clinical Gastoenterology; Oct. 2008 vol. 22, Issue 5, 1pp. (Abstract Only).
Description of ePatch Technology Platform for ECG and EMG, located it http://www.madebydelta.com/imported/images/DELTA_Web/documents/ME/ePatch_ECG_EMG.pdf, Dated Sep. 2, 2010.
Dhar et al., "Electroless nickel plated contacts on porous silicon" Appl. Phys. Lett. 68 (10) pp. 1392-1393 (1996).
Eldek A., "Design of double dipole antenna with enhanced usable bandwidth for wideband phased array applications" Progress in Electromagnetics Research PIER 59, 1-15 (2006).

Evanczuk, S., "PIC MCU software library uses human body for secure communications link"; EDN Network; edn.com; Retrieved from internet Jun. 19, 2013 at http://www.edn.com/electronics-products/other/4407842/PIC-MCU-software-library-uses-human-body-for-secure-communications-link; Feb. 26, 2013; 5 pp.
Fawaz et al., "Enhanced Telemetry System using CP-QPSK Band-Pass Modulation Technique Suitable for Smart Pill Medical Application" IFIP IEEE Dubai Conference Apr. 2008; http://www.asic.fh-offenburg.de/downloads/ePille/IFIP_IEEE_Dubai_Conference.pdf.
Ferguson et al., "Dielectric Constant Studies III Aqueous Gelatin Solutions" J. Chem. Phys. 2, 94 (1934) p. 94-98.
Ferguson et al., "Wireless communication with implanted medical devices using the conductive properties of the body," Expert Rev Med Devices, Jul. 2011, 8(4): 427-433.
Furse C. M., "Dipole Antennas" J. Webster (ed). Wiley Encyclopedia of Electrical and Electronics Engineering (1999) p. 575-581.
Gaglani S. "Put Your Phone, Or Skin, on Vibrate" MedGadget; Mar. 2012 http://medgadget.com/2012/03/put-your-phone-or-skin-on-vibrate.html 8pp.
Gilson, D.R. "Molecular dynamics simulation of dipole interactions", Department of Physics, Hull University, Dec. 2002, p. 1-43.
Given Imaging, "Agile Patency Brochure" (2006) http://www.inclino.no/documents/AgilePatencyBrochure_Global_GMB-0118-01.pdf; 4pp.
Gonzalez-Guillaumin et al., "Ingestible capsule for impedance and pH monitoring in the esophagus" IEEE Trans Biomed Eng; Dec. 2007 54(12) 1pp. (Abstract Only).
Greene, "Edible RFID microchip monitor can tell if you take your medicine" Bloomberg Businessweek; Mar. 2010 2 pp.; http://www.businessweek.com/idg/2010-03-31/edible-rfid-microchip-monitor-can-tell-if-you-take-your-medicine.html.
Greene, "Medicaid Efforts to Incentivize Healthy Behaviours", Center for Health Care Strategies, Inc., Resource Paper, Jul. 2007.
Halthion Medical Technologies "Providing Ambulatory Medical Devices Which Monitor, Measure and Record" webpage. Online website: http://www.halthion.com/; downloaded May 30, 2012; 2 pp.
Heydari et al., "Analysis of the PLL jitter due to power/ground and substrate noise"; IEEE Transactions on Circuits and Systems (2004) 51(12): 2404-16.
Hoeksma, J. "New 'smart pill' to track adherence" E-Health-Insider; http://www.e-health-insider.com/news/5910/new_'smart_pill'_monitors_medicines; May 17, 2010 (2010); 1pp.
Hoover et al., "Rx for health: Engineers design pill that signals it has been swallowed" University of Florida News; Mar. 2010 2pp.; http://news.ufl.edu/2010/03/31/antenna-pill-2/.
Hotz "The Really Smart Phone" The Wall Street Journal, What They Know (2011); 6 pp.; http://online.wsj.com/article/SB10001424052748704547604576263261679848814.html?mod=djemTECH_t.
Intromedic, MicroCam Innovative Capsule Endoscope Pamphlet. (2006) 8 pp (http://www.intromedic.com/en/product/productinfo.asp).
ISFET—Ion Sensitive Field-Effect Transistor; Microsens S.A. pdf document. First cited by Examiner in Office Action dated Jun. 13, 2011 for U.S. Appl. No. 12/238,345; 4pp.
Jimbo et al., "Gastric-fluid-utilized micro battery for micro medical devices" The Sixth International Workshop on Micro and Nanotechnology for Power Geneartion and Energy Conservation Applications, (2006) pp. 97-100.
Jung, S. "Dissolvable 'Transient Electronics' Will Be Good For Your Body and the Environment" MedGadget; Oct. 1, 2012; Onlne website: http://medgadget.com/2012/10/dissolvable-transient-electronics-will-be-good-for-your-body-and-the-environment.html; downloaded Oct. 24, 2012; 4 pp.
Juvenile Diabetes Research Foundation International (JDRF), "Artificial Pancreas Project" Jun. 2010; http://www.artificialpancreasproject.com/; 3 pp.
Kamada K., "Electrophoretic deposition assisted by soluble anode" Materials Letters 57 (2003) 2348-2351.

(56) References Cited

OTHER PUBLICATIONS

Kendle, Earl R. and Morris, Larry A., "Preliminary Studies in the Development of a Gastric Battery for Fish" (1964). Nebraska Game and Parks Commission White Papers, Conference Presentations, & Manuscripts. Paper 22. p. 1-6.
Kim et al., "A Semi-Interpenetrating Network System for a Polymer Membrane"; Eur. Polym. J. vol. 33 No. 7; pp. 1009-1014 (1997).
Li, P-Y, et al. "An electrochemical intraocular drug delivery device", Sensors and Actuators A 143; p. 41-48.; Jul. 2007.
Lifescan, "OneTouch UltraLink™" http://www.lifescan.com/products/meters/ultralink; Jul. 2010 2 pp.
Lin et al., "Do Physiological Data Relate to Traditional Usability Indexes?" Proceedings of OZCHI 2005, Canberra, Australia (2005) 10 pp.
Mackay et al., "Radio Telemetering from within the Body" Inside Information is Revealed by Tiny Transmitters that can be Swallowed or Implanted in Man or Animal Science (1991) 1196-1202; 134; American Association for the Advancement of Science, Washington D.C.
Mackay et al., "Endoradiosonde" Nature, (1957) 1239-1240, 179 Nature Publishing Group.
Mandryk et al., "A physiological approach for continuously modeling user emotion in interactive play environments" Proceedings of Measuring Behavior (2008) (Maastrichtm The Netherlandsm Aug. 26-29) 2 pp.
Mandryk et al., "Objectively Evaluating Entertainment Technology" Simon Fraser University; CHI (2004) ACM 1-58113-703-6/04/0004; 2 pp.
McDermott-Wells, P., "What is Bluetooth?", IEEE Potentials, IEEE, New York, NY, vol. 23, No. 5, Dec. 1, 2004, pp. 33-35.
McKenzie et al., "Validation of a new telemetric core temperature monitor" J. Therm. Biol. (2004) 29(7-8):605-11.
Medtronic, "CareLink Therapy Management Software for Diabetes" Jul. 2010; https://carelink.minimed.com/patient/entry.jsp?bhcp=1; 1 pp.
Medtronic, "Carelink™ USB" (2008) http://www.medtronicdiabetes.com/pdf/carelink_usb_factsheet.pdf 2pp.
Medtronic "The New MiniMed Paradigm® REAL-Time Revel™ System" Aug. 2010 http://www.medtronicdiabetes.com/products/index.html; 2 pp.
Medtronic, "MINI MED Paradigm ® Revel ™ Insulin Pump" Jul. 2010 http://www.medtronicdiabetes.com/products/insulinpumps/index.html; 2 pp.
Medtronic, Mini Med Paradigm™ Veo™ System: Factsheet (2010). http://www.medtronic-diabetes.com.au/downloads/Paradigm%20Veo%20Factsheet.pdf; 4 pp.
Melanson, "Walkers swallow RFID pills for science" Engadget; Jul. 2008; http://www.engadget.com/2008/07/29/walkers-swallow-rfid-pills-for-science/.
Minimitter Co. Inc. "Actiheart" Traditional 510(k) Summary. Sep. 27, 2005.
Minimiter Co. Inc. Noninvasive technology to help your studies succeed. Mini Mitter.com Mar. 31, 2009.
Mini Mitter Co, Inc. 510(k) Premarket Notification Mini-Logger for Diagnostic Spirometer. Sep. 21, 1999.
Mini Mitter Co, Inc. 510(k) Premarket Notification for VitalSense. Apr. 22, 2004.
Minimitter Co. Inc. VitalSense Integrated Physiological Monitoring System. Product Description. Jul. 2005.
Minimitter Co. Inc. VitalSense Wireless Vital Signs Monitoring. Temperatures.com Mar. 31, 2009.
Mojaverian et al., "Estimation of gastric residence time of the Heidelberg capsule in humans: effect of varying food composition" Gastroenterology (1985) 89:(2): 392-7.
O'Brien et al., "The Production and Characterization of Chemically Reactive Porous Coatings of Zirconium Via Unbalanced Magnetron Sputtering" Surface and Coatings Technology (1996) 86-87; 200-206.
Owano, N., "Study proposes smart sutures with sensors for wounds" PHYS.ORG. Aug. 2012. http://phys.org/news/2012-08-smart-sutures-sensors-wounds.html; 2pp.
"PALO Bluetooth Baseband" PALO Bluetooth Resource Center; Retrieved from internet Dec. 12, 2012 at URL:http://palowireless.com/bluearticles/baseband.asp; first cited in Office Action dated Jan. 17, 2013 for EP08853901.0 (2013); 6pp.
Park, "Medtronic to Buy MiniMed for $3.7 Billion" (2001) HomeCare; http://homecaremag.com/mag/medical_medtronic_buy_minimed/; 2 pp.
Platt, D., "Modulation and Deviation" AE6EO, Foothills Amateur Radio Society; Oct. 26, 2007; 61 pp.
Radio Antennae, http://www.erikdeman.de/html/sail018h.htm; (2008) 5 pages.
"RFID "pill" monitors marchers" RFID News; Jul. 2008 http://www.rfidnews.org/2008/07/23/rfid-pill-monitors-marchers/.
Rolison et al., "Electrically conductive oxide aerogels: new materials in electrochemistry" J. Mater. Chem. (2001) 1, 963-980.
Roulstone, et al., "Studies on Polymer Latex Films: 1. A study of latex film morphology" Polymer International 24 (1991) pp. 87-94.
Sanduleanu et al., "Octave tunable, highly linear, RC-ring oscillator with differential fine-coarse tuning, quadrature outputs and amplitude control for fiber optic transceivers" (2002) IEEE MTT-S International Microwave Symposium Digest 545-8.
Santini, J.T. et al., "Microchips as controlled drug delivery-devices", Agnew. Chem. Int. Ed. (2000), vol. 39, p. 2396-2407.
"SensiVida minimally invasive clinical systems" Investor Presentation Oct. 2009 28pp; http://www.sensividamedtech.com/SensiVidaGeneralOctober09.pdf.
Sharma, et al., "The Future is Wireless: Advances in Wireless Diagnostic and Therapeutic Technologies in Gastoenterology," Gastroenterology, Elesevier, Philadelphia, PA, vol. 137, No. 2, Aug. 1, 2009, pp. 434-439.
Shawgo, R.S. et al. "BioMEMS from drug delivery", Current Opinion in Solid State and Material Science 6; May 2002, p. 329-334.
Shin et al., "A Simple Route to Metal Nanodots and Nanoporous Metal Films"; Nano Letters, vol. 2, No. 9 (2002) pp. 933-936.
Shrivas et al., "A New Platform for Bioelectronics-Electronic Pill", Cummins College, (2010).; http://www.cumminscollege.org/downloads/electronics_and_telecommunication/Newsletters/Current%20Newsletters.pdf; First cited in third party client search conducted by Patent Eagle Search May 18, 2010 (2010).
"Smartlife awarded patent for knitted transducer" Innovation in Textiles News: http://www.innovationintextiles.com/articles/208.php; 2pp. Aug. 2009.
"The SmartPill Wireless Motility Capsule" SMARTPILL, The Measure of GI Health; May 2010 http://www.smartpillcorp.com/index.cfm?pagepath=Products/The_SmartPill_Capsule&id=17814.
Solanas et al., "RFID Technology for the Health Care Sector" Recent Patents on Electrical Engineering (2008) 1, 22-31.
Soper, S.A. et al. "Bio-Mems Technologies and Applications", Chapter 12, "MEMS for Drug Delivery", p. 325-346 (2007).
Swedberg, "University Team Sees Ingestible RFID Tag as a Boon to Clinical Trials" RFID Journal Apr. 27, 2010; http://www.rfidjournal.com/article/view/7560/1, 3pp.
Tajalli et al., "Improving the power-delay performance in subthreshold source-coupled logic circuits" Integrated Circuit and System Design. Power and Timing Modeling, Optimization and Simulation, Springer Berlin Heidelberg (2008) 21-30.
Tatbul et al., "Confidence-based data management for personal area sensor networks" ACM International Conference Proceeding Series (2004) 72.
Tierney, M.J. et al. "Electroreleasing Composite Membranes for Delivery of Insulin and other Biomacromolecules", J. Electrochem. Soc., vol. 137, No. 6, Jun. 1990, p. 2005-2006.
Trutag, Technologies, Inc., Spectral Microtags for Authentication and Anti-Counterfeiting; "Product Authentication and Brand Protection Solutions"; http://www.trutags.com/; downloaded Feb. 12, 2013 (2013); 1 pp.
Walkey, "MOSFET Structure and Processing"; 97.398* Physical Electronics Lecture 20.

(56) References Cited

OTHER PUBLICATIONS

Watson, et al., "Determination of the relationship between the pH and conductivity of gastric juice" Physiol Meas. 17 (1996) pp. 21-27.
Winter, J. et al. "The material properties of gelatin gels"; USA Ballistic Research Laboratories, Mar. 1975, p. 1-157.
Wongmanerod et al., "Determination of pore size distribution and surface area of thin porous silicon layers by spectroscopic ellipsometry" Applied Surface Science 172 (2001) 117-125.
Xiaoming et al., "A telemedicine system for wireless home healthcare based on bluetooth and the internet" Telemedicine Journal and e-health (2004) 10(S2): S110-6.
Yang et al., "Fast-switching frequency synthesizer with a discriminator-aided phase detector" IEEE Journal of Solid-State Circuits (2000) 35(10): 1445-52.
Yao et al., "Low Power Digital Communication in Implantable Devices Using Volume Conduction of Biological Tissues" Proceedings of the 28th IEEE, EMBS Annual International Conference, Aug. 30-Sep. 3, 2006.
Zimmerman, "Personal Area Networks: Near-field intrabody communication" IBM Systems Journal (1996) 35 (3-4):609-17.
Zworkin, "A Radio Pill" Nature, (1957) 898, 179 Nature Publishing Group.
Van der Biest, O., et al., "Electrophoretic deposition of materials," Annu. Rev. Mater. Sci. 1999, 29: pp. 327-352.
Aronson, J., "Meyer's Side Effects of Cardiovascular Drugs," Elsevier, Mar. 2, 2009, Medical, 840 pages. (Not Attached).
Chan, Adrian D.C., et al.; "Wavelet Distance Measure for Person Identification Using Electrocardiograms," IEEE Transactions on Instrumentation and Measurement, IEEE Service Center, Piscataway, NJ, US, vol. 57, No. 2, Feb. 1, 2008, pp. 248-253.
Herbig, S.M., "Asymmetric-membrane tablet coatings for osmotic drug delivery", Journal of Controlled Release 35 (1995) 127-136.
Lee, K. B.; "Two-step activation of paper batteries for high power generation: design and fabrication of biofluid- and wateractivated paper batteries"; J. Micromech. Microeng. 16 (2006) 2312-2317.
Lee, K. B.; "Urine-activated paper batteries for Biosystems"; J. Micromech. Microeng. 15 (2005) S21 O-S214.
Sammoura, F. et al., "Water-activated disposable and long shelf life microbatteries", Sensors and Actuators A 111 (2004) 79-86.
VonStetten, F. et al., "Biofuel cells as power generation for implantable devices", Pore. Eurosensors XX, (2006), pp. 22-225.
Zhang, Y-T. et al., "Wireless Biomedical Sensing," Wiley Encyclopedia of Biomedical Engineering, 2006, pp. 1-9.
European Search Report dated Feb. 16, 2022, issued in the corresponding European Patent Application No. 21202781.7, pp. 1-11.

\* cited by examiner

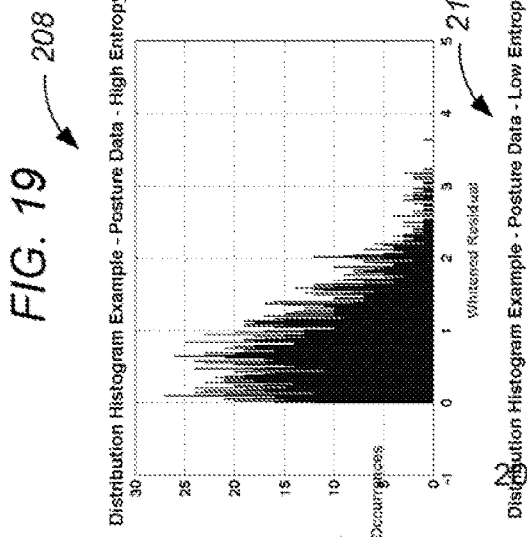
FIG. 18
FIG. 19
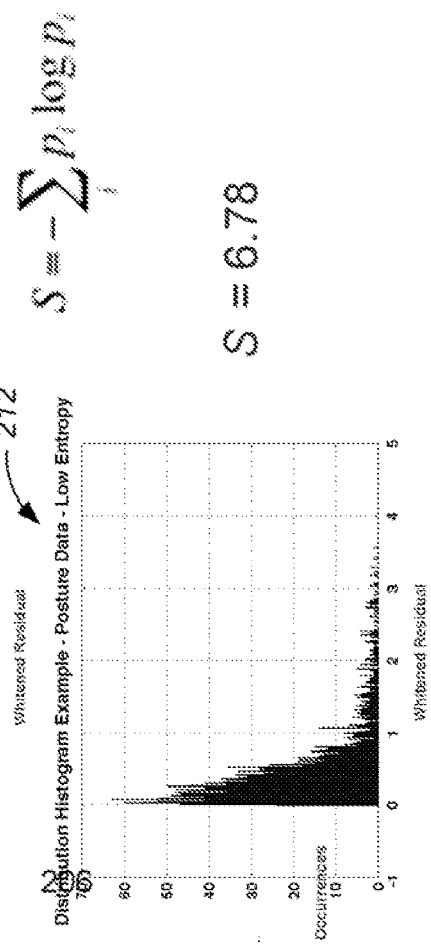
$S = 7.23$
$$S = -\sum p_i \log p_i$$
$S = 6.78$
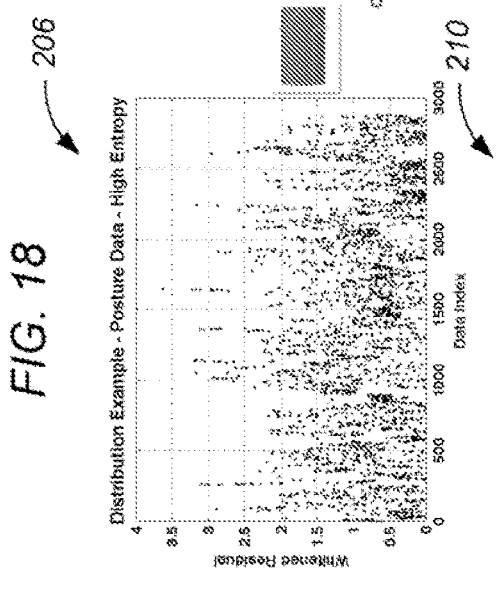
FIG. 20
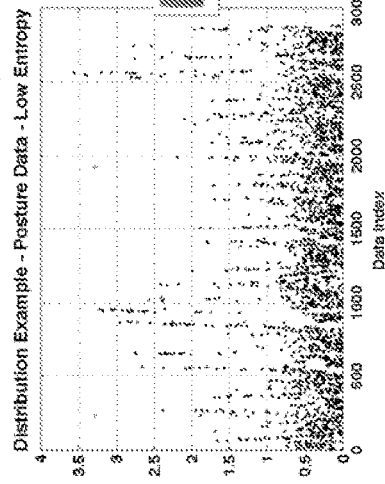
FIG. 21

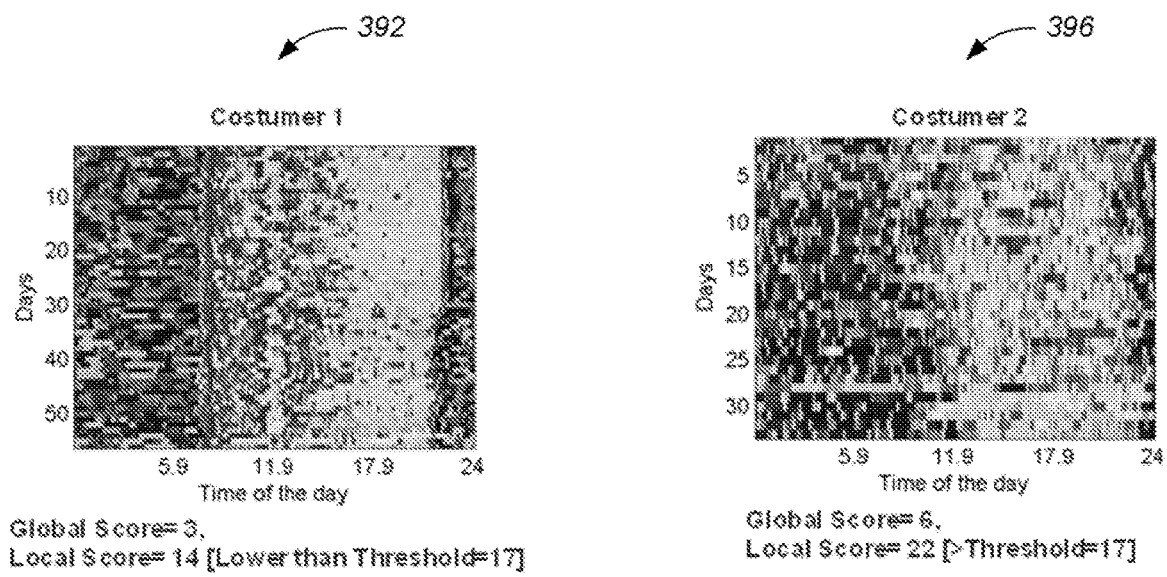
FIG. 53
FIG. 55
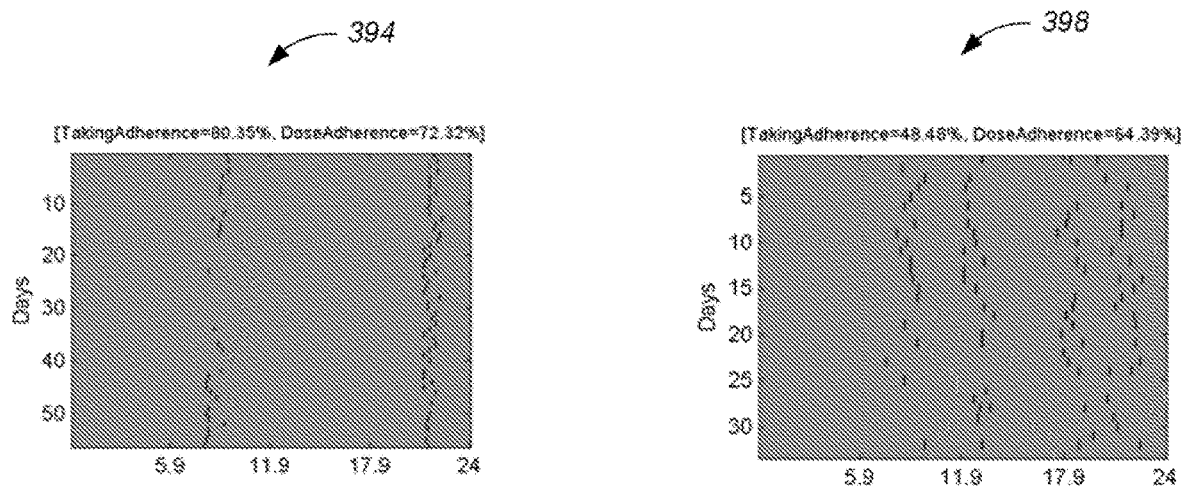
FIG. 54
FIG. 56

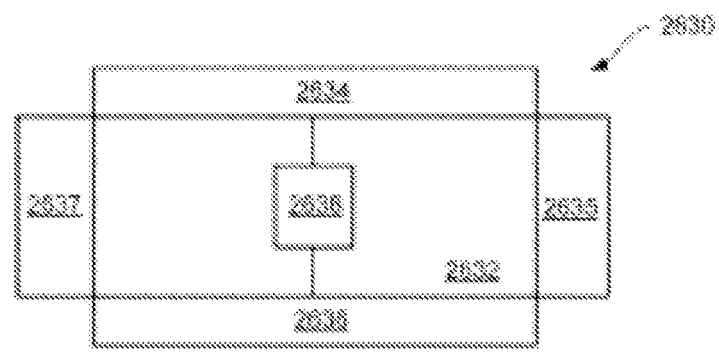
FIG. 71
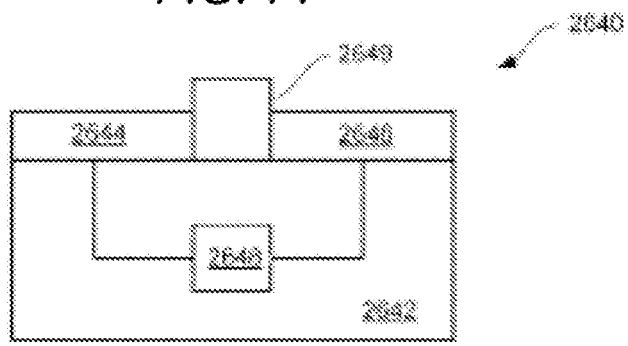
FIG. 72
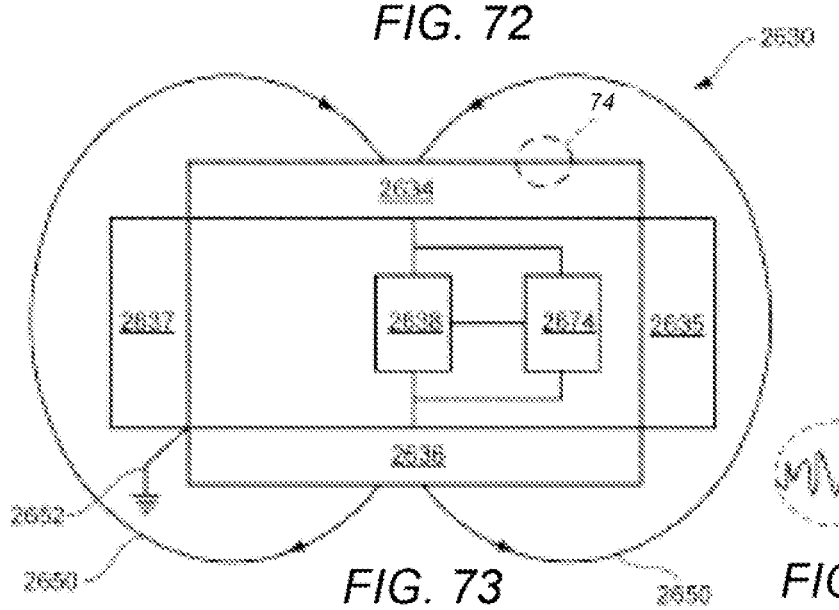 
FIG. 73  FIG. 74

SYSTEM, APPARATUS AND METHODS FOR DATA COLLECTION AND ASSESSING OUTCOMES

CROSS REFERENCE TO RELATED APPLICATIONS

The present application is a U.S. national phase application filed under 35 U.S.C. § 371 of International Patent Application No. PCT/US2014/040570, entitled SYSTEM, APPARATUS AND METHODS FOR DATA COLLECTION AND ASSESSING OUTCOMES, filed Jun. 2, 2014, which application claims the benefit under 35 U.S.C. § 119(e) of U.S. Provisional Application No. 61/831,075 entitled SYSTEM, APPARATUS AND METHODS FOR DATA COLLECTION AND ASSESSING OUTCOMES, filed Jun. 4, 2013, the disclosures of which are herein incorporated by reference.

This application is related to U.S. patent application Ser. No. 13/844,386, filed on Mar. 15, 2013, the disclosure of which application is herein incorporated by reference.

INTRODUCTION

Individual data gathered by a Proteus system (therapy, behavior, physiology) together with publically available data may influence overall health risk and health maintenance of the individual. Such data may include individual demographics, prevalence of disease in a particular geography, proximity to health care service centers, performance (outcomes) associated to HCPs (Health care Provider's) in local, proximity to businesses that might influence healthy behavior (health clubs, restaurants, fast-food, grocery stores, parks, etc).

By combining the data, risk can be properly adjusted for the specific patient situation and appropriate resource can be applied to manage the risk appropriately.

The aggregate patient health risk can be more effectively determined by combining Proteus system data (therapeutic regimen and adherence, behavior, engagement, and physiology) together with one or more data elements.

The data listed above may also be used without a Proteus system data to provide an independent risk-score. By combining the data, risk can be properly adjusted for the specific patient situation and appropriate resource can be applied to manage the risk appropriately. The data might be sourced from a combination of direct capture, public data sources and/or privately available systems/sources.

SUMMARY

In one aspect, a computer-implemented method is disclosed. The computer-implemented method comprises receiving, by a computer system, ingestible event marker (IEM) system information from a receiver worn by a subject, the IEM system information comprising information associated with ingestion of medication by the subject, wherein the receiver is configured to communicate with the computer system; receiving, by the computer system, contextual information associated with the subject; and calculating, by the computer system, a composite risk score based on the IEM system information and the contextual information associated with the subject.

In one aspect, a computer-implemented method is disclosed. The computer-implemented method comprises receiving, by a computer system, daily data from a subject; calculating, by the computer system, the daily data into a dominant circadian pattern; tracking, by the computer system, daily variations between the daily data and the dominant circadian pattern; and calculating, by the computer system, a distribution of the daily variations; and quantifying, by the computer system, the distribution of the daily variations by differential entropy.

In one aspect, a computer-implemented method is disclosed. The computer-implemented method comprises receiving, by a computer system, daily data from a subject; applying, by the computer system, principal component analysis to the received daily data to determine a dominant mode; determining, by the computer system, a variation between the daily data and the dominant mode; and determining, by the computer system, how many samples of the daily data are above a predetermined threshold.

The foregoing summary is illustrative only and is not intended to be in any way limiting. In addition to the illustrative aspects, aspects, and features described above, further aspects, aspects, and features will become apparent by reference to the drawings and the following detailed description.

FIGURES

The novel features of the aspects described herein are set forth with particularity in the appended claims. The aspects, however, both as to organization and methods of operation may be better understood by reference to the following description, taken in conjunction with the accompanying drawings as follows.

Figure 9:
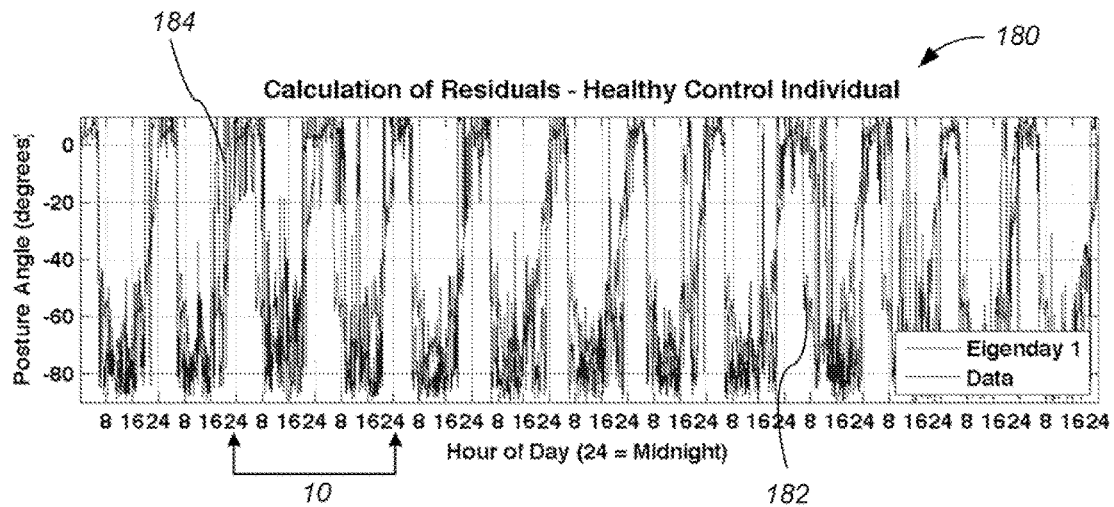

FIG. 9, there is shown a graphical representation of an example Eigenday 1 plotted along with data obtained from a healthy control individual according to one aspect.

Figure 10:
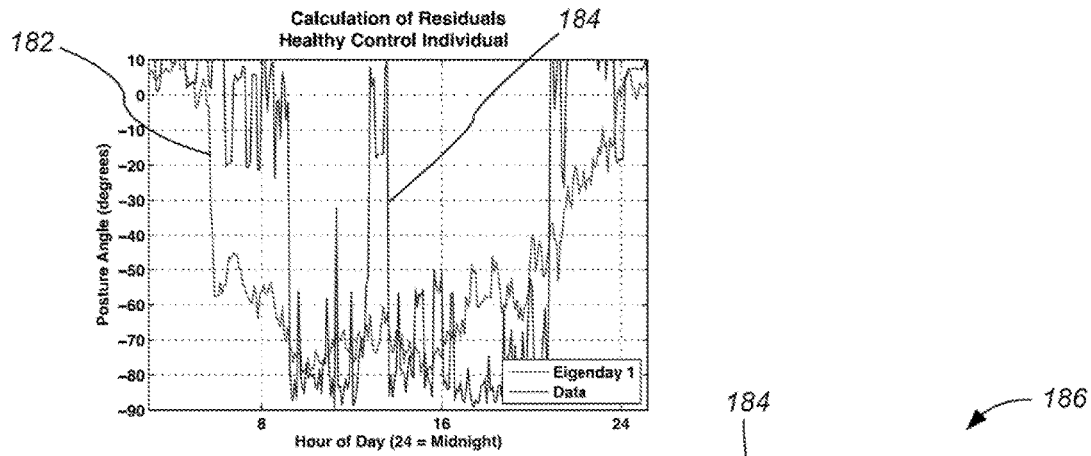

FIG. 10 is a magnified view of the indicated section of the graph shown in FIG. 9 over a 24-hour period.

Figure 11:
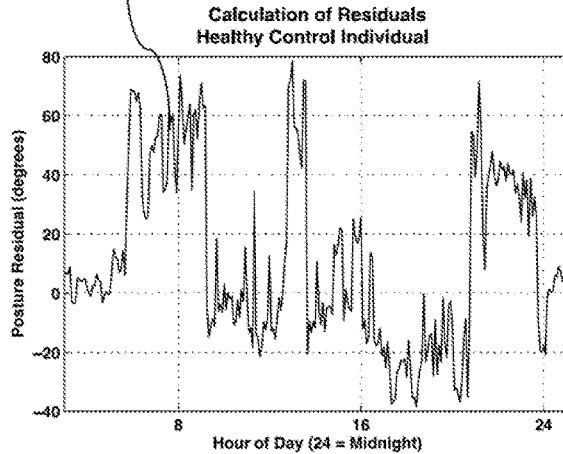

FIG. 11 is a graphical representation showing the residuals calculated by subtracting the baseline Eigenday 1 from each individual's multi-day data set.

Figure 12:
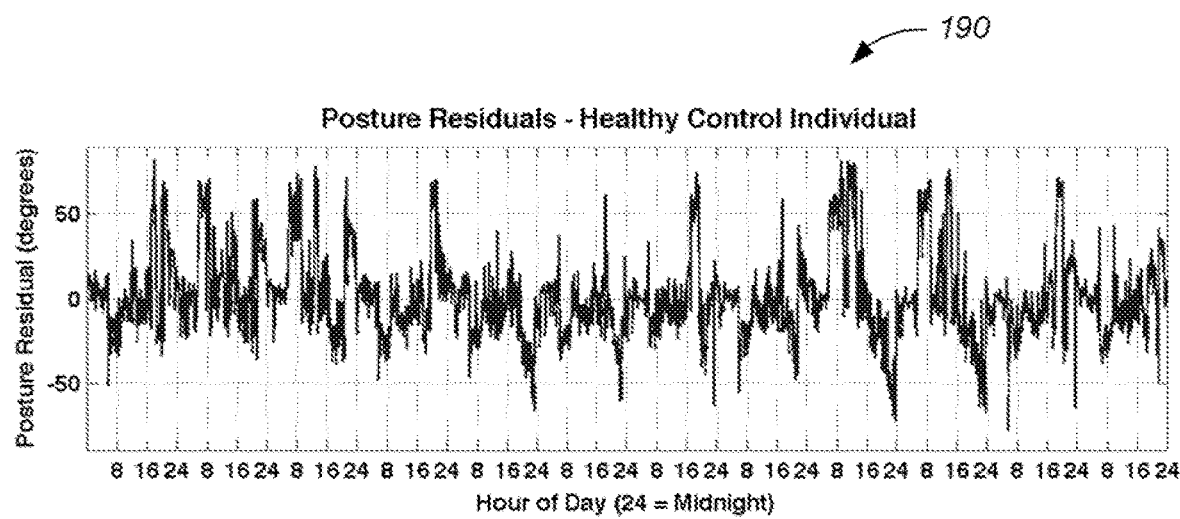

FIG. 12 is a graphical representation of unfiltered data for a healthy control individual according to one aspect.

Figure 13:
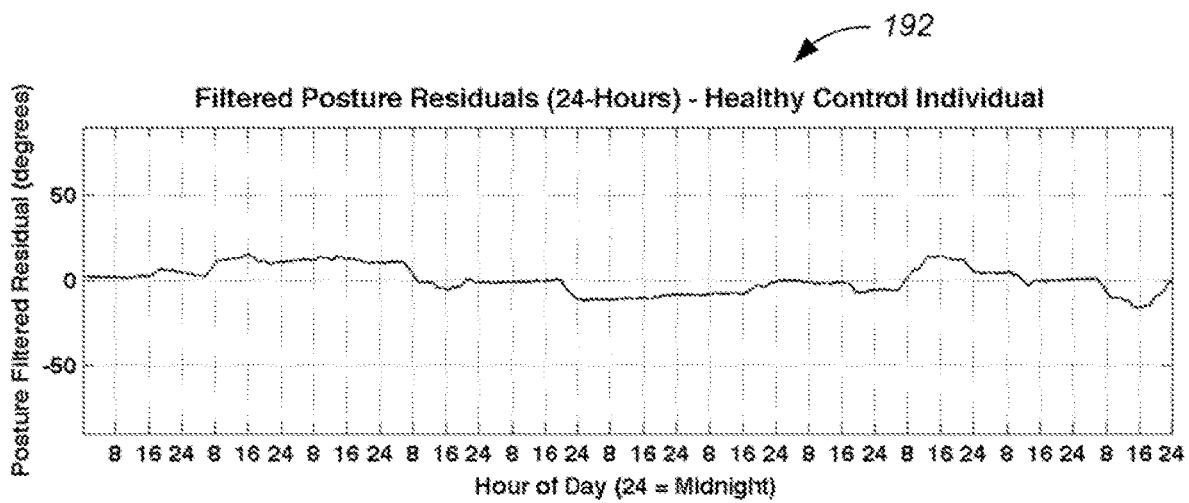

FIG. 13 is a graphical representation of filtered data for a healthy control individual according to one aspect.

Figure 14:
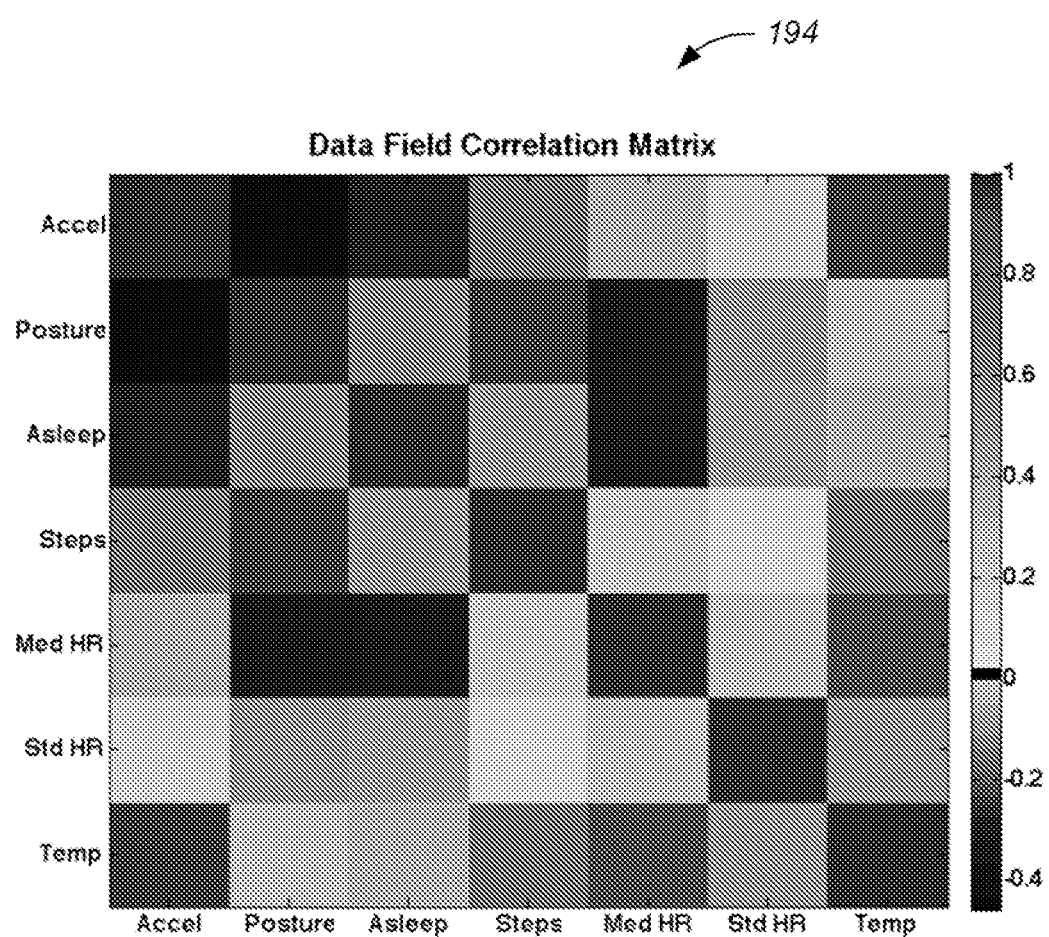

FIG. 14 is a diagram illustrating a data field correlation matrix according to one aspect where the vertical scale to the right of the matrix is a differentially shaded gradient representing the level of correlation.

Figure 15:
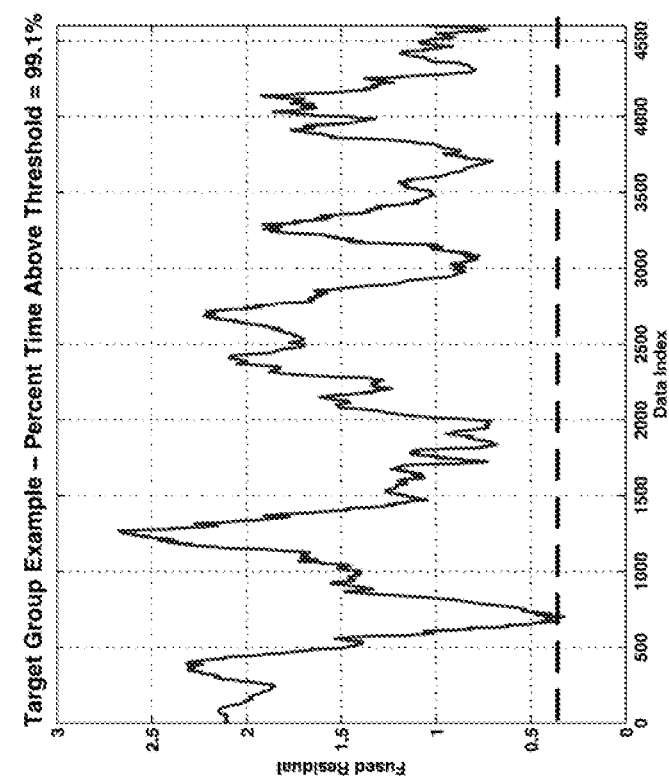

FIG. 15 is a graphical representation target group data showing the amount of time the target group was above the threshold according to one aspect.

Figure 16:
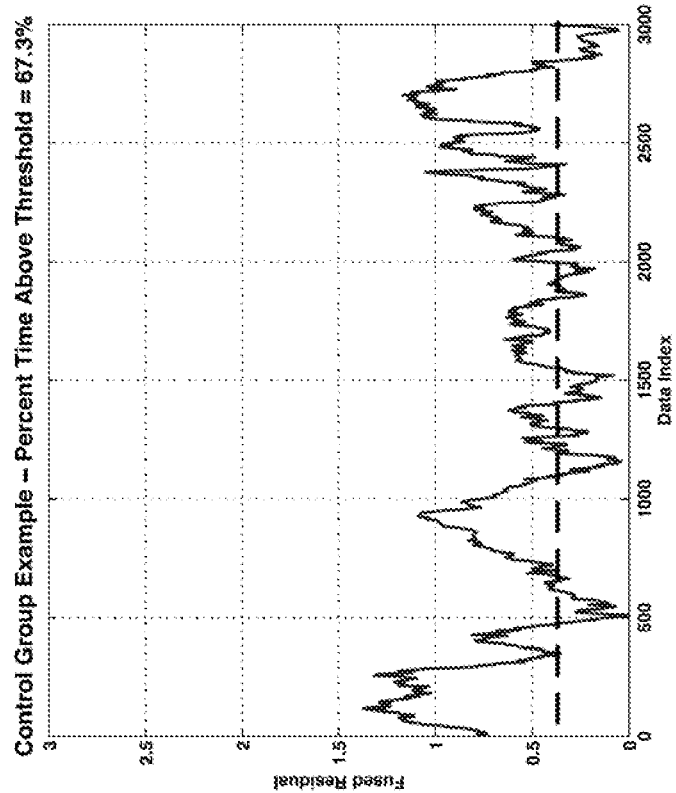

FIG. 16 is a graphical representation of control group data showing the amount of time the control group was above the threshold according to one aspect.

Figure 17:
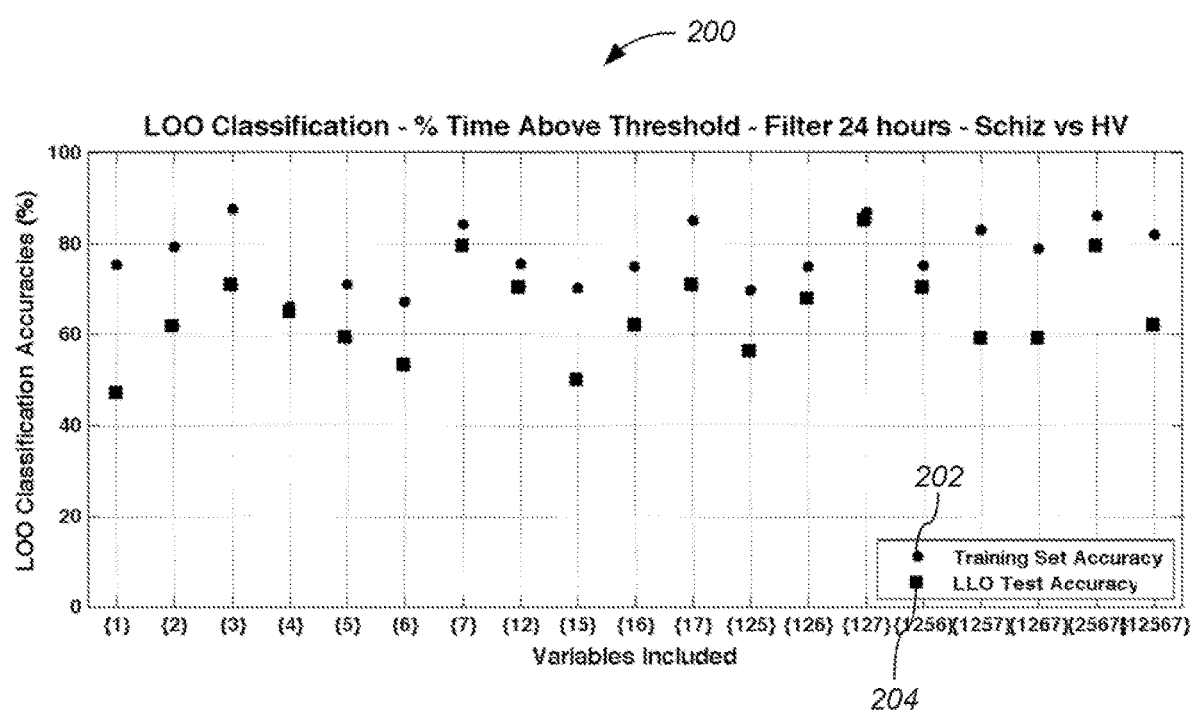

FIG. 17 is a graphical representation of a leave one out (LOO) classification testing according to one aspect showing the time above threshold for schizophrenic vs. healthy control groups.

FIG. 18 is a graphical representation of distribution entropy classification based on features of the posture data distribution based on a high entropy example from a schizophrenic group.

FIG. 19 is a distribution histogram of posture data for the high entropy example.

FIG. 20 is a graphical representation of a distribution entropy classification based on features of the data distribution based on a low entropy example from a control group.

FIG. 21 is a distribution histogram of posture data for the low entropy example.

Figure 22:
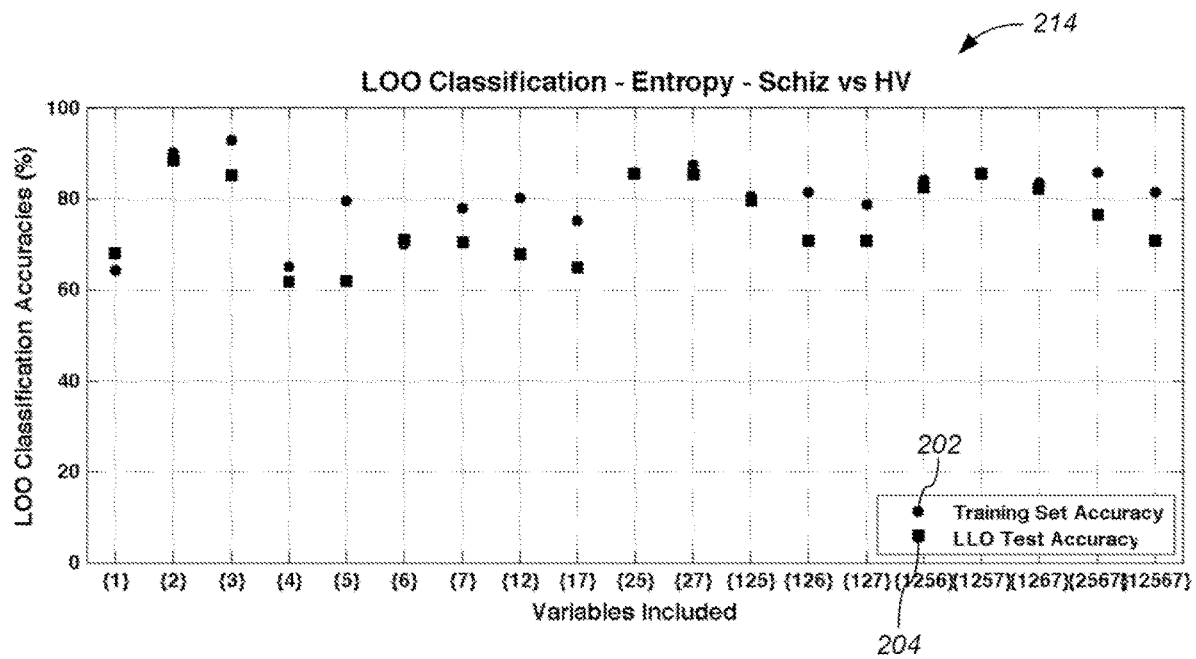

FIG. 22 is a graphical representation of a LOO classification testing according to one aspect showing the distribution entropy for schizophrenic vs. healthy control groups.

Figure 23:
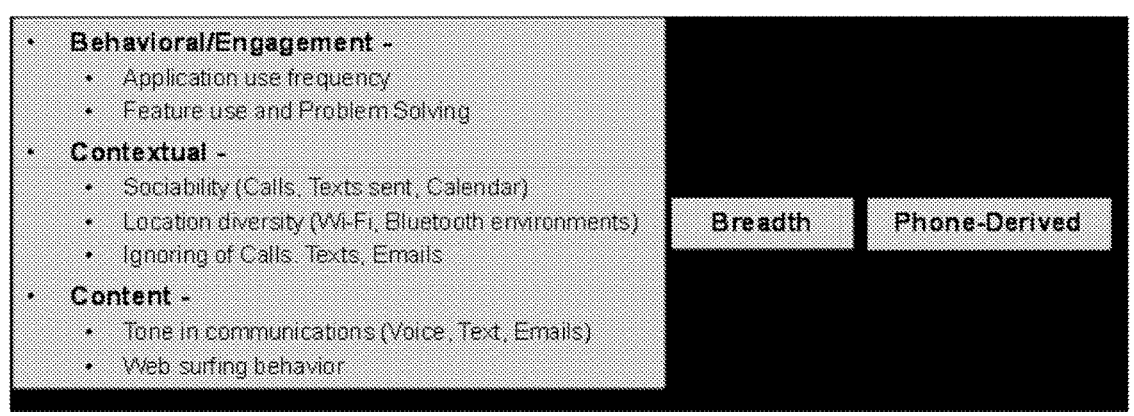

FIG. 23 is a diagram illustrating data characterization for expanded data classes according to one aspect.

Figure 24:
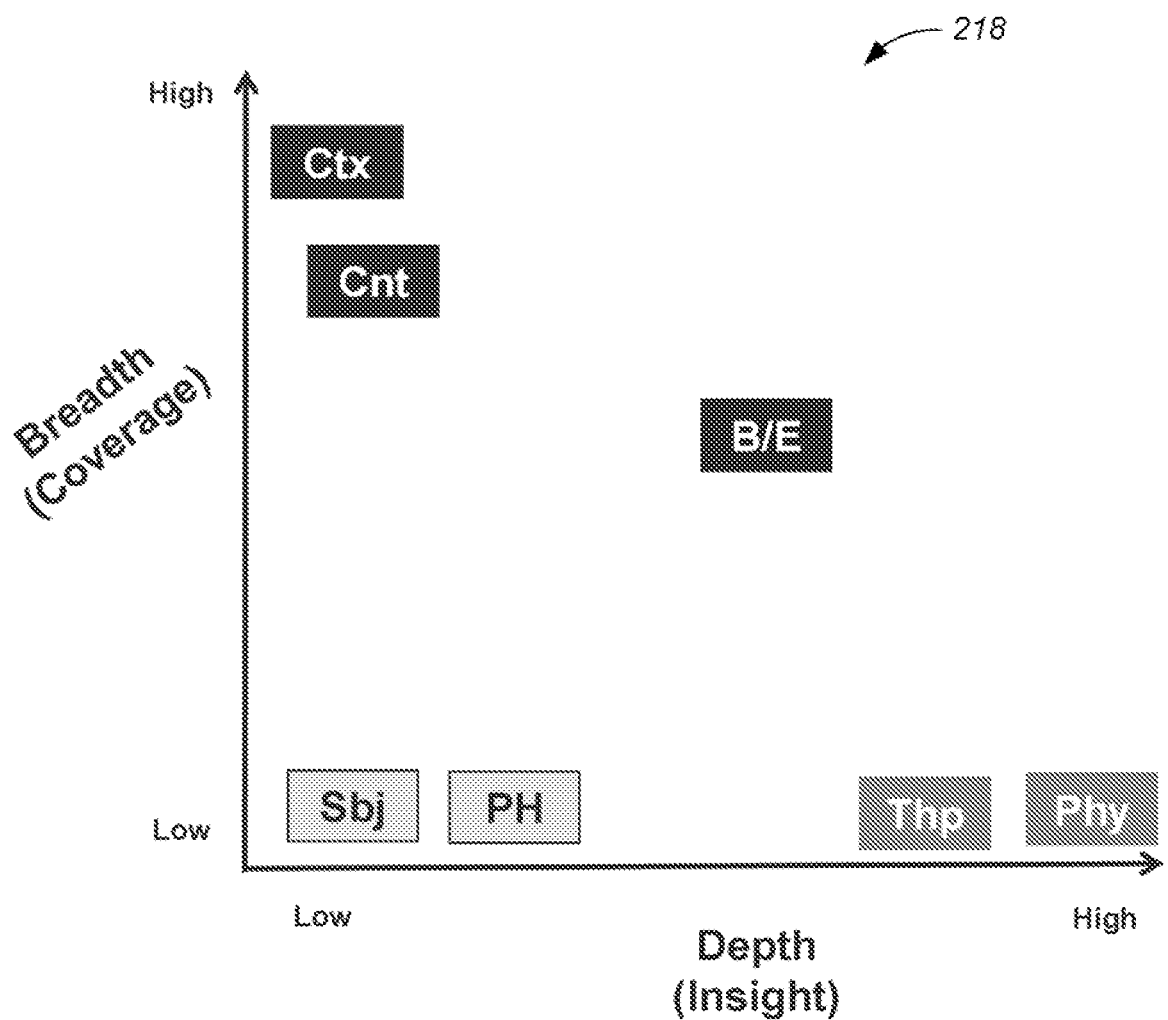

FIG. 24 is a graphical representation of breadth vs. depth framing of data values according to one aspect.

Figure 25:
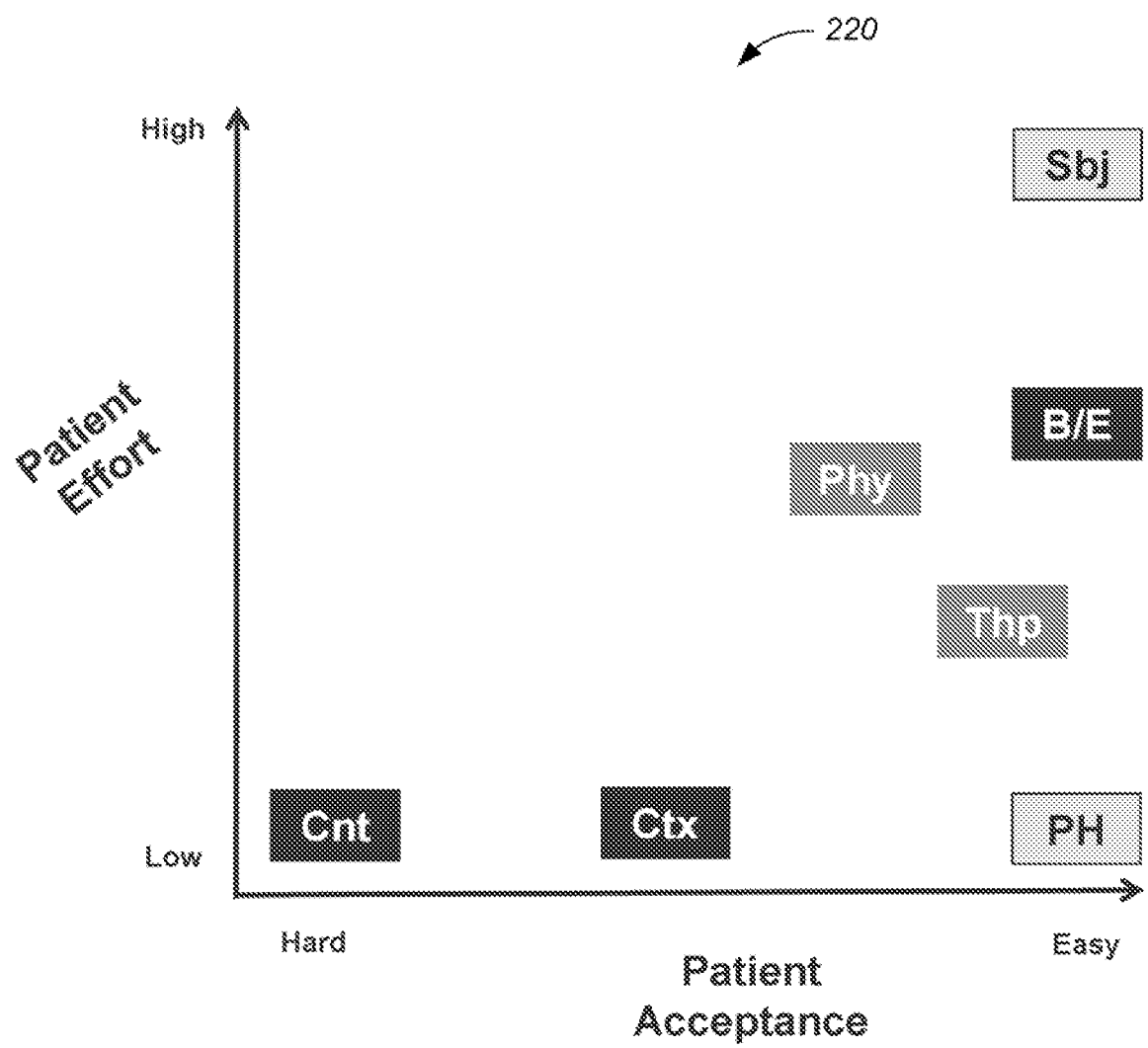

FIG. 25 is a graphical representation patient acceptance vs. patient effort framing of data values according to one aspect.

Figure 26:
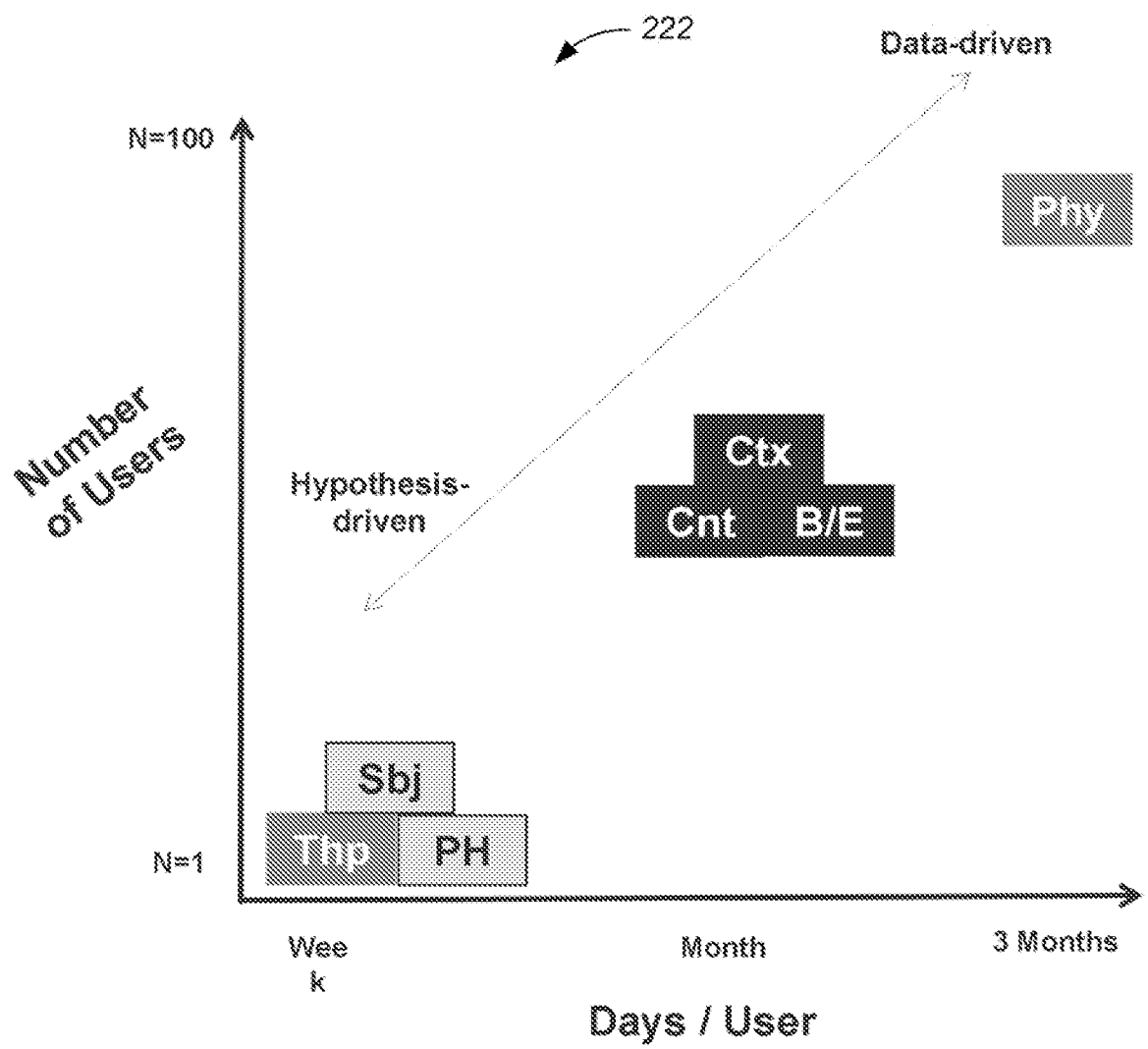

FIG. 26 is a graphical representation of the amount of data needed for framing of data values according to one aspect.

Figure 27:
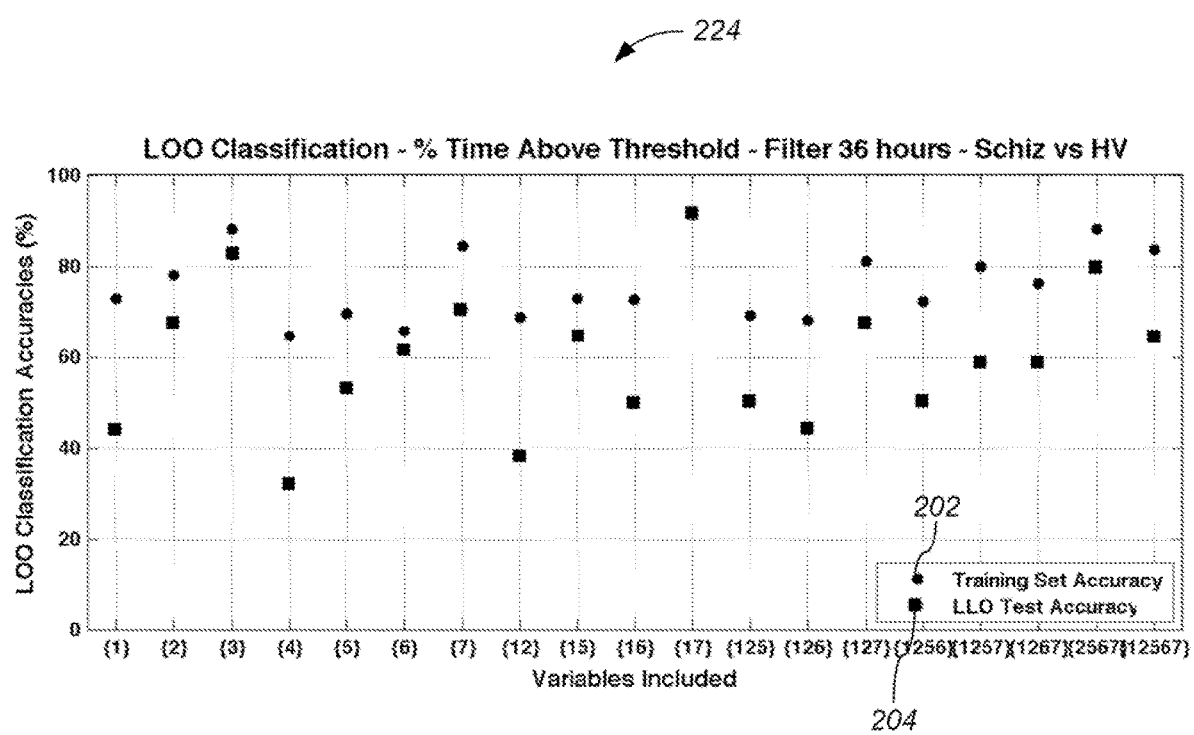

FIG. 27 is a graphical representation of a leave one out (LOO) classification testing showing time above threshold comparing schizophrenic vs. healthy controls according to one aspect.

Figure 28:
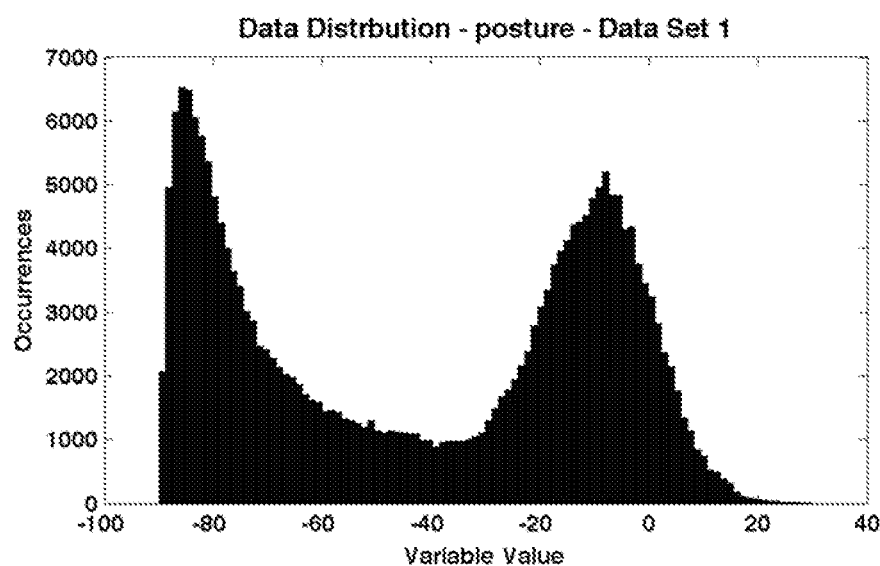

FIG. 28 is a graphical representation of posture data set data distribution according to one aspect.

Figure 29:
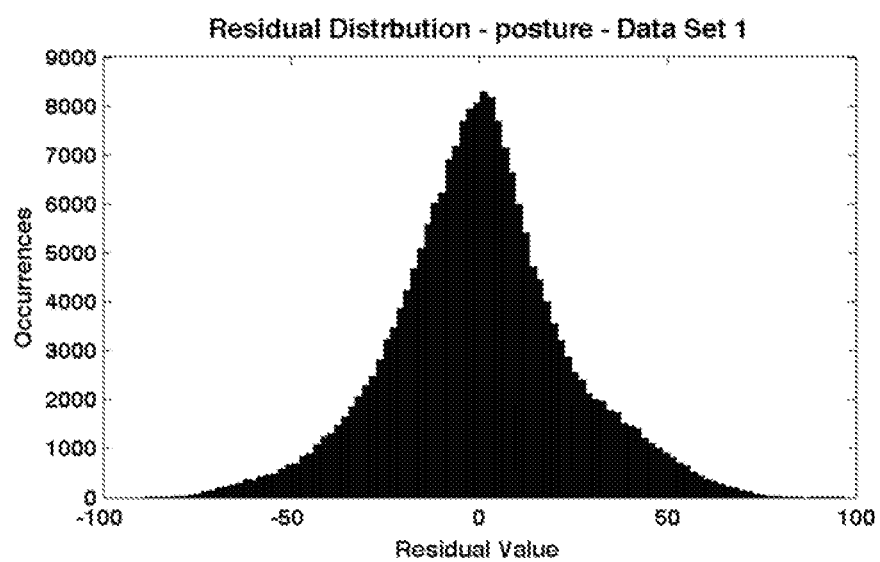

FIG. 29 is a graphical representation of posture data set residual distribution according to one aspect.

Figure 30:
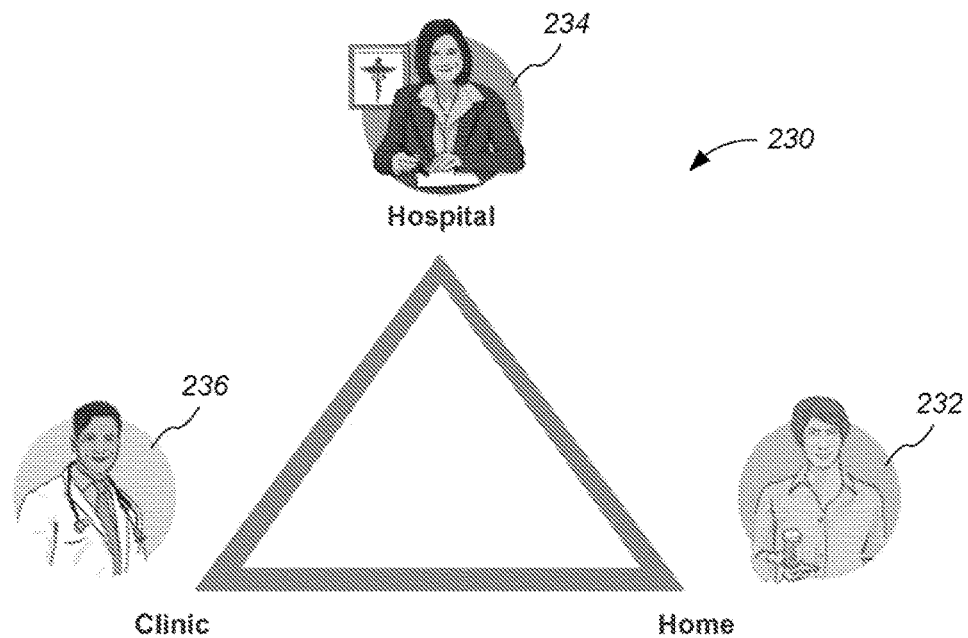

FIG. 30 is a diagram illustrating the continuous patient journey with episodic intervention between home, hospital, and clinic according to one aspect.

Figure 31:
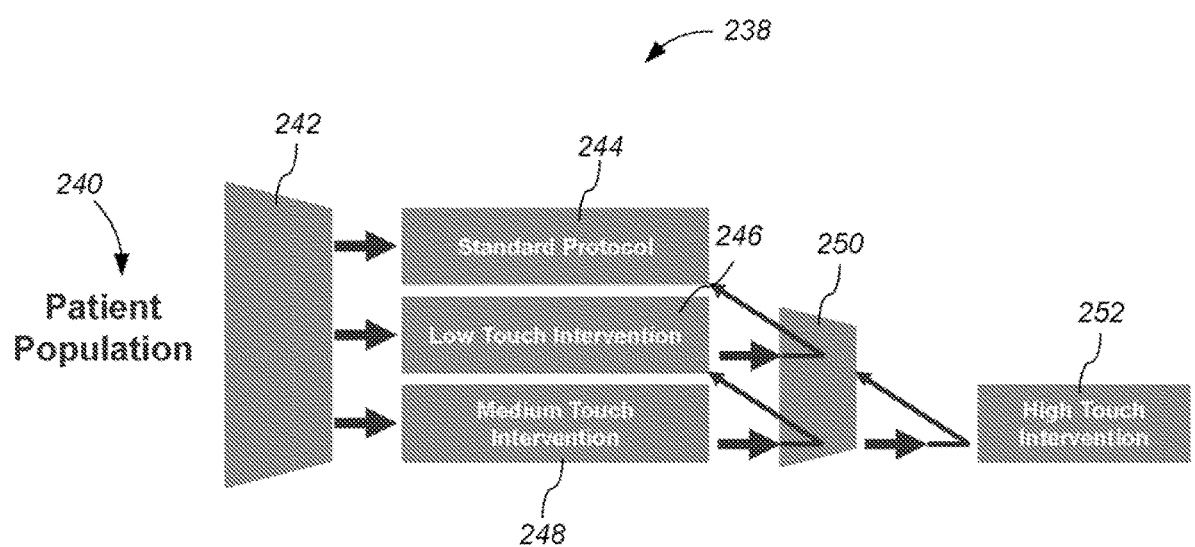

FIG. 31 is a diagram illustrating a comprehensive risk-based product offering that captures all patients throughout their journey according to one aspect.

Figure 32:
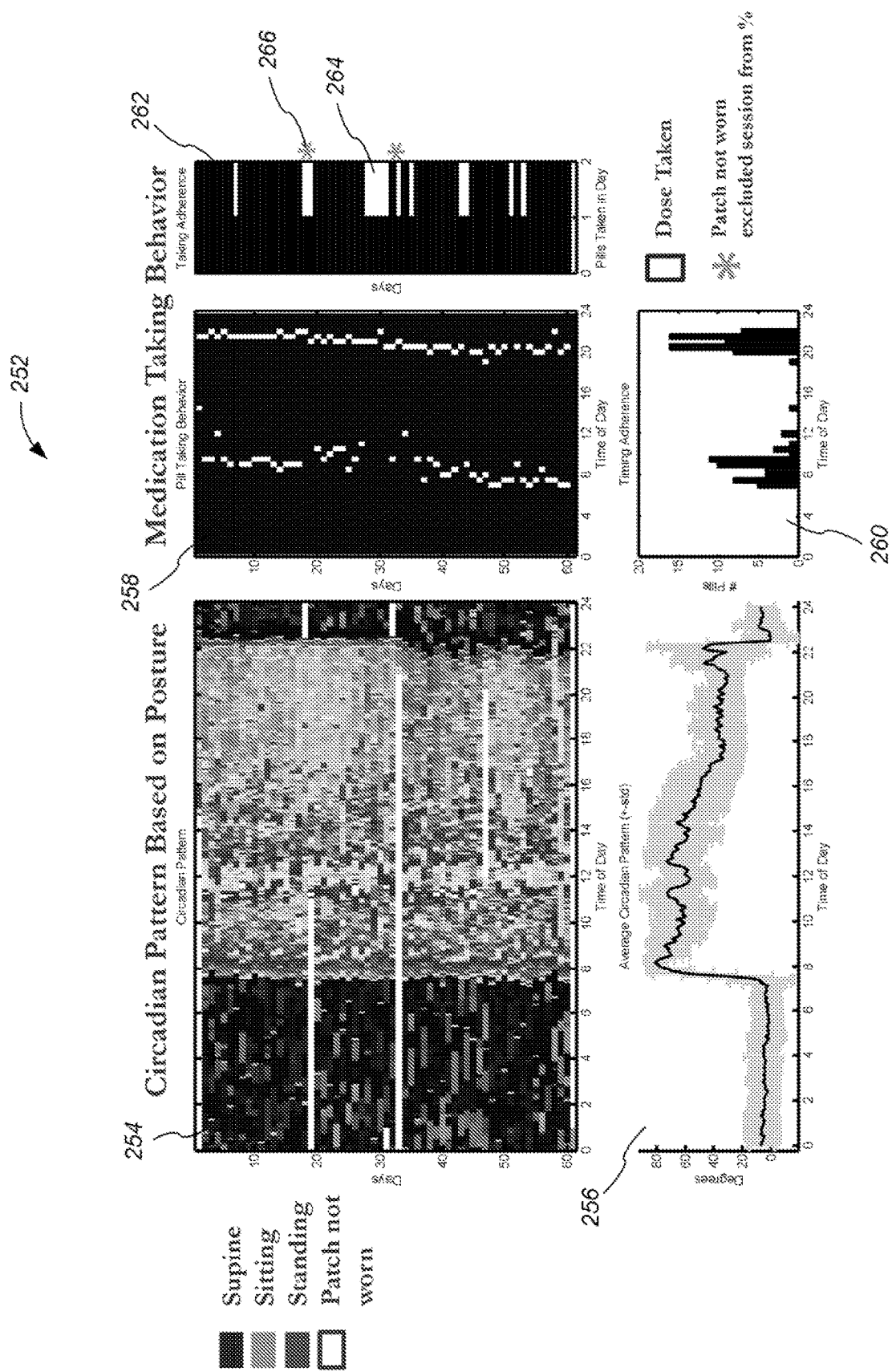

FIG. 32 is a diagram of several graphical representations to assist visualization of longitudinal data according to one aspect.

Figure 33:
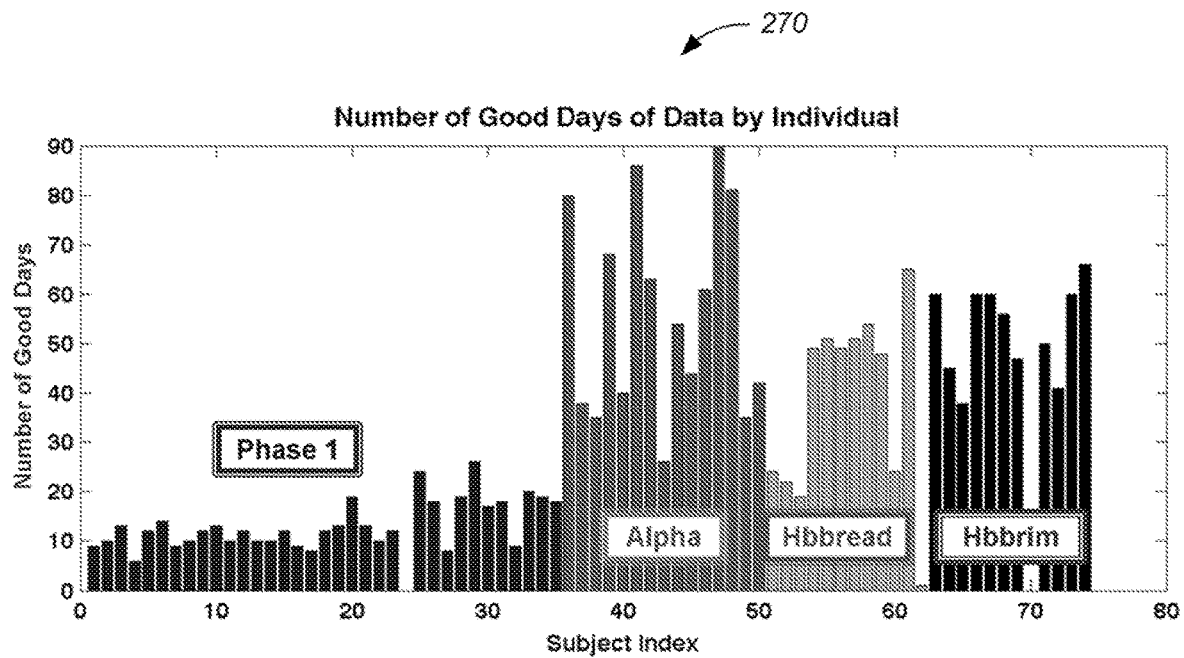

FIG. 33 is a graphical representation of the comparative length of data sets showing the number of good days of data by individual according to one aspect.

Figure 34:
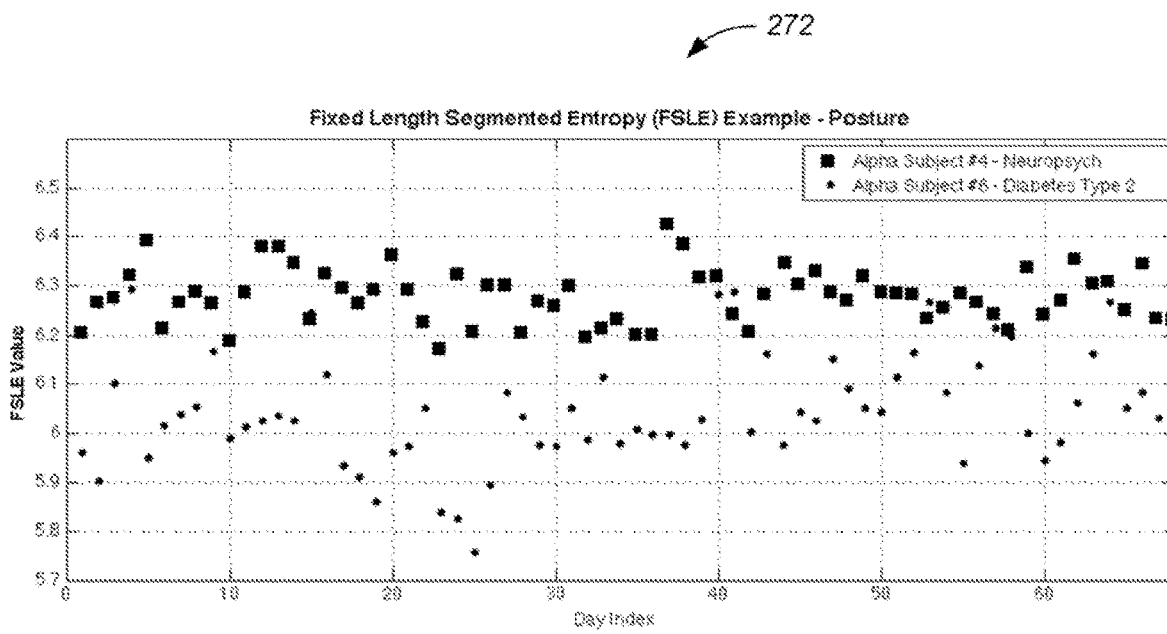

FIG. 34 is a graphical representation of posture entropy metric enhancements for fixed segment length entropy (FSLE) according to one aspect.

Figure 35:
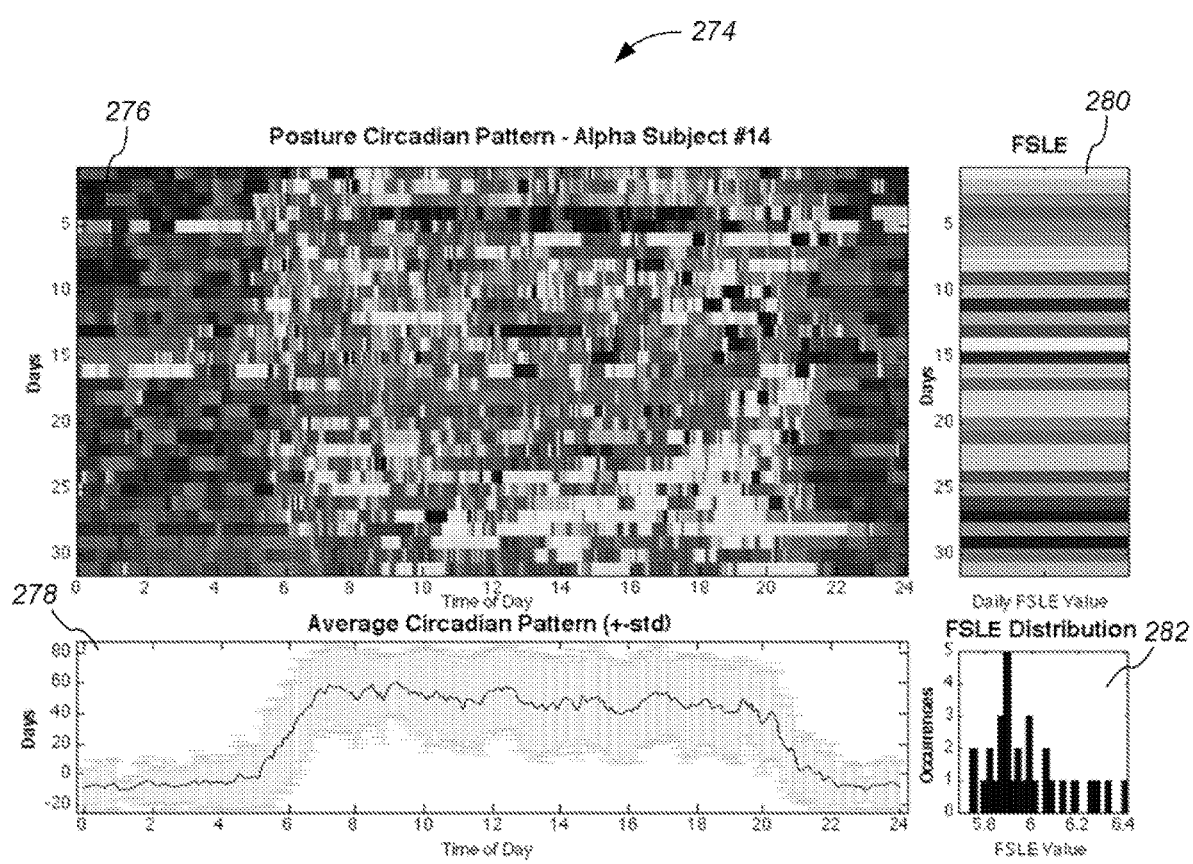

FIG. 35 is a diagram of several graphical representations of an FSLE example depicting abnormalities in circadian posture patterns according to one aspect.

Figure 36:
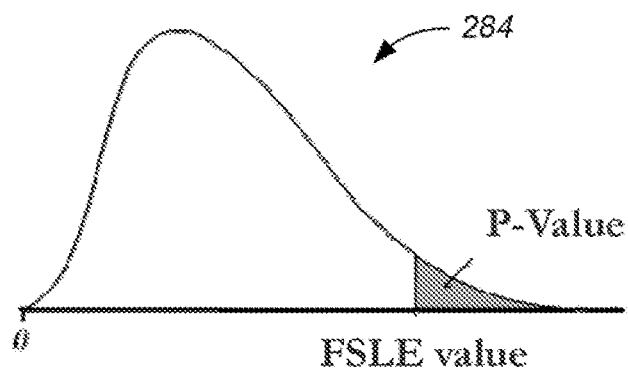

FIG. 36 is a distribution plot indicating the FSLE value and the P-value where the P-value represents the portion of the distribution that is above a given FSLE value.

Figure 37:
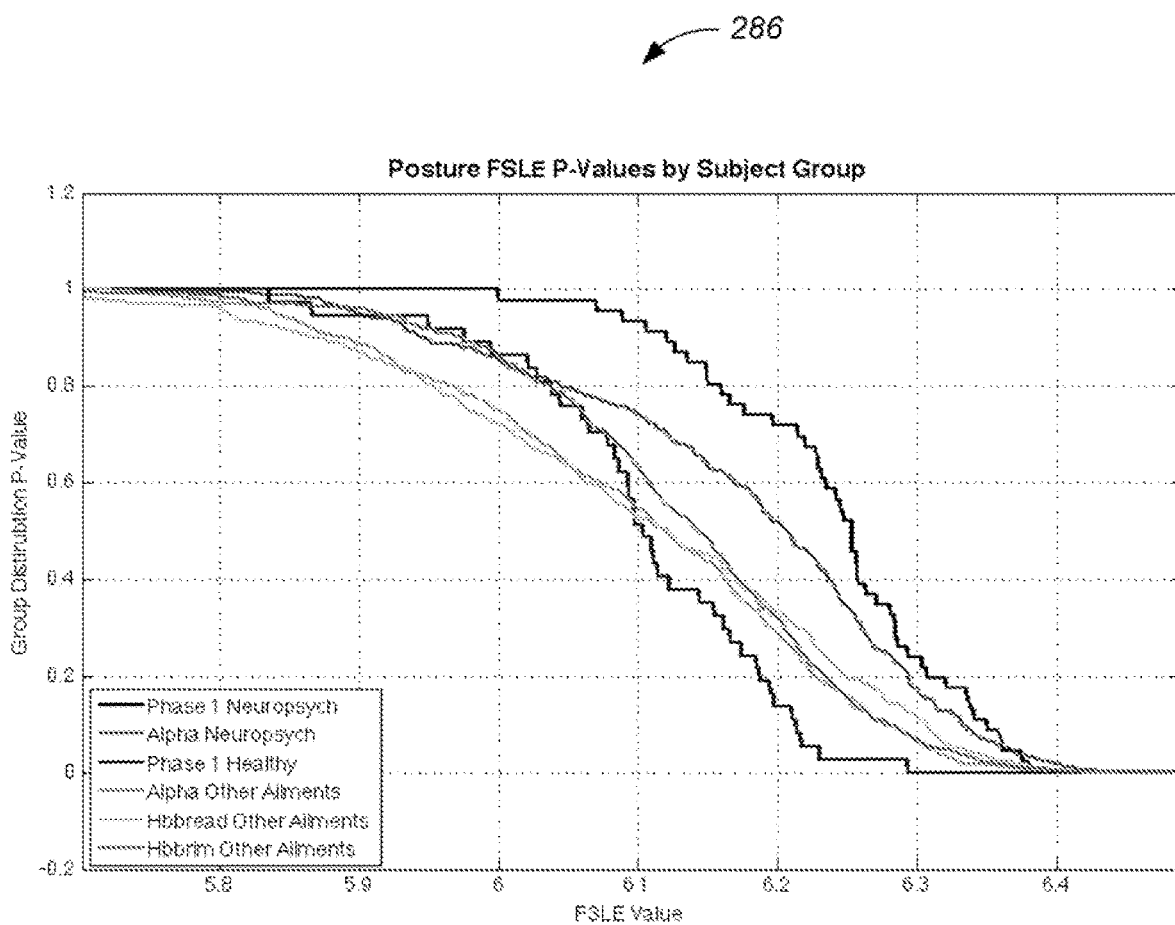

FIG. 37 is a graphical representation of posture FSLE P-values by subject group according to one aspect.

Figure 38:
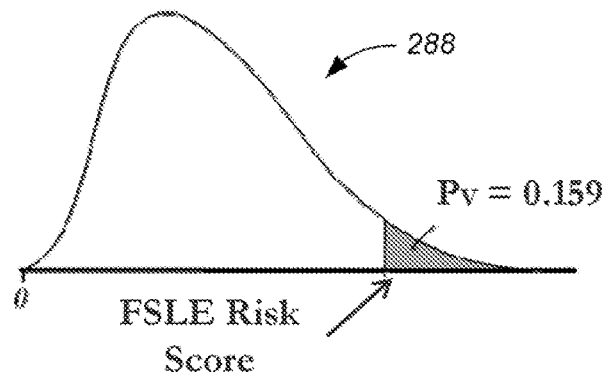

FIG. 38 is a distribution curve of an individual's FSLE risk score.

Figure 39:
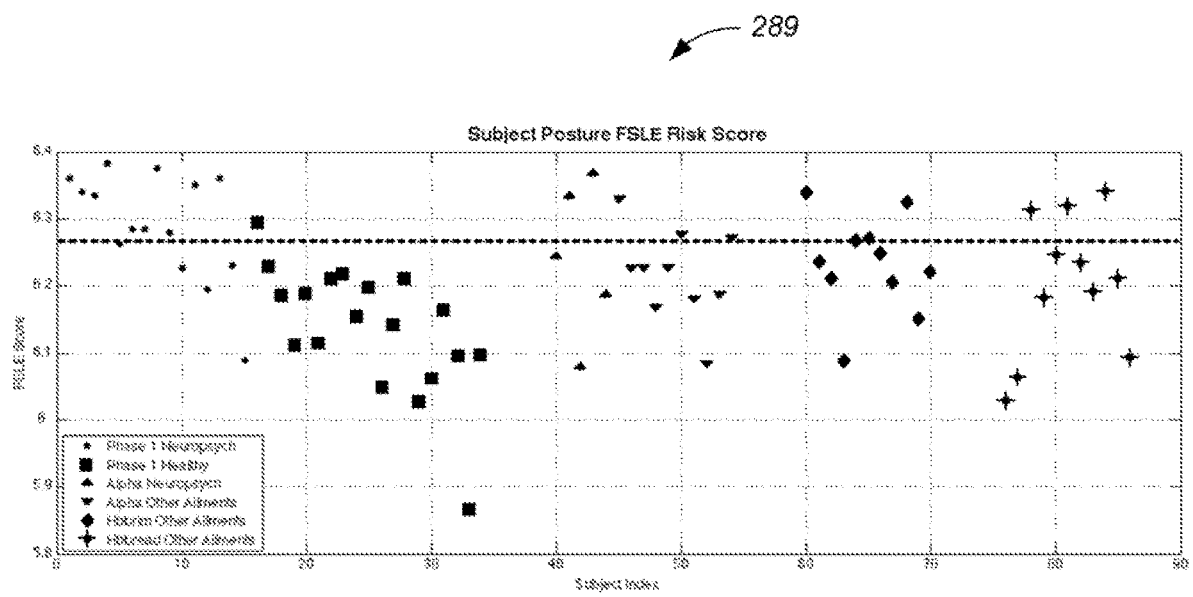

FIG. 39 is a graphical representation of subject posture FSLE risk score according to one aspect.

Figure 40:
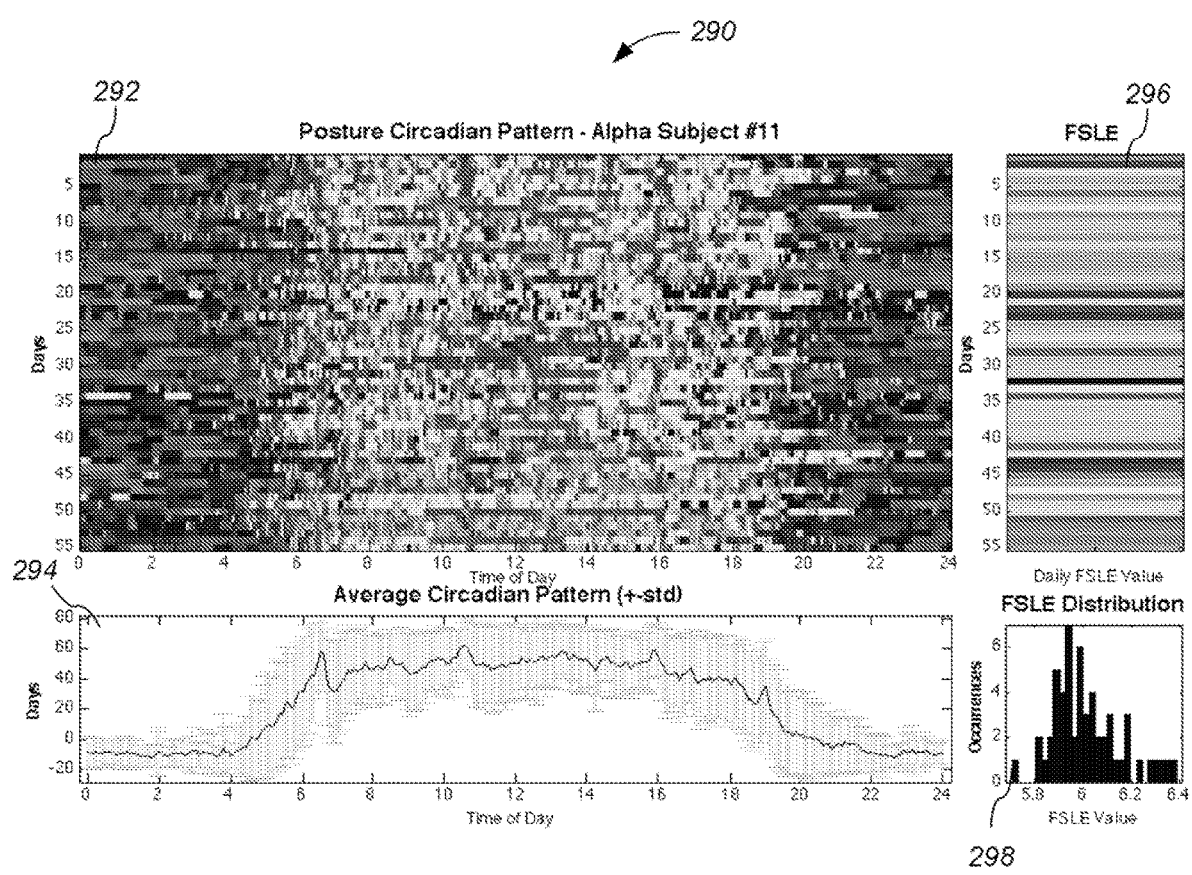

FIG. 40 is a diagram of several graphical representations of posture FSLE used as input to PICO score for Drilldown #1 according to one aspect.

Figure 41:
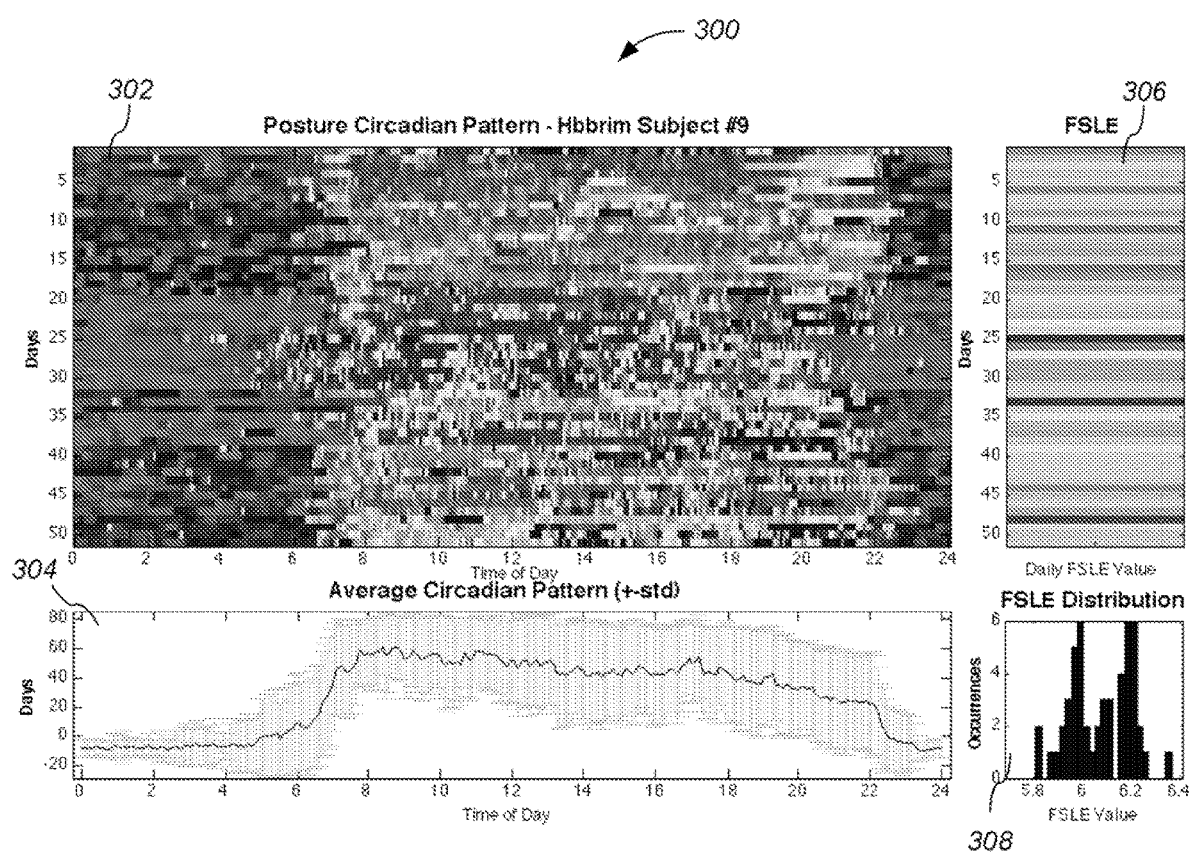

FIG. 41 is a diagram of several graphical representations of posture FSLE used as input to PICO score for Drilldown #2 according to one aspect.

Figure 42:
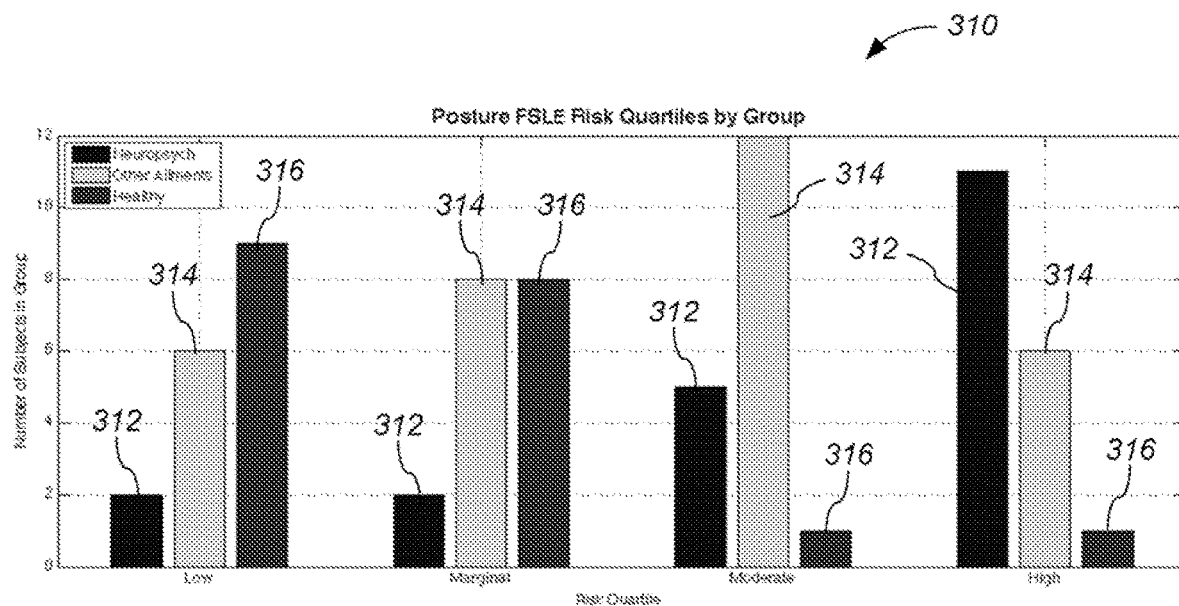

FIG. 42 is a graphical representation of posture FSLE risk ranking across subject groups according to one aspect.

Figure 43:
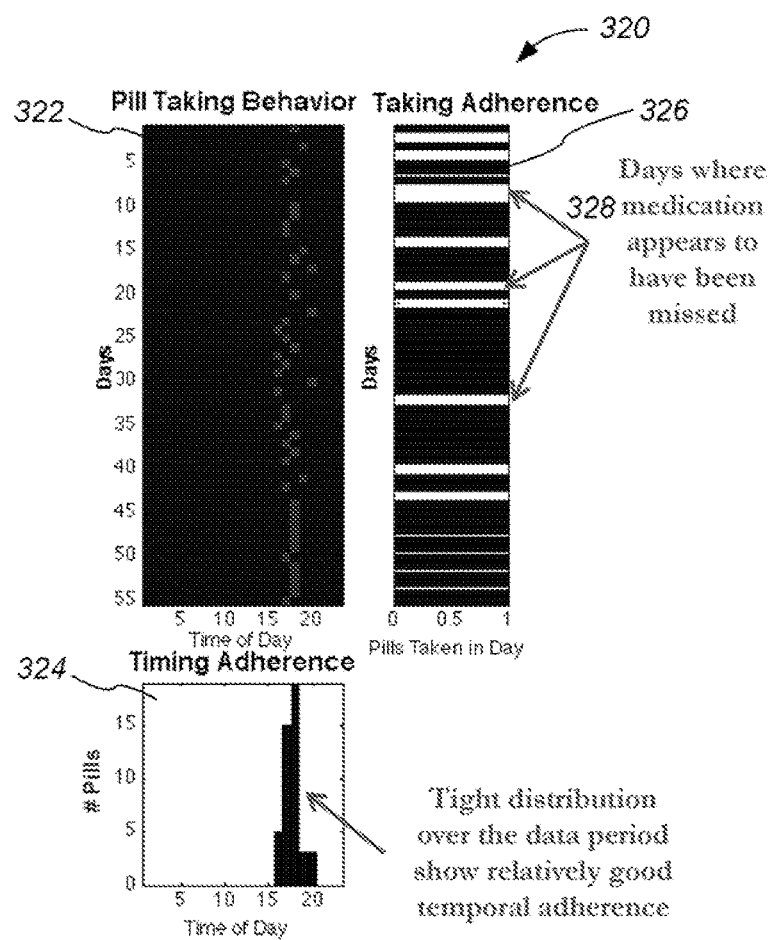

FIG. 43 is a diagram illustrating therapeutic data for additional Proteus indication of clinical outcomes (PICO) risk input according to one aspect.

Figure 44:
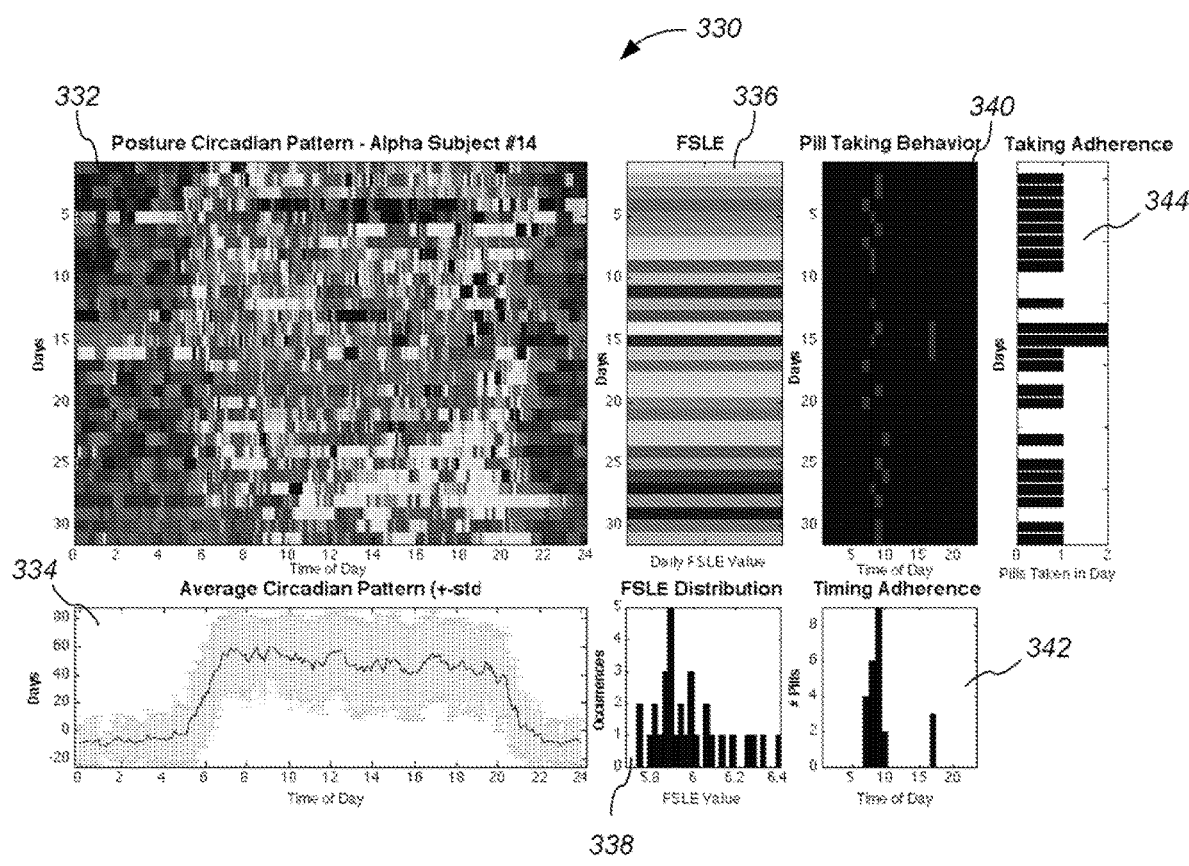

FIG. 44 is a diagram of several graphical representations of the inclusion of IEM data into the PICO score according to one aspect.

Figure 45:
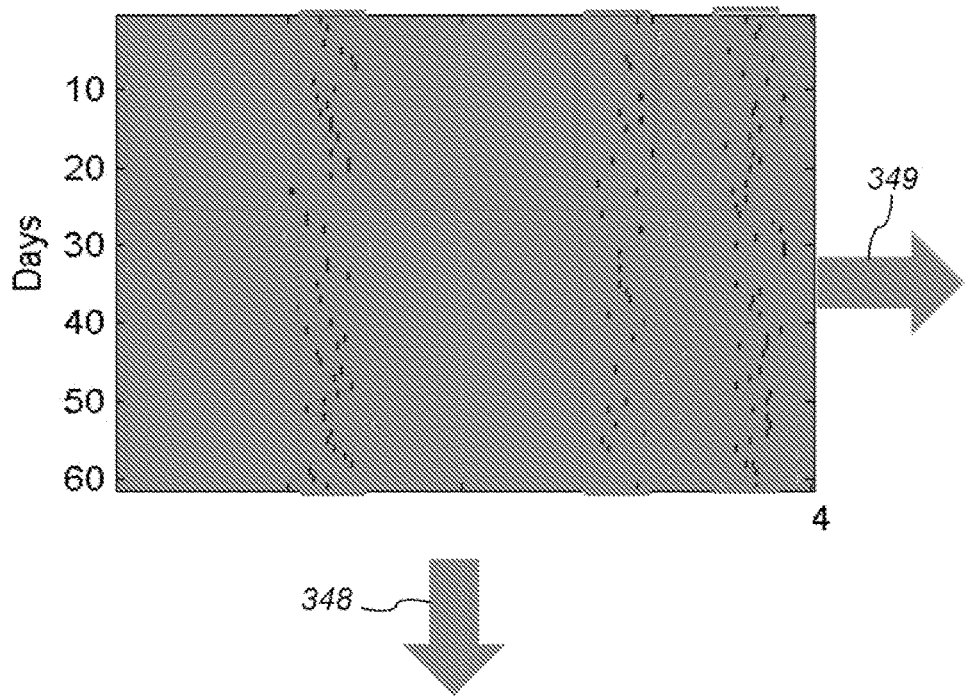

FIG. 45 illustrates a diagram of an IEM ingestion matrix characterization of therapy taking according to one aspect.

Figure 46:
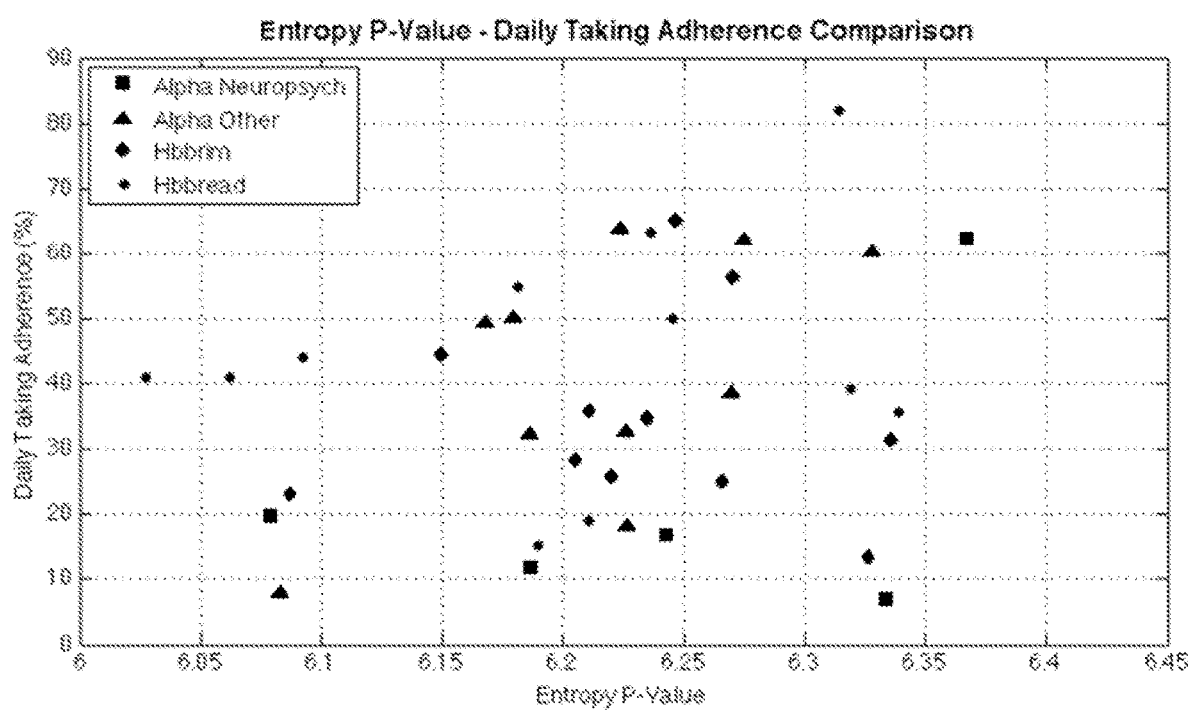

FIG. 46 is graphical representations of the FSLE risk score versus daily adherence according to one aspect.

Figure 47:
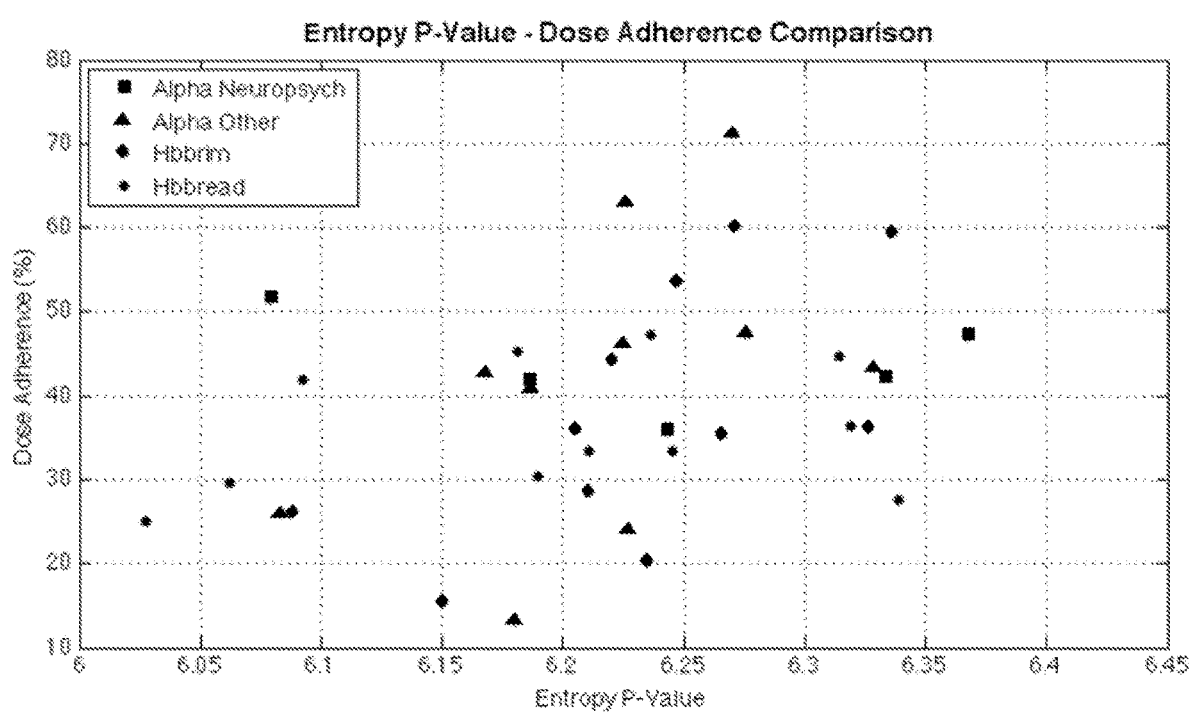

FIG. 47 is graphical representations of the FSLE risk score dose daily adherence according to one aspect.

Figure 48:
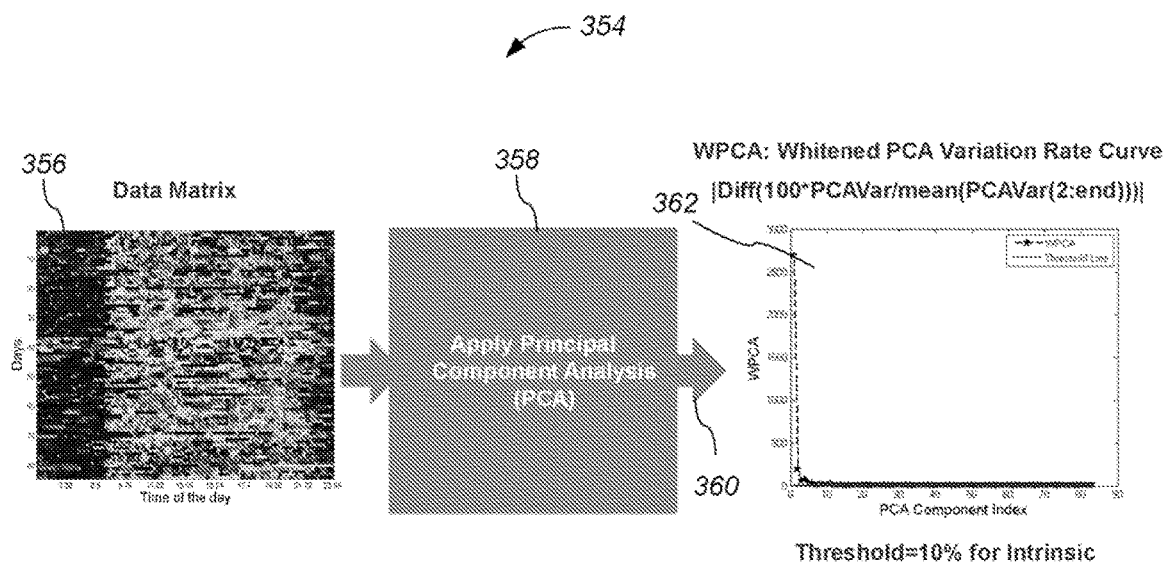

FIG. 48 is a diagram illustrating inter-week (global) variability score intrinsic dimensionality according to one aspect.

Figure 49:
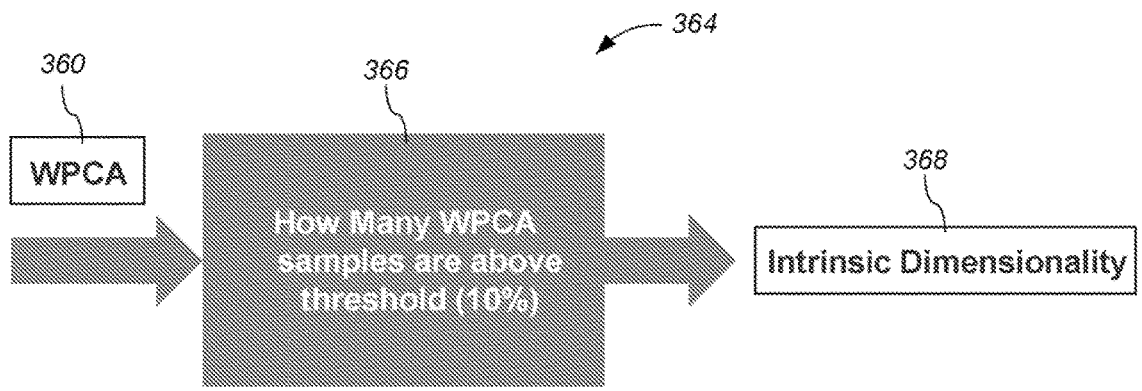

FIG. 49 is a diagram for processing whitened principal component analysis (WPCA) data to determine how many samples are above the intrinsic dimensionality threshold.

Figure 50:
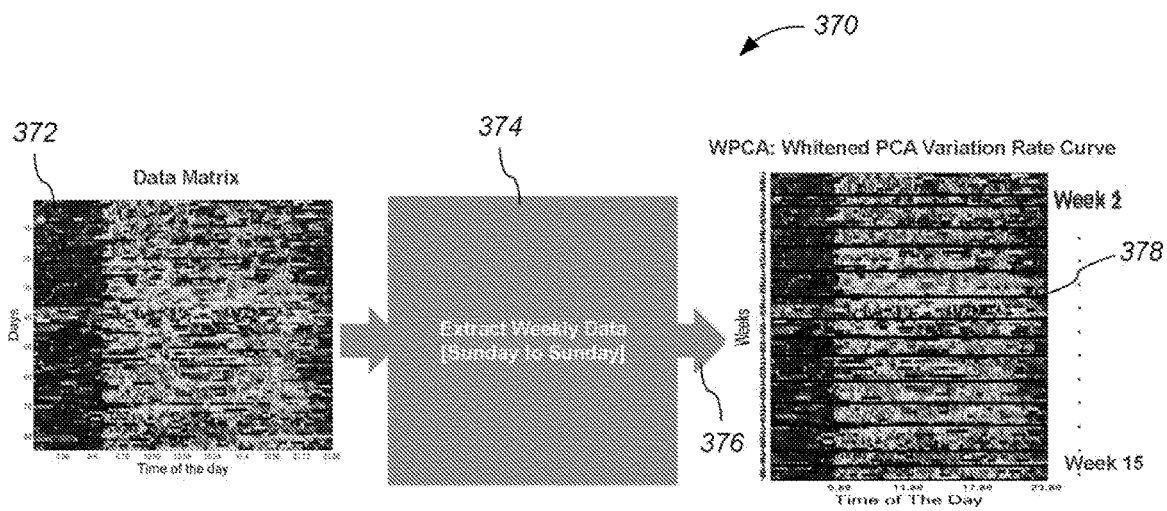

FIG. 50 is a diagram illustrating the intra-week (local) variability scores average deviation from daily pattern according to one aspect.

Figure 51:
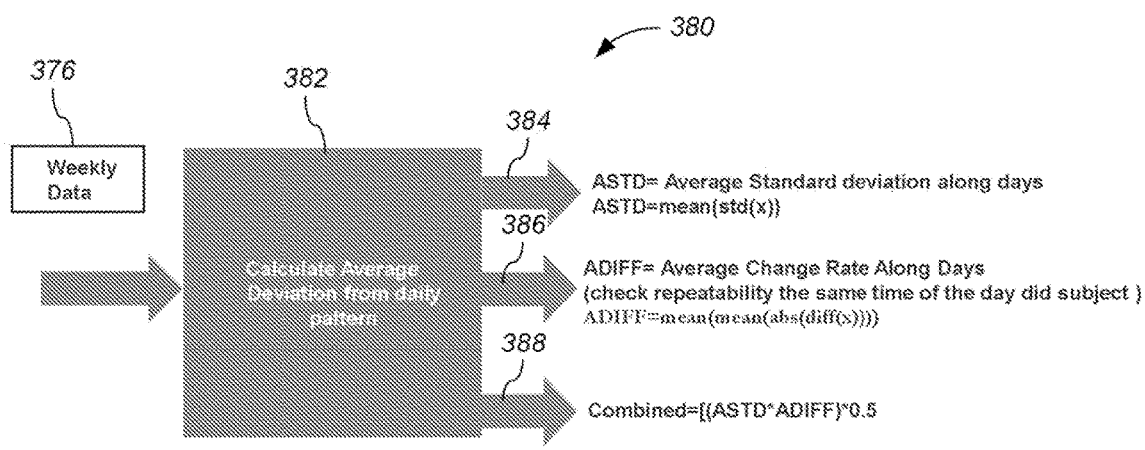

FIG. 51 is diagram for processing the WPCA data 376 into average standard deviation data according to tone aspect.

Figure 52:
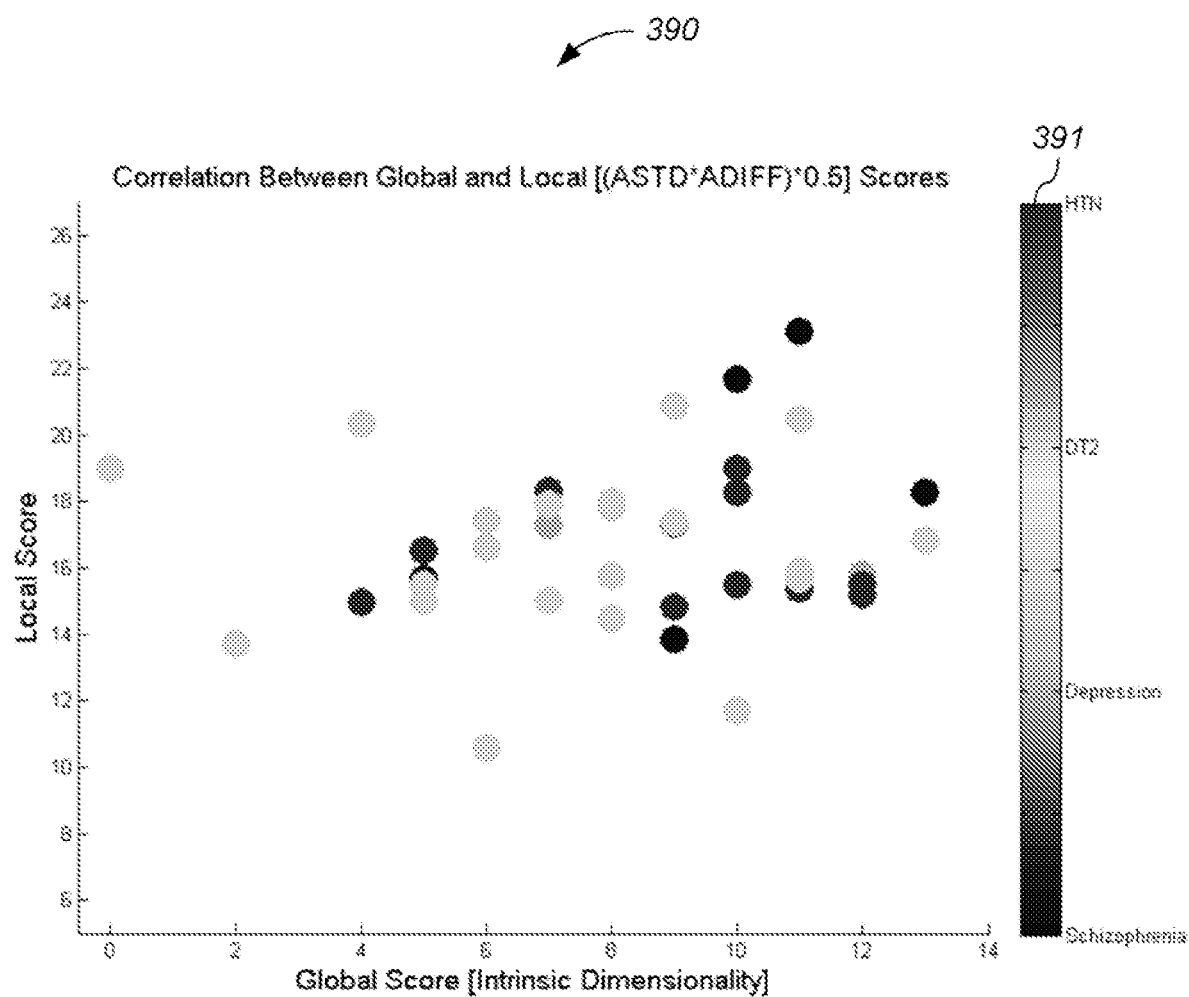

FIG. 52 is a graphical representation of global versus local [(ASTD*ADIFF)]*0.5 according to one aspect.

FIG. 53 is a graphical representation of a data matrix (e.g., posture circadian pattern) of a first subject (Customer 1) according to one aspect.

FIG. 54 is a graphical representation of combined taking adherence and dose adherence according to one aspect.

FIG. 55 is a graphical representation of a data matrix (e.g., posture circadian pattern) of a second subject (Customer 2) according to one aspect.

FIG. 56 is a graphical representation of combined taking adherence and dose adherence according to one aspect.

Figure 57:
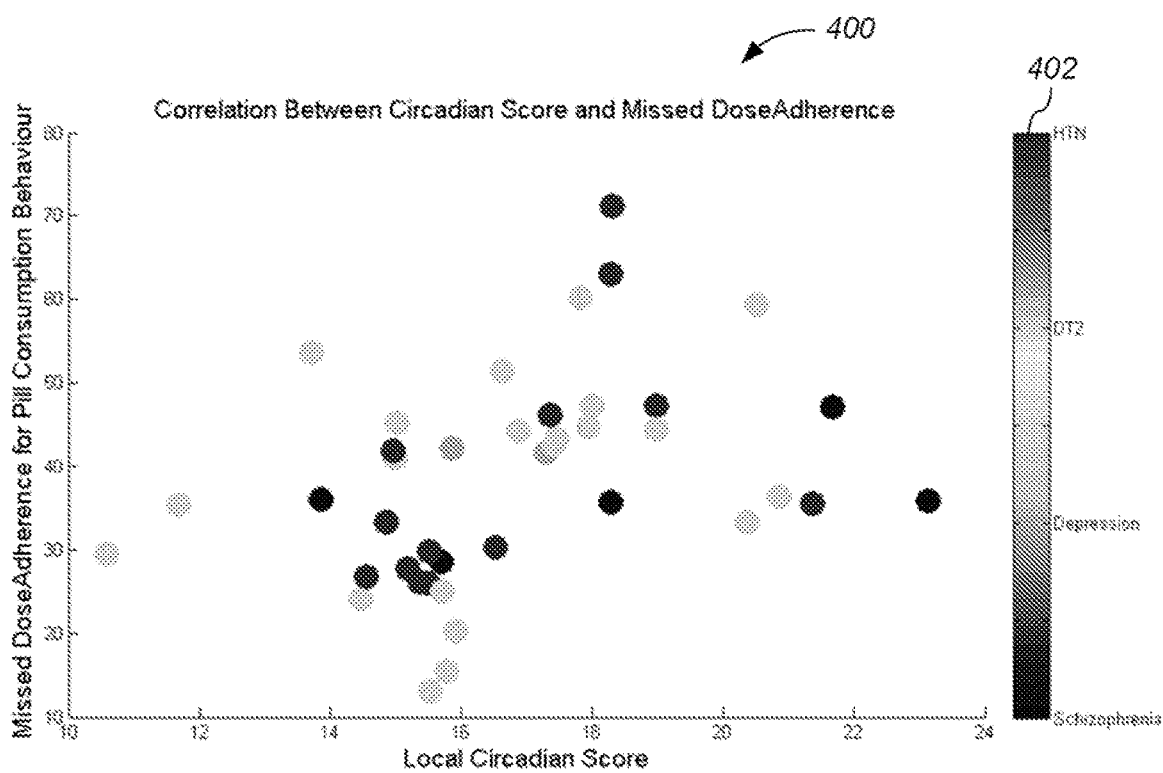

FIG. 57 is a graphical representation of distribution of patient scores according to one embodiment for both subjects (Customer 1 and Customer 2) according to one aspect.

Figure 58:
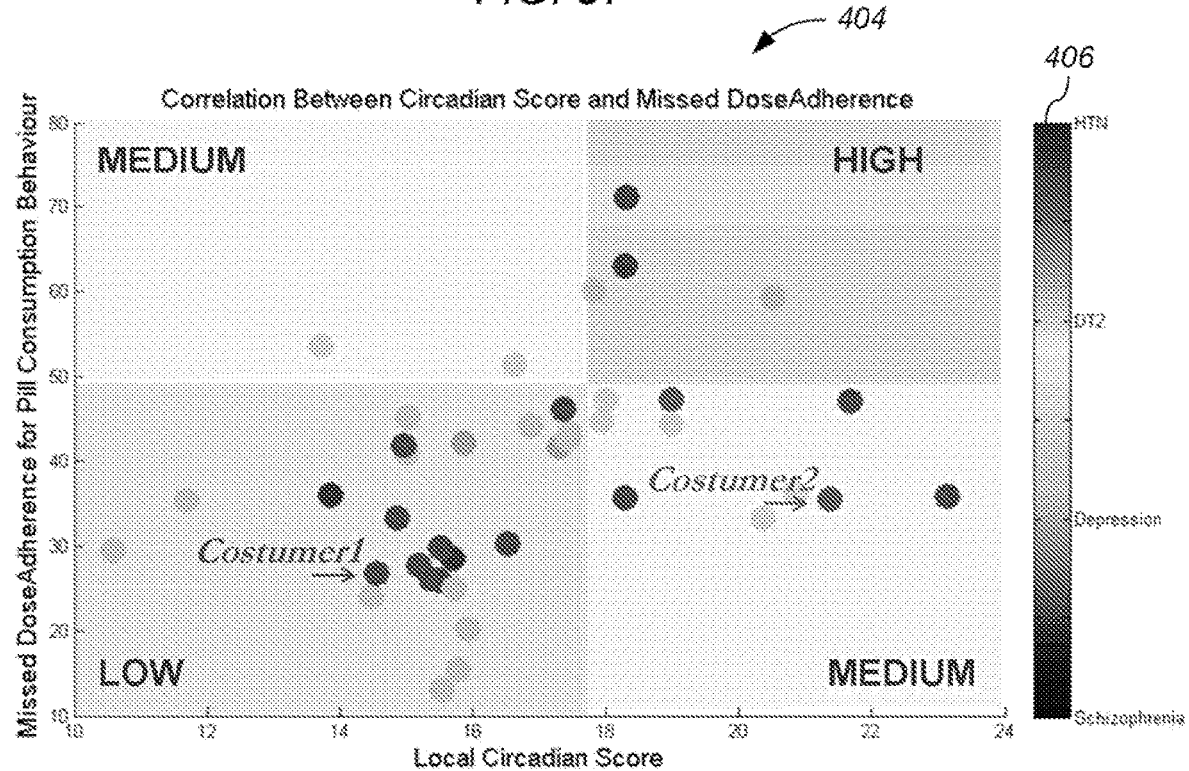

FIG. 58 is a graphical representation showing the correlation between circadian score and missed dose adherence according to one aspect.

Figure 59:
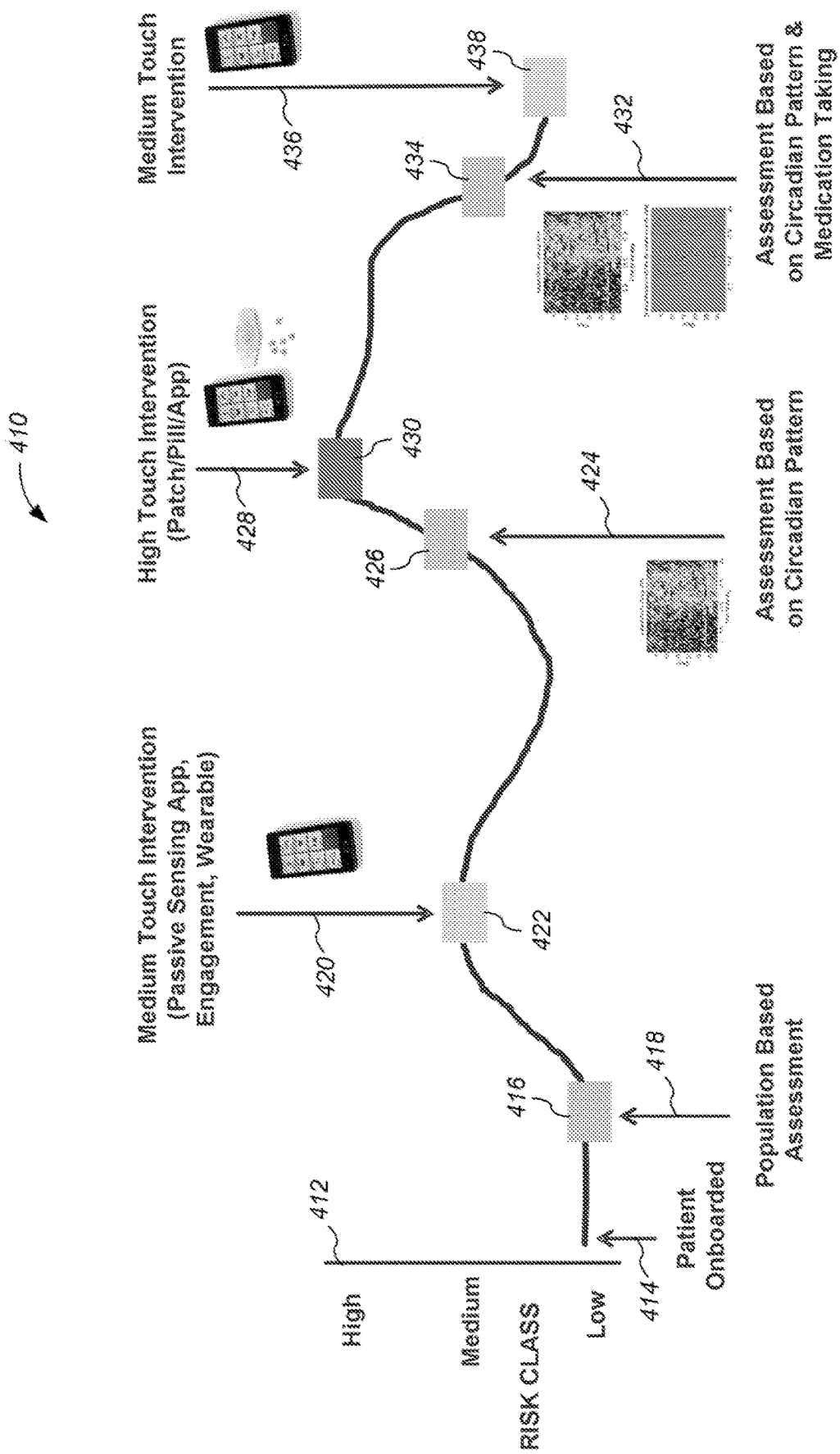

FIG. 59 is a diagram illustrating a comprehensive risk and intervention strategy according to one aspect.

Figure 60:
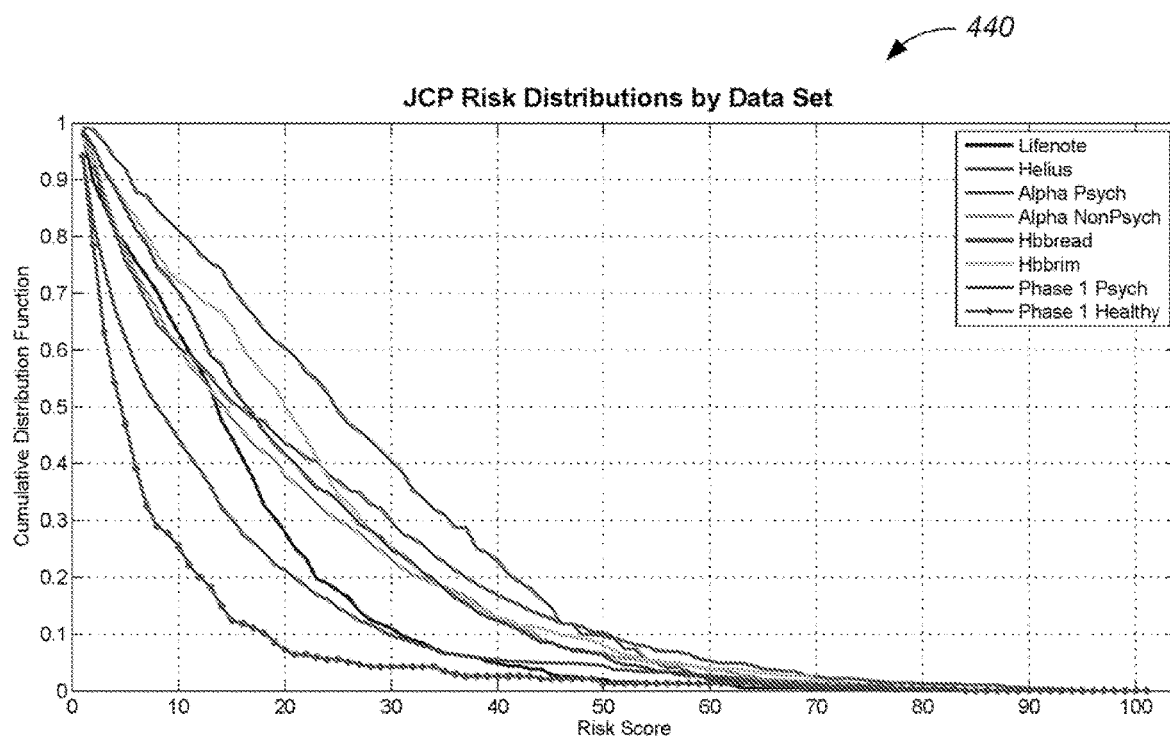

FIG. 60 is a graphical representation of a joint circadian pattern (JCP) risk distribution by data set where the horizontal pattern represents risk score and the vertical axis represents the cumulative distribution function for the various identified groups according to one aspect.

Figure 61:
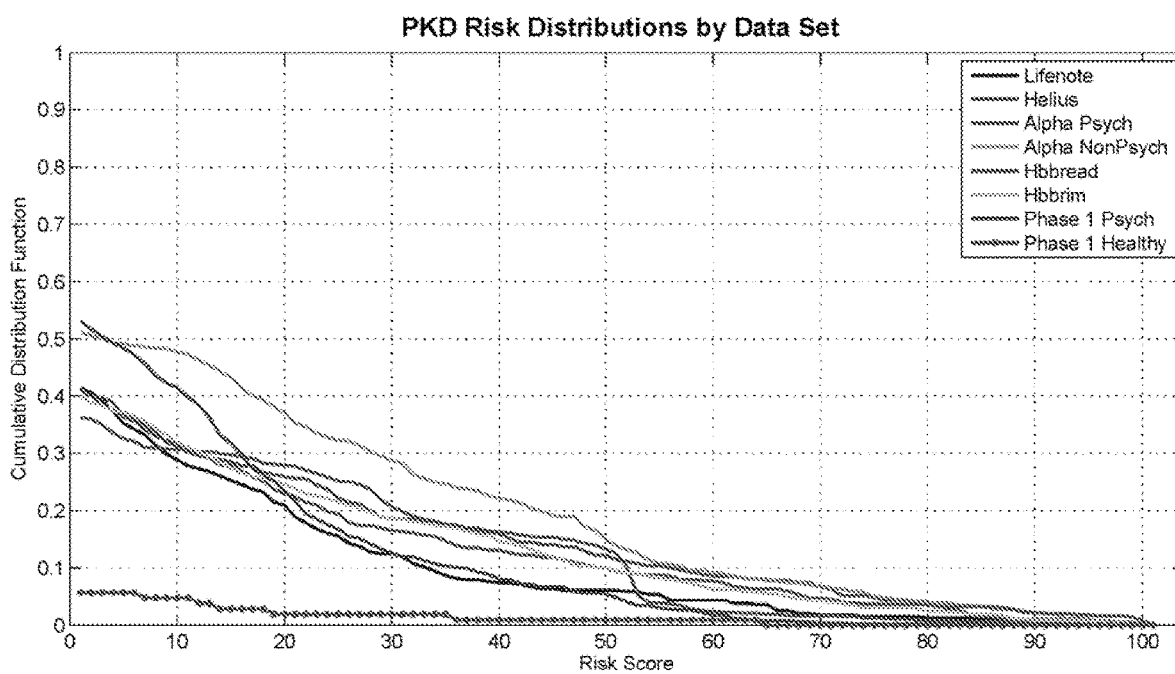

FIG. 61 is a graphical representation of a pharmacokinetic dose (PKD) risk by data set according to one aspect.

Figure 62:
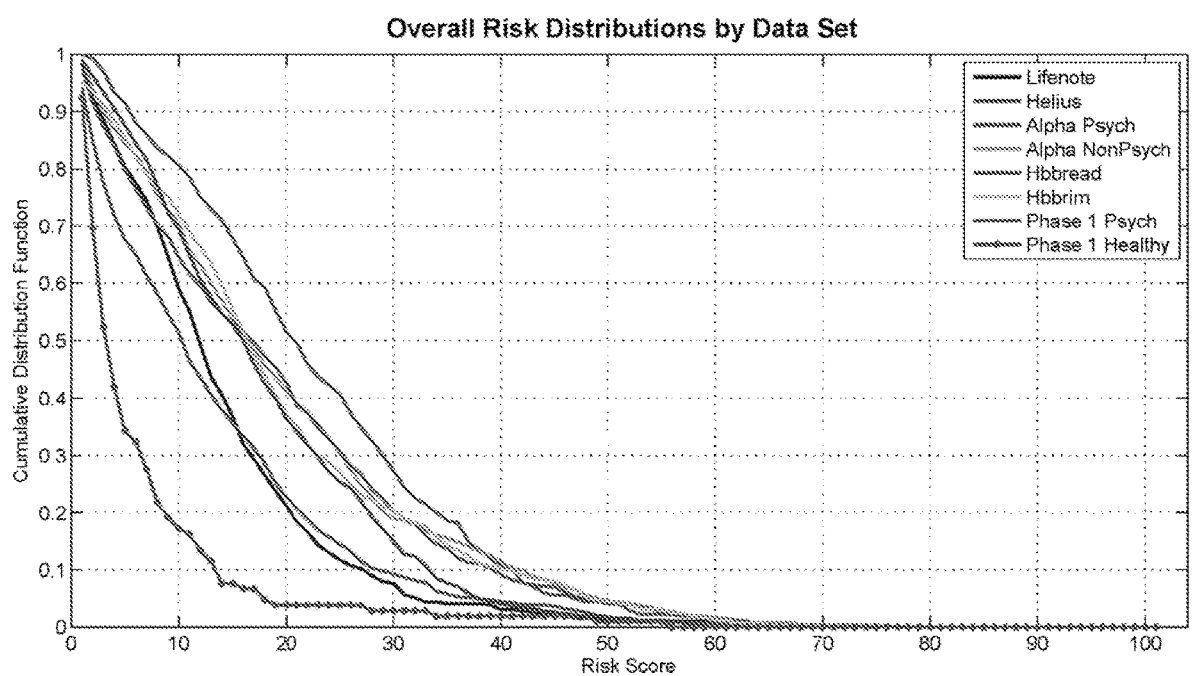

FIG. 62 is a graphical representation of the overall risk distribution by data set according to one aspect.

Figure 63:
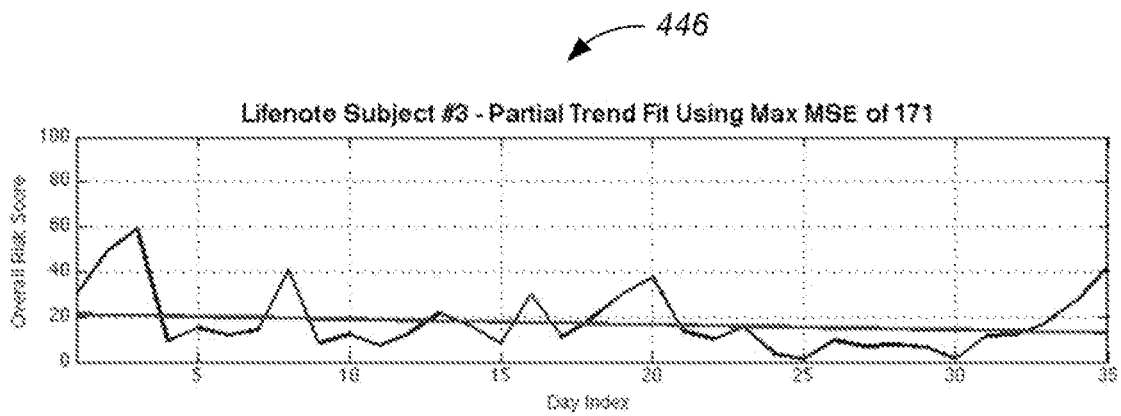

FIG. 63 is a graphical representation of a partial trend analysis of a patient (e.g., Lifenote Subject #3) with a partial trend fit using a maximum standard error (MSE) of 171 according to one aspect.

Figure 64:
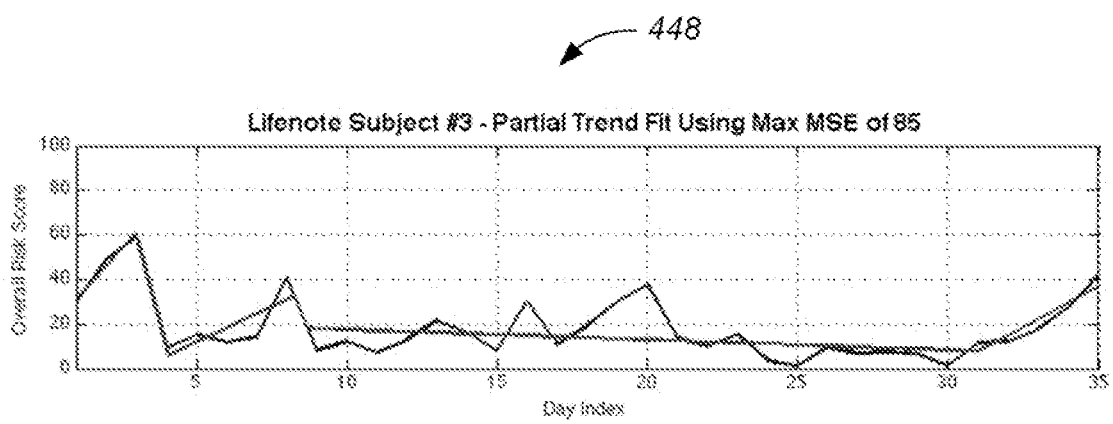

FIG. 64 is a graphical representation of a partial trend analysis of the same patient (e.g., Lifenote Subject #3) with a partial trend fit using a maximum MSE of 85 according to one aspect.

Figure 65:
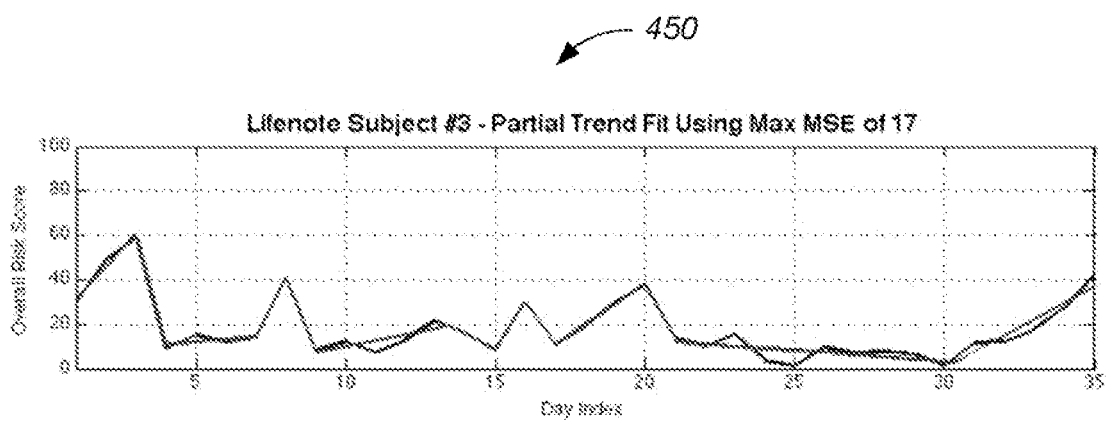

FIG. 65 is a graphical representation of a partial trend analysis of the same patient (e.g., Lifenote Subject #3) with a partial trend fit using a maximum MSE of 17 according to one aspect.

Figure 66:
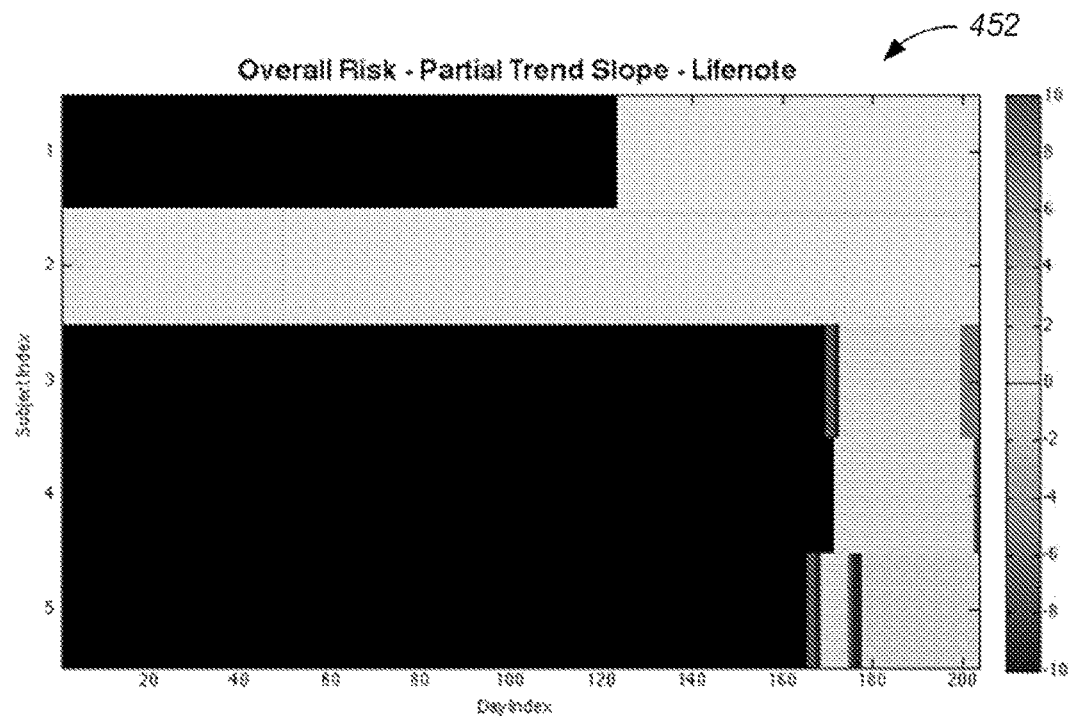

FIG. 66 is a diagram illustrating a partial trend analysis of a Lifenote data set according to one aspect where the horizontal axis represents the day index and the vertical axis represents the subject index.

Figure 67:
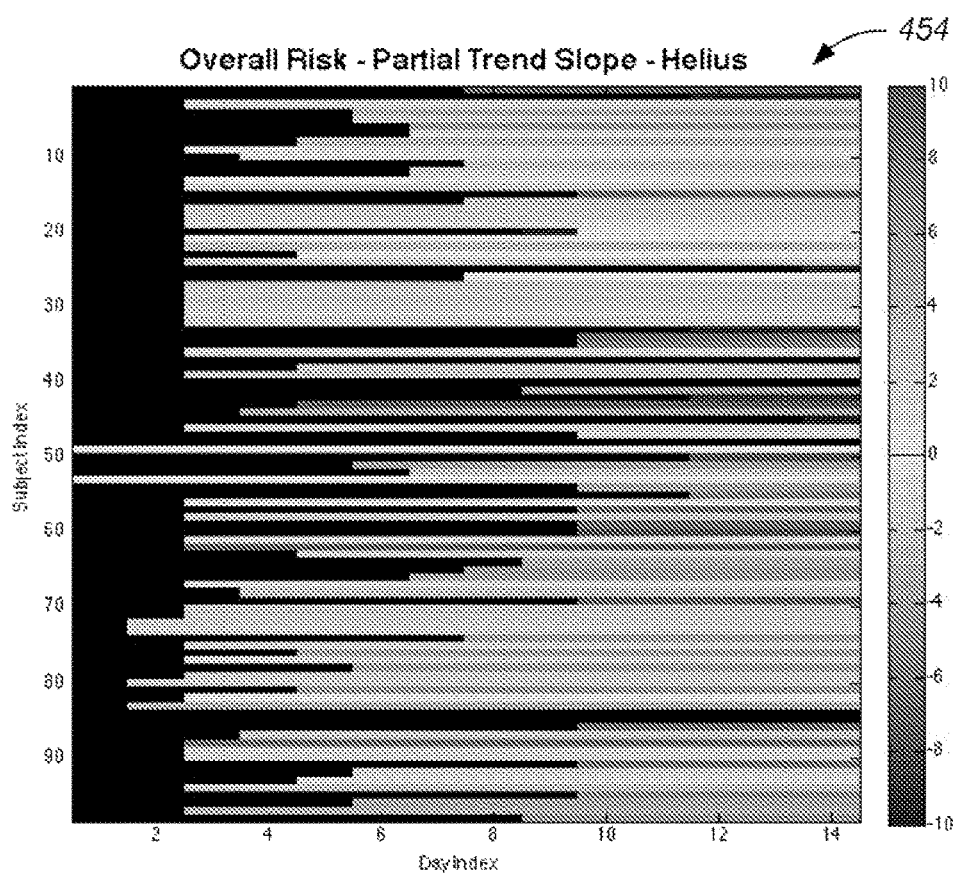

FIG. 67 is diagram illustrating a partial trend analysis of a Helius data set according to one aspect where the horizontal axis represents the day index and the vertical axis represents the subject index.

Figure 68:
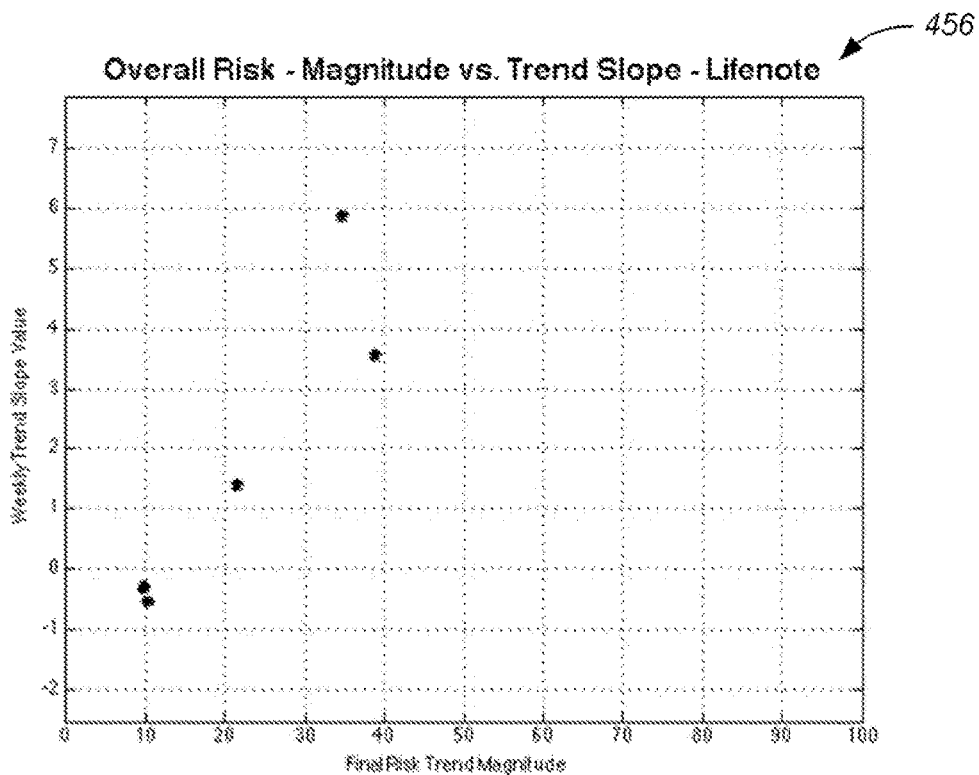

FIG. 68 is a graphical representation of a 2-D scatter plot comparing the final risk trend magnitude and the risk trend slope over the last week of data according to one aspect.

Figure 69:
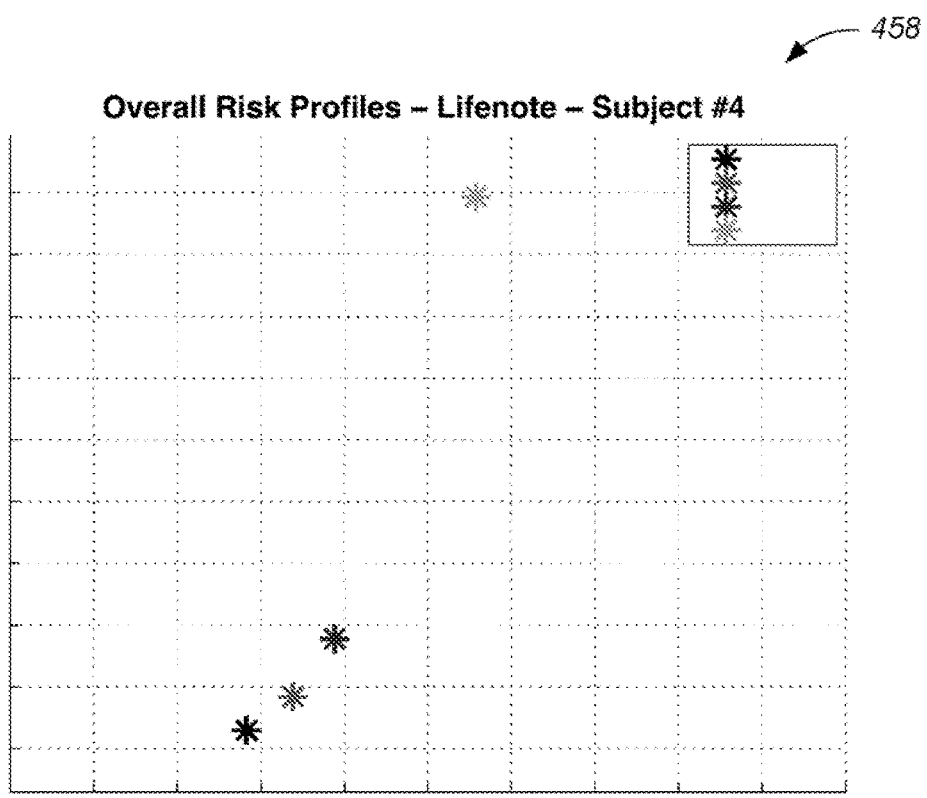

FIG. 69 is a graphical representation of an overall risk profile for an individual according to one aspect.

Figure 70:
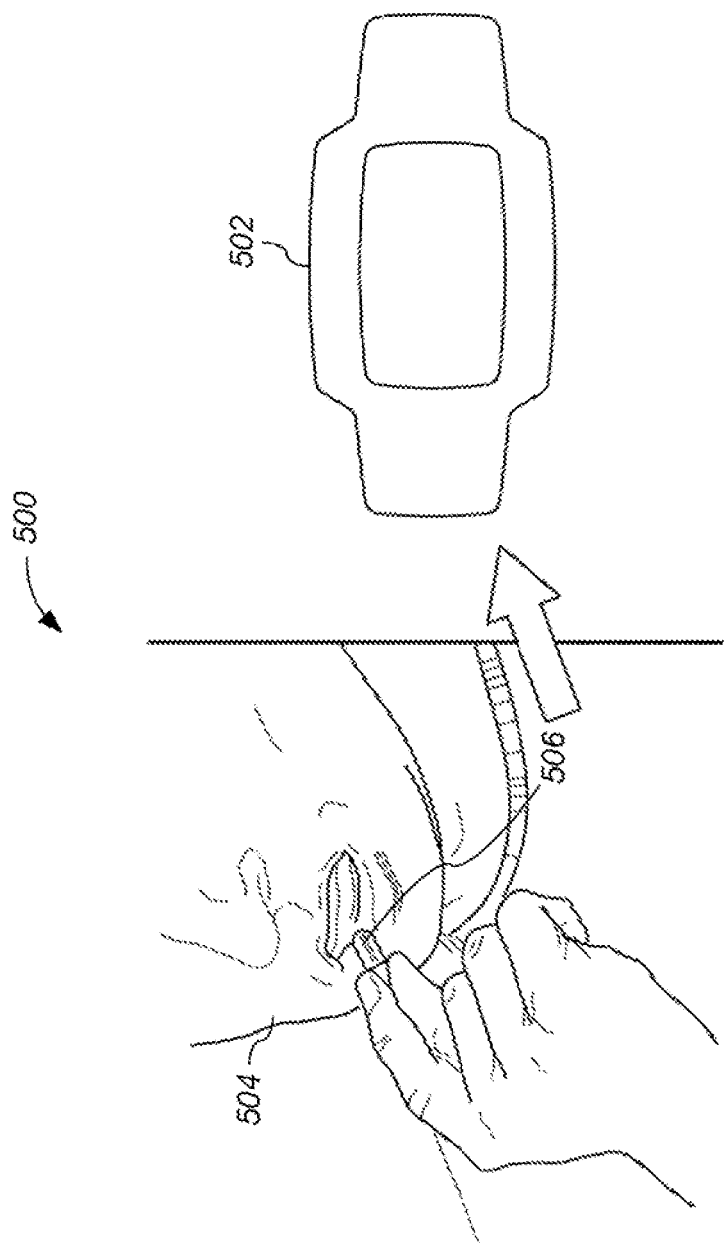

FIG. 70 is conceptual illustration of a system comprising an adhesive patch to receive a signal from an IEM to confirm that the user swallowed the medication according to one aspect.

FIG. 71 is a block diagram representation of an event indicator system with dissimilar metals positioned on opposite ends, according to one aspect.

FIG. 72 is a block diagram representation of the event indicator system with dissimilar metals positioned on the same end and separated by a non-conducting material, according to one aspect.

FIG. 73 shows ionic transfer or the current path through a conducting fluid when the event indicator system of FIG. 71 is in contact with conducting liquid and in an active state according to one aspect.

FIG. 74 shows an exploded view of the surface of dissimilar materials of FIG. 73, according to one aspect.

Figure 75:
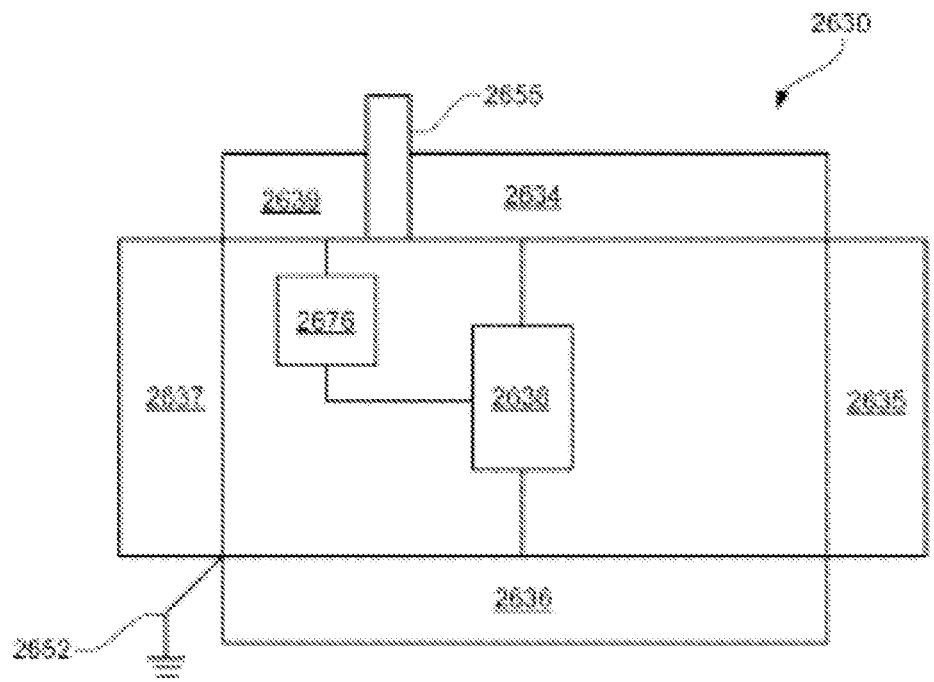

FIG. 75 shows the event indicator system of FIG. 73 with a pH sensor unit, according to one aspect.

Figure 76:
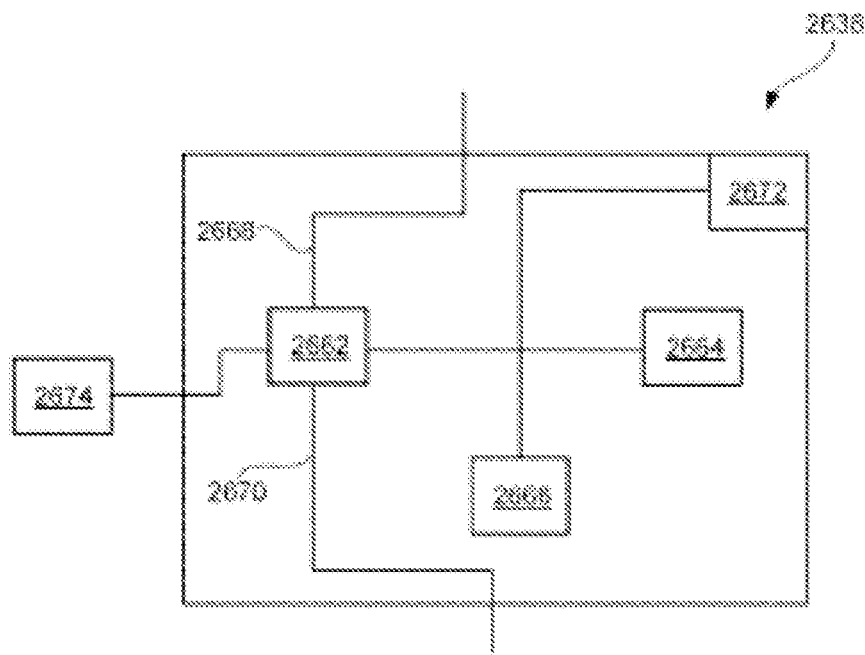

FIG. 76 is a block diagram illustration of the control device used in the system of FIGS. 26 and 27, according to one aspect.

Figure 77:
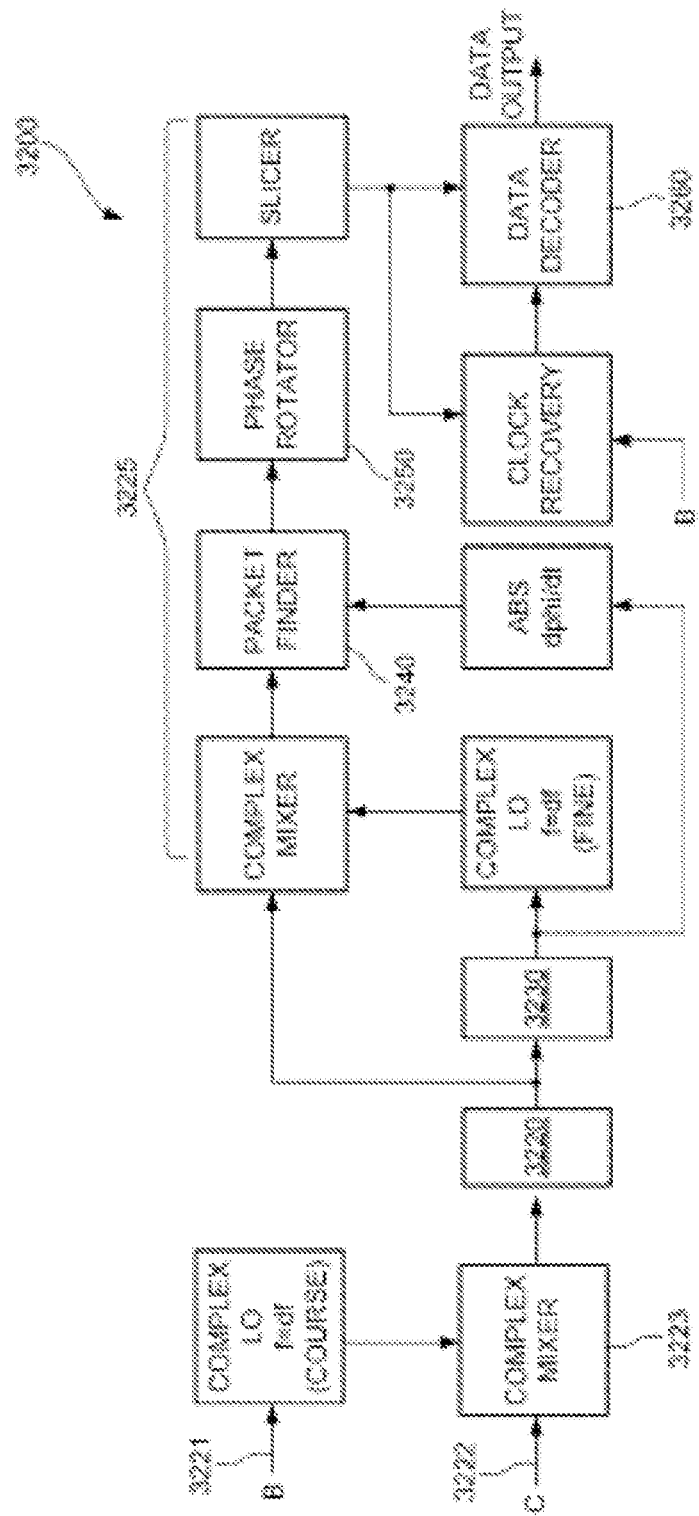

FIG. 77 is a functional block diagram of a demodulation circuit that performs coherent demodulation that may be present in a receiver according to one aspect.

Figure 78:
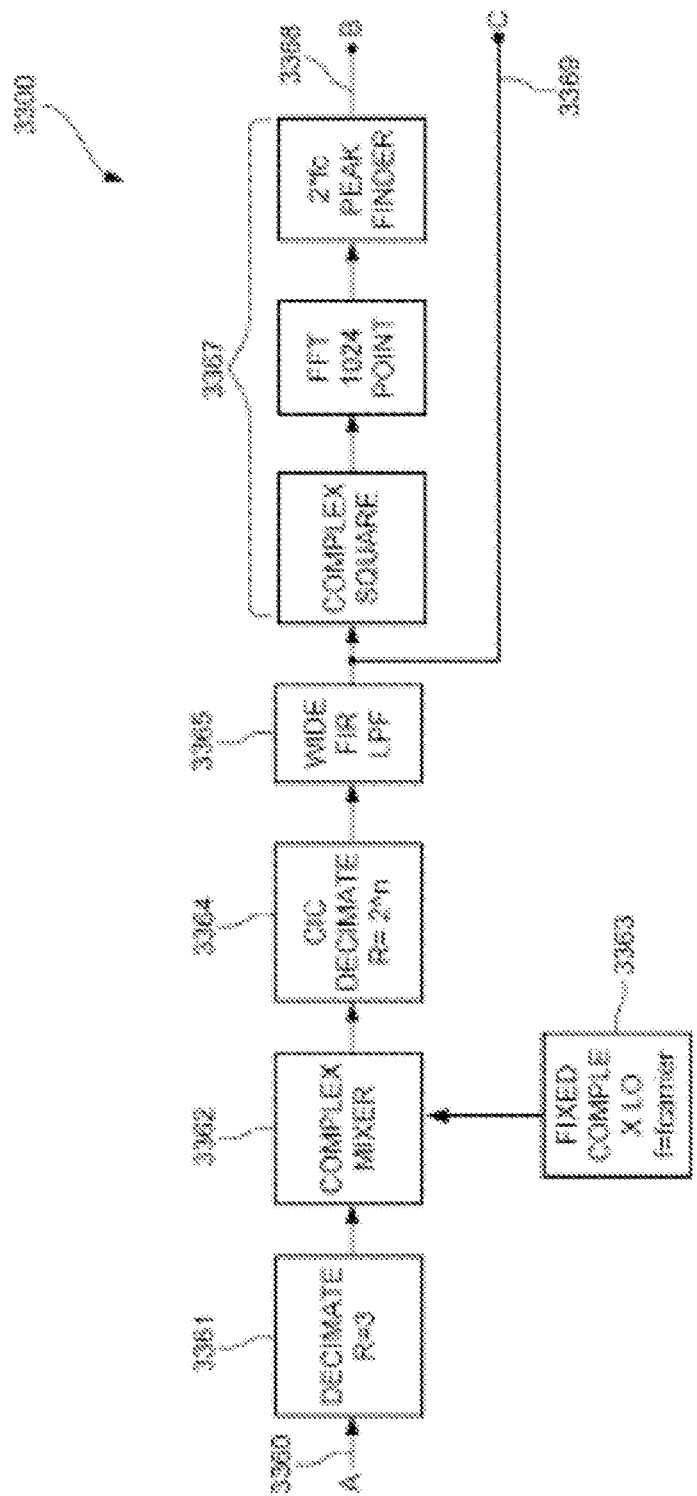

FIG. 78 illustrates a functional block diagram for a beacon module within a receiver, according to one aspect.

Figure 79:
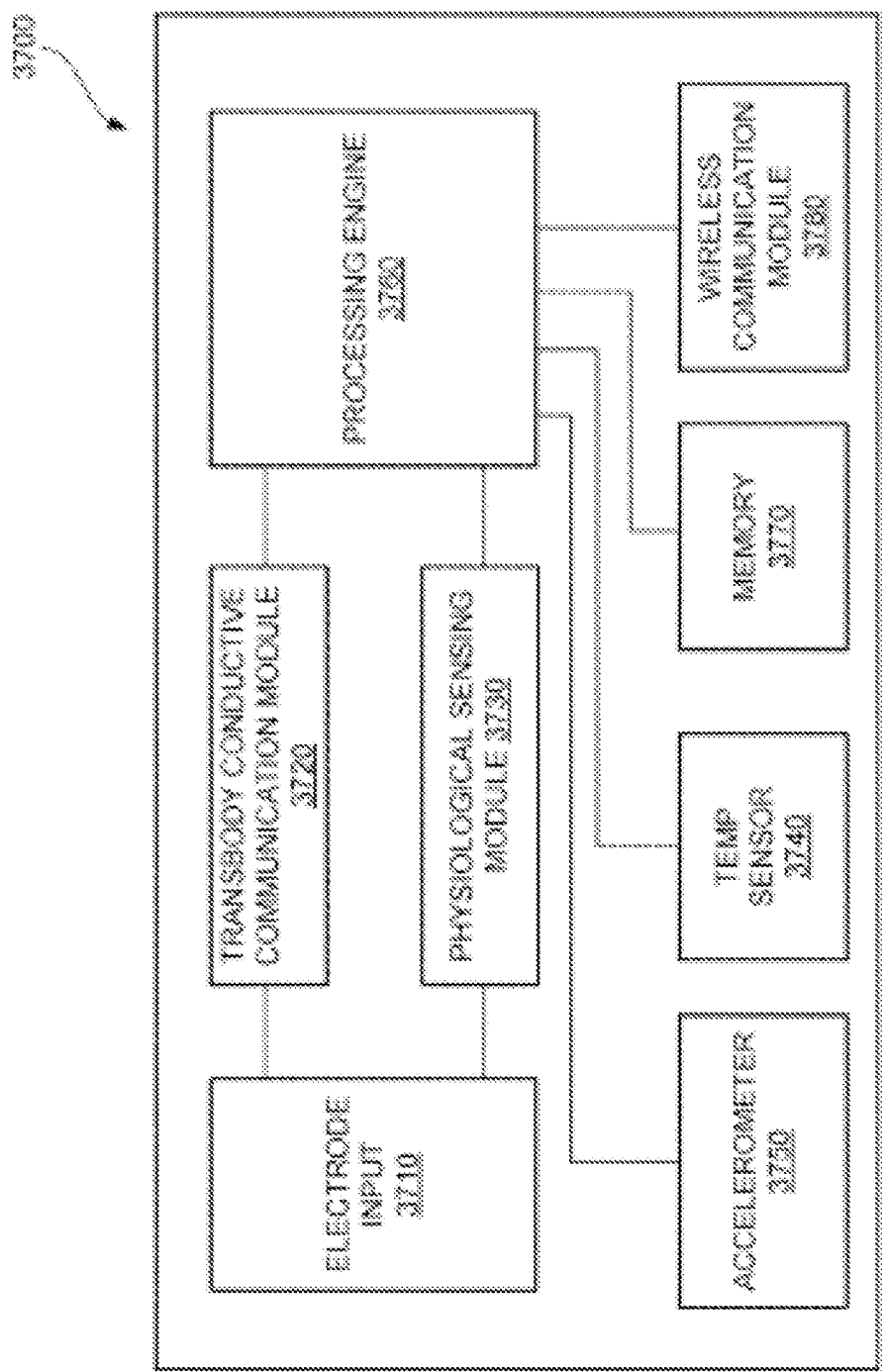

FIG. 79 is a block diagram of the different functional modules that may be present in a receiver, according to one aspect.

Figure 80:
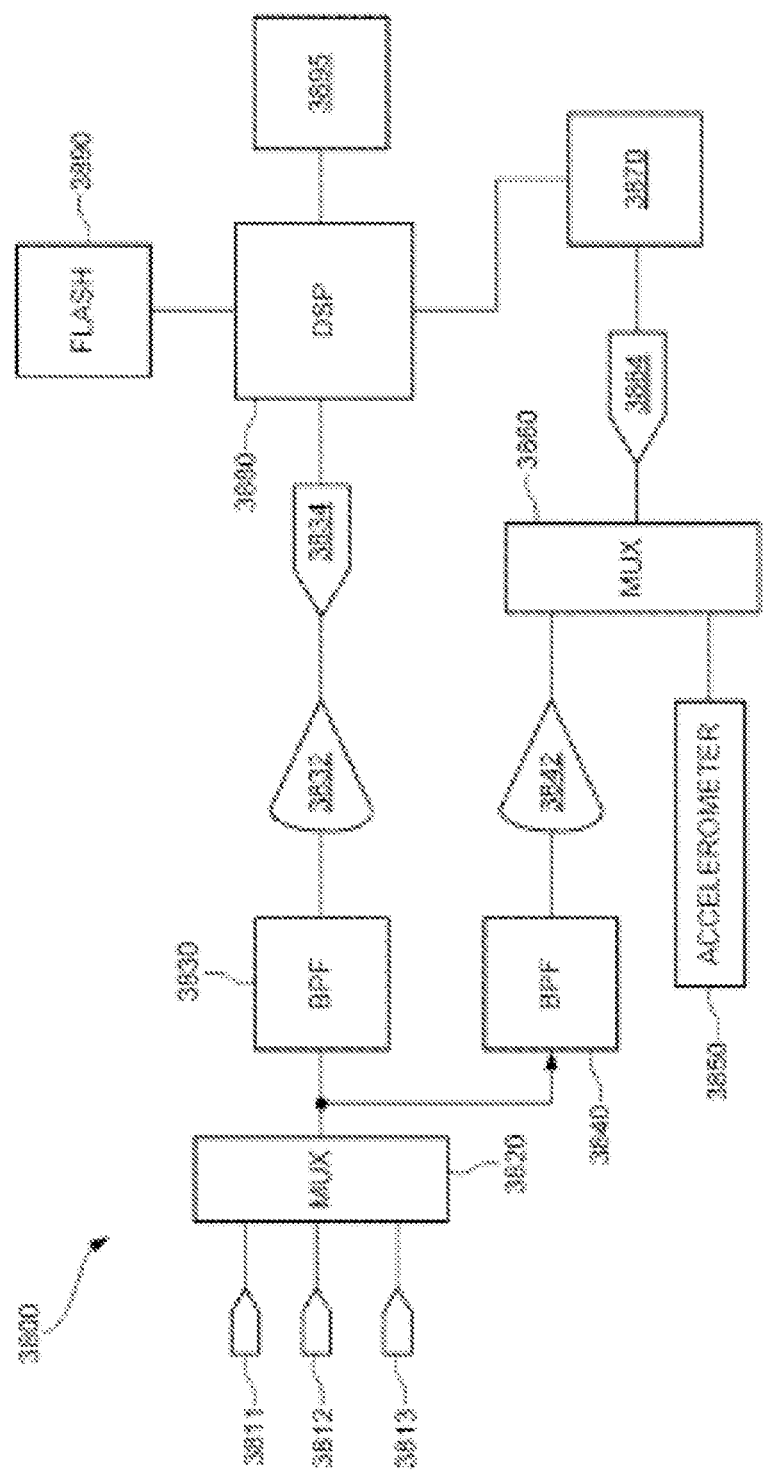

FIG. 80 is a block diagram of a receiver, according to one aspect.

Figure 81:
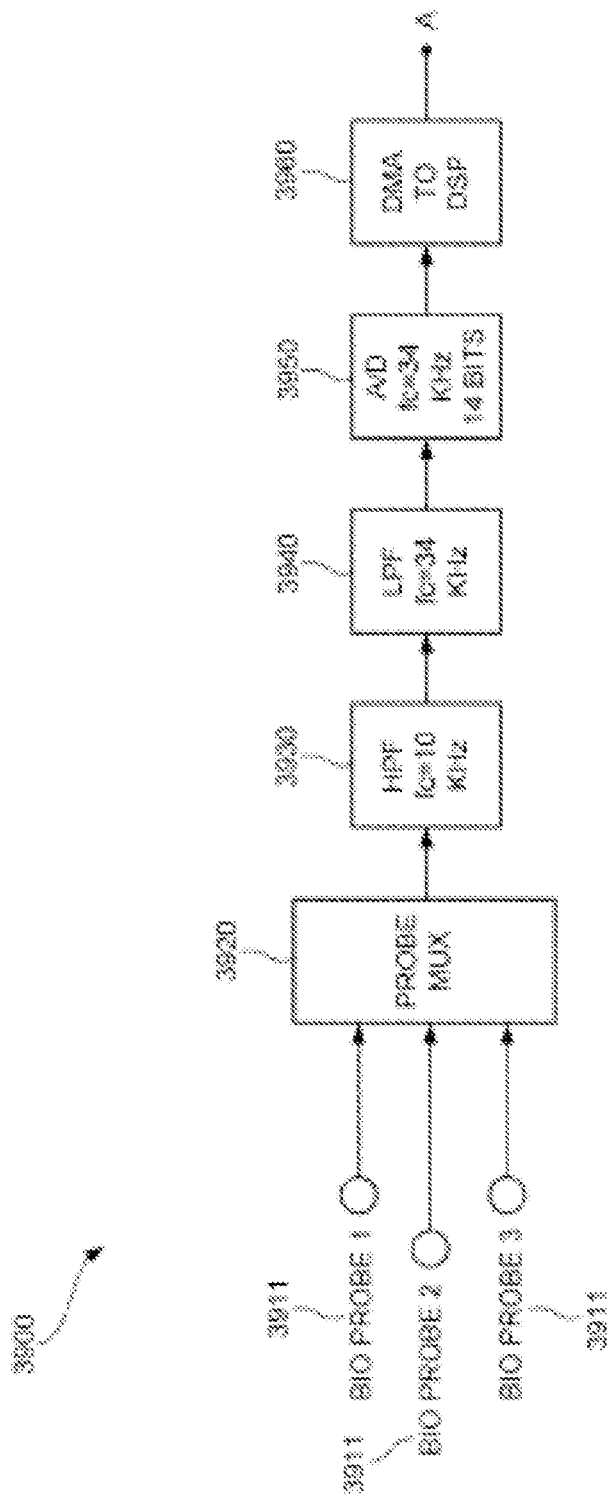

FIG. 81 provides a block diagram of a high frequency signal chain in a receiver, according to one aspect.

Figure 82:
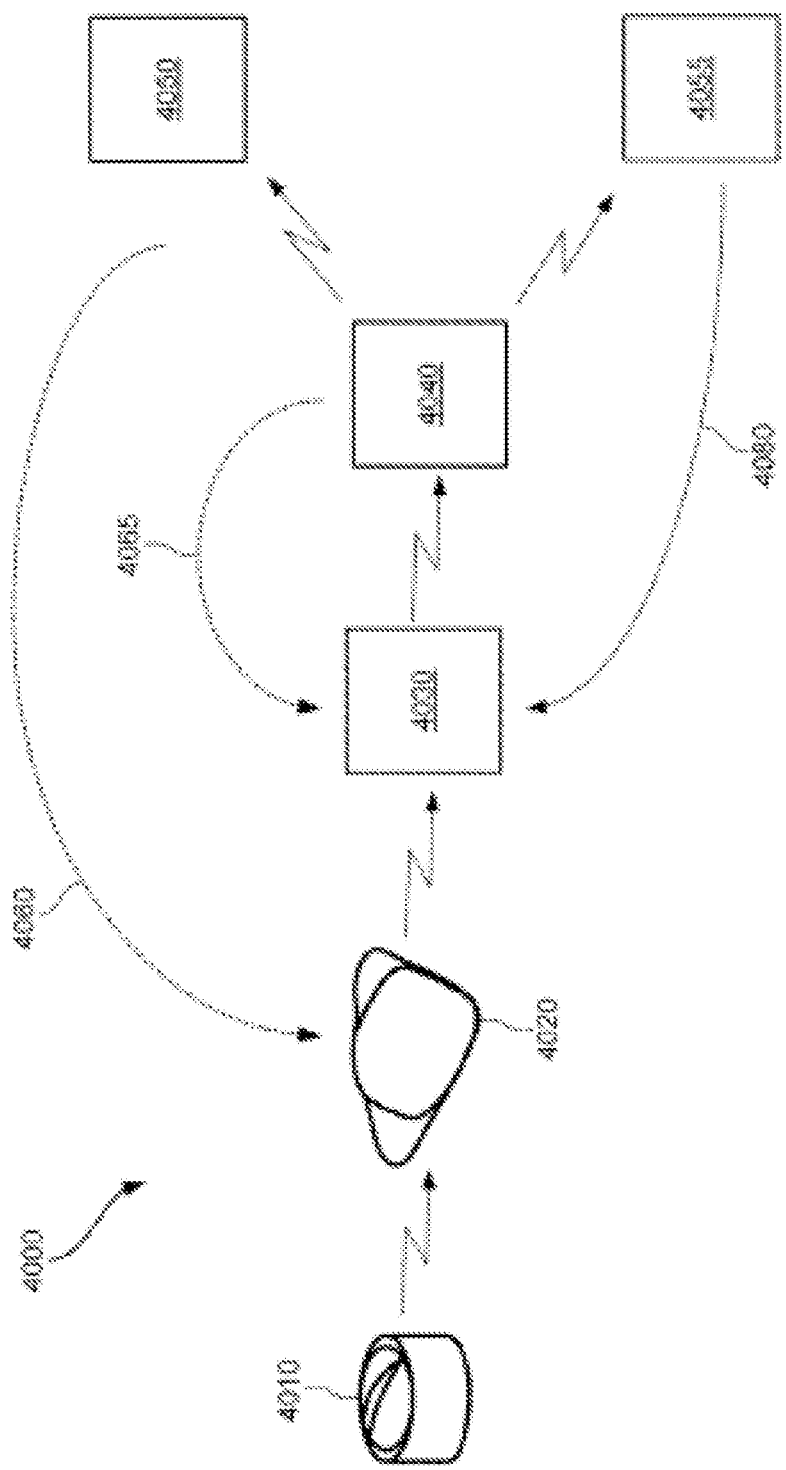

FIG. 82 provides a diagram of how a system that includes a signal receiver and an ingestible event marker may be employed according to one aspect.

Figure 83:
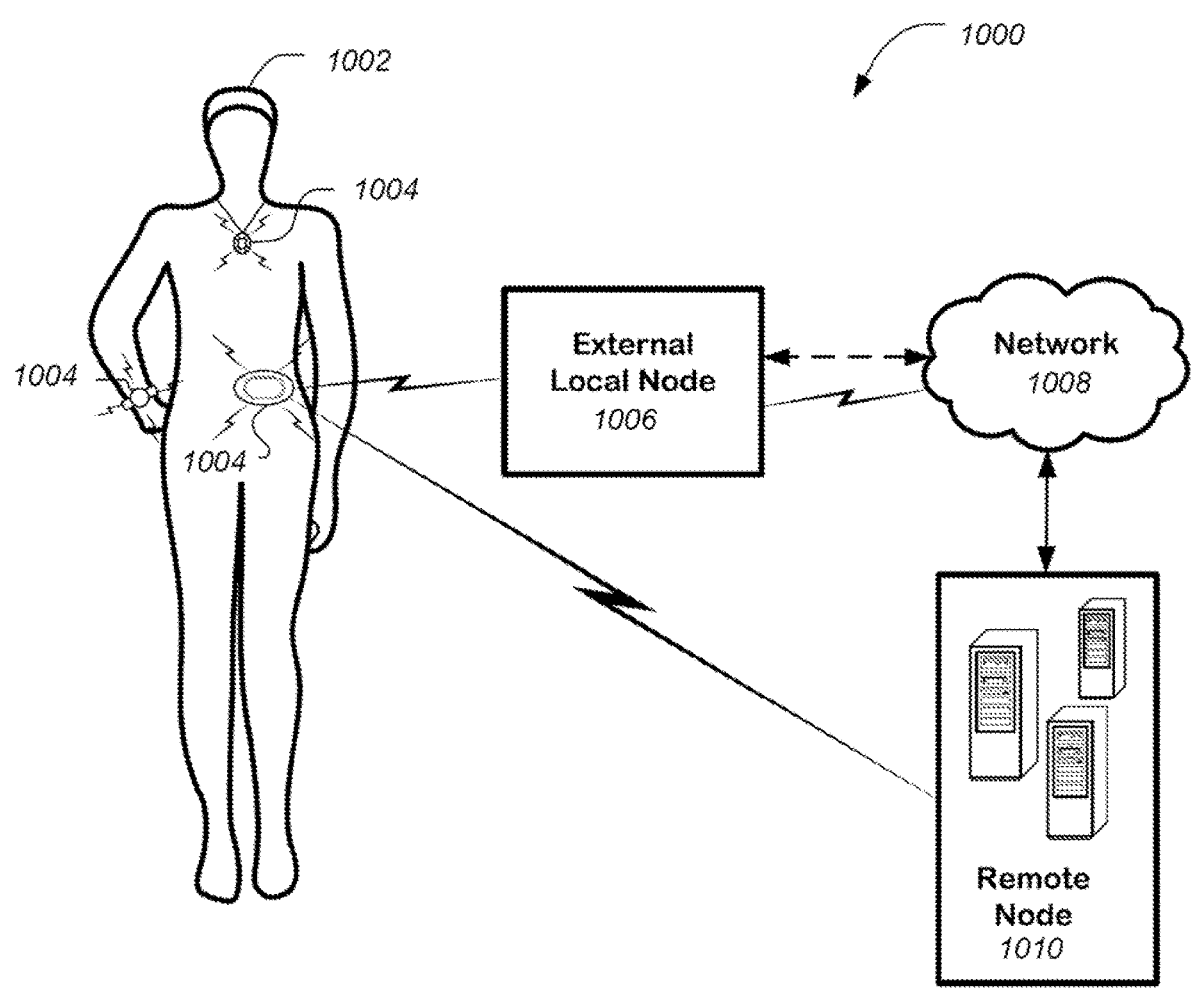

FIG. 83 illustrates one aspect of a personal communication system for obtaining patient physiological and IEM system information into a computer system according to one aspect.

DESCRIPTION

Aspects of the present disclosure include combining individual data gathered by a Proteus system (therapy, behavior, physiology, e.g., as described in greater detail in Appendix A) together with publically available data that might influence overall health risk. Data might include individual demographics, prevalence of disease in a particular geography, proximity to health care service centers, performance (outcomes) associated to HCPs in local, proximity to businesses that might influence healthy behavior (health clubs, restaurants, fast-food, grocery stores, parks, etc).

By combining the data, risk can be properly adjusted for the specific patient situation and appropriate resource can be applied to manage the risk appropriately.

The aggregate patient health risk can be more effectively determined by combining Proteus system data (therapeutic regimen and adherence, behavior, engagement, and physiology) together with one or more of the following data elements:

Demographic (age, ethnicity, etc)
Socioeconomic status
Education level
Living situation
Family situation
Credit history
Prevalence of disease in a particular geography
Proximity to health care service centers
Location
Performance (outcomes) associated to HCPs (doctors, nurses, hospitals, care centers, etc) servicing the local patient population
Geographic composition of businesses that might influence healthy behavior (health clubs, restaurants, fast-food, grocery stores, parks, etc).
Relative HCP load (patients to HCP ratio)
Diagnostic data (e.g. blood pressure measurements in hypertension)
Genomic context (i.e. genomic predisposition to disease)
Medical history
Medication possession ratio
Work situation and schedule
Social environment The data listed above may also be used without a Proteus system data to provide an independent risk-score. By combining the data, risk can be properly adjusted for the specific patient situation and appropriate resource can be applied to manage the risk appropriately. The data might be sourced from a combination of direct capture, public data sources and/or privately available systems/sources.

In one aspect a fusion technique employing Multivariate and Bayesian statistical techniques may be used to determine the combined or composite risk score.

For a basic understanding of the operational details of the Proteus IEM and receiver (patch) system, the reader is directed to FIGS. 71-83 and the accompanying description within the present disclosure, which illustrate and describe a typical Proteus system comprising an ingestible event marker (IEM) (described in connection with FIGS. 71-76) and a receiver "patch" system (described in connection with FIGS. 77-83. For conciseness and clarity of disclosure, the description now turns to a description of various aspects of a system, apparatus, and method for data collection and assessing outcomes employing a Proteus system. Once therapeutic and physiological data is obtained by the Proteus patch system, the data can be communicated to any processing engine configured to analyze the data. For example, the Proteus patch system data can be communicated to a backend computer processing system comprising a server or other suitable computing apparatus, a database, and communication interface as shown and described in connection with FIG. 82, for example. In one aspect, the backend server can be configured as a specialized machine to receive the Proteus patch system data and compute the desired results. These and other aspects will now be described in connection with the figures.

Patch-Derived Data Analytics for Improved Patient Outcomes

One question to be determined is whether feedback from patch-derived data analytics can be utilized to improve outcomes in target patients, such as those suffering from major depressive disorder, bipolar, and/or schizophrenia. In one aspect, the system can identify and quantify individuals at risk using patch-derived data. In a predictive model, the system is configured to determine the likelihood of a patient being hospitalized, being non-compliant, or developing a "new" condition. State monitoring and feedback data can be utilized to determine titration issues, optimization of drug effect, or worsening condition of patient state.

Figure 1:
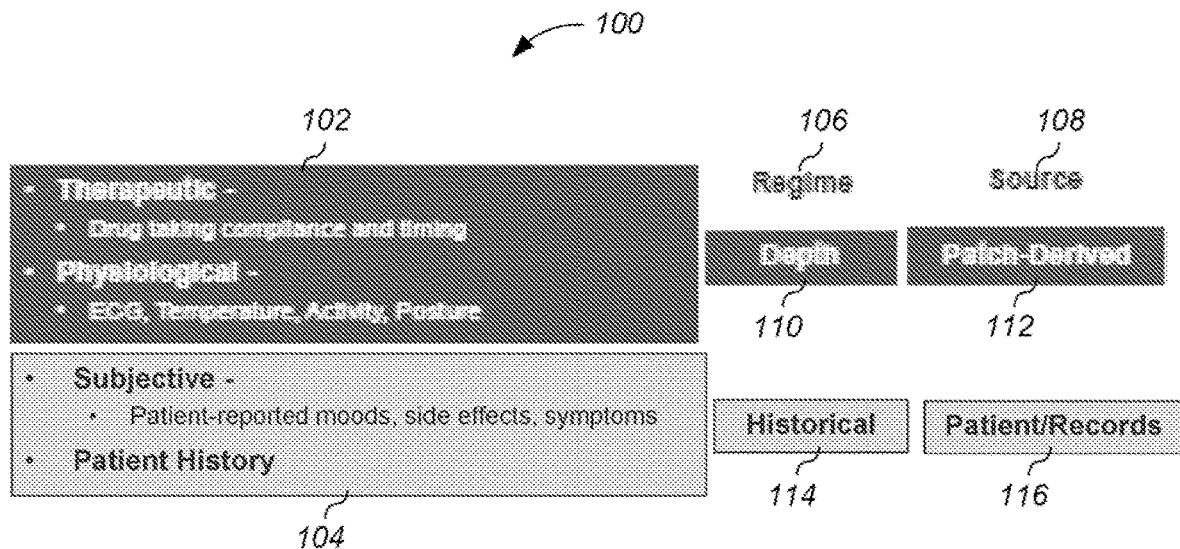
FIG. 1 illustrates a data characterization diagram depicting data types according to one aspect.

FIG. 1 illustrates a data characterization diagram 100 depicting data types according to one aspect. A first data type 102 includes therapeutic data, i.e., drug taking compliance and timing, and physiological data, i.e., electrocardiogram (ECG), Temperature, Activity, Posture, etc. The data regime 106 is depth 110 and the data source 108 is a patch receiver as described below in connection with FIGS. 71 and 77-83. Traditionally, data 104 was subjectively determined from patient-reported moods, side effects, symptoms, etc. and patient history. Thus, traditionally the data regime 106 is historical 114 and the data source 108 is a patient records database 116.

TABLE 1 below, depicts the value of data types in a patient lifecycle management process. The value from a pure data perspective is indicated in the table as Low, Medium, or High.

TABLE 1

| | Patch-Derived | | Patient/Records | |
|---|---|---|---|---|
| Patient State | Therapeutic | Physiological | Subjective | Patient History |
| Pre-Treatment Assessment | Low | High | High | High |
| Treatment Titration | High | High | High | Low |
| Management/ Maintenance | High | High | Medium | Low |

One question associated with patch-derived data analysis is whether patch-derived data fields can be effective for patient identification and classification. Systems according to the present disclosure provide high classification accuracies using patch-derived data fields and data fusion techniques can be used to enhance performance. The data fields used in the patch-derived data analysis include, without limitation, acceleration, posture, steps, temperature, and heart rate—median and standard deviation. An aggregated data field may be employed to determine whether the patent is asleep.

Figure 2:
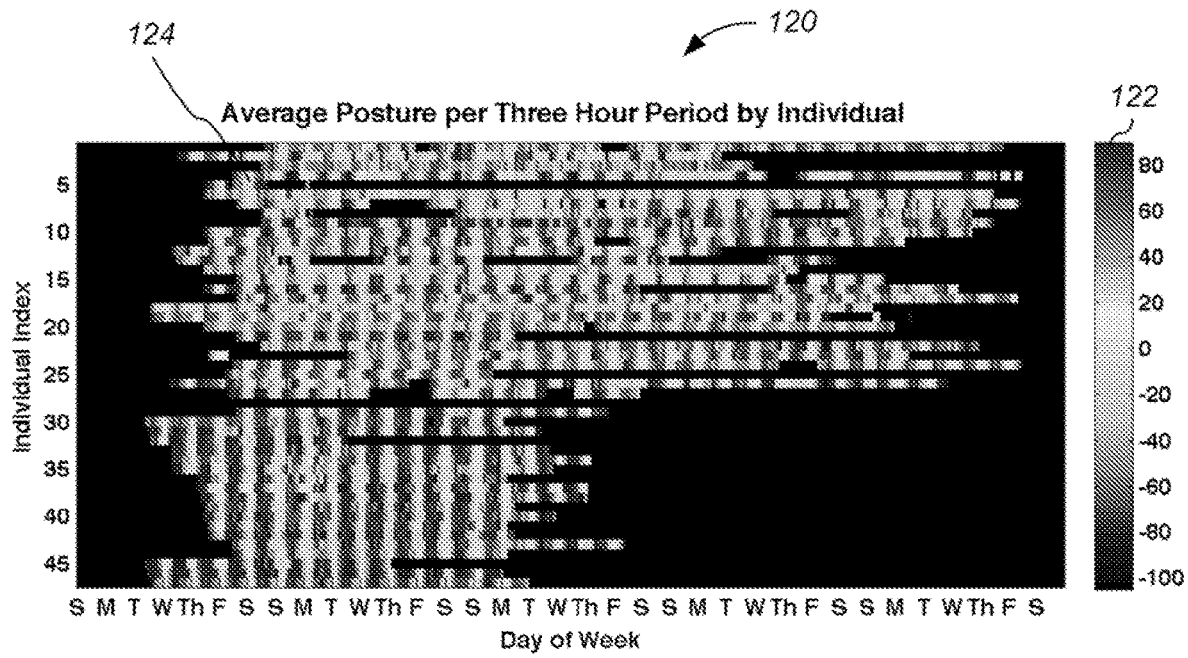
FIG. 2 is a graphical representation of average posture per three hour period by individual according to one aspect.

FIG. 2 is a graphical representation 120 of average posture per three hour period by individual according to one aspect. The horizontal axis represents the day of the week and the vertical axis represents individual patient index. Along the vertical axis, the patients are classified into three groups where Group I patients 1-16 are classified as schizophrenic, Group II patients 17-28 are classified as Bipolar, and Group III patients 29-47 are classified as healthy control. Immediately to the right of the graph 120, a vertical differentially shaded gradient scale 122 represents the individual's posture angle in degrees. The graph 120 provides a visualization of 5-minute data averaged over 3-hour periods. The resting/upright diurnal cycles 124 are visually obvious even though there is significant variance between the individuals. Optimally, each individual would have a separate baseline.

Figure 3:
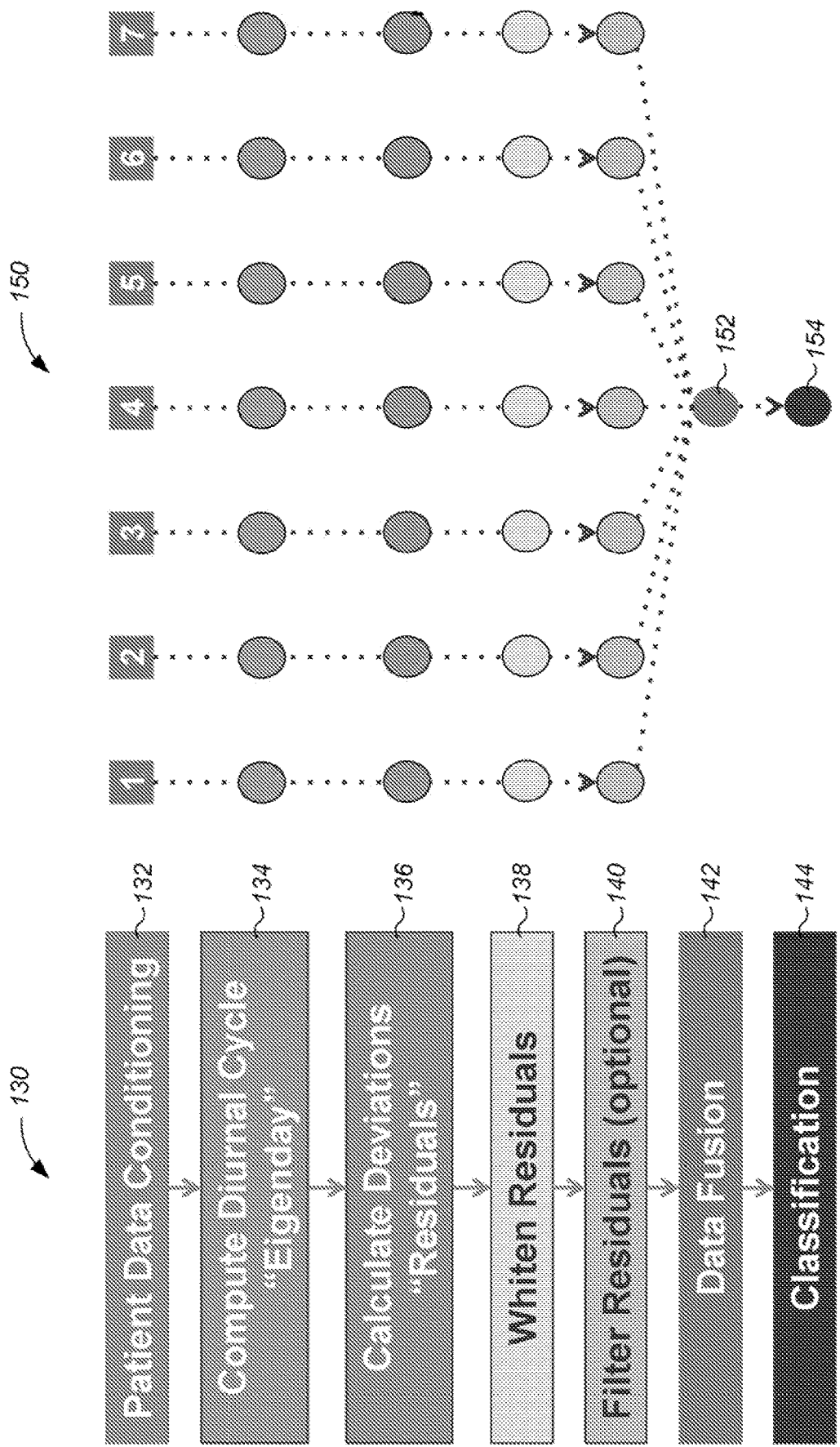
FIG. 3A illustrates a data processing flow diagram employed in determining the classification of each patient according to one aspect.
FIG. 3B illustrates data fields employed in determining the classification of each patient according to one aspect.

FIG. 3A illustrates a data processing flow diagram 130 and FIG. 3B illustrates the corresponding data fields 150 employed in determining the classification of each patient according to one aspect. As shown in the flow diagram 130 of FIG. 3A, the system conditions 132 the patient data using seven data fields, for example. The system then computes 134 diurnal cycle "Eigenday" and stores the results into corresponding seven data fields. The system calculates 136 deviations "residuals" and stores the result in seven corresponding data fields. The system then whitens 138 the residuals and stores the results into seven corresponding data fields 150 shown in FIG. 3B. After the residuals are whitened 138, the system optionally can filter 140 the residuals, storing the results into seven corresponding data fields. The system fuses 142 all the data from the seven fields 150 into a single field 152. Finally, the system classifies 144 the data based on the data fusion 142, represented by 154

Figure 4:
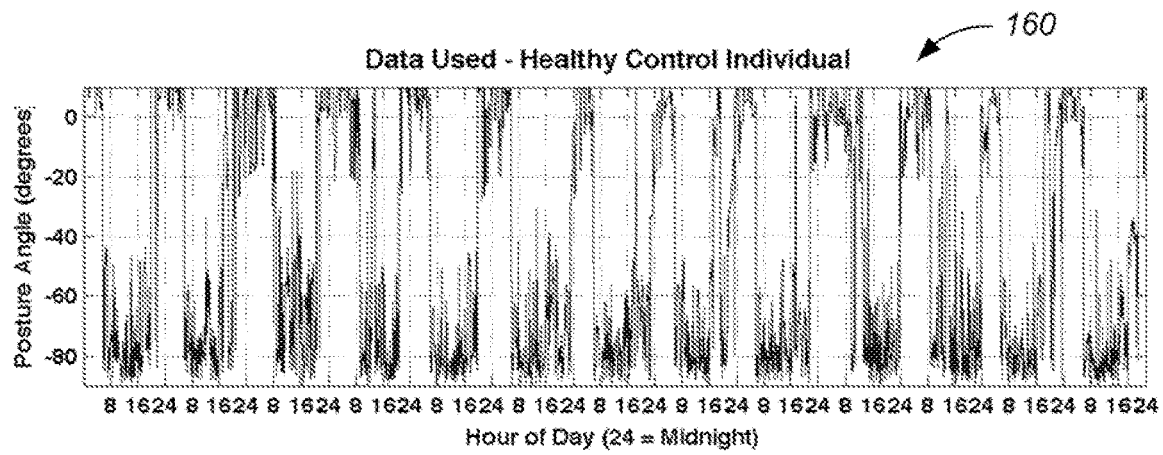
FIG. 4 is a graphical illustration of posture data for a healthy control individual according to one aspect.
Figure 5:
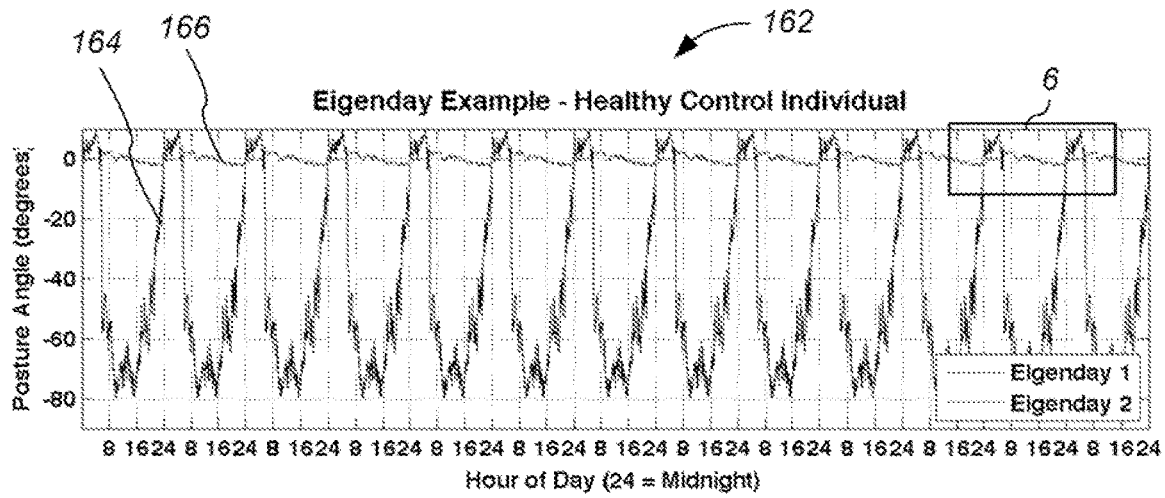
FIG. 5 is a graphical representation of an Eigenday example for a healthy control individual according to one aspect.
Figure 6:
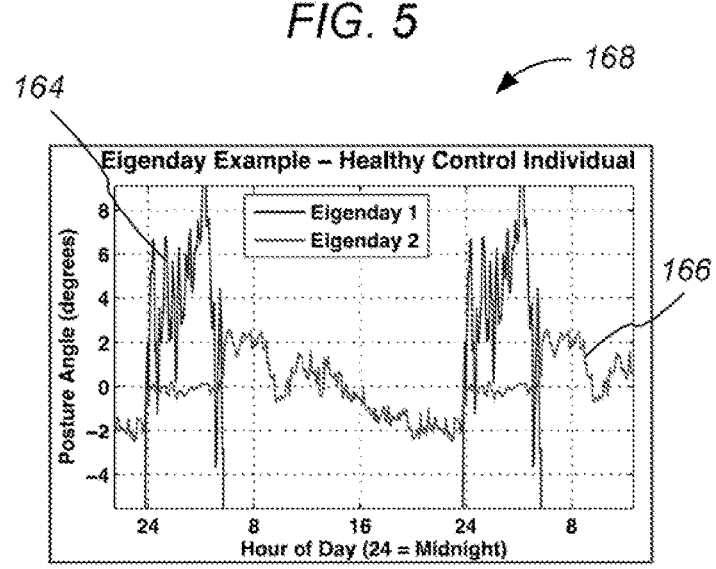
FIG. 6 is a detail view of a section of the Eigenday graphical representation of FIG. 5 showing detail graphs of the Eigenday 1 and Eigenday 2.

FIG. 4 is a graphical illustration 160 of posture data for a healthy control individual according to one aspect. The horizontal axis represents hour of day where 24=midnight and the vertical axis represents posture angle in degrees where zero degrees is resting posture and −90 degrees is completely upright. FIG. 5 is a graphical representation 162 of an Eigenday example for a healthy control individual according to one aspect. Similar to the graphical representation of FIG. 4, the horizontal axis represents hour of day where 24=midnight and the vertical axis represents posture angle in degrees. The graphical representation of FIG. 5, depicts two Eigendays, a first Eigenday 1 164 captures the dominant pattern features. A second, Eigenday 2 166 captures more subtle corrections due to multi-day variations such as sleeping in on weekends. FIG. 6 is a detail view 168 of a section 6 of the Eigenday graphical representation of FIG. 5 showing detail graphs of the Eigenday 1 164 and Eigenday 2 166. As shown in FIGS. 4-6, many days of posture data can be decomposed into patterns to calculate the primary diurnal cycle baseline. These patterns, referred to herein as Eigendays, are ordered according to the dominance of the pattern in the data.

Figure 7:
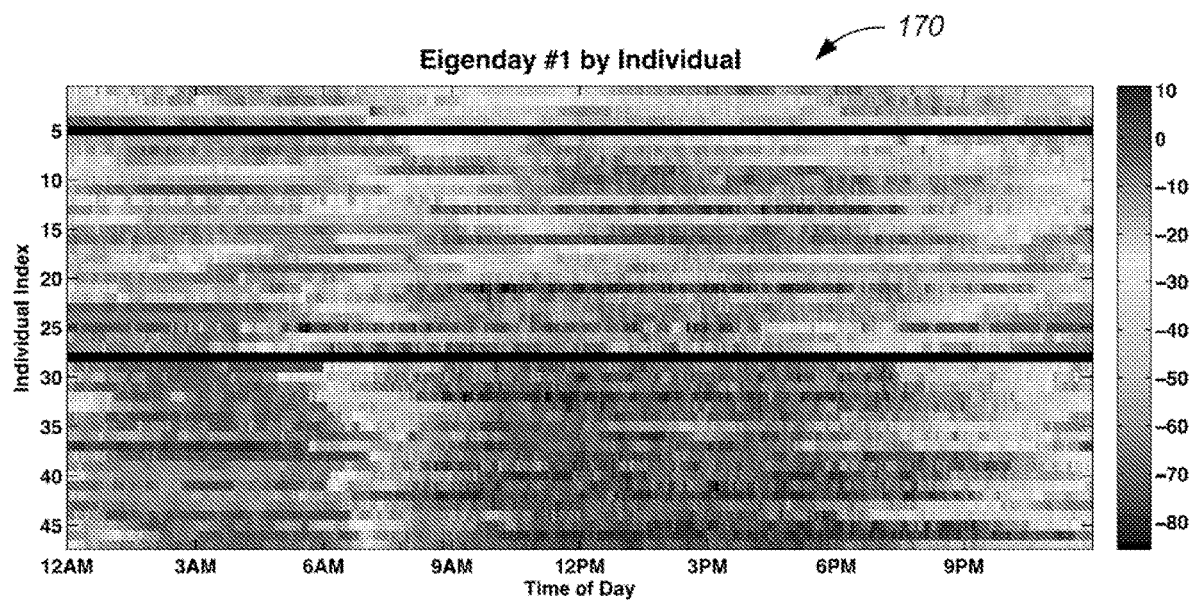
FIG. 7 is a differentially shaded coded graphical representation of primary diurnal cycle—posture Eigenday for Eigenday 1 shown in FIGS. 5-6 by individual.

FIG. 7 is a differentially shaded coded graphical representation 170 of primary diurnal cycle—posture Eigenday for Eigenday 1 shown in FIGS. 5-6 by individual. The horizontal axis represents time of day, the left vertical axis represents the individual index, and the right vertical axis represents posture angle in degrees in differentially shaded coded pattern analogous to a thermal image pattern. The patient class is arranged in three groups: Group I patients 1-16 classified as schizophrenic, Group II patients 17-28 classified as Bipolar, and Group III patients 29-47 classified as healthy control. The dominant posture Eigenday for all individuals is shown in 5-minute data collection interval. The differentially shaded code is configured such that warm differentially shaded portion indicates a laying down posture and cool differentially shaded portion indicates an upright posture.

Figure 8:
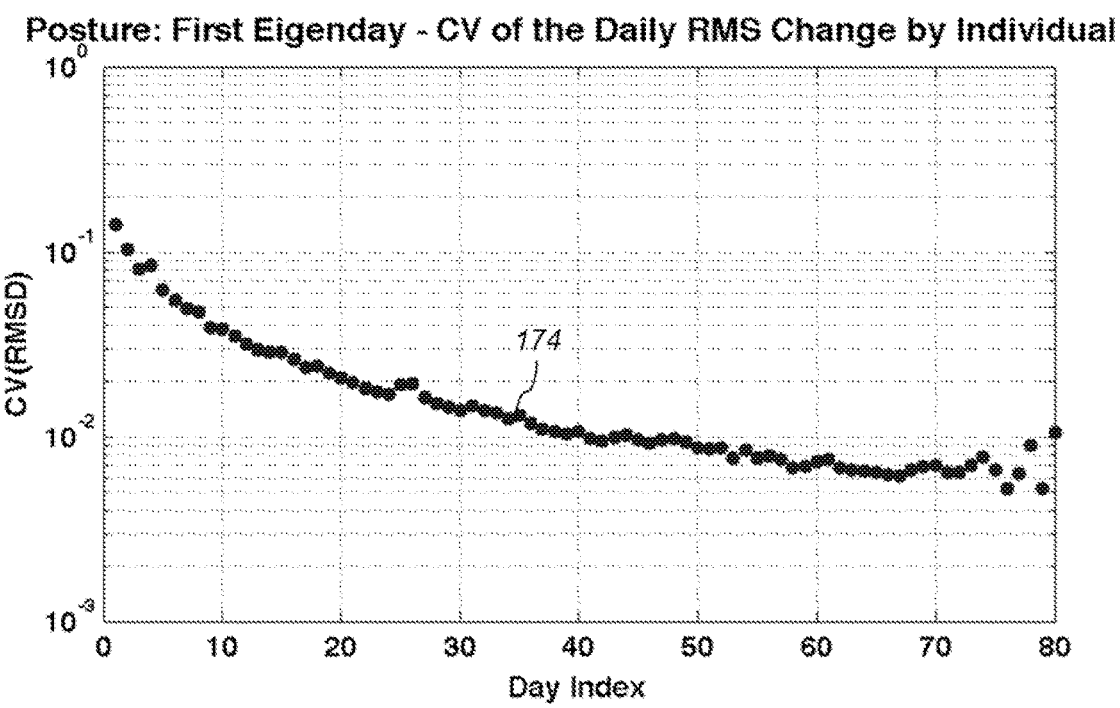
FIG. 8 is a graphical representation of the CV of the daily RMS change by individual of the first Eigenday 1 posture according to one aspect.

FIG. 8 is a graphical representation 172 of the CV of the daily RMS change by individual of the first Eigenday 1 posture according to one aspect. The horizontal axis represents the Day Index and the vertical axis represents the CV (RMSD). The graph 172 illustrates that an adequate baseline may be obtained by increasing the number of days in which data are gathered. As shown in FIG. 8, as more days of data are added to the analysis, the diurnal pattern 174 becomes more accurate. Nevertheless, beyond a certain point the gains in accuracy are small. The graph 172 shows that the convergence slows greatly after a few weeks, e.g., around day 50. The values represented along the vertical axis measure how much the Eigenday 1 value changes due to the inclusion of an extra day of data. The data used to plot the graph 172 was obtained from a longer-term collection from transplant patients so that convergence could be observed on a long time scale.

FIGS. 9-11 are graphical representations of residuals or quantized deviations from a baseline for a healthy control individual. In each of the graphs shown in FIGS. 9-11, the horizontal axis represents the hour of day where 24=midnight and the vertical axis represents posture angle in degrees. Turning now to FIG. 9, there is shown a graphical representation 180 of an example Eigenday 1 182 plotted along with data 184 obtained from a healthy control individual according to one aspect. FIG. 10 is a magnified view of the indicated section 10 of the graph 180 shown in FIG. 9 over a 24-hour period. FIG. 11 is a graphical representation 186 showing the residuals 188 calculated by subtracting the baseline Eigenday 1 182 from each individual's multi-day data 184 set. The resulting residual graph 186 captures events like resting during the day and sleeping late.

FIG. 12 is a graphical representation 190 of unfiltered data for a healthy control individual according to one aspect. FIG. 13 is a graphical representation of filtered data 192 for a healthy control individual according to one aspect. In FIGS. 12-13, the horizontal axis represents the hour of day where 24=midnight and the vertical axis represents posture angle in degrees. As shown in FIGS. 12-13, filtering the residuals enables examination of behavior over long time scales. However, in some cases short-term residual fluctuation includes more noise than useful information. Accordingly, boxcar filtering of the data can reveal persistent long-term residuals which may contain more information for classification. As shown in FIG. 12, in the unfiltered data all the short-term deviations are evident. As shown in FIG. 13, in the filtered data the long-term deviations are illuminated. The filtered data can reveal where the individual was in a laying down position more than usual or in an upright position more than usual.

FIG. 14 is a diagram 194 illustrating a data field correlation matrix according to one aspect where the vertical scale to the right of the matrix is a differentially shaded gradient representing the level of correlation. Data fusion entails combing multiple data fields into one detection/classification metric. In the illustrated example the data fields are provided along the rows and columns of the data field correlation matrix and may include, for example, the following data fields: 1) Acceleration; 2) Posture; 3) Asleep; 4) Steps; 5) Med HR; 6) Std HR; and 7) Temperature. Correlations between data fields are detrimental thus fusing two correlated data sources will emphasize the correlated feature. There are significant correlations between our data fields that must be considered.

Data fusion is the combination of multiple data types into one metric. Fusing multiple data residuals into an "effective residual" can be represented, for example, by the following expression:

$$D_M(\vec{x}) = \sqrt{\vec{x}^T C^{-1} \vec{x}}$$

Where $D_M$ is the "Mahalanobis Distance" and C is the correlation matrix. This expression accounts for the correlations between the data fields to create a "single" residual-type variable that can be used seamlessly with the classification schemes as described in more detail hereinbelow.

A first classification Method 1 classifies the percentage of time the residuals are above a threshold. The time above threshold classification provides an optimal residual threshold that is selected from the training group. The percentage time the residual resides above that threshold is used for classification. FIG. 15 is a graphical representation 196 target group data showing the amount of time the target group was above the threshold according to one aspect. FIG. 16 is a graphical representation 198 of control group data showing the amount of time the control group was above the threshold according to one aspect. In the graphs of FIGS. 15-16, the horizontal axis represents the data index and the vertical axis represents the fused residual. In the illustrated example, the data from the Target and Control Groups is the fusion of the acceleration and temperature data fields. It will be appreciated that other data fields can be fused as shown in the data field correlation matrix of FIG. 14.

FIG. 17 is a graphical representation 200 of a leave one out (LOO) classification testing according to one aspect showing the time above threshold for schizophrenic vs. healthy control groups. The horizontal axis represents variables included and the vertical axis represents the LOO classification accuracies (%). The graph 200 represents the training set accuracy 202 and the LOO test accuracy 204. In the illustrated example, the LOO classification is the percentage of time above threshold, filtered over a 24-hour filter window for schizophrenic vs. healthy control groups. Of the training set 202 and LOO test 204 accuracies shown, the maximum Max LOO test accuracy is ~85.3%. The methodology employs acceleration, posture, and temperature data fields jointly. It will be appreciated that other data fields such as sleep, steps, median HR and standard deviation HR can be employed without limitation.

A second classification Method 2 classifies distribution entropy, which is classifying based on features of the data distribution. FIG. 18 is a graphical representation 206 of distribution entropy classification based on features of the posture data distribution based on a high entropy example from a schizophrenic group. The horizontal axis represents data index and the vertical axis represents whitened residual. To the right of FIG. 18, FIG. 19 is a distribution histogram 208 of posture data for the high entropy example. The horizontal axis represents whitened residual and the vertical axis represents the number of occurrences. Turning to FIG. 20, there is illustrated a graphical representation 210 of a distribution entropy classification based on features of the data distribution based on a low entropy example from a control group. To the right of FIG. 20, FIG. 21 is a distribution histogram 212 of posture data for the low entropy example. The horizontal axis represents whitened residual and the vertical axis represents the number of occurrences. The entropy of a distribution can be used to quantify inherently different distributions. This can be effective as a classifier if different patient classes tend to have different residual distributions.

FIG. 22 is a graphical representation 214 of a leave one out (LOO) classification testing according to one aspect showing the distribution entropy for schizophrenic vs. healthy control groups. The horizontal axis represents variables included and the vertical axis represents the LOO classification accuracies (%). The graph represents the training set accuracy 202 and the LOO test accuracy 204. Unfiltered whitened residuals have a maximum LOO test accuracy 204 of 88.24%. The classification employs only the posture variable. Fusing multiple variables does not provide improved classification in this case. The methodology may employ acceleration, temperature, sleep, steps, median HR and standard deviation HR can be employed without limitation.

In conclusion, high classification accuracies were achieved. Deviations from a unique baseline were calculated for each individual. The deviations or "residuals" appear to possess significant classification power. In addition, the patch-derived data fields worked well for classification. Patch-derived data fields perform as well or better than an aggregate data field for identification and classification of individuals in the study. Finally, data fusion was shown to enhance performance. Fusion of patch-derived data fields provided utility for improving patient classification.

FIG. 23 is a diagram 216 illustrating data characterization for expanded data classes according to one aspect. The expanded data sets are in addition to the Therapeutic, Physiological, Subjective, and Patient History data classes shown in FIG. 1. In FIG. 23, the expanded data classes include Behavioral Engagement, Contextual, and Content. The regime is breadth and the source is phone-derived. The Behavioral Engagement data class may include application use frequency, feature use, and problem solving. The Contextual data class includes sociability (Calls, Texts sent, and Calendar), location diversity (Wi-Fi and Bluetooth environments), ignoring of calls, texts, emails. The Content data class includes tone in communications (Voice, Text, and Emails) and web surfing behavior.

FIG. 24 is a graphical representation 218 of breadth vs. depth framing of data values according to one aspect. The horizontal axis represents depth (insight) ranging from low to high and the vertical axis represents breadth (coverage) ranging from low to high. The Therapeutic and Physiological data classes are patch-derived, whereas the contextual, content, and behavioral engagement data classes are phone-derived. The subjective and patient history data classes are patient-derived. As can be seen in FIG. 24, the phone-derived data types add complementary analytical coverage of patient state to the patch-derived and patient data. As also shown in FIG. 24, the patch-derived data types are high depth (insight) and low breadth (coverage). The contextual and content phone-derived data types are high breadth (coverage) and low depth (insight). The patient-derived data types are both low depth (insight) and low breadth (coverage). The behavioral engagement phone-derived data types strike a balance between depth (insight) and breadth (coverage). Key data types include therapeutic (Thp), physiologic (Phy), behavioral/engagement (B/E), contextual (Ctx), content (Cnt), subjective (Sbj), and patient history (PH), among others, for example.

FIG. 25 is a graphical representation 220 patient acceptance vs. patient effort framing of data values according to one aspect. The horizontal axis represents patient acceptance and the vertical axis represents patient effort. As in FIG. 24, the Therapeutic and Physiological data classes are patch-derived, whereas the contextual, content, and behavioral engagement data classes are phone-derived. The patient acceptance of the phone-derived data type collection could be problematic although it requires little effort. As can be seen in FIG. 25, the content phone-derived data type has hard patient acceptance and low patient effort. The contextual phone-derived data type has medium acceptance and low effort. The physiologic patch-derived data type has medium acceptance and medium effort. The patient history patient-derived data type has easy acceptance and low effort. The therapeutic patch-derived data type has easy acceptance but slightly higher effort than the physiologic data type. The behavioral engagement phone-derived data type has easy acceptance and medium effort. The subjective patient-derived data type has easy acceptance and high effort. Key data types include therapeutic (Thp), physiologic (Phy), behavioral/engagement (B/E), contextual (Ctx), content (Cnt), subjective (Sbj), and patient history (PH), among others, for example.

FIG. 26 is a graphical representation 222 of the amount of data needed fro framing of data values according to one aspect. The horizontal axis represents days/users ranging from a week to 3 months and the vertical axis represents number of users ranging from 1 to 100. As shown in FIG. 26, the therapeutic, subjective, and physiologic data types are hypothesis driven and have low time and low number of users. The contextual, content, and behavioral/engagement data types are between hypothesis and data driven over a month with a medium number of users. The physiological data types are data driven over three months and have a large number of users. The phone-derived data analyses will be more hypothesis-driven than the data-driven physiological analysis. Key data types include therapeutic (Thp), physiologic (Phy), behavioral/engagement (B/E), contextual (Ctx), content (Cnt), subjective (Sbj), and patient history (PH), among others, for example.

TABLE 2 below, depicts the value of the expanded data types in a patient lifecycle management process. The phone-derived data adds value in the management/maintenance patient state.

TABLE 2

| Patient State | Patch-Derived | | | Phone-Derived | | Patient/Records | |
| --- | --- | --- | --- | --- | --- | --- | --- |
| | Therapeutic | Physiological | Behavioral Engagement | Contextual | Content | Subjective | Patient History |
| Pre-Treatment Assessment | Low | High | Low | Low | Low | High | High |
| Treatment Titration | High | High | Low | Low | Low | High | Low |
| Management/ Maintenance | High | High | High | High | High | Medium | Low |

FIG. 27 is a graphical representation 224 of a leave one out (LOO) classification testing showing time above threshold comparing schizophrenic vs. healthy controls. The data was gathered over a 36-hour filter window. The maximum LOO test accuracy is 91.18% using only acceleration and temperature data fields. The horizontal axis represents variables included and the vertical axis represents LOO classification accuracies (%). Additional data fields include posture, sleep, steps, median HR, and standard deviation HR, without limitation.

FIG. 28 is a graphical representation 226 of posture data set data distribution according to one aspect. The horizontal axis represents variable value and the vertical axis represents occurrences. FIG. 29 is a graphical representation 228 of posture data set residual distribution according to one aspect. The horizontal axis represents residual value and the vertical axis represents occurrence. Residuals are calculated by subtracting the baseline Eigenday from each individual's multi-day data set. The patch-derived posture data compiled over the data set shows a bi-modal distribution corresponding to resting/upright states. The residual distribution over the same data is unimodal. This deviation from normal is used for classification.

PICO: Proteus Indication of Clinical Outcomes—A Risk-Based Approach Based on Therapeutic and Physiologic Data FIG. 30 is a diagram illustrating 230 the continuous patient journey with episodic intervention between home 232, hospital 234, and clinic 236 according to one aspect. The key question is how to identify who is in need of attention and apply the right resources to the right person at the right time. FIG. 31 is a diagram 238 illustrating a comprehensive risk-based product offering that captures all patients throughout their journey according to one aspect. The patient population 240 is assessed 242 based on patient population data such as medical history, demographics, socio-economic, HCP performance, geography, education, behavioral history, among other data. A risk-based intervention class includes standard protocol 244, low touch intervention 246, and medium touch intervention 248. Subsequently, the data is assessed 250 based on individual data is performed, such as therapy, behavior, physiology, genomic, diagnostic, among other assessment techniques. Feedback may be provided from the medium touch intervention 248 to the low touch intervention 246 and from the low touch intervention 246 to the standard protocol 244. From the assessment stage 250 the patient proceeds to the high touch intervention 252 stage with feedback to the assessment stage 250 if necessary. Thus, a risk based approach based on complex algorithms can be applied to composite data sets to determine PICO scores. PICO scores are somewhat analogous to the Fair-Issac Corporation (FICO) score employed as the global standard for assessing consumer credit risk that drives millions of credit decisions daily. The FICO scoring system is used by 90 of the 100 largest financial institutions in the U.S., and all the 100 largest U.S. credit card issuers. FICO fraud systems protect more than two billion card accounts worldwide and 23 million consumers in the US pay for real-time access to their FICO scores.

Accordingly, in one aspect, the present disclosure provides a patch-derived data analytics system to contribute to constructing a health equivalent of a FICO score referred to herein as a PICO score, for example. The PICO score provides an assessment of patient risk and stability across therapeutic areas and enables automated data-driven clinical decision making. This system can provide effective drug therapy management and improved therapeutic program effectiveness at reduced cost. In one aspect, metrics may be derived that are suitable for quantifying the patch-derived data as input to the PICO score. The PICO score system may be employed to predict whether the patient is likely to be hospitalized or non-compliant or developing "new" condition. The PICO score system may provide patient state monitoring and feedback, titration issues, optimization of drug effect, or worsening condition of patient state.

FIG. 32 is a diagram 252 of several graphical representations to assist visualization of longitudinal data according to one aspect. A first graph 254 illustrates a patient's circadian pattern based on posture where the horizontal axis represents the time of day and the vertical axis represents the number of days. The first graph 254 is differentially shaded coded pattern analogous to a thermal image pattern. The dark or black areas indicate that the patient is in a supine position, the light blue areas indicate that the patient is in a sitting position, the red areas indicate that the patient is in a standing position, and the white areas indicate that the patient was not wearing the patch. A second graph 256 immediately below the first graph 254 illustrates the patient's average circadian pattern where the horizontal axis represents time of day and the vertical axis represents degrees. A third graph 258 illustrates the medication that the patient is taking representing pill taking behavior where the horizontal axis represents the time of day and the vertical axis represents the number of days. A fourth graph 260 immediately below illustrates the timing adherence in time of day versus number of pills taken where the horizontal axis represents the time of day and the vertical axis represents the number of pills taken. A fifth graph 262 illustrates how many pills were taken in a day representing pill taking adherence where the horizontal axis represents the number of pills taken in a day and the vertical axis represents the number of days. The white spaces 264 denote the dose taken and the asterisk 266 denotes that the patch was not worn and thus excluded the session from the percentage (%). Accordingly, at a glance, one can obtain a visualization of long term data based on the patient's circadian pattern based on posture and medication taking behavior.

The disclosure now turns briefly to an overview of the patch-derived data analytics for patient risk assessment over two phases. In phase 1, high classification accuracies were achieved with patch-derived data. The "Residual Entropy" method enabled patient classification accuracy of 88.24% as previously described in connection with FIG. 22 for N=34 subjects (15 neuropsych/19 healthy volunteers. The data fusion of multiple physiological parameters was shown to provide performance enhancement for some cases. In phase 2, the residual entropy metric was enhanced for input into PICO score. For this study the patch-derived posture data was used and refined to be time-window specific and agnostic to data set length and sample rate. This provided strong utility to catch subject instabilities. The therapeutic patch-derived data (IEM) studied for utility towards PICO score provided two degrees of freedom identified to enable risk quantification and of potential correlation between therapeutic and physiological abnormalities in the data.

In addition to the original phase 1 data set, three new data sets were used and there were some key differences between the data sets. The new data sets consisted entirely for institutionalized subjects with severe health issues. Phase 1 subjects were not institutionalized and the subjects that were not in the neuropsych group were healthy volunteers. The new data sets were collected with an updated version of the patch where many of the sampling rates were higher. These additional data sets are summarized in TABLE 3.

TABLE 3

| Data Summary | # of Subjects | Neuropsych | Healthy | Other Ailments | Institutionalized |
|---|---|---|---|---|---|
| Phase 1 | 35 | X | X | | |
| Alpha | 15 | X | | X | X |
| Hbbread | 12 | | | X | X |
| Hbbrim | 12 | | | X | X |

FIG. 33 is a graphical representation 270 of the comparative length of data sets showing the number of good days of data by individual according to one aspect. The horizontal axis represents the subject index and the vertical represents the number of good days. The data sets Phase 1, Alpha, Hbbbread, and Hbbrim are graphed as histograms. The newer data sets Alpha, Hbbbread, and Hbbrim are much longer in general than the Phase 1 data set. Statistical metrics can be dependent on the length of the data set and can lead to the development of a new metric related to the Phase 1 but allowing for disparate data set lengths.

The PICO entropy metric quantifies the variability in the subject's circadian patterns where the dominant circadian patterns are calculated from subject's historical data. The higher the entropy of the variations from the baseline circadian patterns the larger the subject's variability. With reference to FIG. 4, the daily data can be decomposed into dominant circadian patterns as shown in FIG. 6. The daily variations that are tracked as shown in FIG. 9 can be illustrated as distributions of variations quantified by differential entropy as shown in FIGS. 19 and 21, for example.

FIG. 34 is a graphical representation 272 of posture entropy metric enhancements for fixed segment length entropy (FSLE) according to one aspect. The horizontal axis represents the day index and the vertical axis FSLE value. One set of data is for Alpha Subject #4—Neuropsych and another set of data is for Alpha Subject #6—Diabetes type 2. Previously a single entropy value for whole data set was calculated. The FSLE technique provides a series of entropy values over fixed time intervals and allows temporal assessment of patient stability.

FIG. 35 is a diagram 274 of several graphical representations of an FSLE example depicting abnormalities in circadian posture patterns according to one aspect. The diagram 274 illustrates that spikes in FSLE values are indicative of days when the subject's posture pattern is highly variable. A first graph 276 illustrates the posture circadian pattern for Alpha subject #14. The red areas of the differentially shaded coded pattern indicate that the patient is in standing upright position and the dark blue areas indicate that the patient is in a supine position. Intermediate differentially shaded pattern indicates that the patient is in an intermediate position between upright and supine. The horizontal axis represents time of day and the vertical axis represents the number of days. Immediately below the first graph 276 is a second graph 278 illustrating the average circadian pattern where the horizontal axis still represents time of day and the vertical axis represents the number of days. Immediately to the right of the first graph 276 is a third graph 280 depicting FSLE where the horizontal axis represents a daily FSLE vale and the vertical axis represents the number of days. The third graph 280 can show a robust capture of aberrations in the circadian posture pattern. Immediately below the third graph 280 is a fourth graph 282 depicting the FSLE distribution where the horizontal axis represents the FSLE value and the vertical axis represents the number of occurrences.

Posture FSLE distributions may be obtained by subject group. The FSLE distributions from aggregated subject group values can be plotted and different therapeutic areas can be clustered together. FIG. 36 is a distribution plot 284 indicating the FSLE value and the P-value where the P-value represents the portion of the distribution that is above a given FSLE value. FIG. 37 is a graphical representation 286 of posture FSLE P-values by subject group according to one aspect. The horizontal axis represents FSLE value and the vertical axis represents group distribution P-value. The subject groups are Phase 1 Neuropsych, Alpha Neuropsych, Phase 1 Healthy, Alpha Other Ailments, Hbbread Other Ailments, and Hbbrim Other Ailments. The two target neuropsych groups have the highest P-values of entire set. The healthy Phase 1 group has much lower overall P-values. The three 3 institutionalized groups with other ailments cluster together in the middle.

The posture FSLE can be used as an input into the PICO score. FIG. 38 is a distribution curve 288 of an individual's FSLE risk score. As shown in FIG. 38, an individual subject's FSLE distribution curve 288 can be quantified as a scalar for input into a PICO score where the FSLE Score is chosen where the P-Value=0.159 and one standard deviation above the distribution mean. FIG. 39 is a graphical representation 289 of subject posture FSLE risk score according to one aspect. The horizontal axis represents the subject index and the vertical axis represents the FSLE score. As illustrative examples, the subsequent disclosure drills down into two specific cases Drilldown #1 for Alpha subject #11 and Drilldown #2 for Hbbrim subject #9.

FIG. 40 is a diagram 290 of several graphical representations of posture FSLE used as input to PICO score for Drilldown #1 according to one aspect. The diagram 290 illustrates the Drilldown #1 for Alpha subject #11 a Neuropsych with lower risk score and a relatively stable posture circadian pattern. A first graph 292 illustrates the posture circadian pattern for the Alpha subject #11 where the horizontal axis represents time of day and the vertical axis represents the number of days. The red areas of the differentially shaded coded pattern indicate that the patient is in standing upright position and the dark blue areas indicate that the patient is in a supine position. Intermediate differentially shaded pattern indicates that the patient is in an intermediate position between upright and supine. The horizontal axis represents time of day and the vertical axis represents the number of days. Immediately below the first graph 292 is a second graph 294 illustrating the average circadian pattern where the horizontal axis still represents time of day and the vertical axis represents the number of days. Immediately to the right of the first graph 292 is a third graph 296 depicting FSLE where the horizontal axis represents a daily FSLE vale and the vertical axis represents the number of days. The third graph 296 shows a robust capture of aberrations in the circadian posture pattern. Immediately below the third graph 296 is a fourth graph 298 depicting the FSLE distribution where the horizontal axis represents the FSLE value and the vertical axis represents the number of occurrences. The daily FSLE captured a brief period of unstable circadian patterns.

FIG. 41 is a diagram 300 of several graphical representations of posture FSLE used as input to PICO score for Drilldown #2 according to one aspect. The diagram 300 illustrates the Drilldown #2 for Hbbrim subject #9 a hypercholesterolemia, hypertension, ischemic heart disease with higher risk score. A first graph 302 illustrates the posture circadian pattern for the Hbbrim subject #9 where the horizontal axis represents time of day and the vertical axis represents the number of days. The red areas of the differentially shaded coded pattern indicate that the patient is in standing upright position and the dark blue areas indicate that the patient is in a supine position. Intermediate differentially shaded pattern indicates that the patient is in an intermediate position between upright and supine. Immediately below the first graph 302 is a second graph 304 illustrating the average circadian pattern where the horizontal axis still represents time of day and the vertical axis represents the number of days. Immediately to the right of the first graph 302 is a third graph 306 depicting FSLE where the horizontal axis represents a daily FSLE vale and the vertical axis represents the number of days. The third graph can show a robust capture of aberrations in the circadian posture pattern. Immediately below the third graph 306 is a fourth graph 308 depicting the FSLE distribution where the horizontal axis represents the FSLE value and the vertical axis represents the number of occurrences. The daily FSLE shows a period of stable circadian patterns characterized by low FSLE values and as the circadian patterns become unstable the FSLE values increase accordingly.

FIG. 42 is a graphical representation 310 of posture FSLE risk ranking across subject groups according to one aspect. The graph 310 represents the posture FSLE risk quartiles by group where the horizontal axis represents risk quartile and the vertical axis represents the number of subjects in the group. The blue bars 312 represent the Neurpsych group, the green bars 314 represent the Other Ailments group, and the Brown 316 bars represent the Healthy groups. The groups 312, 314, 316 are ranked according to risk from left to right: low risk, marginal risk, moderate risk, and high risk. Ranking of subject risk shows the utility of FSLE as a risk measure. Neuropsych subjects strongly tend towards high risk. Healthy control subjects are strongly low risk. "Other ailment" groups spread more evenly with Moderate Risk the highest.

FIG. 43 is a diagram 320 illustrating therapeutic data for additional PICO risk input according to one aspect. IEM data is used as medication adherence risk indicator. Predictive medication adherence provides substantial added value to the overall PICO risk score. A first graph 322 illustrates pill taking behavior where the horizontal axis represents time of day and the vertical axis represents the number of days. Immediately below the first graph 322 is a second graph 324 that illustrates timing adherence where the horizontal axis represents the time of day and the vertical axis represents the number of pills. The second graph 324 indicates a tight distribution over the data period, which shows relatively good temporal adherence. Immediately to the right of the first graph 322 is a third graph 326 illustrating taking adherence where the horizontal axis represents the number of pills taken in a day and the vertical axis represents the number of days. As shown in the third graph 326, the white horizontal bars 328 indicate days where the medication appears to have been missed. As shown in FIG. 44 there are two degrees of freedom daily adherence and temporal (timing) adherence. Daily adherence refers to the number of pills that are prescribed versus the number that are actually taken per day. Temporal (timing) adherence refers to the timing regularity with which the medications are taken. Temporal adherence is a good indicator of the patient's discipline and reliability with respect to medication adherence.

FIG. 44 is a diagram 330 of several graphical representations of the inclusion of IEM data into the PICO score according to one aspect. The diagram 330 illustrates that high FSLE values coincide with IEM abnormalities. A first graph 332 illustrates the posture circadian pattern for the Alpha subject #14 where the horizontal axis represents time of day and the vertical axis represents the number of days. The red areas of the differentially shaded coded pattern indicates that the patient is in standing upright position and the dark blue areas indicate that the patient is in a supine position. Intermediate differentially shaded pattern indicates that the patient is in an intermediate position between upright and supine. Immediately below the first graph 332 is a second graph 334 illustrating the average circadian pattern where the horizontal axis still represents time of day and the vertical axis represents the number of days. Immediately to the right of the first graph 332 is a third graph 336 depicting FSLE where the horizontal axis represents a daily FSLE vale and the vertical axis represents the number of days. Immediately below the third graph 338 is a fourth graph 340 depicting the FSLE distribution where the horizontal axis represents the FSLE value and the vertical axis represents the number of occurrences. Immediately to the right of the third graph 326 is a fifth graph 340 depicting pill taking behavior where the horizontal axis represents the time of day and the vertical axis represents the number of days. Immediately below the fifth graph 340 is a sixth graph 342 depicting timing adherence where the horizontal axis represents the time of day and the vertical axis represents the number of pills. In the illustrated graph six 342, the diagram shows good consistency on timing adherence. Immediately to the right of the fifth graph 340 is a seventh graph 344 that represents taking adherence where the horizontal axis represents pills taken in a day and the vertical axis represents the number of days. In the illustrated graph seven 344, the abnormalities (+/−) appear to slightly precede a period of high FSLE values.

Turning now to FIG. 45, there is illustrated a diagram 346 of an IEM ingestion matrix characterization of therapy taking according to one aspect. The vertical axis represents the number of days. The large arrow 348 pointing vertically downward represents dose adherence rate (DAR), which is the percentage (%) of doses taken within +/−1 hour from the expected time. The large arrow pointing horizontally 349 rightward represents daily taking adherence (DTA), which is the percentage (%) of days all expected doses are taken.

FIG. 46 is graphical representations 350 of the FSLE risk score versus daily adherence according to one aspect. The horizontal axis represents FSLE risk score and the vertical axis represents 100-daily taking adherence (%). Four groups were plotted. The Alpha Neuropsych, Alpha Other, Hbbrim, and Hbbread.

FIG. 47 is graphical representations 352 of the FSLE risk score dose daily adherence according to one aspect. The horizontal axis represents FSLE risk score and the vertical axis represents 100-dose adherence (%). Four groups were plotted. The Alpha Neuropsych, Alpha Other, Hbbrim, and Hbbread.

FIG. 48 is a diagram 354 illustrating inter-week (global) variability score intrinsic dimensionality according to one aspect. Data from a data matrix 356 on the left is provided to a functional computation module 358 (e.g., computer, server, processor, engine, platform, and the like) on the right which is configured to apply principal component analysis (PCA) to the data matrix. The output of the functional computation module 358 is a whitened PCA (WPCA) data 360 that is used to generate the variation rate curve 362 |Diff(100*PCAVar/mean(PCAVar(2:end)))|. The threshold is 10% for intrinsic dimensionality.

FIG. 49 is a diagram 364 for processing the WPCA data 360 to determine how many samples are above the intrinsic dimensionality 368 threshold. As shown in FIG. 49, the WPCA data 360 is provided to another functional computation module 366 which is configured to determine how many WPCA samples are above the threshold (10%) for intrinsic dimensionality 368.

FIG. 50 is a diagram 370 illustrating the intra-week (local) variability scores average deviation from daily pattern according to one aspect. In the illustrated diagram 370, data from a data matrix 372 on the left is provided to a functional computation module 374 which is configured to extract weekly data (e.g., Sunday to Sunday). The output of the functional computation module 374 is WPCA data 376 plotted to represent a variation rate curve from week 2 to week 15 in the form of a differentially shaded coded matrix 378, as shown in the illustrated example.

FIG. 51 is diagram 380 for processing the WPCA data 376 into average standard deviation data according to tone aspect. As shown in FIG. 51, the weekly data 376 is provided to another functional computation module 382 which is configured to calculate average deviation from the daily pattern. The output of the functional computation module 382 is ASTD=Average Standard deviation 384 along days ASTD=mean(std(x)) 384, ADIFF=Average Change Rate Along Days 386 (check repeatability the same time of the day did subject) ADIFF=mean(mean(abs(diff(x)))), and Combined=[(ASTD*ADIFF)]*0.5 388, as shown in the illustrated example.

FIG. 52 is a graphical representation 390 of global versus local [(ASTD*ADIFF)*0.5 according to one embodiment. The horizontal axis represents the global score (intrinsic dimensionality) and the vertical axis represents the local score. A differentially shaded coded vertical scale 391 to the right of the graph represents Schizophrenia, Depression, DT2, and HTN, for example.

FIG. 53 is a graphical representation 392 of a data matrix (e.g., posture circadian pattern) of a first subject (Customer 1) and FIG. 54 is a graphical representation 394 of combined taking adherence and dose adherence according to various aspects. As shown in the illustrated example, the Global Score=3 and the Local Score=14, which is less than the threshold=17. The taking adherence=80.35% and the dose adherence=72.32%.

FIG. 55 is a graphical representation 396 of a data matrix (e.g., posture circadian pattern) of a second subject (Customer 2) and FIG. 56 is a graphical representation 398 of combined taking adherence and dose adherence according to various aspects. As shown in the illustrated example, the Global Score=6 and the Local Score=22, which is greater than the threshold=17. The taking adherence=48.48% and the dose adherence=64.39%.

FIG. 57 is a graphical representation 400 of distribution of patient scores according to one embodiment for both subjects (Customer 1 and Customer 2) according to one aspect. The graph 400 depicts correlation between circadian score and missed dose adherence where the horizontal axis represents the local circadian score and the vertical axis represents the missed dose adherence for pill consumption behavior. A differentially shaded coded vertical scale 402 to the right of the graph represents Schizophrenia, Depression, DT2, and HTN, for example. As shown, Customer 1 has a local circadian score of 14 and Customer 2 has a local circadian score of 22.

FIG. 58 is a graphical representation 404 showing the correlation between circadian score and missed dose adherence according to one aspect. The horizontal axis represents local circadian score and the vertical axis represents missed dose adherence for pill consumption behavior. A differentially shaded coded vertical scale 406 to the right of the graph represents Schizophrenia, Depression, DT2, and HTN, for example. The graph 400 shown in FIG. 57 has been superimposed with four risk quadrants labeled low, medium, high, and medium. Thus, the patients or subjects can be classified in a particular risk class.

FIG. 59 is a diagram 410 illustrating a comprehensive risk and intervention strategy according to one aspect. Once the patients are classified in a risk class 412 (low, medium, high) the patient is on-boarded 414 and a population based assessment 418 is made at node 416. A medium touch intervention 420 is made (passive sensing application, engagement, wearable) at node 422 for medium risk class patients. Another assessment 424 based on circadian pattern is made at node 426 and a high touch intervention 428 is made (patch, pill, application) at node 430 for high risk class patients. Another assessment 432 can be made at node 434 based on circadian pattern and medication taking. A medium touch intervention 436 can be made at node 438 to medium risk class patients.

Accordingly, patch-derived data is well-suited as a foundation for patient risk quantification. Circadian pattern analysis using posture data is an effective component of a PICO risk score. Risk quantified at the subject group level segmented the groups into appropriate risk groupings. Individual cases illustrated the utility of patch-derived metrics to track subject temporal risk state. Additionally, therapeutic medication adherence data has potential as an additional risk input into PICO. Daily medication taking and timing adherence patterns show prospective added value through individual case analysis. Many cases where medication adherence and circadian pattern abnormalities co-exist.

In connection with data analysis, the system can extend posture-based risk metric procedure to other patch-derived data such as other physiological data (heart rate, temperature, acceleration) and IEM ingestion data. Risk metrics can be modified according to known issues such as when IEM ingestion is not 100% detected and fuzzy data fusion techniques can be employed to merge physiological and therapeutic data types. The therapeutic effect of individual pills (pharmacodynamics) should be accounted for since not all pills can be treated equally.

In connection with risk score training, the system requires subject data with outcomes, including Lifenote project data, and the inclusion of different data types into risk score such as behavioral analytics, passive sensing, contextual data, and patient data.

PICO Risk Score Distributions and Trend Analysis

In accordance with the techniques described herein, a joint circadian pattern (JCP) risk distribution by data set can be developed. In one aspect, four basic groupings Phase 1 Healthy group contains the lowest risk scores (as is expected). Lifenote and Helius groups comprise the middle grouping. Phase 1 Psych and Phase 2 Alpha NonPsych, Hbbread, Hbbrim group together. Alpha Psych group possesses highest risk score distribution. FIG. 60 is a graphical representation 440 of a joint circadian pattern (JCP) risk distribution by data set where the horizontal pattern represents risk score and the vertical axis represents the cumulative distribution function for the various identified groups according to one aspect.

FIG. 61 is a graphical representation 442 of a pharmacokinetic dose (PKD) risk by data set according to one aspect. The horizontal pattern represents risk score and the vertical axis represents the cumulative distribution function for the various identified groups. The PKD technique provides less obvious clustering. As shown, the Phase 1 Healthy group again has the lowest risk scores. Lifenote and Phase 1 Psych groups seem to have similar behavior above 20. Hbbread, Hbbrim are similar with Alpha groups possessing the highest risk behavior. Although Alpha NonPsych has a fatter distribution in Risk Score range of 10-50. Helius has an anomalous bump around 50—possibly due to shorter data sets.

FIG. 62 is a graphical representation 444 of the overall risk distribution by data set according to one aspect. The horizontal axis represents risk score and the vertical axis represents the cumulative distribution function for the various identified groups. As before, there are four basic groupings where Phase 1 Healthy has the lowest overall risk scores, Lifenote and Helius groups cluster with the next lowest risk distribution behavior, Hbbread, Hbbrim, Alpha Non Psych, and Phase 1 Psych have the second to highest risk distributions, and Alpha Psych has the highest risk distribution.

In accordance with the aforementioned risk scores trend analysis techniques, the present disclosure provides a method of singling out patients for closer scrutiny and/or physician follow-up. A substantial risk score spike may be a temporary occurrence and not necessarily an indicator that a patient is in danger. Observing trends in the risk score time series provides a better indication of a patient's risk state. Other methods including methods of "Partial Trend Analysis" enable the dominant trends in subsets of the time series to be calculated based on minimizing the trend fit error. This result is parametric and may allow more or less detail into the Partial Trend by varying the maximum amount of error allowed. Thus this method can provide both the general trend (with little details) over the entire time series or a set of very short trends that closely approximate the details of the time series. An example is discussed in connection with the next three figures.

FIGS. 63-65 are graphical representations 446, 448, 450 of partial trend analysis according to various aspects. The horizontal axis represents the day risk and the vertical axis represents the overall risk score. The graphs 446, 448, 450 show plots of a subject's raw PICO risk score along with three different Partial Trend approximations. The approximations were calculated using different maximum error values. Accordingly, FIG. 63 is a graphical representation 446 of a partial trend analysis of a patient (e.g., Lifenote Subject #3) with a partial trend fit using a maximum standard error (MSE) of 171 according to one aspect. FIG. 64 is a graphical representation 448 of a partial trend analysis of the same patient (e.g., Lifenote Subject #3) with a partial trend fit using a maximum MSE of 85. FIG. 65 is a graphical representation 450 of a partial trend analysis of the same patient (e.g., Lifenote Subject #3) with a partial trend fit using a maximum MSE of 17. As shown in FIGS. 63-65, the larger the allowed error in the fit, the smoother the partial trend fit becomes. The smaller allowed errors results in a greater number of partial trends which tend to capture the details in the time series. Thus the maximum allowed error serves to fine tune the level detail that is deemed important to the analysis.

FIG. 66 is a diagram 452 illustrating a partial trend analysis of a Lifenote data set according to one aspect where the horizontal axis represents the day index and the vertical axis represents the subject index. A lot of information can be gleaned by observing the partial trend slopes over a set of data. Here the MSE threshold is set at 103 (60% of maximum observed). Immediately it can be seen that subjects #1, #3 and #4 risk is trending upward toward the end of the data set. Although risk magnitude is also critical, it is not presented in this visualization.

FIG. 67 is diagram 454 illustrating a partial trend analysis of a Helius data set according to one aspect where the horizontal axis represents the day index and the vertical axis represents the subject index. Over shorter data sets the partial trend heat map immediately shows which subjects increased risk over the time period. Subjects with increasing risk at present (to the data set) are 12, 13, 22, 26, and 87. However, as noted on previous slide risk magnitude is critical. Another visualization provides a combination of both magnitude and slope.

In the context of risk magnitude versus risk trend based on a Lifenote data set, FIG. 68 is a graphical representation 456 of a 2-D scatter plot comparing the final risk trend magnitude and the risk trend slope over the last week of data according to one aspect. The horizontal axis represents final risk trend magnitude and the vertical axis represents weekly trend slope value. The risk trend magnitude data helps separate partial trend slope values and pinpoint which patient has higher risk values that are trending up. Subjects #3 and 4 appear to have significant risk scores that are strongly trending upwards. Plots for other data sets are not shown for conciseness and clarity of disclosure.

Within the context of risk magnitude versus risk trend based on a risk profile for an individual, FIG. 69 is a graphical representation 458 of an overall risk profile for an individual according to one aspect. For an individual subject it is illuminating to observe risk magnitude vs. trend for a few given time periods. As can be seen, for one of the subjects singled out in FIG. 68—Lifenote subject #4—the temporal Risk profile is shown in the graph of FIG. 69. The risk trend slope and magnitudes are plotted for periods of 28, 14, 7, and 3 days. It can be quickly determined if the Trend Slope/Magnitude is getting better or worse.

Proteus IEM/Receiver (Patch) System

FIG. 70 is conceptual illustration of a system 500 comprising an adhesive patch 502 to receive a signal from an IEM to confirm that the user 504 swallowed the medication 506 according to one aspect. Upon ingestion of the medication 506, the patch receives a signal from the IEM and records the ingestion event. The patch 502 is configured to communicate with other communication devices such as cell phones, smart phones, access points, Wi-Fi hot spots, or any suitable wireless communication system that can connect the patch 502 with a computer processing system to perform the data analysis discussed in connection with FIGS. 1-69.

Various enabling aspects of the IEM are illustrated in FIGS. 71-76 below. It is appreciated that the IEM may be a system which comprises a partial power source that can be activated when in contact with conductive liquid and is capable of controlling conductance to mark an event. In the instance where the system is used with the product that is ingested by the living organism, when the product that includes the system is taken or ingested, the device comes into contact with the conducting liquid of the body. When the system of the present disclosure comes into contact with the body fluid, a voltage potential is created and the system is activated. A portion of the power source is provided by the device, while another portion of the power source is provided by the conducting fluid. That is, once ingested, the system comes into contact with body liquids and the system is activated. The system uses the voltage potential difference to power up and thereafter modulates conductance to create a unique and identifiable current signature. Upon activation, the system controls the conductance and, hence, current flow to produce the current signature. In addition, various enabling aspects of the receiver/detector are illustrated in FIGS. 77-82 below.

With reference to FIG. 71, there is shown one aspect of an ingestible device event indicator system with dissimilar metals positioned on opposite ends as system 2630. The system 2630 can be used in association with any pharmaceutical product, as mentioned above, to determine when a patient takes the pharmaceutical product. As indicated above, the scope of the present disclosure is not limited by the environment and the product that is used with the system 2630. For example, the system 2630 may be placed within a capsule and the capsule is placed within the conducting liquid. The capsule would then dissolve over a period of time and release the system 2630 into the conducting liquid. Thus, in one aspect, the capsule would contain the system 2630 and no product. Such a capsule may then be used in any environment where a conducting liquid is present and with any product. For example, the capsule may be dropped into a container filled with jet fuel, salt water, tomato sauce, motor oil, or any similar product. Additionally, the capsule containing the system 2630 may be ingested at the same time that any pharmaceutical product is ingested in order to record the occurrence of the event, such as when the product was taken.

In the specific example of the system 2630 combined with the pharmaceutical product, as the product or pill is ingested, the system 2630 is activated. The system 2630 controls conductance to produce a unique current signature that is detected, thereby signifying that the pharmaceutical product has been taken. The system 2630 includes a framework 2632. The framework 2632 is a chassis for the system 2630 and multiple components are attached to, deposited upon, or secured to the framework 2632. In this aspect of the system 2630, a digestible material 2634 is physically associated with the framework 2632. The material 2634 may be chemically deposited on, evaporated onto, secured to, or built-up on the framework all of which may be referred to herein as "deposit" with respect to the framework 2632. The material 2634 is deposited on one side of the framework 2632. The materials of interest that can be used as material 2634 include, but are not limited to: Cu or CuI. The material 2634 is deposited by physical vapor deposition, electrodeposition, or plasma deposition, among other protocols. The material 2634 may be from about 0.05 to about 500 μm thick, such as from about 5 to about 100 μm thick. The shape is controlled by shadow mask deposition, or photolithography and etching. Additionally, even though only one region is shown for depositing the material, each system 2630 may contain two or more electrically unique regions where the material 2634 may be deposited, as desired.

At a different side, which is the opposite side as shown in FIG. 71, another digestible material 2636 is deposited, such that materials 2634 and 2636 are dissimilar. Although not shown, the different side selected may be the side next to the side selected for the material 2634. The scope of the present disclosure is not limited by the side selected and the term "different side" can mean any of the multiple sides that are different from the first selected side. Furthermore, even though the shape of the system is shown as a square, the shape maybe any geometrically suitable shape. Material 2634 and 2636 are selected such that they produce a voltage potential difference when the system 2630 is in contact with conducting liquid, such as body fluids. The materials of interest for material 2636 include, but are not limited to: Mg, Zn, or other electronegative metals. As indicated above with respect to the material 2634, the material 2636 may be chemically deposited on, evaporated onto, secured to, or built-up on the framework. Also, an adhesion layer may be necessary to help the material 2636 (as well as material 2634 when needed) to adhere to the framework 2632. Typical adhesion layers for the material 2636 are Ti, TiW, Cr or similar material. Anode material and the adhesion layer may be deposited by physical vapor deposition, electrodeposition or plasma deposition. The material 2636 may be from about 0.05 to about 500 μm thick, such as from about 5 to about 100 μm thick. However, the scope of the present disclosure is not limited by the thickness of any of the materials nor by the type of process used to deposit or secure the materials to the framework 2632.

Thus, when the system 2630 is in contact with the conducting liquid, a current path, an example is shown in FIG. 73, is formed through the conducting liquid between material 2634 and 2636. A control device 2638 is secured to the framework 2632 and electrically coupled to the materials 2634 and 2636. The control device 2638 includes electronic circuitry, for example control logic that is capable of controlling and altering the conductance between the materials 2634 and 2636.

The voltage potential created between the materials 2634 and 2636 provides the power for operating the system as well as produces the current flow through the conducting fluid and the system. In one aspect, the system operates in direct current mode. In an alternative aspect, the system controls the direction of the current so that the direction of current is reversed in a cyclic manner, similar to alternating current. As the system reaches the conducting fluid or the electrolyte, where the fluid or electrolyte component is provided by a physiological fluid, e.g., stomach acid, the path for current flow between the materials 2634 and 2636 is completed external to the system 2630; the current path through the system 2630 is controlled by the control device 2638. Completion of the current path allows for the current to flow and in turn a receiver can detect the presence of the current and recognize that the system 2630 has been activated and the desired event is occurring or has occurred.

In one aspect, the two materials 2634 and 2636 are similar in function to the two electrodes needed for a direct current power source, such as a battery. The conducting liquid acts as the electrolyte needed to complete the power source. The completed power source described is defined by the physical chemical reaction between the materials 2634 and 2636 of the system 2630 and the surrounding fluids of the body. The completed power source may be viewed as a power source that exploits reverse electrolysis in an ionic or a conductive solution such as gastric fluid, blood, or other bodily fluids and some tissues. Additionally, the environment may be something other than a body and the liquid may be any conducting liquid. For example, the conducting fluid may be salt water or a metallic based paint.

In certain aspects, these two materials are shielded from the surrounding environment by an additional layer of material. Accordingly, when the shield is dissolved and the two dissimilar materials are exposed to the target site, a voltage potential is generated.

Referring again to FIG. 71, the materials 2634 and 2636 provide the voltage potential to activate the control device 2638. Once the control device 2638 is activated or powered up, the control device 2638 can alter conductance between the materials 2634 and 2636 in a unique manner. By altering the conductance between materials 2634 and 2636, the control device 2638 is capable of controlling the magnitude of the current through the conducting liquid that surrounds the system 2630. This produces a unique current signature that can be detected and measured by a receiver, which can be positioned internal or external to the body. In addition to controlling the magnitude of the current path between the materials, non-conducting materials, membrane, or "skirt" are used to increase the "length" of the current path and, hence, act to boost the conductance path, as disclosed in the U.S. patent application Ser. No. 12/238,345 filed Sep. 25, 2608, published 2609-0082645, and entitled, "In-Body Device with Virtual Dipole Signal Amplification", the entire content of which is incorporated herein by reference. Alternatively, throughout the disclosure herein, the terms "non-conducting material," "membrane," and "skirt" are interchangeably with the term "current path extender" without impacting the scope or the present aspects and the claims herein. The skirt, shown in portion at 2635 and 2637, respectively, may be associated with, e.g., secured to, the framework 2632. Various shapes and configurations for the skirt are contemplated as within the scope of the present disclosure. For example, the system 2630 may be surrounded entirely or partially by the skirt and the skirt maybe positioned along a central axis of the system 2630 or off-center relative to a central axis. Thus, the scope of the present disclosure as claimed herein is not limited by the shape or size of the skirt. Furthermore, in other aspects, the materials 2634 and 2636 may be separated by one skirt that is positioned in any defined region between the materials 2634 and 2636.

Referring now to FIG. 72, in another aspect of an ingestible device is shown in more detail as system 2640. The system 2640 includes a framework 2642. The framework 2642 is similar to the framework 2632 of FIG. 26. In this aspect of the system 2640, a digestible or dissolvable material 2644 is deposited on a portion of one side of the framework 2642. At a different portion of the same side of the framework 2642, another digestible material 2646 is deposited, such that materials 2644 and 2646 are dissimilar. More specifically, material 2644 and 2646 are selected such that they form a voltage potential difference when in contact with a conducting liquid, such as body fluids. Thus, when the system 2640 is in contact with and/or partially in contact with the conducting liquid, then a current path, an example is shown in FIG. 28, is formed through the conducting liquid between material 2644 and 2646. A control device 2648 is secured to the framework 2642 and electrically coupled to the materials 2644 and 2646. The control device 2648 includes electronic circuitry that is capable of controlling part of the conductance path between the materials 2644 and 2646. The materials 2644 and 2646 are separated by a non-conducting skirt 2649. Various examples of the skirt 2649 are disclosed in U.S. Provisional Application No. 61/173,511 filed on Apr. 28, 2609 and entitled "HIGHLY RELIABLE INGESTIBLE EVENT MARKERS AND METHODS OF USING SAME" and U.S. Provisional Application No. 61/173,564 filed on Apr. 28, 2609 and entitled "INGESTIBLE EVENT MARKERS HAVING SIGNAL AMPLIFIERS THAT COMPRISE AN ACTIVE AGENT"; as well as U.S. application Ser. No. 12/238,345 filed Sep. 25, 2608, published 2609-0082645, entitled "IN-BODY DEVICE WITH VIRTUAL DIPOLE SIGNAL AMPLIFICATION"; the entire disclosure of each is incorporated herein by reference.

Once the control device 2648 is activated or powered up, the control device 2648 can alter conductance between the materials 2644 and 2646. Thus, the control device 2648 is capable of controlling the magnitude of the current through the conducting liquid that surrounds the system 2640. As indicated above with respect to system 2630, a unique current signature that is associated with the system 2640 can be detected by a receiver to mark the activation of the system 2640. In order to increase the "length" of the current path the size of the skirt 2649 is altered. The longer the current path, the easier it may be for the receiver to detect the current.

Referring now to FIG. 73, the system 2630 of FIG. 71 is shown in an activated state and in contact with conducting liquid. The system 2630 is grounded through ground contact 2652. The system 2630 also includes a sensor module 2674, which is described in greater detail with respect to FIG. 72. Ion or current paths 2650 form between material 2634 to material 2636 through the conducting fluid in contact with the system 2630. The voltage potential created between the material 2634 and 2636 is created through chemical reactions between materials 2634/2636 and the conducting fluid.

FIG. 74 shows an exploded view of the surface of the material 2634. The surface of the material 2634 is not planar, but rather an irregular surface 2654 as shown. The irregular surface 2654 increases the surface area of the material and, hence, the area that comes in contact with the conducting fluid.

In one aspect, at the surface of the material 2634, there is chemical reaction between the material 2634 and the surrounding conducting fluid such that mass is released into the conducting fluid. The term "mass" as used herein refers to protons and neutrons that form a substance. One example includes the instant where the material is CuCl and when in contact with the conducting fluid, CuCl becomes Cu (solid) and Cl— in solution. The flow of ions into the conduction fluid is depicted by the ion paths 2650. In a similar manner, there is a chemical reaction between the material 2636 and the surrounding conducting fluid and ions are captured by the material 2636. The release of ions at the material 2634 and capture of ion by the material 2636 is collectively referred to as the ionic exchange. The rate of ionic exchange and, hence the ionic emission rate or flow, is controlled by the control device 2638. The control device 2638 can increase or decrease the rate of ion flow by altering the conductance, which alters the impedance, between the materials 2634 and 2636. Through controlling the ion exchange, the system 2630 can encode information in the ionic exchange process. Thus, the system 2630 uses ionic emission to encode information in the ionic exchange.

The control device 2638 can vary the duration of a fixed ionic exchange rate or current flow magnitude while keeping the rate or magnitude near constant, similar to when the frequency is modulated and the amplitude is constant. Also, the control device 2638 can vary the level of the ionic exchange rate or the magnitude of the current flow while keeping the duration near constant. Thus, using various combinations of changes in duration and altering the rate or magnitude, the control device 2638 encodes information in the current flow or the ionic exchange. For example, the control device 2638 may use, but is not limited to any of the following techniques namely, Binary Phase-Shift Keying (PSK), Frequency modulation, Amplitude modulation, on-off keying, and PSK with on-off keying.

As indicated above, the various aspects disclosed herein, such as systems 2630 and 2640 of FIGS. 71 and 72, respectively, include electronic components as part of the control device 2638 or the control device 2648. Components that may be present include but are not limited to: logic and/or memory elements, an integrated circuit, an inductor, a resistor, and sensors for measuring various parameters. Each component may be secured to the framework and/or to another component. The components on the surface of the support may be laid out in any convenient configuration. Where two or more components are present on the surface of the solid support, interconnects may be provided.

As indicated above, the system, such as system 2630 and 2640, control the conductance between the dissimilar materials and, hence, the rate of ionic exchange or the current flow. Through altering the conductance in a specific manner the system is capable of encoding information in the ionic exchange and the current signature. The ionic exchange or the current signature is used to uniquely identify the specific system. Additionally, the systems 2630 and 2640 are capable of producing various different unique exchanges or signatures and, thus, provide additional information. For example, a second current signature based on a second conductance alteration pattern may be used to provide additional information, which information may be related to the physical environment. To further illustrate, a first current signature may be a very low current state that maintains an oscillator on the chip and a second current signature may be a current state at least a factor of ten higher than the current state associated with the first current signature.

Referring now to FIG. 76, a block diagram representation of the control device 2638 is shown. The device 2638 includes a control module 2662, a counter or clock 2664, and a memory 2666. Additionally, the device 2638 is shown to include a sensor module 2672 as well as the sensor module 2674, which was referenced in FIG. 73. The control module 2662 has an input 2668 electrically coupled to the material 2634 and an output 2670 electrically coupled to the material 2636. The control module 2662, the clock 2664, the memory 2666, and the sensor modules 2672/2674 also have power inputs (some not shown). The power for each of these components is supplied by the voltage potential produced by the chemical reaction between materials 2634 and 2636 and the conducting fluid, when the system 2630 is in contact with the conducting fluid.

The control module 2662 controls the conductance through logic that alters the overall impedance of the system 2630. The control module 2662 is electrically coupled to the clock 2664. The clock 2664 provides a clock cycle to the control module 2662. Based upon the programmed characteristics of the control module 2662, when a set number of clock cycles have passed, the control module 2662 alters the conductance characteristics between materials 2634 and 2636. This cycle is repeated and thereby the control device 2638 produces a unique current signature characteristic. The control module 2662 is also electrically coupled to the memory 2666. Both the clock 2664 and the memory 2666 are powered by the voltage potential created between the materials 2634 and 2636.

The control module 2662 is also electrically coupled to and in communication with the sensor modules 2672 and 2674. In the aspect shown, the sensor module 2672 is part of the control device 2638 and the sensor module 2674 is a separate component. In alternative aspects, either one of the sensor modules 2672 or 2674 can be used without the other, and the scope of the present disclosure is not limited by the structural or functional location of the sensor modules 2672 or 2674. Additionally, any component of the system 2630 may be functionally or structurally moved, combined, or repositioned without limiting the scope of the present disclosure as claimed. Thus, it is possible to have one single structure, for example a processor, which is designed to perform the functions of all of the following modules: the control module 2662, the clock 2664, the memory 2666, and the sensor module 2672 or 2674. On the other hand, it is also within the scope of the present disclosure to have each of these functional components located in independent structures that are linked electrically and able to communicate.

Referring again to FIG. 76, the sensor modules 2672 or 2674 can include any of the following sensors: temperature, pressure, pH level, and conductivity. In one aspect, the sensor modules 2672 or 2674 gather information from the environment and communicate the analog information to the control module 2662. The control module then converts the analog information to digital information and the digital information is encoded in the current flow or the rate of the transfer of mass that produces the ionic flow. In another aspect, the sensor modules 2672 or 2674 gather information from the environment and convert the analog information to digital information and then communicate the digital information to control module 2662. In the aspect shown in FIG. 73, the sensor modules 2674 is shown as being electrically coupled to the material 2634 and 2636 as well as the control device 2638. In another aspect, as shown in FIG. 76, the sensor module 2674 is electrically coupled to the control device 2638 at a connection. The connection acts as both a source for power supply to the sensor module 2674 and a communication channel between the sensor module 2674 and the control device 2638.

Referring now to FIG. 75, the system 2630 includes a pH sensor module 2676 connected to a material 2639, which is selected in accordance with the specific type of sensing function being performed. The pH sensor module 2676 is also connected to the control device 2638. The material 2639 is electrically isolated from the material 2634 by a non-conductive barrier 2655. In one aspect, the material 2639 is platinum. In operation, the pH sensor module 2676 uses the voltage potential difference between the materials 2634/2636. The pH sensor module 2676 measures the voltage potential difference between the material 2634 and the material 2639 and records that value for later comparison. The pH sensor module 2676 also measures the voltage potential difference between the material 2639 and the material 2636 and records that value for later comparison. The pH sensor module 2676 calculates the pH level of the surrounding environment using the voltage potential values. The pH sensor module 2676 provides that information to the control device 2638. The control device 2638 varies the rate of the transfer of mass that produces the ionic transfer and the current flow to encode the information relevant to the pH level in the ionic transfer, which can be detected by a receiver. Thus, the system 2630 can determine and provide the information related to the pH level to a source external to the environment.

As indicated above, the control device 2638 can be programmed in advance to output a pre-defined current signature. In another aspect, the system can include a receiver system that can receive programming information when the system is activated. In another aspect, not shown, the switch 2664 and the memory 2666 can be combined into one device.

In addition to the above components, the system 2630 may also include one or other electronic components. Electrical components of interest include, but are not limited to: additional logic and/or memory elements, e.g., in the form of an integrated circuit; a power regulation device, e.g., battery, fuel cell or capacitor; a sensor, a stimulator, etc.; a signal transmission element, e.g., in the form of an antenna, electrode, coil, etc.; a passive element, e.g., an inductor, resistor, etc.

FIG. 77 provides a functional block diagram of how a receiver may implement a coherent demodulation protocol, according to one aspect of the disclosure. It should be noted that only a portion of the receiver is shown in FIG. 77. FIG. 77 illustrates the process of mixing the signal down to baseband once the carrier frequency (and carrier signal mixed down to carrier offset) is determined. A carrier signal 3221 is mixed with a second carrier signal 3222 at mixer 3223. A narrow low-pass filter 3220 is applied of appropriate bandwidth to reduce the effect of out-of-bound noise. Demodulation occurs at functional blocks 3225 in accordance with the coherent demodulation scheme of the present disclosure. The unwrapped phase 3230 of the complex signal is determined. An optional third mixer stage, in which the phase evolution is used to estimate the frequency differential between the calculated and real carrier frequency can be applied. The structure of the packet is then leveraged to determine the beginning of the coding region of the BPSK signal at block 3240. Mainly, the presence of the sync header, which appears as an FM porch in the amplitude signal of the complex demodulated signal is used to determine the starting bounds of the packet. Once the starting point of the packet is determined the signal is rotated at block 3250 on the IQ plane and standard bit identification and eventually decoded at block 3260.

In addition to demodulation, the transbody communication module may include a forward error correction module, which module provides additional gain to combat interference from other unwanted signals and noise. Forward error correction functional modules of interest include those described in PCT Application Serial No. PCT/US2007/024325 published as WO/2008/063626; the disclosure of which is herein incorporated by reference. In some instances, the forward error correction module may employ any convenient protocol, such as Reed-Solomon, Golay, Hamming, BCH, and Turbo protocols to identify and correct (within bounds) decoding errors.

Receivers of the disclosure may further employ a beacon functionality module. In various aspects, the beacon switching module may employ one or more of the following: a beacon wakeup module, a beacon signal module, a wave/frequency module, a multiple frequency module, and a modulated signal module.

The beacon switching module may be associated with beacon communications, e.g., a beacon communication channel, a beacon protocol, etc. For the purpose of the present disclosure, beacons are typically signals sent either as part of a message or to augment a message (sometimes referred to herein as "beacon signals"). The beacons may have well-defined characteristics, such as frequency. Beacons may be detected readily in noisy environments and may be used for a trigger to a sniff circuit, such as described below.

In one aspect, the beacon switching module may comprise the beacon wakeup module, having wakeup functionality. Wakeup functionality generally comprises the functionality to operate in high power modes only during specific times, e.g., short periods for specific purposes, to receive a signal, etc. An important consideration on a receiver portion of a system is that it be of low power. This feature may be advantageous in an implanted receiver, to provide for both small size and to preserve a long-functioning electrical supply from a battery. The beacon switching module enables these advantages by having the receiver operate in a high power mode for very limited periods of time. Short duty cycles of this kind can provide optimal system size and energy draw features.

In practice, the receiver may "wake up" periodically, and at low energy consumption, to perform a "sniff function" via, for example, a sniff circuit. For the purpose of the present application, the term "sniff function" generally refers to a short, low-power function to determine if a transmitter is present. If a transmitter signal is detected by the sniff function, the device may transition to a higher power communication decode mode. If a transmitter signal is not present, the receiver may return, e.g., immediately return, to sleep mode. In this manner, energy is conserved during relatively long periods when a transmitter signal is not present, while high-power capabilities remain available for efficient decode mode operations during the relatively few periods when a transmit signal is present. Several modes, and combination thereof, may be available for operating the sniff circuit. By matching the needs of a particular system to the sniff circuit configuration, an optimized system may be achieved.

Another view of a beacon module is provided in the functional block diagram shown in FIG. 78. The scheme outlined in FIG. 78 outlines one technique for identifying a valid beacon. The incoming signal 3360 represents the signals received by electrodes, bandpass filtered (such as from 10 KHz to 34 KHz) by a high frequency signaling chain (which encompasses the carrier frequency), and converted from analog to digital. The signal 3360 is then decimated at block 3361 and mixed at the nominal drive frequency (such as, 12.5 KHz, 20 KHz, etc.) at mixer 3362. The resulting signal is decimated at block 3364 and low-pass filtered (such as 5 KHz BW) at block 3365 to produce the carrier signal mixed down to carrier offset-signal 3369. Signal 3369 is further processed by blocks 3367 (fast Fourier transform and then detection of two strongest peaks) to provide the true carrier frequency signal 3368. This protocol allows for accurate determination of the carrier frequency of the transmitted beacon.

FIG. 79 provides a block functional diagram of an integrated circuit component of a signal receiver according to an aspect of the disclosure. In FIG. 79, a receiver 3700 includes electrode input 3710. Electrically coupled to the electrode input 3710 are transbody conductive communication module 3720 and physiological sensing module 3730. In one aspect, transbody conductive communication module 3720 is implemented as a high frequency (HF) signal chain and physiological sensing module 3730 is implemented as a low frequency (LF) signal chain. Also shown are CMOS temperature sensing module 3740 (for detecting ambient temperature) and a 3-axis accelerometer 3750. Receiver 3700 also includes a processing engine 3760 (for example, a microcontroller and digital signal processor), non-volatile memory 3770 (for data storage) and wireless communication module 3780 (for data transmission to another device, for example in a data upload action).

FIG. 80 provides a more detailed block diagram of a circuit configured to implement the block functional diagram of the receiver depicted in FIG. 79, according to one aspect of the disclosure. In FIG. 80, a receiver 3800 includes electrodes e1, e2 and e3 (3811, 3812 and 3813) which, for example, receive the conductively transmitted signals by an IEM and/or sense physiological parameters or biomarkers of interest. The signals received by the electrodes 3811, 3812, and 3813 are multiplexed by multiplexer 3820 which is electrically coupled to the electrodes.

Multiplexer 3820 is electrically coupled to both high band pass filter 3830 and low band pass filter 3840. The high and low frequency signal chains provide for programmable gain to cover the desired level or range. In this specific aspect, high band pass filter 3830 passes frequencies in the 10 KHz to 34 KHz band while filtering out noise from out-of-band frequencies. This high frequency band may vary, and may include, for example, a range of 3 KHz to 300 KHz. The passing frequencies are then amplified by amplifier 3832 before being converted into a digital signal by converter 3834 for input into high power processor 3880 (shown as a DSP) which is electrically coupled to the high frequency signal chain.

Low band pass filter 3840 is shown passing lower frequencies in the range of 0.5 Hz to 150 Hz while filtering out out-of-band frequencies. The frequency band may vary, and may include, for example, frequencies less than 300 Hz, such as less than 200 Hz, including less than 150 Hz. The passing frequency signals are amplified by amplifier 3842. Also shown is accelerometer 3850 electrically coupled to second multiplexer 3860. Multiplexer 3860 multiplexes the signals from the accelerometer with the amplified signals from amplifier 3842. The multiplexed signals are then converted to digital signals by converter 3864 which is also electrically coupled to low power processor 3870.

In one aspect, a digital accelerometer (such as one manufactured by Analog Devices), may be implemented in place of accelerometer 3850. Various advantages may be achieved by using a digital accelerometer. For example, because the signals the digital accelerometer would produce signals already in digital format, the digital accelerometer could bypass converter 3864 and electrically couple to the low power microcontroller 3870—in which case multiplexer 3860 would no longer be required. Also, the digital signal may be configured to turn itself on when detecting motion, further conserving power. In addition, continuous step counting may be implemented. The digital accelerometer may include a FIFO buffer to help control the flow of data sent to the low power processor 3870. For instance, data may be buffered in the FIFO until full, at which time the processor may be triggered to turn awaken from an idle state and receive the data.

Low power processor 3870 may be, for example, an MSP430 microcontroller from Texas Instruments. Low power processor 3870 of receiver 3800 maintains the idle state, which as stated earlier, requires minimal current draw—e.g., 10 µA or less, or 1 µA or less.

High power processor 3880 may be, for example, a VC5509 digital signal process from Texas Instruments. The high power processor 3880 performs the signal processing actions during the active state. These actions, as stated earlier, require larger amounts of current than the idle state—e.g., currents of 30 µA or more, such as 50 µA or more—and may include, for example, actions such as scanning for conductively transmitted signals, processing conductively transmitted signals when received, obtaining and/or processing physiological data, etc.

The receiver may include a hardware accelerator module to process data signals. The hardware accelerator module may be implemented instead of, for example, a DSP. Being a more specialized computation unit, it performs aspects of the signal processing algorithm with fewer transistors (less cost and power) compared to the more general purpose DSP. The blocks of hardware may be used to "accelerate" the performance of important specific function(s). Some architectures for hardware accelerators may be "programmable" via microcode or VLIW assembly. In the course of use, their functions may be accessed by calls to function libraries.

The hardware accelerator (HWA) module comprises an HWA input block to receive an input signal that is to be processed and instructions for processing the input signal; and, an HWA processing block to process the input signal according to the received instructions and to generate a resulting output signal. The resulting output signal may be transmitted as needed by an HWA output block.

Also shown in FIG. 80 is flash memory 3890 electrically coupled to high power processor 3880. In one aspect, flash memory 3890 may be electrically coupled to low power processor 3870, which may provide for better power efficiency.

Wireless communication element 3895 is shown electrically coupled to high power processor 3880 and may include, for example, a BLUETOOTH™ wireless communication transceiver. In one aspect, wireless communication element 3895 is electrically coupled to high power processor 3880. In another aspect, wireless communication element 3895 is electrically coupled to high power processor 3880 and low power processor 3870. Furthermore, wireless communication element 3895 may be implemented to have its own power supply so that it may be turned on and off independently from other components of the receiver—e.g., by a microprocessor.

FIG. 81 provides a view of a block diagram of hardware in a receiver according to an aspect of the disclosure related to the high frequency signal chain. In FIG. 81, receiver 3900 includes receiver probes (for example in the form of electrodes 3911, 3912 and 3913) electrically coupled to multiplexer 3920. Also shown are high pass filter 3930 and low pass filter 3940 to provide for a band pass filter which eliminates any out-of-band frequencies. In the aspect shown, a band pass of 10 KHz to 34 KHz is provided to pass carrier signals falling within the frequency band. Example carrier frequencies may include, but are not limited to, 12.5 KHz and 20 KHz. One or more carriers may be present. In addition, the receiver 3900 includes analog to digital converter 3950—for example, sampling at 500 KHz. The digital signal can thereafter be processed by the DSP. Shown in this aspect is DMA to DSP unit 3960 which sends the digital signal to dedicated memory for the DSP. The direct memory access provides the benefit of allowing the rest of the DSP to remain in a low power mode.

As stated earlier, for each receiver state, the high power functional block may be cycled between active and inactive states accordingly. Also, for each receiver state, various receiver elements (such as circuit blocks, power domains within processor, etc.) of a receiver may be configured to independently cycle from on and off by the power supply module. Therefore, the receiver may have different configurations for each state to achieve power efficiency.

An example of a system of the disclosure is shown in FIG. 82. In FIG. 82, system 4000 includes a pharmaceutical composition 4010 that comprises an IEM. Also present in the system 4000 is signal receiver 4020. Signal receiver 4020 is configured to detect a signal emitted from the identifier of the IEM 4010. Signal receiver 4020 also includes physiologic sensing capability, such as ECG and movement sensing capability. Signal receiver 4020 is configured to transmit data to a patient's an external device or PDA 4030 (such as a smart phone or other wireless communication enabled device), which in turn transmits the data to a server 4040. Server 4040 may be configured as desired, e.g., to provide for patient directed permissions. For example, server 4040 may be configured to allow a family caregiver 4050 to participate in the patient's therapeutic regimen, e.g., via an interface (such as a web interface) that allows the family caregiver 4050 to monitor alerts and trends generated by the server 4040, and provide support back to the patient, as indicated by arrow 4060. The server 4040 may also be configured to provide responses directly to the patient, e.g., in the form of patient alerts, patient incentives, etc., as indicated by arrow 4065 which are relayed to the patient via PDA 4030. Server 4040 may also interact with a health care professional (e.g., RN, physician) 4055, which can use data processing algorithms to obtain measures of patient health and compliance, e.g., wellness index summaries, alerts, cross-patient benchmarks, etc., and provide informed clinical communication and support back to the patient, as indicated by arrow 4080.

FIG. 83 illustrates one aspect of a personal communication system 1000 for obtaining patient physiological and IEM system information into a computer system according to one aspect. As illustrated in FIG. 83, a receiver, otherwise referred to herein as a body-associated personal communicator 1004 or patch, is positioned on a living subject 1002.

The living subject 1002 may be a human or non-human being. In various aspects, the body-associated personal communicator 1004 may be realized in many forms and configurations including sensor-enabled patches, watches, and jewelry, as shown in FIG. 83, for example, as well as a bandage with an adhesive portion, wristbands, earrings, bracelets, rings, pendants, clothing, undergarments, hats, caps, scarves, pins, accessories, belts, shoes, eyeglasses, contact lenses, hearing-aides, subcutaneous implants, and other devices that are wearable, implantable, or semi-implantable on or in the living subject 1002 without limitation. The body-associated personal communicator 1004 is configured to communicate with the living subject 1002 and an external local node 1006. The external local node 1006 is configured to communicate with a remote node 1010 via a network 1008. In one aspect, the body-associated personal communicator 1004 is configured to communicate with the remote node 1010 directly. It will be appreciated that in the context of the present disclosure, communication is intended to encompass communications to and from the personal communicator 1004 and the external local node 1006. Likewise, communication is intended to encompass communications to and from the body-associated personal communicator 1004 and the remote node 1010 as well as communications to and from the external local node 1006 and the remote node 1010.

The body-associated personal communicator 1004 may comprise any number of distinct physiologic parameter or biomarker collecting and/or sensing capabilities. The number of distinct parameters or biomarker collecting and/or sensing capabilities may vary e.g., one or more, two or more, three or more, four or more, five or more, ten or more, and so on. In certain configurations, the body-associated personal communicator 1004 comprises one or more active components that are able to dynamically monitor and record individual physiologic parameters and/or biomarkers associated with the living subject 1002. Such components include, without limitation, sensors, electronic recording devices, processors, memory, communication components. In one aspect, the body-associated personal communicator 1004 may include an on-board battery to supply electrical power to the active components. The physiologic parameter or biomarker sensing abilities may include sensing cardiodata, including heart rate, (ECG, and the like, respiration rate, temperature, pressure, chemical composition of fluid, e.g., analyte in blood, fluid state, blood flow rate, physical activity, sleep, accelerometer motion data, without limitation, for example.

In one aspect, the body-associated personal communicator 1004 provides specific information about the physiologic state of the subject 1002. In another aspect, some of this information may be derived from sensors embedded in the body-associated personal communicator 1004. The subject 1002 may obtain the body-associated personal communicator 1004 with a prescription, for example, and then wear the body-associated personal communicator 1004 for a prescribed period, e.g., hours, days, weeks, months, years.

In one aspect, the body-associated personal communicator 1004 includes, is configured to (a) monitor and record individual physiology, e.g., physical activity, heart rate, respiration, temperature, sleep, etc., of the living subject 1002 and (b) communicate these parameters beyond the body of the living subject 1002 to other client devices, e.g., mobile phones, computers, internet servers, etc., in order to (c) enable support and collaboration for fitness, wellbeing, disease management, sport, entertainment, gaming, and other applications on a social media platform. A challenge for such body-associated personal communicators 104 is creating a compelling rationale for the individual 1002 to wear or use the body-associated personal communicator 1004 on a continuous basis—for example, to apply an adhesive bandage-based body-associated personal communicator 1004 to their skin for weeks, months and potentially years and accept the possibility of its inconveniences and limitations, such as (i) potential skin irritation, (ii) the burden of frequent application and removal, and (iii) a feeling of intrusiveness into the wearer's daily life. An opportunity for the personal communicator 1004 is to exploit fundamental "intimacy" advantages they have over other sensor-enabled and communication devices that are not worn on or in the body—a body-associated personal communicator 1004 interface with the individual 1002 is by definition highly personal and tangible, with the ability to have private, communication between the individual and the personal communicator (leveraging physical, tactile "body language" or other signals), where the communication is substantially undetectable by others. In this manner, the body-associated personal communicator 1004 may enable product and service possibilities not feasible with other approaches. The body language opportunity seeks to overcome at least some of the challenges and burdens of the body-associated personal communicator 1004 to create a compelling rationale to make the body-associated personal communicator 1004 as indispensable to a consumer as the mobile phone as an extension of their mind and body. In one aspect, discreet communications between the body-associated personal communicator 1004 and the living subject 1002 can be auditory via a small earpiece placed inside the ear canal, or visual via images projected on specialized eye glasses worn by living subject 1002. In other aspects, discreet modes of communication between the living subject 1002 and the personal communicator 1004 include, without limitation, visual, auditory, vibratory, tactile, olfactory, and taste as described in the form of illustrative examples hereinbelow.

In one aspect, the body-associated personal communicator 1004, for example a sensor patch that adheres to the skin of an individual such as the living subject 1002, communicates with its wearer by sending and receiving tactile or other signals. The default settings may be modified such that the body-associated personal communicator 1004 discreetly vibrates or pulses in a specific manner or pattern, e.g., time or space based, to remind the subject 1002 of important events or to communicate important personalized messages to the wearer. The default settings also may be modified such that the subject 1002 can transmit and record meaningful inputs and messages to the body-associated personal communicator 1004 by communicating a simple language of finger taps, jiggles, scratches or other physical inputs initiated by the subject 1002. Through the body-associated personal communicator 1004 communications architecture, e.g., a BLUETOOTH™ or other communication links to other devices beyond the body, the composite set of sensed physiology, tactile inputs, and outputs can be transmitted to other individuals, groups, caregivers, and related products, e.g., online games, of the subject's 1002 choosing via the external local node 1006, network 1008, and/or the remote node 1010. The features of the body-associated personal communicator 1004 are based on a sustained behavior change mechanism and it increases the value and potential of body-associated personal communicators 1004 and the likelihood that consumers will seek out, use, and benefit from such body-associated personal communicators 1004.

In-body communications include any communication of data or information via the body of the living subject 1002, i.e., communication via or associated with inter-body aspects, intra-body aspects, and a combination of the same. For example, inter-body aspects include communications associated with devices designed to attach to a body surface. Intra-body aspects include communications associated with data generated from within the body, e.g., by the body itself or by a device implanted, ingested, or otherwise locatable in, or partially in, the body. For example, intra-body communications are disclosed in the U.S. Provisional Patent Application No. 61/251,088, the entire content of which is hereby incorporated by reference.

Communications include and/or may be associated with software, hardware, circuitry, various devices, and combinations thereof.

The devices include devices associated with physiologic data generation, transmission, reception, communication. The devices further include various implantable, ingestible, insertable, and/or attachable devices associated with the human body or other living organisms. The devices still further include multimedia devices such as telephones, stereos, audio players, PDAs, handheld devices, and multimedia players.

The system for incorporating physiologic data enables exchange, transmission, receipt, manipulation, management, storage, and other activities and events related to physiologic data. Such activities and events may be contained within the system for incorporating physiologic data, partially integrated with the system for incorporating physiologic data, or associated with externalities, e.g., activities, systems, components, and the like which are external to the system for incorporating physiologic data.

The physiologic data environment includes any source of information or data, including remote computer systems, local computer devices. The information or data may comprise physiologic data in whole or in part, e.g., aggregated or generated with other types of data. The physiologic data may be pure or refined, e.g., physiologic data from which inferences are drawn.

As shown in FIG. 83, the body-associated personal communicator 1004, regardless of form factor or implementation is in communication with an external local node 1006. In one aspect, the body-associated personal communicator 1004 includes the capability of communicating, e.g., receiving, transmitting, generating, and recording data directly or indirectly from the living subject 1002. Although the data may include physiologic data, it is not limited as such. Any data of a physiologic nature may be associated with the living subject 1002. The physiologic data may include, for example, heart rate, heart rate variability, respiration rate, body temperature, temperature of local environment, three-axis measurement of activity and torso angle, as well as other physiologic data, metrics, inertial measurements comprising at least an accelerometer, a gyroscope, and a magnetometer, and indicators associated with one or more individuals. The physiologic data may be communicated at various times or time intervals to the external local node 1006. For example, the communication may be real-time, i.e., in close temporal proximity to a time in which the physiologic data were generated, measured, ascertained, or on an historical basis, i.e., in far temporal proximity to a time in which the physiologic data was generated, measured, ascertained. In various aspects, the physiologic data may be associated with a variety of devices, e.g., cardiac device.

In one aspect, the external local node 1006 may be configured as a communication hub and may include any hardware device, software, and/or communications component(s), as well as systems, subsystems, and combinations of the same which generally function to communicate physiologic and non-physiologic data between the personal communicator 1004 and the external local node 1006. Communication of the data includes receiving, storing, manipulating, displaying, processing, and/or transmitting the data to the remote node 1010 via the network 1008.

In various aspects, the external local node 1006 also functions to communicate, e.g., receive and transmit, non-physiologic data. Example of non-physiologic data include gaming rules and data generated by a separate cardiac-related device such as an implanted pacemaker and communicated to the hub directly or indirectly, e.g., via the personal communicator 104.

Broad categories of external local nodes 1006 include, for example, base stations, personal communication devices, handheld devices, and mobile telephones. In various aspects, the external local node 1006 may be implemented as a handheld portable device, computer, mobile telephone, sometimes referred to as a smartphone, tablet personal computer (PC), kiosk, desktop computer, laptop computer, game console, or any combination thereof. Although some aspects of the external local node 1006 may be described with a mobile or fixed computing device implemented as a smart phone, personal digital assistant, laptop, desktop computer by way of example, it may be appreciated that the various aspects are not limited in this context. For example, a mobile computing device may comprise, or be implemented as, any type of wireless device, mobile station, or portable computing device with a self-contained power source, e.g., battery, such as the laptop computer, ultra-laptop computer, personal digital assistant (PDA), cellular telephone, combination cellular telephone/PDA, mobile unit, subscriber station, user terminal, portable computer, handheld computer, palmtop computer, wearable computer, media player, pager, messaging device, data communication device, and so forth. A fixed computing device, for example, may be implemented as a desk top computer, workstation, client/server computer, and so forth.

The external local node 1006 comprises personal communication devices including, for example, devices having communication and computer functionality and typically intended for individual use, e.g., mobile computers, sometimes referred to as "handheld devices." Base stations comprise any device or appliance capable of receiving data such as physiologic data. Examples include computers, such as desktop computers and laptop computers, and intelligent devices/appliances. Intelligent devices/appliances include consumer and home devices and appliances that are capable of receipt of data such as physiologic data. Intelligent devices/appliances may also perform other data-related functions, e.g., transmit, display, store, and/or process data. Examples of intelligent devices/appliances include refrigerators, weight scales, toilets, televisions, door frame activity monitors, bedside monitors, bed scales. Such devices and appliances may include additional functionality such as sensing or monitoring various physiologic data, e.g., weight, heart rate. Mobile telephones include telephonic communication devices associated with various mobile technologies, e.g., cellular networks.

In various aspects, the external local node 1006 may provide voice and/or data communications functionality in accordance with different types of cellular radiotelephone systems. Examples of cellular radiotelephone systems may include Code Division Multiple Access (CDMA) systems, Global System for Mobile Communications (GSM) systems, North American Digital Cellular (NADC) systems, Time Division Multiple Access (TDMA) systems, Extended-TDMA (E-TDMA) systems, Narrowband Advanced Mobile Phone Service (NAMPS) systems, 3G systems such as Wide-band CDMA (WCDMA), CDMA-2000, Universal Mobile Telephone System (UMTS) systems, WiMAX (Worldwide Interoperability for Microwave Access, LTE (Long Term Evolution) and so forth.

In various embodiments, the external local node 1006 may be configured to provide voice and/or data communications functionality in accordance with different types of wireless network systems or protocols. Examples of suitable wireless network systems offering data communication services may include the Institute of Electrical and Electronics Engineers (IEEE) 802.xx series of protocols, such as the IEEE 802.1a/b/g/n series of standard protocols and variants (also referred to as "WiFi"), the IEEE 802.16 series of standard protocols and variants (also referred to as "WiMAX"), the IEEE 802.20 series of standard protocols and variants, and so forth. A mobile computing device may also utilize different types of shorter range wireless systems, such as a Bluetooth system operating in accordance with the Bluetooth Special Interest Group (SIG) series of protocols, including Bluetooth Specification versions v1.0, v1.1, v1.2, v1.0, v2.0 with Enhanced Data Rate (EDR), as well as one or more Bluetooth Profiles, and so forth. Other examples may include systems using infrared techniques or near-field communication techniques and protocols, such as electromagnetic induction (EMI) techniques.

In one aspect, the external local node 1006, for example, the hub, includes a software application associated with a mobile telephone of a patient. The application and mobile telephone function to receive physiologic data from a receiver, which, in turn, receives the physiologic data directly from an individual or indirectly, e.g., via a device. Examples of devices include cardiac devices and ingestible devices. The hub stores, manipulates, and/or forwards the data, alone or in combination with other data, via the network 1008 to a remote node 1010.

In various aspects, the external local node 1006 (hub) receives, generates, communicates, and/or transmits, physiologic data, alone or in combination with other data, i.e., non-physiologic data such as ingestion information from IEMs or various sources. Communication from the external local node 106 includes any transmission means or carriers, and combinations thereof, including wireless, wired, RF, conductive, etc. as is known in the art or as may become available in the future.

In various aspects, the handheld device includes software, e.g., a software agent/application, associated with the physiologic data. In various aspects of the handheld device, the software is preconfigured, i.e., configurable by the manufacturer/retailer; configurable by the consumer, i.e., downloadable from a website; or a combination of the same.

The base station includes systems, subsystems, devices, and/or components that receive, transmit, and/or relay the physiologic data. In various aspects, the base station communicably interoperates with a receiver such as the body-associated personal communicator 1004 and a communications network 1008 such as the Internet. Examples of base stations are computers, e.g., servers, personal computers, desktop computers, laptop computers, intelligent devices/appliances, etc. as heretofore discussed.

In various aspects, the base station may be embodied as an integrated unit or as distributed components, e.g., a desktop computer and a mobile telephone in communication with one another and in communication with a patch receiver and the Internet.

In various aspects, the base station includes the functionality to wirelessly receive and/or wirelessly transmit data, e.g., physiologic data received from and transmitted to the body-associated personal communicator 1004 and the Internet.

Further, in various aspects, the base station may incorporate and/or be associated with, e.g., communicate with, various devices. Such devices may generate, receive, and/or communicate data, e.g., physiologic data. The devices include, for example, "intelligent" devices such as gaming devices, e.g., electronic slot machines, handheld electronic games, electronic components associated with games and recreational activities.

The mobile telephone includes, for example, devices such as a short-range, portable electronic device used for mobile voice or data communication over a network of specialized cell site base stations. The mobile telephone is sometimes known as or referred to as "mobile," "wireless," "cellular phone," "cell phone," or "hand phone (HP)."

In addition to the standard voice function of a telephone, various aspects of mobile telephones may support many additional services and accessories such as short message service (SMS) for text messaging, email, packet switching for access to the Internet, Java gaming, wireless, e.g., short range data/voice communications, infrared, camera with video recorder, and multimedia messaging system (MMS) for sending and receiving photos and video. Some aspects of mobile telephones connect to a cellular network of base stations (cell sites), which is, in turn, interconnected to the public switched telephone network (PSTN) or satellite communications in the case of satellite phones. Various aspects of mobile telephones can connect to the Internet, at least a portion of which can be navigated using the mobile telephones.

In various aspects, the mobile telephone includes software, e.g., a software agent/application, associated with the physiologic data. One example is an auto refill application related to or integrated with an auto refill system to facilitate automated prescription refill functions. In various aspects of the mobile telephone, the software is preconfigured, i.e., configurable by the manufacturer/retailer; configurable by the consumer, i.e., downloadable from a website; or a combination of the same.

Further, various aspects of the hub include combinations of devices. One such combination is the body-associated personal communicator 1004 in communication with the handheld device or the mobile telephone. Thus, for example, the body-associated personal communicator 1004 wirelessly transmits physiologic data to the mobile telephone having a receiver and a software agent available thereon. The receiver of the mobile telephone receives the physiologic data. A software agent, e.g., an application, processes the physiologic data and displays various information related to the physiologic data via, for example, a customized graphical user interface (GUI). In various aspects, the software agent generates displays with a predetermined "look and feel," i.e., recognizable to a user as belonging to a predetermined group of software programs, GUIs, source devices, communities, gaming software, etc.

More particularly, the personal communication system 1000 includes any environment having therein, or associated with, data or communication of physiologic data for a gaming or recreational purpose. Communication includes any method, act, or vehicle of communication, and/or combinations thereof. For example, communication methods include manual, wired, and wireless. Wireless technologies include radio signals, such as x-rays, ultraviolet light, the visible spectrum, infrared, microwaves, and radio waves, etc. Wireless services include voice and messaging, handheld and other Internet-enabled devices, data networking.

Vehicles of communication include the network 1008. In various aspects, the network 1008 comprises local area networks (LAN) as well as wide area networks (WAN) including without limitation Internet, wired channels, wireless channels, communication devices including telephones, computers, wire, radio, optical or other electromagnetic channels, and combinations thereof, including other devices and/or components capable of/associated with communicating data. For example, the communication environments include in-body communications, various devices, various modes of communications such as wireless communications, wired communications, and combinations of the same.

Wireless communication modes include any mode of communication between points that utilizes, at least in part, wireless technology including various protocols and combinations of protocols associated with wireless transmission, data, and devices. The points include, for example, wireless devices such as wireless headsets, audio and multimedia devices and equipment, such as audio players and multimedia players, telephones, including mobile telephones and cordless telephones, and computers and computer-related devices and components, such as printers.

Wired communication modes include any mode of communication between points that utilizes wired technology including various protocols and combinations of protocols associated with wired transmission, data, and devices. The points include, for example, devices such as audio and multimedia devices and equipment, such as audio players and multimedia players, telephones, including mobile telephones and cordless telephones, and computers and computer-related devices and components, such as printers.

In one aspect, the remote node 1010 comprises social network systems, commercial systems, healthcare systems, pharmacy systems, university systems, financial transaction systems, web communities, physician systems, family caregiver systems, regulatory agency systems, wholesaler/retailer systems as described in U.S. patent application Ser. No. 12/522,249 titled "INGESTIBLE EVENT MARKER DATA SYSTEM," the disclosure of which is herein incorporated by reference in its entirety. In other aspects, the remote node 110 comprises state games, behavioral reflective games, psychological response games, synchronization games, actual progress games, and recreational games as described in PCT Patent Application No. PCT/US09/60713 dated Oct. 14, 2009 titled "METHOD AND SYSTEM FOR INCORPORATING PHYSIOLOGIC DATA IN A GAMING ENVIRONMENT" and published as WO 2010/045385, the disclosure of which is herein incorporated by reference in its entirety.

In various aspects, a computer system associated with the server 4040 or the server 4040 itself described in connection with FIG. 82 and/or a computer system associated with the external local node 1006 and/or the remote node 1010 may be configured to implement a computer-implemented method as described hereinbelow. The computer system architectural or component comprises one or more processors (such as for instance a microprocessor or microcontroller). The computing system further comprises a storage medium, having operating logic, in coupled to the one or more processors. The computing system further comprises a communication interface coupled to the one or more processors.

The processor may be configured to execute the operating logic. The processor may be any one of a number of single or multi-core processors known in the art. The storage may comprise volatile and non-volatile storage media configured to store persistent and temporal copies of the operating logic.

In various aspects, the operating logic may be configured to calculate a composite risk score as described hereinbelow. In various aspects, the operating logic may be implemented in instructions supported by the instruction set architecture (ISA) of the processor, or in higher level languages and compiled into the supported ISA. The operating logic may comprise on or more logic units or modules. The operating logic may be implemented in an object oriented manner. The operating logic may be configured to be executed in a multi-tasking and/or multi-threaded manner. In other embodiments, the operating logic may be implemented in hardware, such as a gate array.

In various aspects, the communication interface may be configured to facilitate communication between external systems or network-connected systems and the computing system. The communication may include transmission of the at least two distinct digitally watermarked copies and/or the pattern that represents a unique identifier. In various embodiments, the communication interface may be a wired or a wireless communication interface. An example of a wired communication interface may include, but is not limited to, a serial interface, a parallel interface, an Ethernet interface, or a Universal Serial Bus (USB) interface. An example of a wireless communication interface may include, but is not limited to, an interface implementing any variant of the 802.11 wireless protocol, an interface implementing a cellular network protocol, or a Bluetooth interface.

For various aspects, the processor may be packaged together with the operating logic. In various aspects, the processor may be packaged together with the operating logic to form a System in Package (SiP). In various embodiments, the processor may be integrated on the same die with the operating logic. In various embodiments, the processor may be packaged together with the operating logic to form a System on Chip (SoC).

Accordingly, a computer system associated with the server 4040 or the server 4040 itself described in connection with FIG. 82 and/or a computer system associated with the external local node 1006 and/or the remote node 1010 comprising the above architecture may be configured to implement a computer-implemented method to receive ingestible event marker (IEM) system information from a receiver 1004 worn by a subject 1002, the IEM system information comprising physiological information and information associated with ingestion of medication by the subject 1002, wherein the receiver 1004 is configured to communicate with the computer system, receive contextual information associated with the subject 1002, and calculate a composite risk score based on a combination of the IEM system information and the contextual information associated with the subject 1002. The composite risk score being calculated in connection with the description associated with FIGS. 1-69 herein. The computer-implemented method also may be configured to receive patient history information associated with the subject 1002 and calculate the composite risk score based on the patient history information.

In another aspect, the computer system may be configured to classify the subject 1002 into a predetermined risk group based on the composite risk score. The computer system also can be configured to dynamically reclassify the subject 1002 into a predetermined risk group based on the risk score.

In another aspect, the computer system may be configured to determine a circadian pattern from the contextual information received from the subject, calculate variability of the circadian pattern, and quantify the variability of the circadian pattern. The computer system also may be configured to determine a dominant circadian pattern, determine a deviation between the dominant circadian pattern and the circadian pattern, calculate a distribution of the deviations, and quantify the distribution of deviations by differential entropy. The computer system also may be configured to determine the dominant circadian pattern using principal component analysis. The computer system also may be configured to determine the composite risk score based at least in part on the variability of the circadian pattern.

In another aspect, the a computer system associated with the server 4040 or the server 4040 described in connection with FIG. 82 and/or a computer system associated with the external local node 1006 and/or the remote node 1010 comprising the architecture described above may be configured to implement a computer-implemented method to receive daily data from a subject 1002, calculate the daily data into a dominant circadian pattern, track daily variations between the daily data and the dominant circadian pattern, calculate a distribution of the daily variations, and quantify the distribution of the daily variations by differential entropy.

In another aspect, the computer system may be configured to calculate a composite risk score based on the quantified distribution of the daily variations. The computer system also may be configured to classify subjects 1002 into high risk or low risk classes based on the composite risk score. The computer system also can be implemented to temporarily classify subjects 1002 into high risk or low risk classes based on the composite risk score when the subjects' 1002 data temporarily increases in variability.

In another aspect, the a computer system associated with the server 4040 or the server 4040 described in connection with FIG. 82 and/or a computer system associated with the external local node 1006 and/or the remote node 1010 comprising the architecture described above may be configured to implement a computer-implemented method to receive daily data from a subject 1002, apply principal component analysis to the received daily data to determine a dominant mode, determine a variation between the daily data and the dominant mode, and determine how many samples of the daily data are above a predetermined threshold.

In another aspect, the computer system may be configured to whiten the variation between the daily data and the dominant mode. The computer system also may be configured to determine how many whitened principal component analysis samples are above the predetermined threshold. The computer system may be configured to determine a variability score based how many samples of the daily data are above the predetermined threshold.

In another aspect, the a computer system associated with the server 4040 or the server 4040 described in connection with FIG. 82 and/or a computer system associated with the external local node 1006 and/or the remote node 1010 comprising the architecture described above may be configured to implement a computer-implemented method to receive daily data from a subject for at least one week, extract at least one week of data from the received data, whiten the at least one week of data, and calculate an average deviation between the daily data and the weekly data.

The computer system also may be configured to determine a variability score based how many samples of the daily data are above the predetermined threshold. The computer system also may be configured to calculate a composite risk score based on the average deviation between the daily data and the weekly data. The computer system also may be configured to assess a risk associated with a subject based on the composite risk score.

The present invention may be defined by way of the following clauses. It will be understood that the features recited are interchangeable defined by the following clauses and their dependencies. That is, the features of the clauses may be combined to define the present invention.

Clauses

1. A computer-implemented method, comprising:
receiving, by a computer system, ingestible event marker (IEM) system information from a receiver worn by a subject, the IEM system information comprising physiological information and information associated with ingestion of medication by the subject, wherein the receiver is configured to communicate with the computer system;
receiving, by the computer system, contextual information associated with the subject; and
calculating, by the computer system, a composite risk score based on a combination of the IEM system information and the contextual information associated with the subject.

2. The computer-implemented method of Clause 1, comprising:
receiving, by the computer system, patient history information associated with the subject; and
calculating the composite risk score based on the patient history information.

3. The computer-implemented method of Clause 1 or Clause 2, comprising classifying the subject into a predetermined risk group based on the composite risk score.

4. The computer-implemented method of Clause 3, comprising dynamically reclassifying the subject into a predetermined risk group based on the risk score.

5. The computer-implemented method of any of Clauses 1 to 5, comprising:
determining, by the computer system, a circadian pattern from the contextual information received from the subject;
calculating, by the computer system, variability of the circadian pattern; and
quantifying, by the computer system, the variability of the circadian pattern.

6. The computer-implemented method of Clause 5, comprising:
determining, by the computer system, a dominant circadian pattern;
determining, by the computer system, a deviation between the dominant circadian pattern and the circadian pattern;
calculating, by the computer system, a distribution of the deviations; and
quantifying, by the computer system, the distribution of deviations by differential entropy.

7. The computer-implemented method of Clause 6, comprising, by the computer system, determining the dominant circadian pattern using principal component analysis.

8. The computer-implemented method of Clause 5, further comprising determining, by the computer system, the composite risk score based at least in part on the variability of the circadian pattern.

9. A computer-implemented method, comprising:
receiving, by a computer system, daily data from a subject;
calculating, by the computer system, the daily data into a dominant circadian pattern;
tracking, by the computer system, daily variations between the daily data and the dominant circadian pattern;
calculating, by the computer system, a distribution of the daily variations; and
quantifying, by the computer system, the distribution of the daily variations by differential entropy.

10. The computer-implemented method of Clause 9, comprising calculating, by the computer system, a composite risk score based on the quantified distribution of the daily variations.

11. The computer-implemented method of Clause 10, comprising classifying, by the computer system, subjects into high risk or low risk classes based on the composite risk score.

12. The computer-implemented method of Clause 10, comprising temporarily classifying, by the computer system, subjects into high risk or low risk classes based on the composite risk score when the subjects' data temporarily increases in variability.

13. A computer-implemented method, comprising:
receiving, by a computer system, daily data from a subject;
applying, by the computer system, principal component analysis to the received daily data to determine a dominant mode;
determining, by the computer system, a variation between the daily data and the dominant mode; and
determining, by the computer system, how many samples of the daily data are above a predetermined threshold.

14. The computer-implemented method of Clause 13, comprising, by the computer system, whitening the variation between the daily data and the dominant mode.

15. The computer-implemented method of Clause 14, comprising determining, by the computer system, how many whitened principal component analysis samples are above the predetermined threshold.

16. The computer-implemented method of Clause 13, comprising determining, by the computer system, a variability score based how many samples of the daily data are above the predetermined threshold.

17. A computer-implemented method, comprising:
receiving, by a computer system, daily data from a subject for at least one week;
extracting, by the computer system, at least one week of data from the received data;
whitening, by the computer, the at least one week of data; and
calculating, by the computer, an average deviation between the daily data and the weekly data.

18. The computer-implemented method of Clause 17, comprising determining, by the computer system, a variability score based how many samples of the daily data are above the predetermined threshold.

19. The computer-implemented method of Clause 17 or Clause 18, comprising calculating, by the computer system, a composite risk score based on the average deviation between the daily data and the weekly data.

20. The computer-implemented method of Clause 19, comprising assessing, by the computer system, a risk associated with a subject based on the composite risk score.

21. A system, comprising:
a computer system, comprising:
a processor; and
a memory coupled to the processor, wherein the memory stores program instructions, which when executed from the memory cause the processor to:
receive ingestible event marker (IEM) system information from a receiver worn by a subject, the IEM system information comprising physiological information and information associated with ingestion of medication by the subject, wherein the receiver is configured to communicate with the computer system;
receive contextual information associated with the subject; and
calculate a composite risk score based on a combination of the IEM system information and the contextual information associated with the subject.

22. The system of Clause 21, wherein the stored program instructions, when executed by the processor, cause the processor to:
receive patient history information associated with the subject; and
calculate the composite risk score based on the patient history information.

23. The system of Clause 21, wherein the stored program instructions, when executed by the processor, cause the processor to classify the subject into a predetermined risk group based on the composite risk score.

24. The system of Clause 23, wherein the stored program instructions, when executed by the processor, cause the processor to dynamically reclassify the subject into a predetermined risk group based on the risk score.

25. The system of Clause 21, wherein the stored program instructions, when executed by the processor, cause the processor to
determine a circadian pattern from the contextual information received from the subject;
calculate variability of the circadian pattern; and
quantify the variability of the circadian pattern.

26. The system of Clause 25, wherein the stored program instructions, when executed by the processor, cause the processor to:
determine a dominant circadian pattern;
determine a deviation between the dominant circadian pattern and the circadian pattern;
calculate a distribution of the deviations; and
quantify the distribution of deviations by differential entropy.

27. The system of Clause 26, wherein the stored program instructions, when executed by the processor, cause the processor to determine the dominant circadian pattern using principal component analysis.

28. The system of Clause 25, wherein the stored program instructions, when executed by the processor, cause the processor to determine the composite risk score based at least in part on the variability of the circadian pattern.

29. A system, comprising:
a computer system, comprising:
a processor; and
a memory coupled to the processor, wherein the memory stores program instructions, which when executed from the memory cause the processor to:
receive daily data from a subject;
calculate the daily data into a dominant circadian pattern;
track daily variations between the daily data and the dominant circadian pattern;

calculate a distribution of the daily variations; and quantify the distribution of the daily variations by differential entropy.

30. The system of Clause 29, wherein the stored program instructions, when executed by the processor, cause the processor to calculate a composite risk score based on the quantified distribution of the daily variations.

31. The system of Clause 29 or Clause 30, wherein the stored program instructions, when executed by the processor, cause the processor to classify subjects into high risk or low risk classes based on the composite risk score.

32. The system of Clause 29 or Clause 30, wherein the stored program instructions, when executed by the processor, cause the processor to temporarily classify subjects into high risk or low risk classes based on the composite risk score when the subjects' data temporarily increases in variability.

33. A system, comprising:
a computer system, comprising:
a processor; and
   a memory coupled to the processor, wherein the memory stores program instructions, which when executed from the memory cause the processor to:
   receive daily data from a subject;
   apply principal component analysis to the received daily data to determine a dominant mode;
   determine a variation between the daily data and the dominant mode; and
   determine how many samples of the daily data are above a predetermined threshold.

34. The system of Clause 33, wherein the stored program instructions, when executed by the processor, cause the processor to whiten the variation between the daily data and the dominant mode.

35. The system of Clause 34, wherein the stored program instructions, when executed by the processor, cause the processor to determine how many whitened principal component analysis samples are above the predetermined threshold.

36. The system of any of Clauses 33 to 35, wherein the stored program instructions, when executed by the processor, cause the processor to determine a variability score based how many samples of the daily data are above the predetermined threshold.

37. A system, comprising:
a computer system, comprising:
a processor; and
   a memory coupled to the processor, wherein the memory stores program instructions, which when executed from the memory cause the processor to:
   receive daily data from a subject for at least one week;
   extract least one week of data from the received data;
   whiten the at least one week of data; and
   calculate an average deviation between the daily data and the weekly data.

38. The system of Clause 37, wherein the stored program instructions, when executed by the processor, cause the processor to determine a variability score based how many samples of the daily data are above the predetermined threshold.

39. The system of Clause 37 or Clause 38, wherein the stored program instructions, when executed by the processor, cause the processor to calculate a composite risk score based on the average deviation between the daily data and the weekly data.

40. The system of Clause 39, wherein the stored program instructions, when executed by the processor, cause the processor to assess a risk associated with a subject based on the composite risk score.

While various details have been set forth in the foregoing description, it will be appreciated that the various aspects of system, apparatus and methods for data collection and assessing outcomes may be practiced without these specific details. For example, for conciseness and clarity selected aspects have been shown in block diagram form rather than in detail. Some portions of the detailed descriptions provided herein may be presented in terms of instructions that operate on data that is stored in a computer memory. Such descriptions and representations are used by those skilled in the art to describe and convey the substance of their work to others skilled in the art. In general, an algorithm refers to a self-consistent sequence of steps leading to a desired result, where a "step" refers to a manipulation of physical quantities which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities.

It is to be understood that this disclosure is not limited to particular aspects described, and as such may vary. It is also to be understood that the terminology used herein is for the purpose of describing particular aspects only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided may be different from the actual publication dates which may need to be independently confirmed.

Unless specifically stated otherwise as apparent from the foregoing discussion, it is appreciated that, throughout the foregoing description, discussions using terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

It is worthy to note that any reference to "one aspect," "an aspect," "one aspect," or "an aspect" means that a particular feature, structure, or characteristic described in connection with the aspect is included in at least one aspect. Thus, appearances of the phrases "in one aspect," "in an aspect," "in one aspect," or "in an aspect" in various places throughout the specification are not necessarily all referring to the same aspect. Furthermore, the particular features, structures or characteristics may be combined in any suitable manner in one or more aspects.

Although various aspects have been described herein, many modifications, variations, substitutions, changes, and equivalents to those aspects may be implemented and will occur to those skilled in the art. Also, where materials are disclosed for certain components, other materials may be used. It is therefore to be understood that the foregoing description and the appended claims are intended to cover all such modifications and variations as falling within the scope of the disclosed aspects. The following claims are intended to cover all such modification and variations.

Some or all of the aspects described herein may generally comprise technologies for various aspects of content traceability using segmented watermark encoding, or otherwise according to technologies described herein. In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

The foregoing detailed description has set forth various aspects of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one aspect, several portions of the subject matter described herein may be implemented via Application Specific Integrated Circuits (ASICs), Field Programmable Gate Arrays (FPGAs), digital signal processors (DSPs), or other integrated formats. Those skilled in the art will recognize, however, that some aspects of the aspects disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative aspect of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

As will be apparent to those of skill in the art upon reading this disclosure, each of the individual aspects described and illustrated herein has discrete components and features which may be readily separated from or combined with the features of any of the other several aspects without departing from the scope of the present disclosure. Any recited method can be carried out in the order of events recited or in any other order which is logically possible.

Although the foregoing disclosure has been described in some detail by way of illustration and example for purposes of clarity of understanding, it is readily apparent to those of ordinary skill in the art in light of the teachings of this disclosure that certain changes and modifications may be made thereto without departing from the scope of the appended claims.

Accordingly, the preceding merely illustrates the principles of the disclosure. It will be appreciated that those skilled in the art will be able to devise various arrangements which, although not explicitly described or shown herein, embody the principles of the disclosure and are included within its scope. Furthermore, all examples and conditional language recited herein are principally intended to aid the reader in understanding the principles of the disclosure and the concepts contributed by the inventors to furthering the art, and are to be construed as being without limitation to such specifically recited examples and conditions. Moreover, all statements herein reciting principles, aspects, and aspects of the disclosure as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present disclosure, therefore, is not intended to be limited to the example aspects shown and described herein. Rather, the scope of present disclosure is embodied by the appended claims.

Although various aspects have been described herein, many modifications, variations, substitutions, changes, and equivalents to those aspects may be implemented and will occur to those skilled in the art. Also, where materials are disclosed for certain components, other materials may be used. It is therefore to be understood that the foregoing description and the appended claims are intended to cover all such modifications and variations as falling within the scope of the disclosed aspects. The following claims are intended to cover all such modification and variations.

The invention claimed is:

1. A computer-implemented method, comprising:
receiving, by a computer system, ingestible event marker (IEM) system information wirelessly transmitted from a receiver worn by a subject, the IEM comprising a partial power source of an anode and cathode that is activated in the presence of a conductive liquid, the IEM configured to transmit the IEM system information to the receiver via a conductive signal using the conductive liquid as a transmitting medium, the IEM system information comprising at least IEM-derived medication ingestion compliance information providing an indication that medication containing the IEM has been ingested by the subject, wherein the receiver comprises one or more electrodes that touches the subject to receive the conductive signal from the IEM, and one or more physiologic parameter sensors, and is configured to communicate with the computer system;
receiving, by the computer system, receiver-derived contextual information comprising periodic data of the subject's posture angle, wherein the receiver-derived contextual information is obtained using the one or more physiologic parameter sensors monitoring the subject;
determining, by the computer system, a circadian pattern from the contextual information received from the receiver, the circadian pattern reflecting at least a pattern of the subject's posture across a 24-hour period;
calculating, by the computer system, variability of the circadian pattern, the variability comprising a plurality of ranges in posture angle at regular intervals across the 24-hour period;
quantifying, by the computer system, the variability of the circadian pattern;
determining, by the computer system, a dominant circadian pattern by determining a posture angle for each interval of the regular intervals across the 24-hour period that reduces trend fit error of the dominant circadian pattern when fitted to circadian pattern;
determining, by the computer system, a plurality of deviations between the dominant circadian pattern and the circadian pattern;
calculating, by the computer system, a distribution of the plurality of deviations;
quantifying, by the computer system, the distribution of the plurality of deviations by differential entropy;
calculating, by the computer system, a composite risk score representing an assessment of what type of additional medical intervention is needed, if any, to improve the subject's health, based on a combination of the IEM system information and the quantified plurality of deviations between the dominant circadian pattern and the circadian pattern; and
providing, by the computer system, a recommendation for a medical intervention, if any, to improve the subject's health, based on the composite risk score.

2. The computer-implemented method of claim 1, further comprising:
accessing, by the computer system, database-derived patient history information comprising self-reported, historical health information by the subject; and
calculating the composite risk score based further on the database-derived patient history information.

3. The computer-implemented method of claim 1, further comprising classifying the subject into a predetermined risk group based on the composite risk score.

4. The computer-implemented method of claim 3, further comprising dynamically reclassifying the subject into a predetermined risk group based on the composite risk score.

5. The computer-implemented method of claim 1, further comprising, by the computer system, determining the dominant circadian pattern using principal component analysis.

6. The computer-implemented method of claim 1, further comprising determining, by the computer system, the composite risk score based at least in part on the variability of the circadian pattern.

7. A system, comprising:
a computer system, comprising:
a processor; and
a memory coupled to the processor, wherein the memory stores program instructions, which when executed from the memory cause the processor to:
receive ingestible event marker (IEM) system information from a receiver worn by a subject, the IEM comprising a partial power source of an anode and cathode that is activated in the presence of a conductive liquid, the IEM configured to transmit the IEM system information to the receiver via a conductive signal using the conductive liquid as a transmitting medium, the IEM system information comprising at least IEM-derived medication ingestion compliance information providing an indication that medication containing the IEM has been ingested by the subject, wherein the receiver comprises one or more electrodes that touches the subject to receive the conductive signal from the IEM, and one or more physiologic parameter sensors, and is configured to communicate with the computer system;
receive receiver-derived contextual information comprising periodic data of the subject's posture angle, wherein the receiver-derived contextual information is obtained using the one or more physiologic parameter sensors monitoring the subject;
determine a circadian pattern from the contextual information received from the receiver, the circadian pattern reflecting at least a pattern of the subject's posture across a 24-hour period;
calculate variability of the circadian pattern, the variability comprising a plurality of ranges in posture angle at regular intervals across the 24-hour period;
quantify the variability of the circadian pattern;
determine a dominant circadian pattern by determining a posture angle for each interval of the regular intervals across the 24-hour period that reduces trend fit error of the dominant circadian pattern when fitted to circadian pattern;
determine a plurality of deviations between the dominant circadian pattern and the circadian pattern;
calculate a distribution of the plurality of deviations;
quantify the distribution of the plurality of deviations by differential entropy;

calculate a composite risk score representing an assessment of what type of additional medical intervention is needed, if any, to improve the subject's health, based on a combination of the IEM system information and the quantified plurality of deviations between the dominant circadian pattern and the circadian pattern; and provide a recommendation for a medical intervention, if any, to improve the subject's health, based on the composite risk score.

8. The system of claim 7, wherein the stored program instructions, when executed by the processor, further cause the processor to:

access database-derived patient history information comprising self-reported, historical health information by the subject; and calculate the composite risk score based further on the database-derived patient history information.

9. The system of claim 7, wherein the stored program instructions, when executed by the processor, further cause the processor to classify the subject into a predetermined risk group based on the composite risk score.

10. The system of claim 9, wherein the stored program instructions, when executed by the processor, further cause the processor to dynamically reclassify the subject into a predetermined risk group based on the composite risk score.

11. The system of claim 7, wherein the stored program instructions, when executed by the processor, further cause the processor to determine the dominant circadian pattern using principal component analysis.

12. A system, comprising:
a computer system, comprising:
a processor; and
a memory coupled to the processor, wherein the memory stores program instructions, which when executed from the memory cause the processor to:

receiving, by the computer system, ingestible event marker (IEM) system information wirelessly transmitted from a receiver worn by a subject, the IEM comprising a partial power source of an anode and cathode that is activated in the presence of a conductive liquid, the IEM configured to transmit the IEM system information to the receiver via a conductive signal using the conductive liquid as a transmitting medium, the IEM system information comprising at least IEM-derived medication ingestion compliance information providing an indication that medication containing the IEM has been ingested by the subject, receive, from the receiver comprising one or more electrodes that touches a subject, and one or more physiologic parameter sensors, daily data of regularly recorded posture angle associated with a circadian rhythm from a subject for at least one week, the daily data obtained from using the one or more physiologic parameter sensors monitoring the subject;

extract at least one week of data from the received data;

whiten the at least one week of data by performing a matrix transformation on the at least one week of data;

calculate an average deviation between the daily data and the weekly data;

calculate the daily data into a dominant circadian pattern by determining a posture angle at regular intervals across 24 hours in the daily data that reduces trend fit error of the dominant circadian pattern when fitted to the daily data;

track daily variations between the daily data and the dominant circadian pattern at each interval of the regular intervals;

calculate a distribution of the daily variations;

quantify the distribution of the daily variations by differential entropy; and provide a recommendation for a medical intervention, if any, to improve the subject's health, based on the quantified distribution of the daily variations.

13. The system of claim 12, wherein the stored program instructions, when executed by the processor, further cause the processor to determine a variability score based how many samples of the daily data are above a predetermined threshold.

14. The system of claim 12, wherein the stored program instructions, when executed by the processor, further cause the processor to calculate a composite risk score based on the average deviation between the daily data and the weekly data.

15. The system of claim 14, wherein the stored program instructions, when executed by the processor, further cause the processor to assess a risk associated with a subject based on the composite risk score.

* * * * *